(12) United States Patent
Kim et al.

(10) Patent No.: US 10,851,056 B2
(45) Date of Patent: Dec. 1, 2020

(54) COMPOUND FOR ORGANIC OPTOELECTRONIC DEVICE, ORGANIC OPTOELECTRONIC DEVICE AND DISPLAY APPARATUS

(71) Applicant: Samsung SDI Co., Ltd., Yongin-si (KR)

(72) Inventors: Byungku Kim, Suwon-si (KR); Hyung Sun Kim, Suwon-si (KR); Eun Sun Yu, Suwon-si (KR); Sangshin Lee, Suwon-si (KR); Yuna Jang, Suwon-si (KR); Chunkeun Jang, Suwon-si (KR); Sung-Hyun Jung, Suwon-si (KR); Ho-Kuk Jung, Suwon-si (KR)

(73) Assignee: Samsung SDI Co., Ltd., Yongin-Si (KR)

( * ) Notice: Subject to any disclaimer, the term of this patent is extended or adjusted under 35 U.S.C. 154(b) by 274 days.

(21) Appl. No.: 16/075,428

(22) PCT Filed: Apr. 18, 2016

(86) PCT No.: PCT/KR2016/004019
§ 371 (c)(1),
(2) Date: Aug. 3, 2018

(87) PCT Pub. No.: WO2017/135510
PCT Pub. Date: Aug. 10, 2017

(65) Prior Publication Data
US 2018/0339967 A1    Nov. 29, 2018

(30) Foreign Application Priority Data

Feb. 4, 2016 (KR) .................. 10-2016-0014448

(51) Int. Cl.
*H01L 51/50* (2006.01)
*C07D 209/82* (2006.01)
(Continued)

(52) U.S. Cl.
CPC ......... *C07D 209/82* (2013.01); *C07D 239/36* (2013.01); *C07D 251/24* (2013.01);
(Continued)

(58) Field of Classification Search
None
See application file for complete search history.

(56) References Cited

U.S. PATENT DOCUMENTS 7,001,676 B2   2/2006  Igarashi et al.
2002/0045061 A1   4/2002  Hosokawa

FOREIGN PATENT DOCUMENTS

CN    101654430 A    2/2010
CN    102036957 A    4/2011
(Continued)

OTHER PUBLICATIONS

European Search Report dated Jun. 3, 2019.
Chinese Office action dated Jun. 2, 2020.

*Primary Examiner* — Gregory D Clark
(74) *Attorney, Agent, or Firm* — Lee IP Law, PC

(57) ABSTRACT

The present invention relates to a compound for an organic optoelectronic device represented by chemical formula 1, an organic optoelectronic device employing the same and a display device apparatus. The details of chemical formula 1 are as defined in the specification.

15 Claims, 2 Drawing Sheets

(51) Int. Cl.
*C07D 251/24* (2006.01)
*C09K 11/06* (2006.01)
*H01L 51/00* (2006.01)
*C07D 239/36* (2006.01)

(52) U.S. Cl.
CPC .............. *C09K 11/06* (2013.01); *H01L 51/00* (2013.01); *H01L 51/0072* (2013.01); *H01L 51/50* (2013.01); *H01L 51/5064* (2013.01); *H01L 51/5072* (2013.01); *H01L 51/0037* (2013.01)

(56) References Cited

FOREIGN PATENT DOCUMENTS

| | | | | |
|---|---|---|---|---|
| CN | 104498025 A | 4/2015 | | |
| JP | 2003-027048 A | 1/2003 | | |
| JP | 2004-244400 A | 9/2004 | | |
| JP | 2005-268022 | * | 9/2005 | ............. H05B 33/22 |
| JP | 2005-268022 A | 9/2005 | | |
| JP | 2006-135184 A | 5/2006 | | |
| JP | 4003824 B2 | 11/2007 | | |
| JP | 2011523644 A | 8/2011 | | |
| JP | 2013006838 A | 1/2013 | | |
| JP | 5206907 B2 | 6/2013 | | |
| JP | 2014508114 | 4/2014 | | |
| KR | 10-2014-0120975 A | 10/2014 | | |
| WO | WO 2006-097717 A1 | 9/2006 | | |
| WO | WO 2008/119666 A1 | 10/2008 | | |
| WO | WO 2009/142870 A1 | 11/2009 | | |

* cited by examiner

【Figure 1】
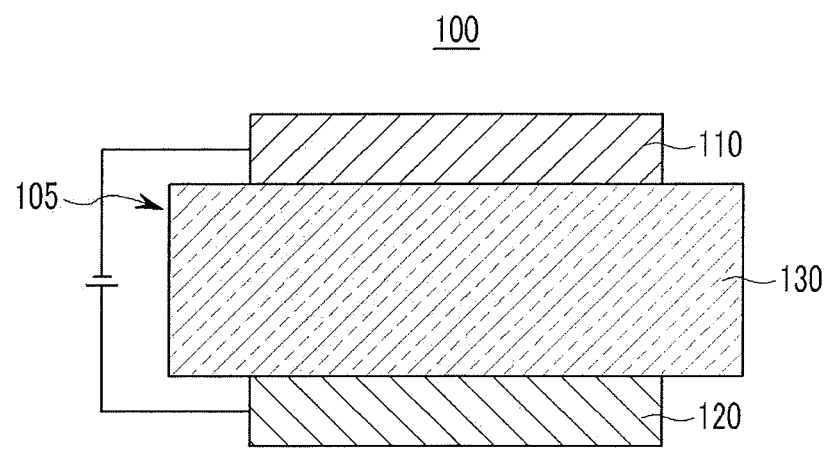
【Figure 2】
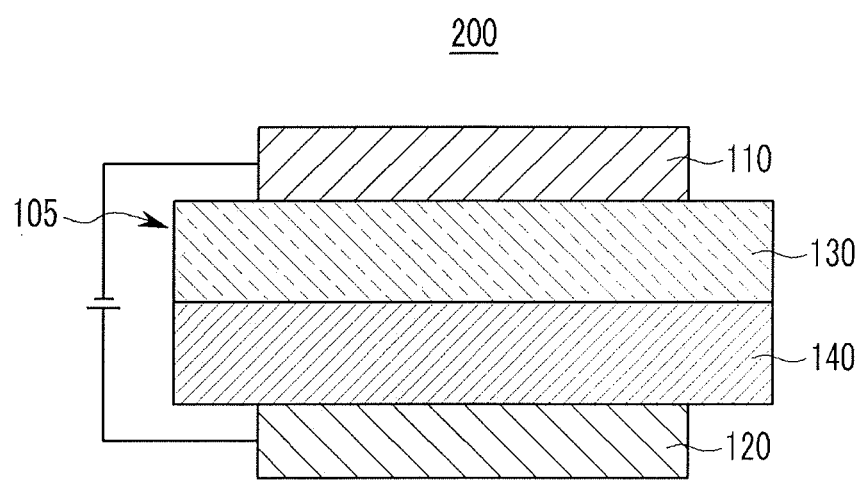

【Figure 3】
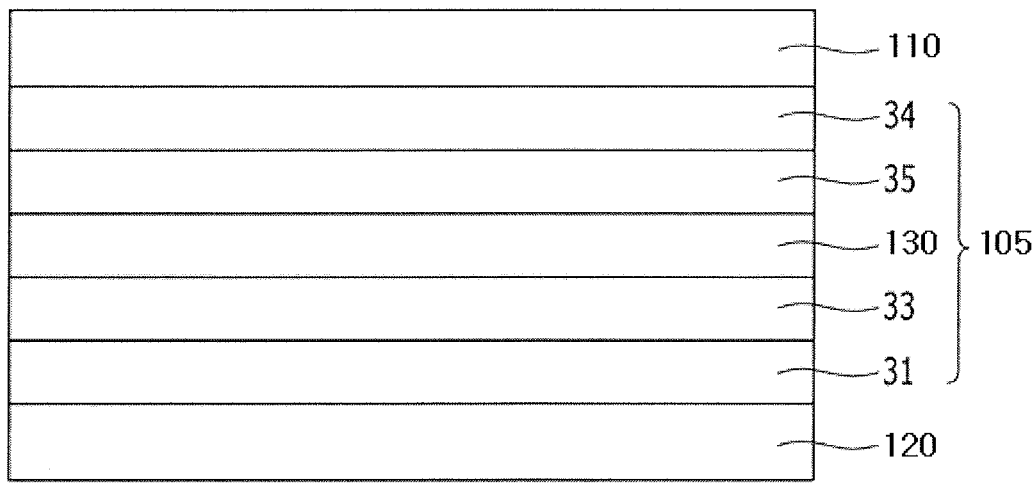
【Figure 4】
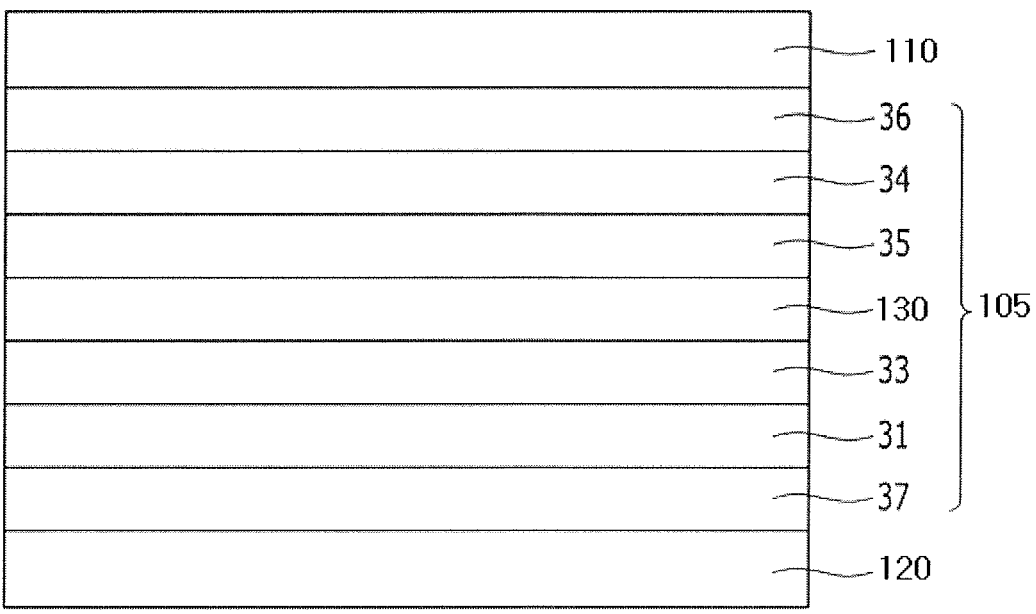

COMPOUND FOR ORGANIC OPTOELECTRONIC DEVICE, ORGANIC OPTOELECTRONIC DEVICE AND DISPLAY APPARATUS

CROSS REFERENCE TO RELATED APPLICATIONS

This is the U.S. national phase application based on PCT Application No. PCT/KR2016/004019, filed Apr. 18, 2016, which is based on Korean Patent Application No. 10-2016-0014448, filed Feb. 4, 2016, the entire contents of all of which are hereby incorporated by reference.

TECHNICAL FIELD

A compound for an organic optoelectronic device, an organic optoelectronic device, and a display device are disclosed.

BACKGROUND ART

An organic optoelectronic device is a device that converts electrical energy into photoenergy, and vice versa.

An organic optoelectronic device may be classified as follows in accordance with its driving principles. One is an optoelectronic device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode. Herein, the organic layer may include an emission layer and optionally an auxiliary layer, and the auxiliary layer may be, for example at least one selected from a hole injection layer, a hole transport layer, an electron blocking layer, an electron transport layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectronic device capable of realizing an organic optoelectronic device having high efficiency and long life-span.

Another embodiment provides an organic optoelectronic device including the compound for an organic optoelectronic device.

Yet another embodiment provides a display device including the organic optoelectronic device.

Technical Solution

According to an embodiment, a compound for an organic optoelectronic device is represented by Chemical Formula 1.

[Chemical Formula 1]

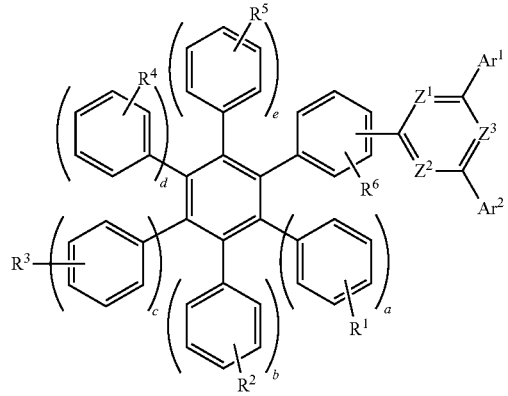

In Chemical Formula 1, $R^1$ to $R^5$ are independently hydrogen, a deuterium, a substituted or unsubstituted C1 to C4 alkyl group, or a phenyl group, $Z^1$ to $Z^3$ are independently $CR^a$ or N, at least two of $Z^1$ to $Z^3$ are N, $R^a$ and $R^6$ are hydrogen, a deuterium, a substituted or unsubstituted C1 to C10 alkyl group, or a substituted or unsubstituted C6 to C12 aryl group, $Ar^1$ and $Ar^2$ are independently hydrogen, a deuterium, a substituted or unsubstituted C1 to C10 alkyl group, or a substituted or unsubstituted C6 to C18 aryl group, a, b, c, d, and e are independently an integer of 0 or 1, $4 \leq a+b+c+d+e \leq 5$, and the "substituted" refers to replacement of at least one hydrogen by deuterium, a C1 to C4 alkyl group, or a C6 to C12 aryl group.

According to another embodiment, an organic optoelectronic device includes an anode and a cathode facing each other, at least one organic layer between the anode and the cathode, wherein the organic layer includes the compound for an organic optoelectronic device.

According to yet another embodiment, a display device including the organic optoelectronic device is provided.

Advantageous Effects

An organic optoelectronic device having high efficiency and long life-span may be realized.

DESCRIPTION OF THE DRAWINGS

FIGS. 1 to 4 are cross-sectional views showing organic light emitting diodes according to an embodiment.

DESCRIPTION OF SYMBOLS

100, 200, 300, 400: organic light emitting diode
105: organic layer, 110: cathode 120: anode
130: emission layer
140: hole auxiliary layer
10: organic light emitting diode
31: hole transport layer
33: hole transport auxiliary layer
34: electron transport layer
35: electron transport auxiliary layer
36: electron injection layer
37: hole injection layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, the term "substituted" refers to one substituted with a deuterium, a halogen, a hydroxyl group, an amino group, a substituted or unsubstituted C1 to C30 amine group, a nitro group, a substituted or unsubstituted C1 to C40 silyl group, C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, or a cyano group, instead of at least one hydrogen of a substituent or a compound.

In the present specification, when specific definition is not otherwise provided, "hetero" refers to one including 1 to 3 hetero atoms selected from the group consisting of N, O, S, P, and Si, and remaining carbons in one compound or substituent.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification "aryl group" refers to a group including at least one hydrocarbon aromatic moiety, and
all the elements of the hydrocarbon aromatic moiety have p-orbitals which form conjugation, for example a phenyl group, a naphthyl group, and the like,
two or more hydrocarbon aromatic moieties may be linked by a sigma bond and may be, for example a biphenyl group, a terphenyl group, a quarterphenyl group, and the like, and
two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

For example, a "heteroaryl group" may refer to an aryl group including at least one hetero atom selected from N, O, S, P, and Si and remaining carbon. Two or more heteroaryl groups are linked by a sigma bond directly, or when the heteroaryl group includes two or more rings, the two or more rings may be fused. When the heteroaryl group is a fused ring, each ring may include 1 to 3 hetero atoms.

Specific examples of the heteroaryl group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment is represented by Chemical Formula 1.

[Chemical Formula 1]

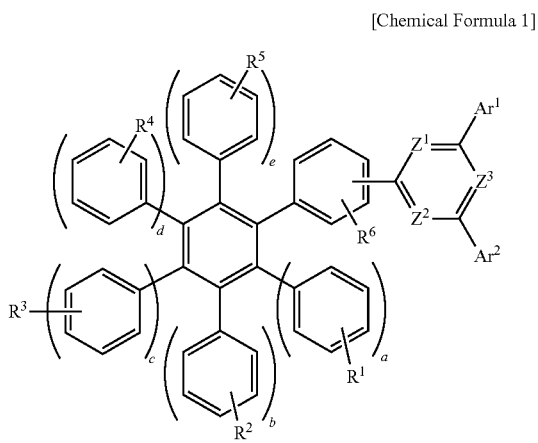

In Chemical Formula 1, $R^1$ to $R^5$ are independently hydrogen, a deuterium, a substituted or unsubstituted C1 to C4 alkyl group, or a phenyl group, $Z^1$ to $Z^3$ are independently $CR^a$ or N, at least two of $Z^1$ to $Z^3$ are N, $R^a$ and $R^6$ are hydrogen, a deuterium, a substituted or unsubstituted C1 to C10 alkyl group, or a substituted or unsubstituted C6 to C12 aryl group, $Ar^1$ and $Ar^2$ are independently hydrogen, a deuterium, a substituted or unsubstituted C1 to C10 alkyl group, or a substituted or unsubstituted C6 to C18 aryl group, a, b, c, d, and e are independently an integer of 0 or 1, 4≤a+b+c+d+e≤5, and the "substituted" refers to replacement of at least one hydrogen by deuterium, a C1 to C4 alkyl group, or a C6 to C12 aryl group.

The compound for an organic optoelectronic device represented by Chemical Formula 1 has a structure that a bulky aromatic group moiety substituted with four or more phenyl groups is connected with a nitrogen-containing 6-membered ring through a phenyl linker.

The nitrogen-containing 6-membered ring plays a role of easing injection or transport of electrons in a device, and the bulky aromatic group moiety plays a role of helping injection and transport of holes or increasing a glass transition temperature of the compound, suppresses an interaction among molecules and thus increases luminous efficiency and decreases deposition temperature of the compound relative a molecular weight. Accordingly, the compound for an organic optoelectronic device represented by Chemical Formula 1 exhibits improved packing of nitrogen-containing 6-membered rings having a relatively flatter structure than the bulky aromatic group moiety, when used to form a film in the device and thus eases the injection and transport of electrons in the device. Accordingly, the compound for an organic optoelectronic device represented by Chemical Formula 1 may decrease a driving voltage of the device due to improved electron transport characteristics when particularly used to form an electron injection auxiliary layer and increase luminous efficiency due to rapid injection of electrons into an emission layer. On the other hand, when the compound is mixed with a material having improved hole injection and transport to form an emission layer, a driving voltage is decreased due to improved electron transport, and improved luminous efficiency may be obtained due to the decreased interaction among molecules by the bulky aromatic group moiety. In addition, the compound for an organic optoelectronic device represented by Chemical Formula 1 has improved solubility and thus may be usefully applied to both deposition and solution processes as well as may lower a deposition temperature due to spherical shape structure of the bulky aromatic group moiety.

In particular, the nitrogen-containing 6-membered ring connected with the bulky aromatic group through a linker may play a role of increasing prerotation among bonds and decreasing crystallinity and also increase solubility of molecules due to the bulky aromatic group and the linker, which may enable a solution process.

In addition, the linker is fixed by a phenyl group and thus shortens a distance between the nitrogen-containing 6-membered ring and the bulky aromatic group and resultantly, may realize a more spherically shape of molecules and thus lower a deposition temperature and bring about improved thermal resistant stability.

The Chemical Formula 1 may be represented by one of Chemical Formulae 1-I to 1-IV according to the number of the phenyl group in the bulky aromatic group moiety.

[Chemical Formula 1-I]

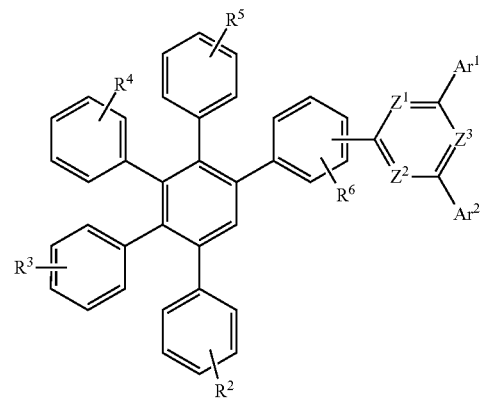

[Chemical Formula 1-II]

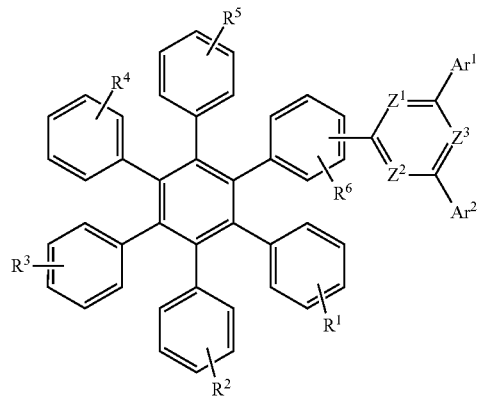

[Chemical Formula 1-III]

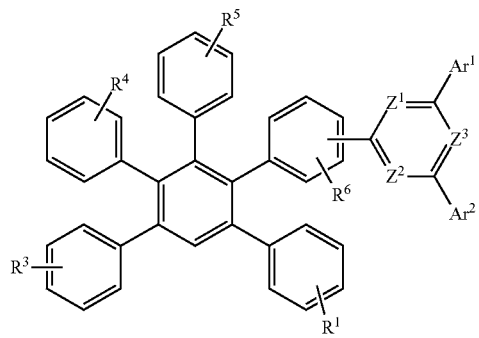

[Chemical Formula 1-Ib]

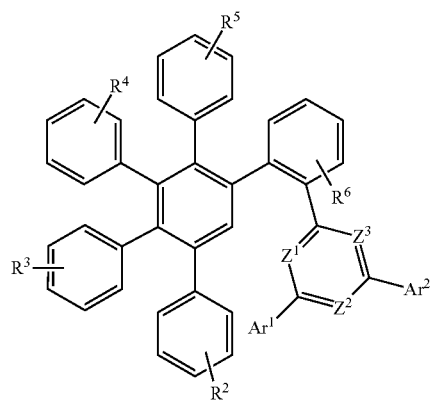

[Chemical Formula 1-IV]

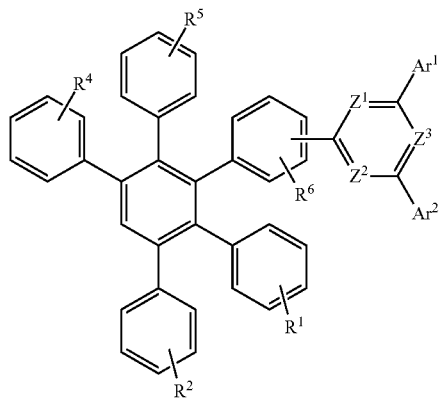

[Chemical Formula 1-Ic]

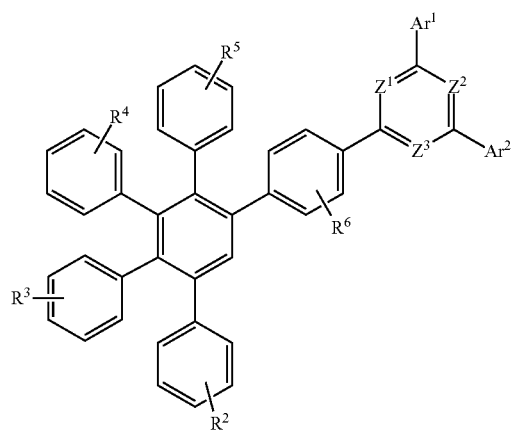

In Chemical Formulae 1-I to 1-IV, $R^1$ to $R^6$, $Z^1$ to $Z^3$, $Ar^1$ and $Ar^2$ are the same as described above.

The Chemical Formula 1-I may be represented by one of Chemical Formula 1-I a, 1-I b, or 1-I c according to the linkers connected in a meta, ortho, or para position.

The Chemical Formula 1-II may also be represented by one of Chemical Formulae 1-II a, 1-II b, or 1-II c according to the linkers connected in a meta, ortho, or para position.

[Chemical Formula 1-Ia]

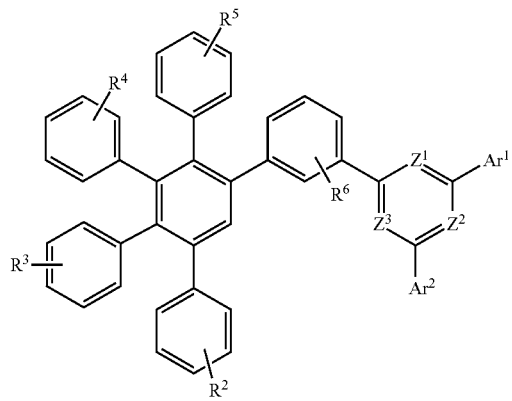

[Chemical Formula 1-IIa]

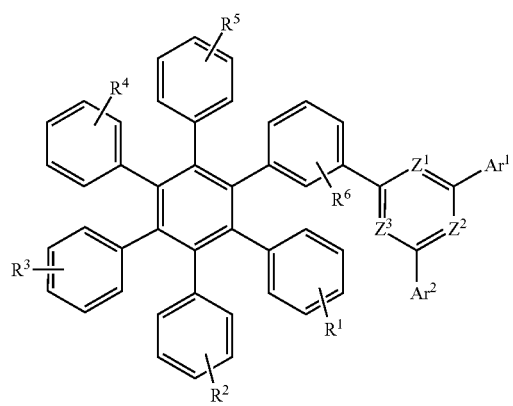

[Chemical Formula 1-IIb]

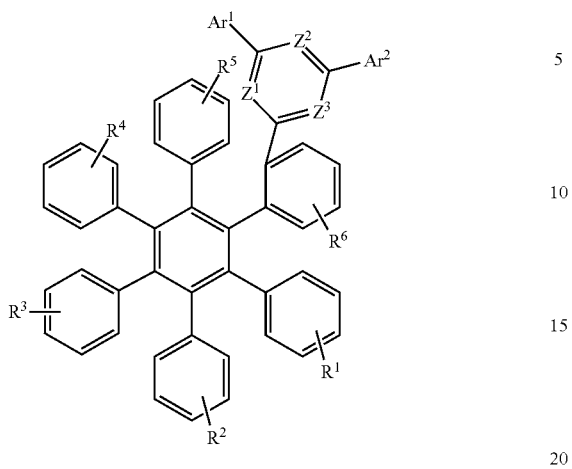

[Chemical Formula 1-IIc]

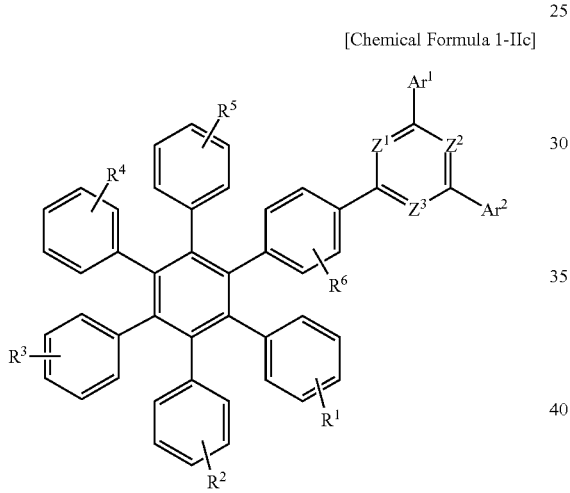

[Chemical Formula 1-Id]

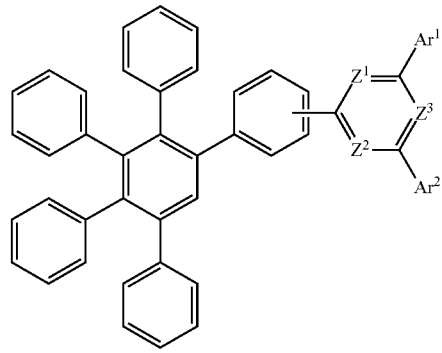

[Chemical Formula 1-Ie]

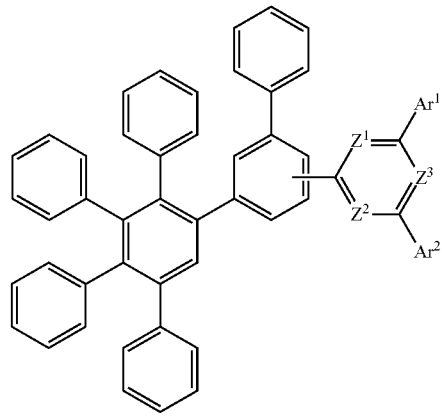

In examples of the present invention, a compound for an organic optoelectronic device may be represented by Chemical Formula 1-I a, 1-I b, 1-I c, 1-II a, or 1-II c.

In the Chemical Formulae 1-I a, 1-I b, 1-I c, 1-II a, 1-II b and 1-II c, $R^1$ to $R^6$, $Z^1$ to $Z^3$, $Ar^1$, and $Ar^2$ are the same as described above.

In an embodiment of the present invention, the $R^1$ to $R^5$ are independently hydrogen, a deuterium, a substituted or unsubstituted C1 to C4 alkyl group, or a phenyl group. Specifically, the $R^1$ to $R^5$ may be hydrogen, a methyl group, an ethyl group, a propyl group, an isopropyl group, or a phenyl group, for example all the $R^1$ to $R^5$ may be hydrogen.

The $R^6$ may be hydrogen, a deuterium, a substituted or unsubstituted C1 to C10 alkyl group, or a substituted or unsubstituted C6 to C12 aryl group. Specifically, the $R^6$ may be hydrogen, or a substituted or unsubstituted C6 to C12 aryl group, and may more specifically be hydrogen, a phenyl group, a biphenyl group, for example hydrogen, or a phenyl group.

As more specific examples, the Chemical Formula 1-I may be represented by Chemical Formula 1-I d or 1-I e, and the Chemical Formula 1-II may be represented by Chemical Formula 1-II d or 1-II e.

[Chemical Formula 1-IId]

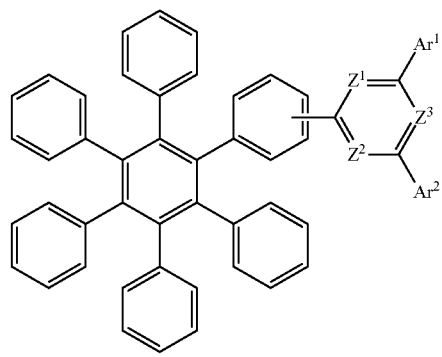

-continued

[Chemical Formula 1-IIe]

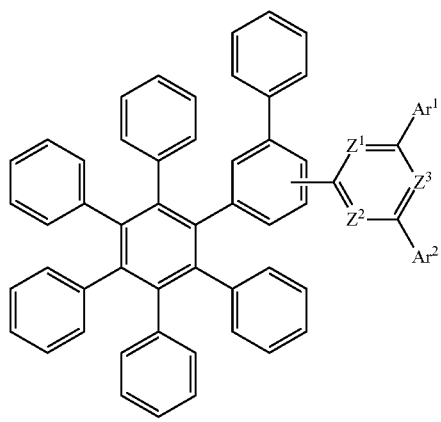

In one example of the present invention, the compound for an organic optoelectronic device may be represented by Chemical Formula 1-I d, 1-I e, or 1-II d.

In Chemical Formulae 1-I d, 1-I e, 1-II d and 1-II e, $Z^1$ to $Z^3$, $Ar^1$ and $Ar^2$ are the same as described above.

In an embodiment of the present invention, at least two of the $Z^1$ to $Z^3$ may be N. For example, $Z^1$ and $Z^3$ may be N or $Z^1$ and $Z^2$ are N to provide a pyrimidinyl group, and $Z^1$ to $Z^3$ may be N to provide a triazinyl group.

In an embodiment of the present invention, the $Ar^1$ and $Ar^2$ may independently be a substituted or unsubstituted C6 to C18 aryl group. Specifically, $Ar^1$ and $Ar^2$ may independently be a substituted or unsubstituted phenyl group, a substituted or unsubstituted biphenyl group, a substituted or unsubstituted terphenyl group, or a substituted or unsubstituted naphthyl group, for example one of substituents of Group 1.

[Group 1]

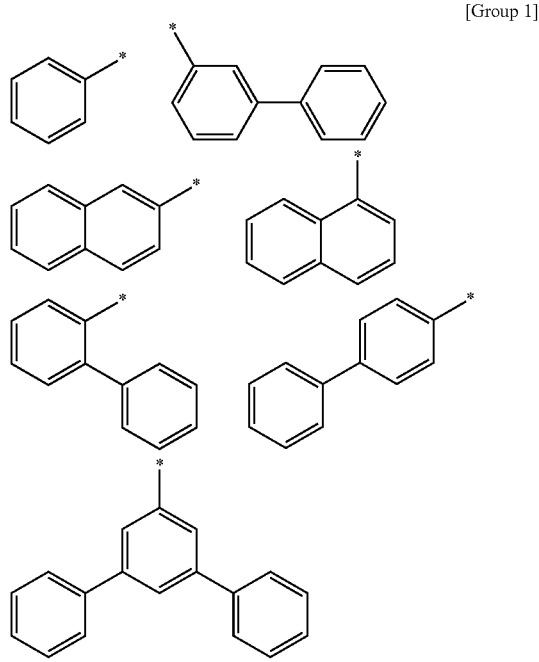

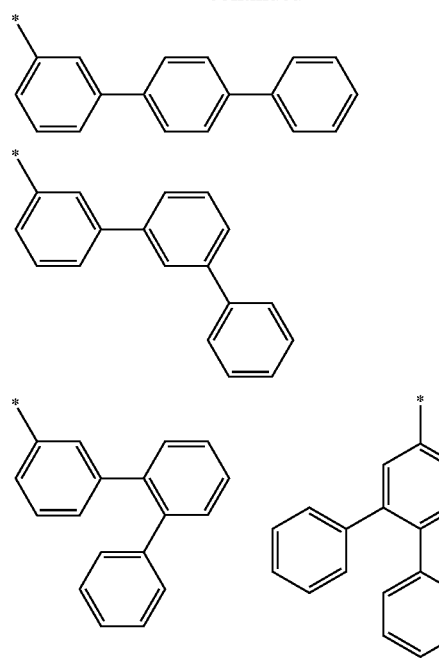

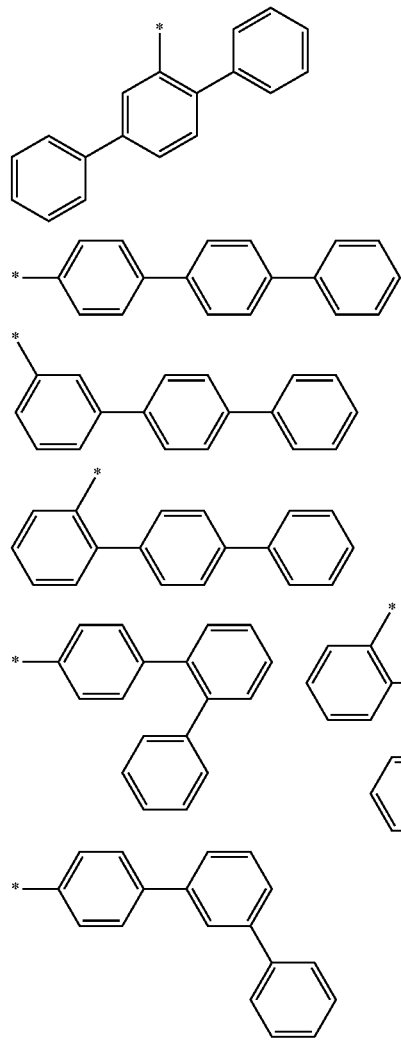

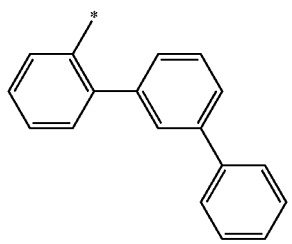
In Group 1, * is a linking point.
In Chemical Formula 1, specific examples of
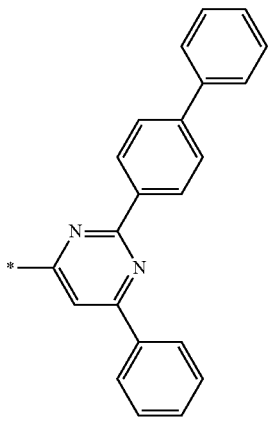
may be selected from substituents of Group A.
[Group A]
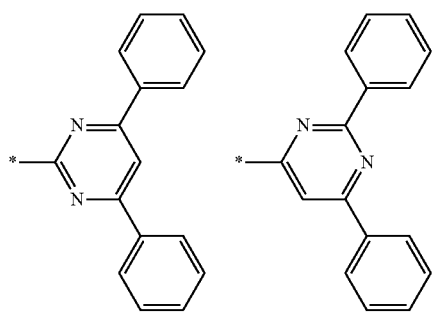
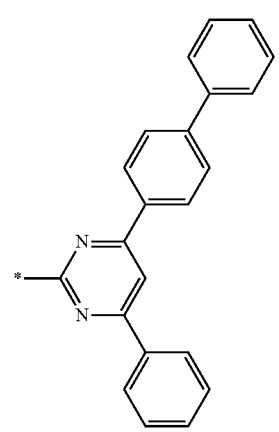
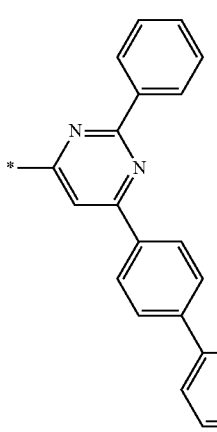
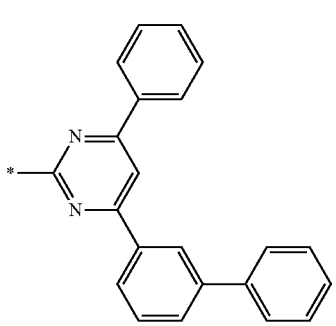
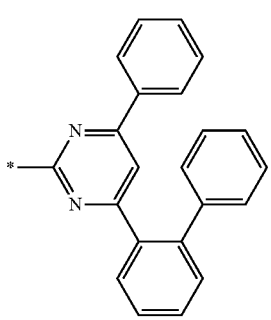

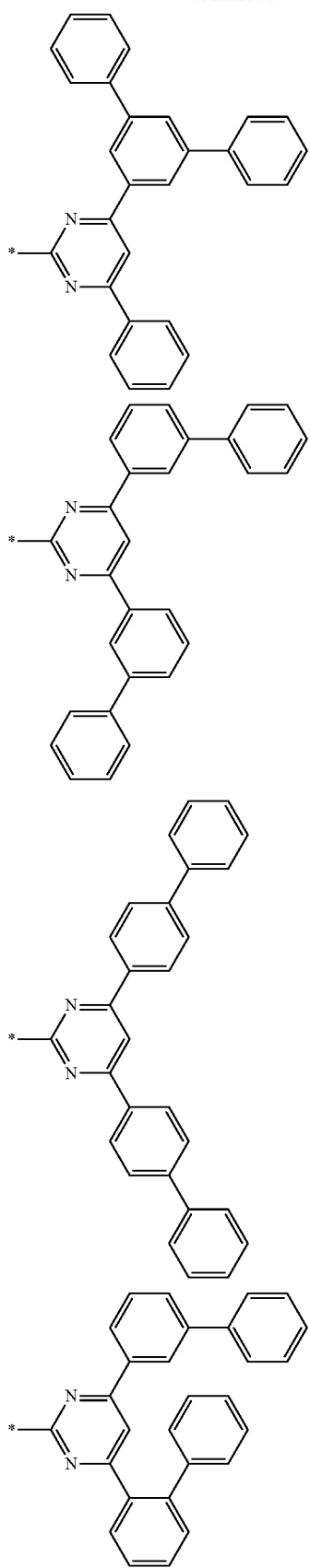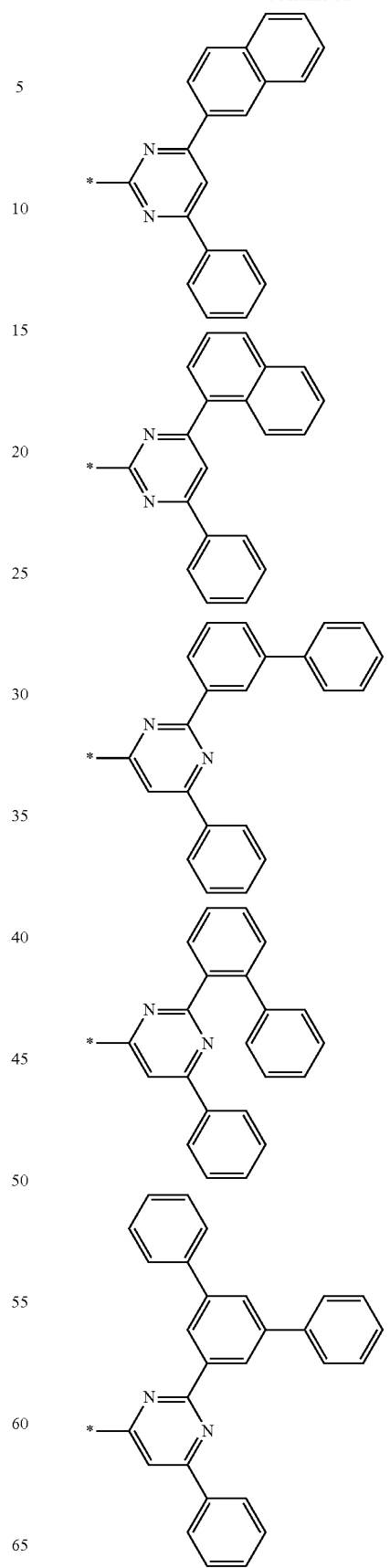

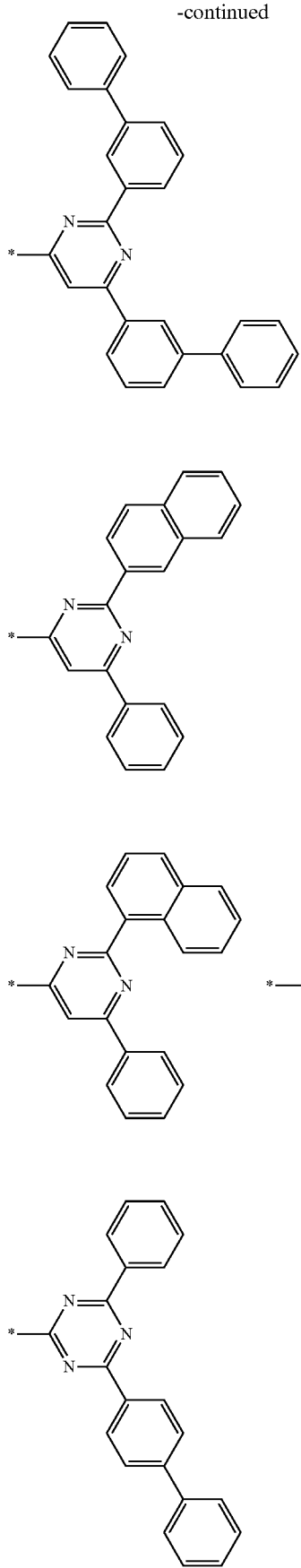
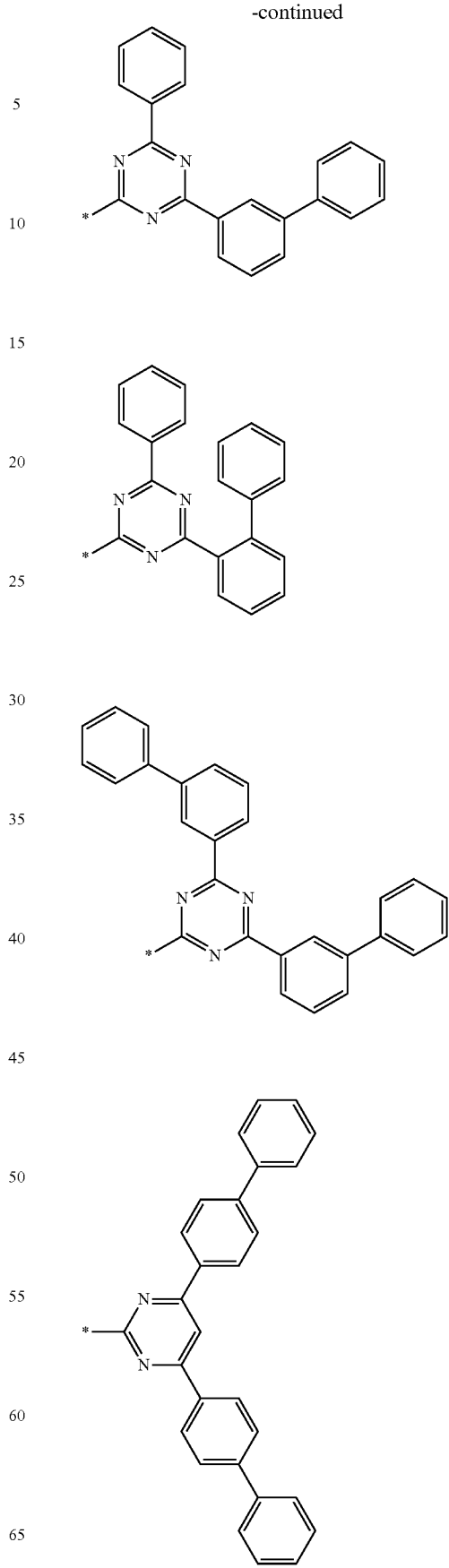

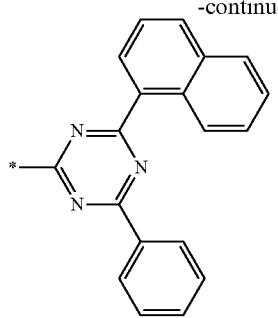
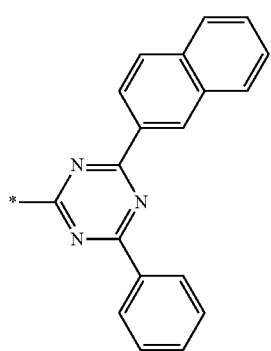
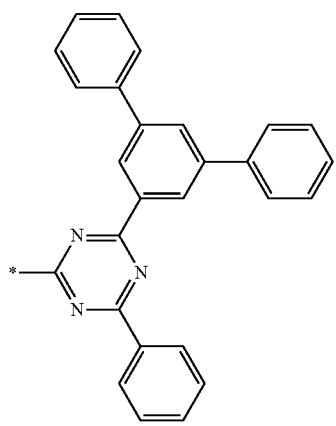
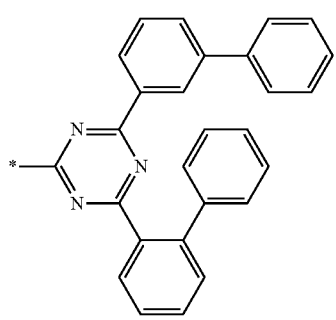
In Group A, * is a linking point.
The compound for an organic optoelectronic device may be, for example selected from compounds of Group 2, but is not limited thereto.
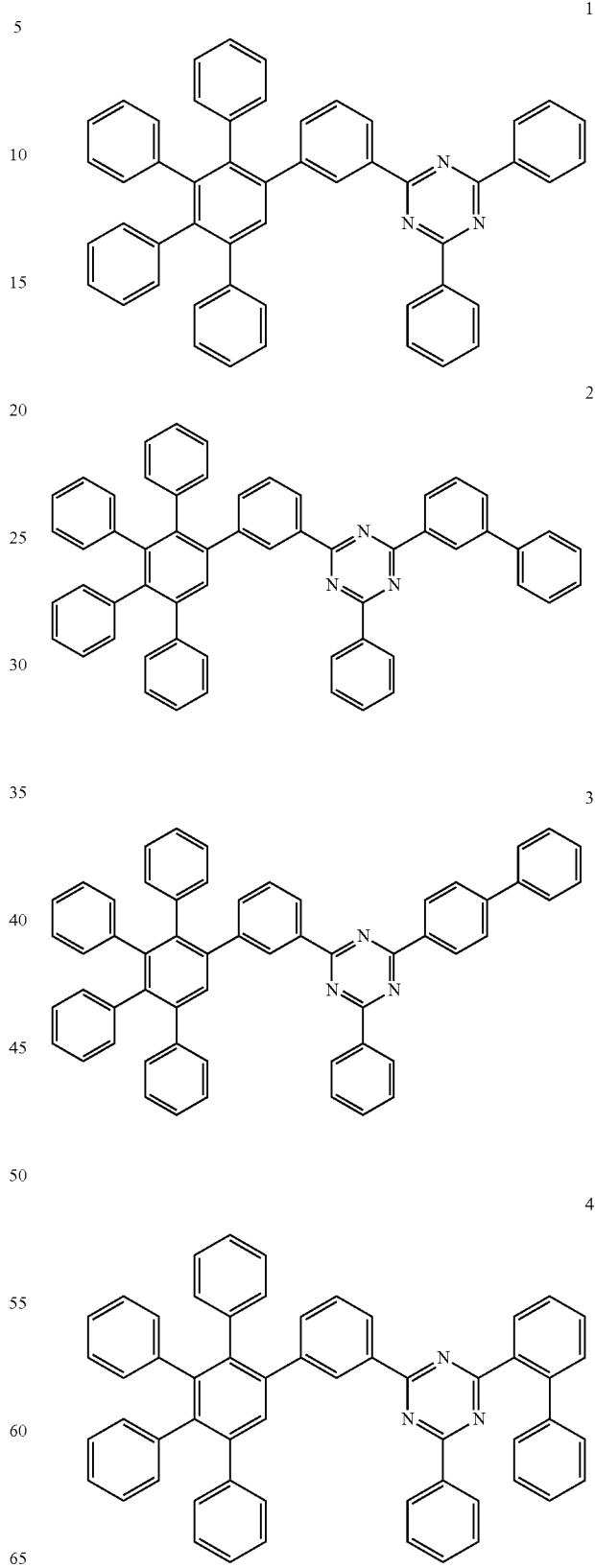

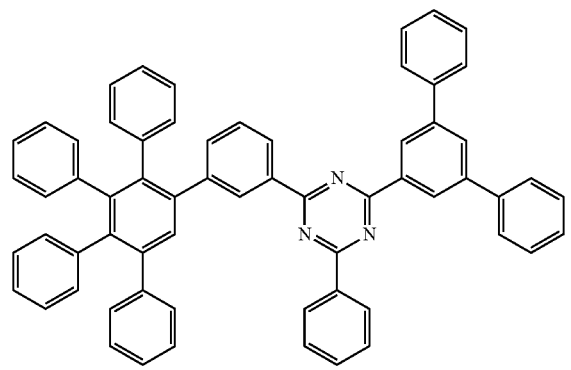
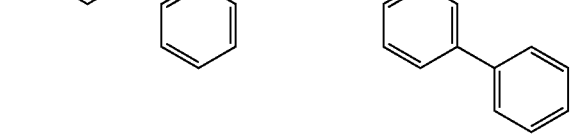
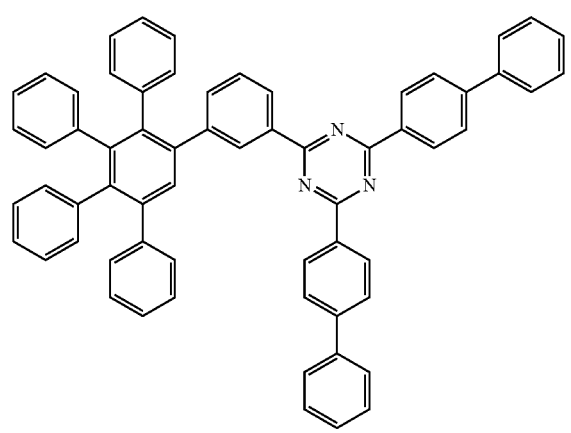
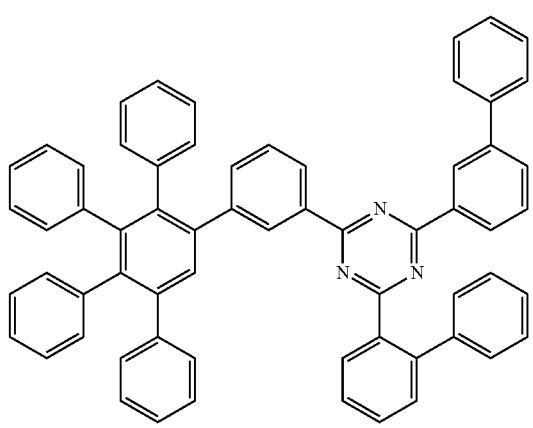
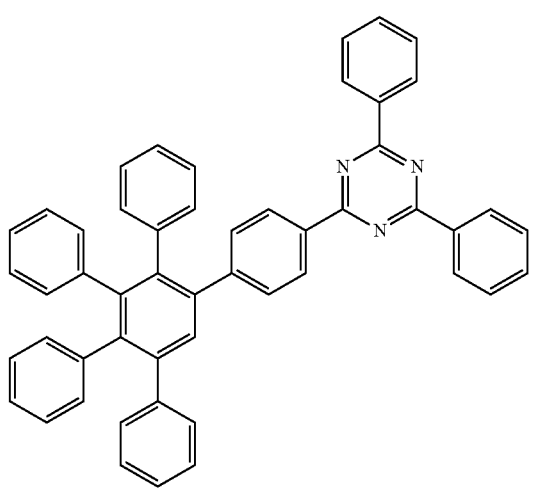
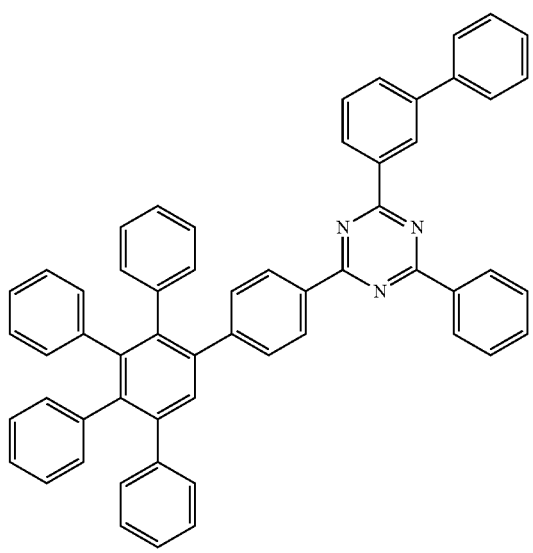

11
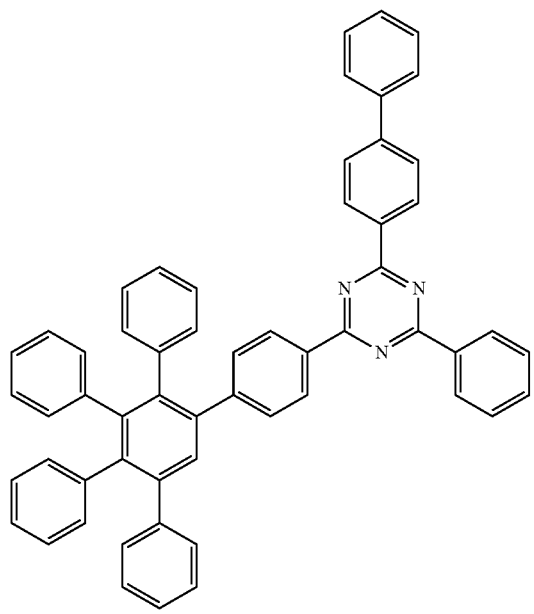
12
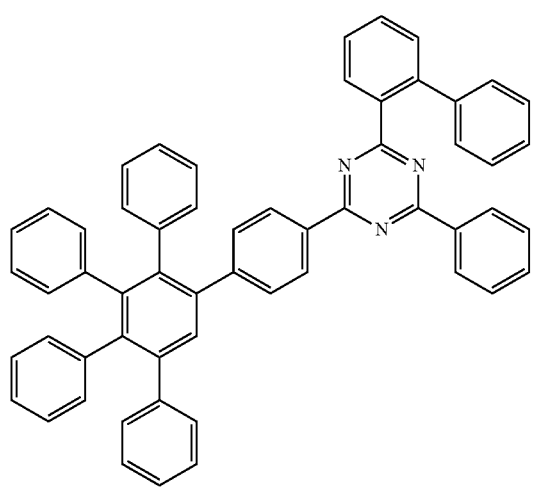
13
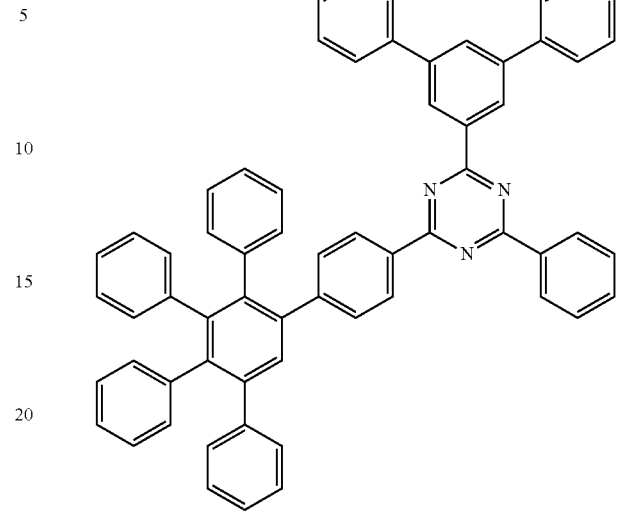
14
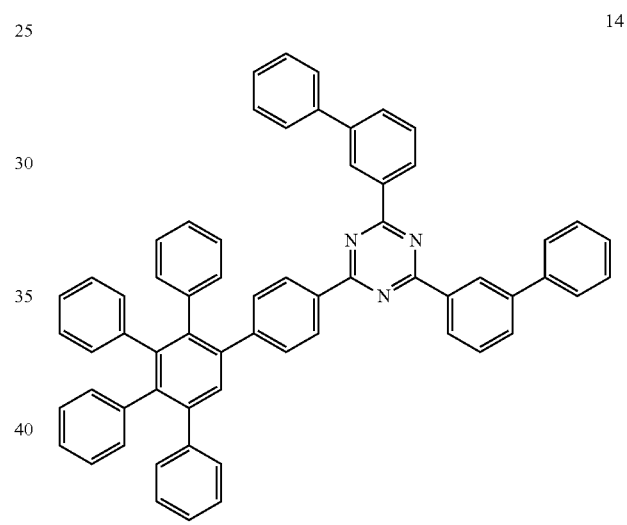
15
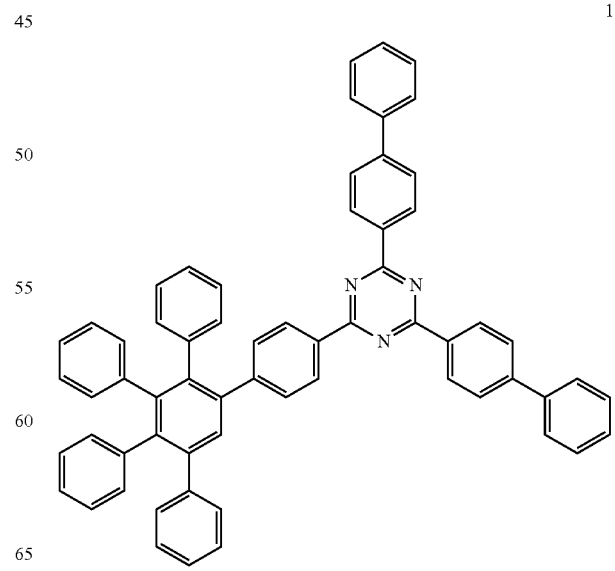

-continued
16
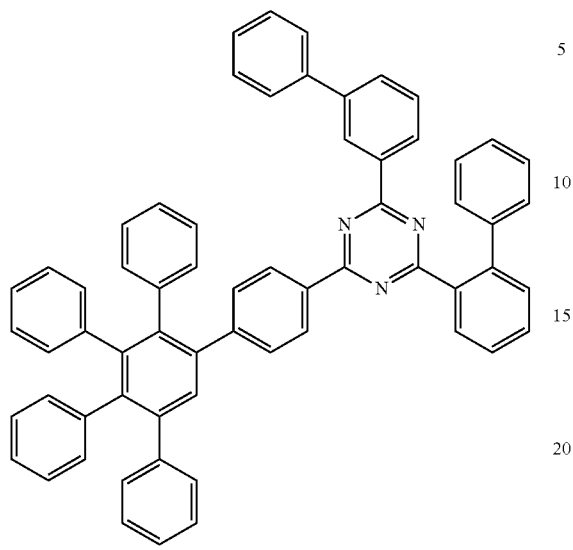
17
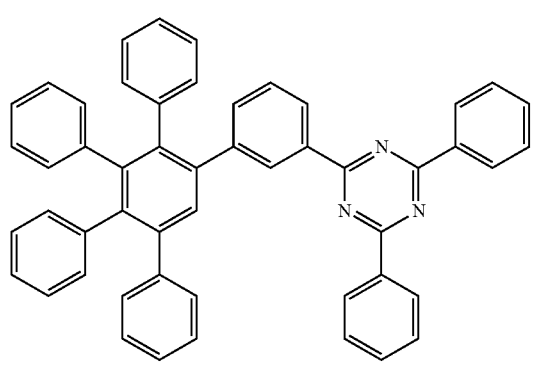
18
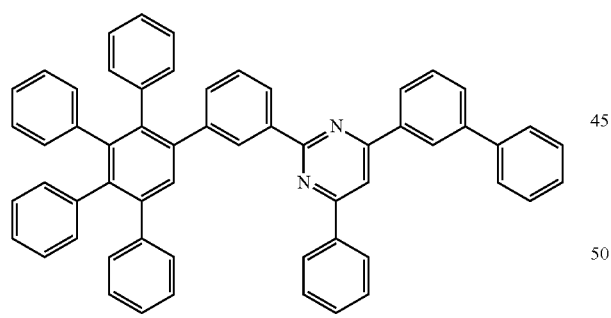
19
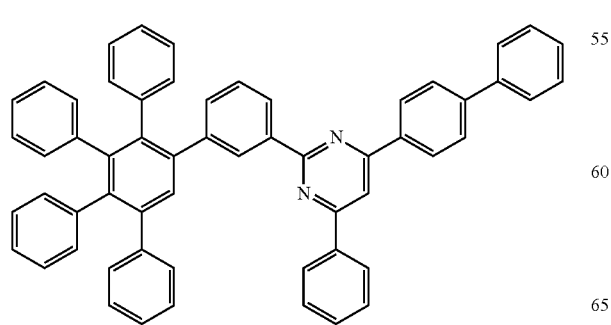
-continued
20
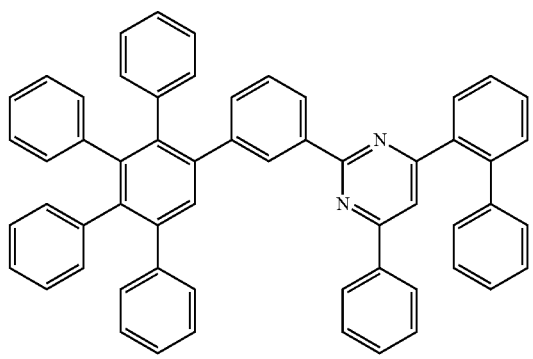
21
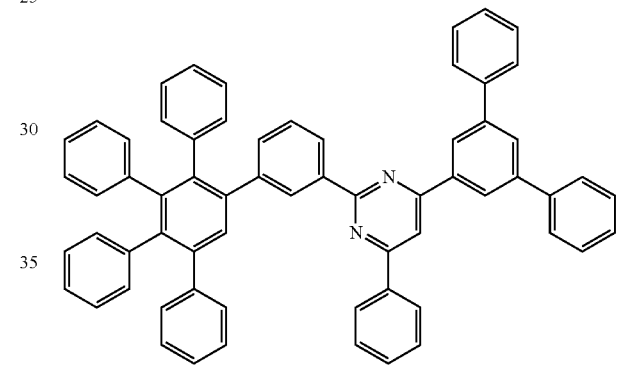
22
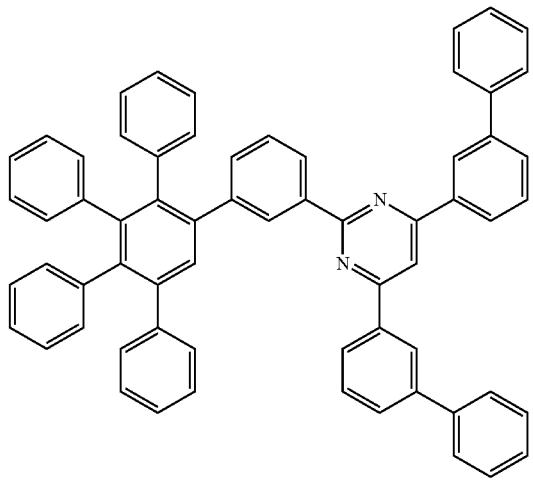

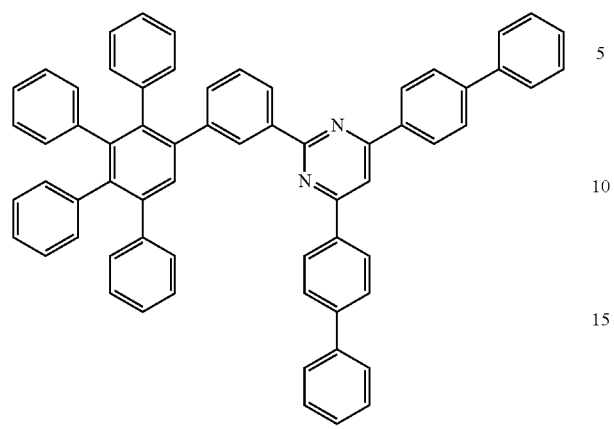
23
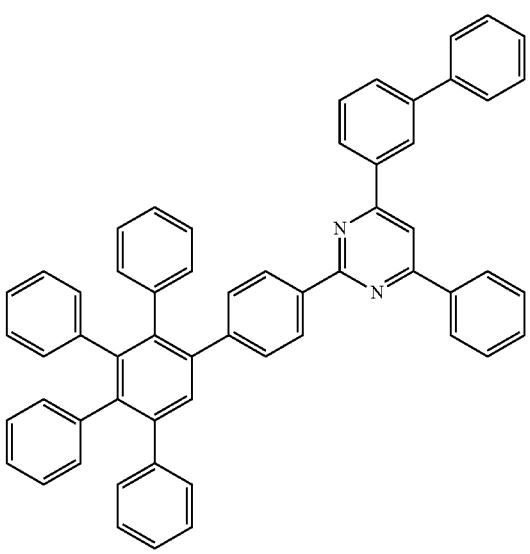
26
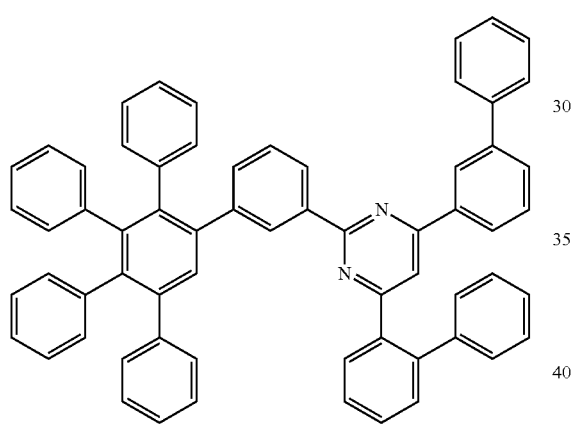
24
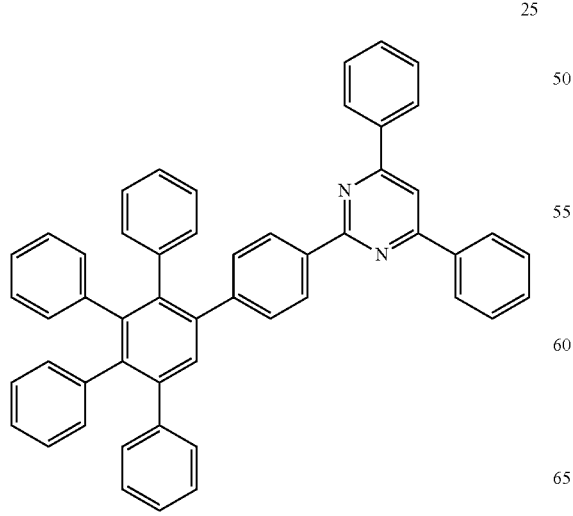
25

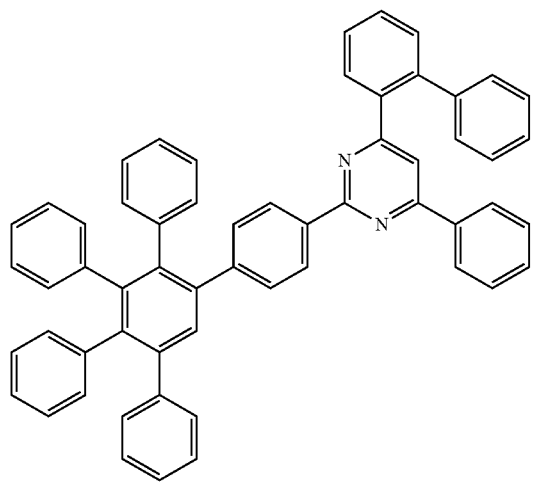
28
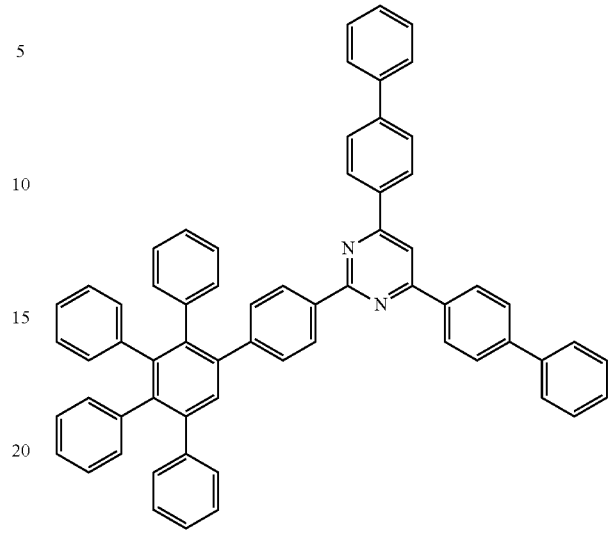
31
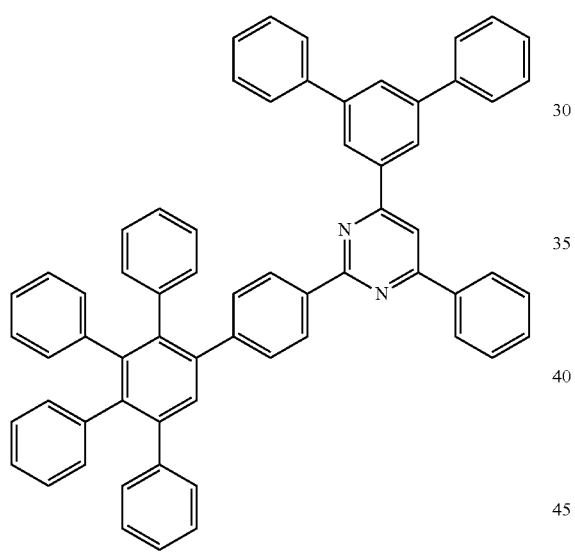
29
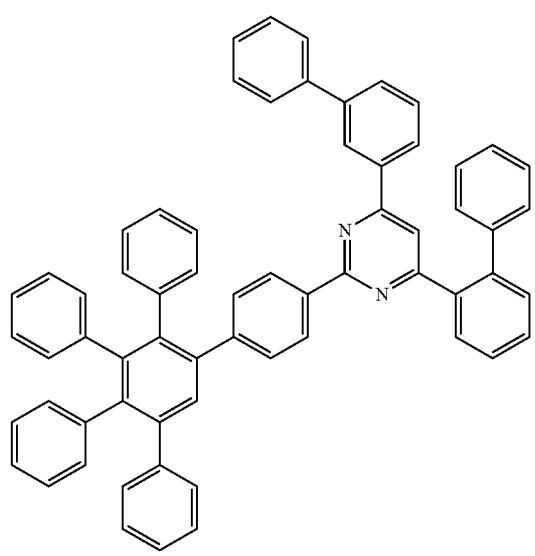
32
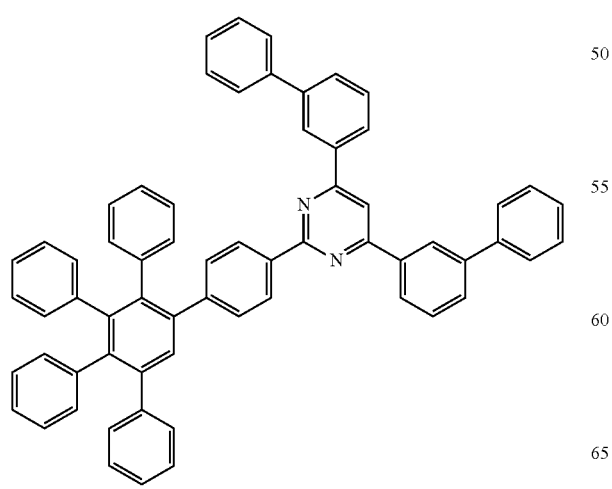
30
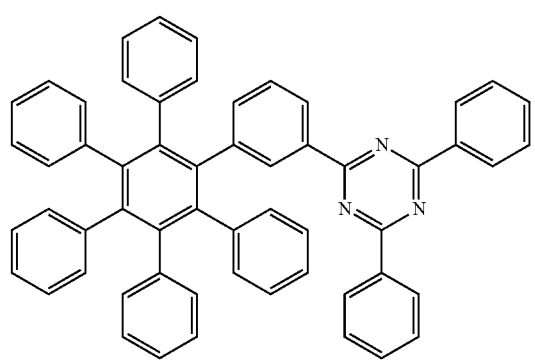
33

34
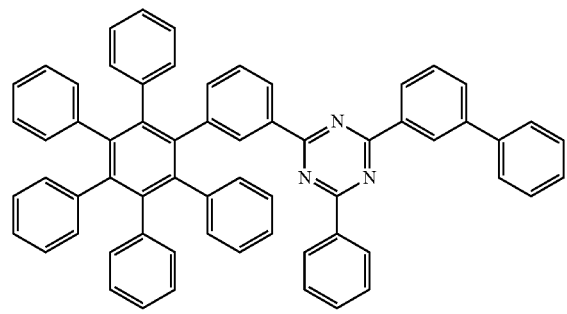
35
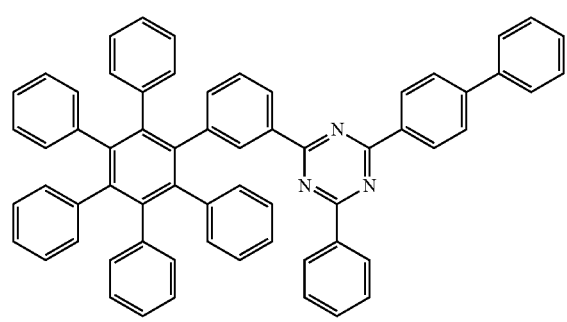
36
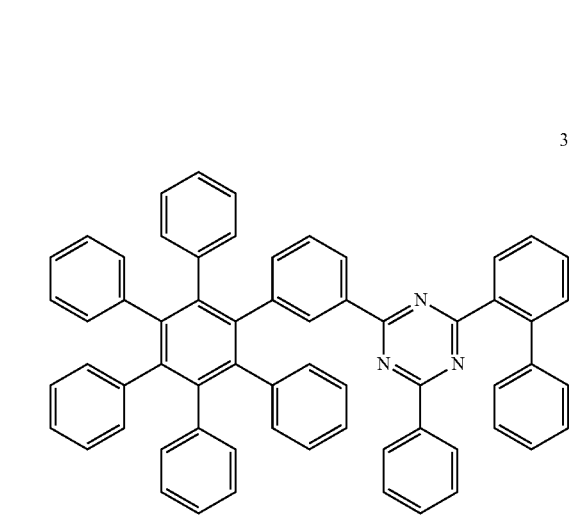
37
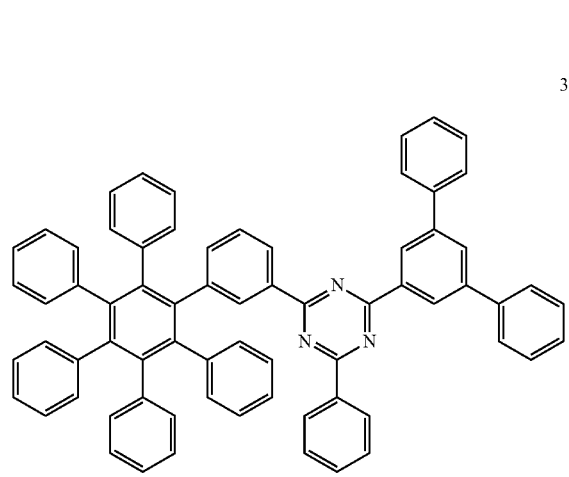
38
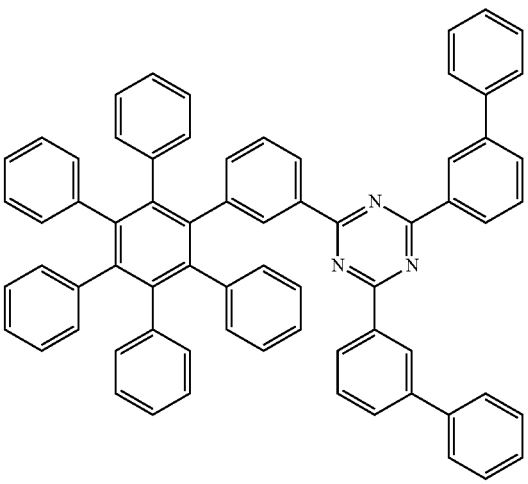
39
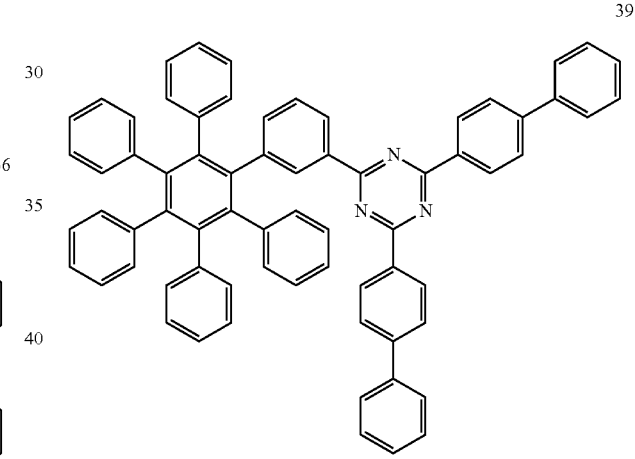
40
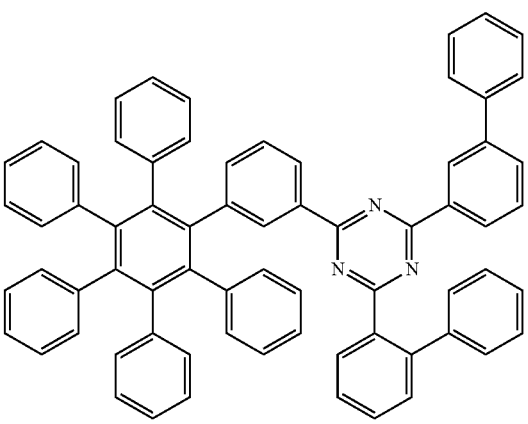

41
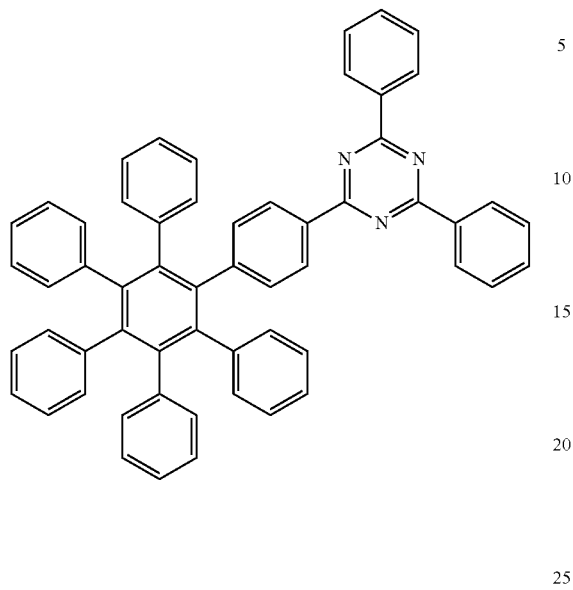
43
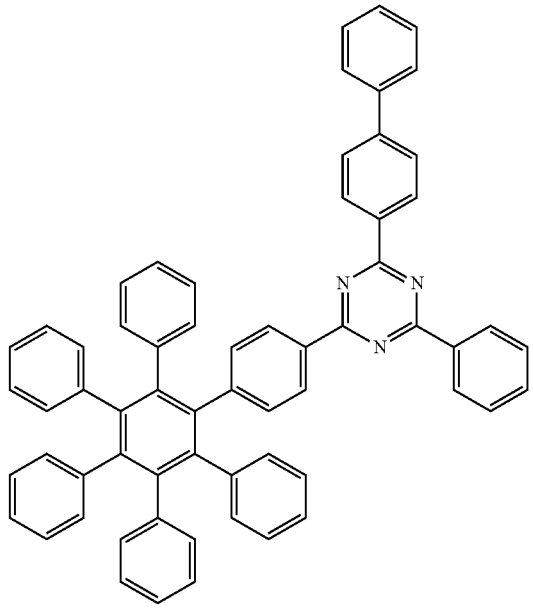
42
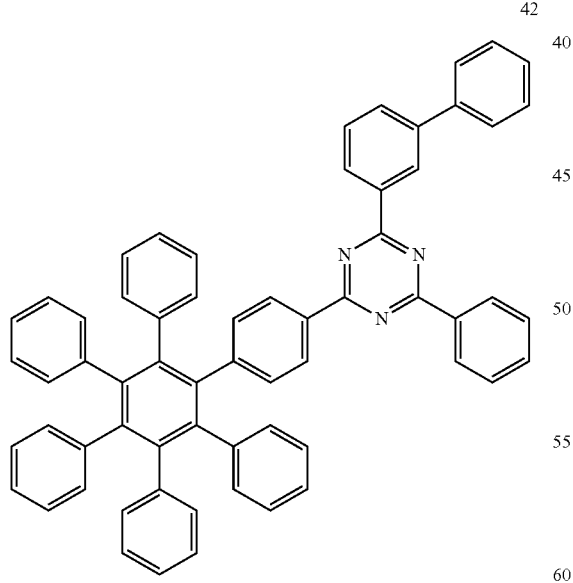
44
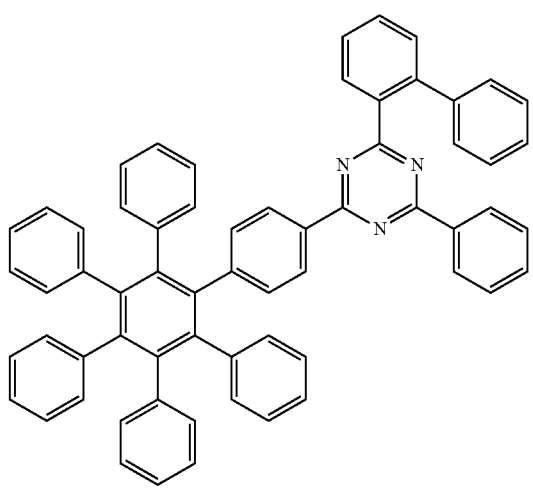

45
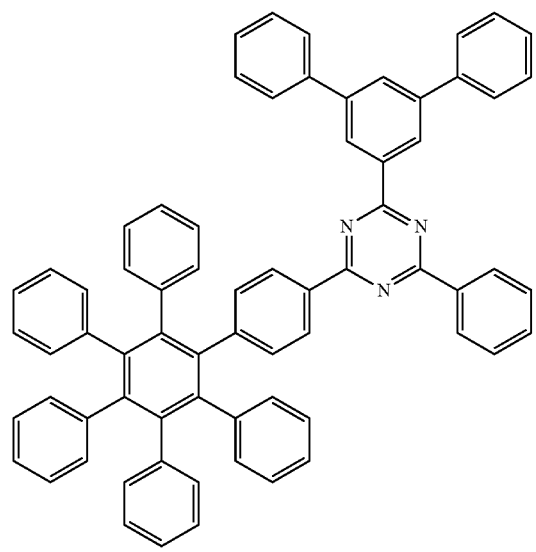
46
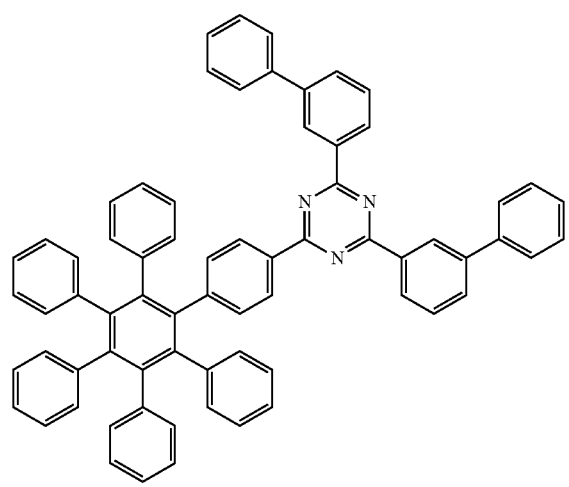
47
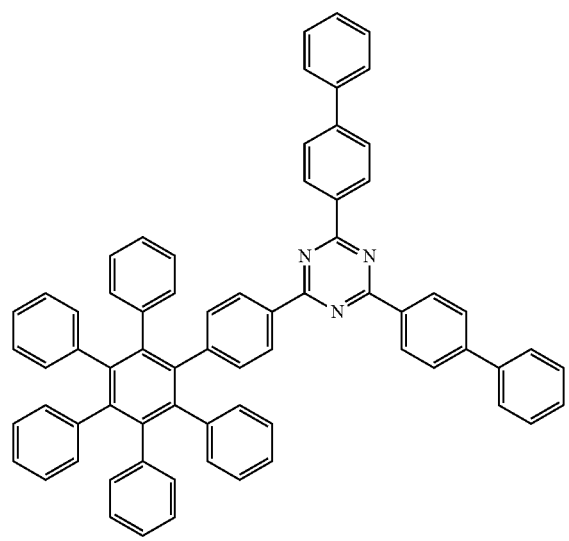
48
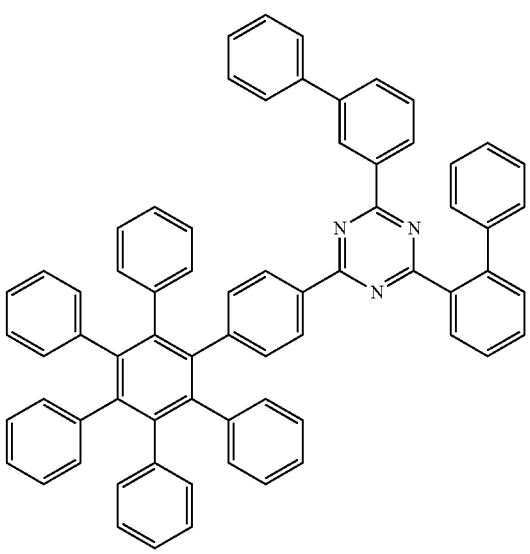
49
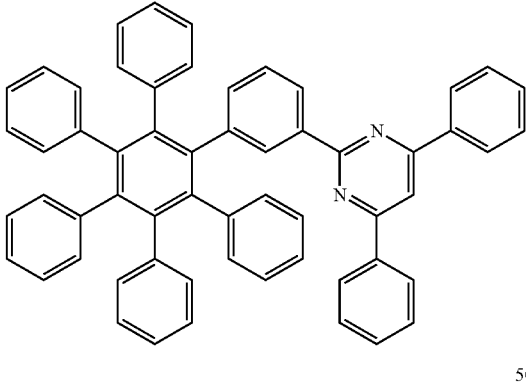
50
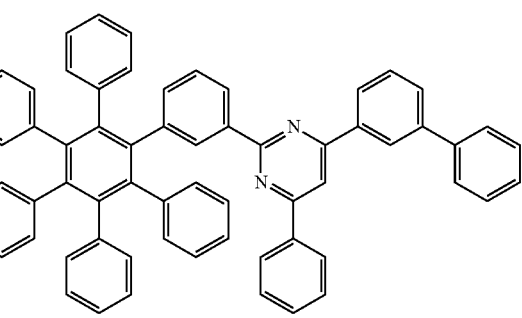
51
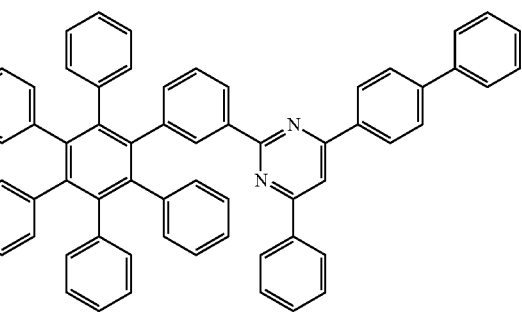

52
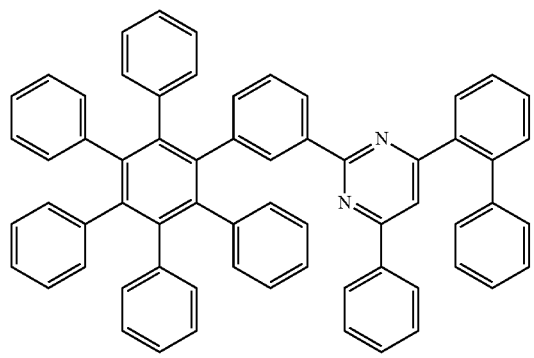
53
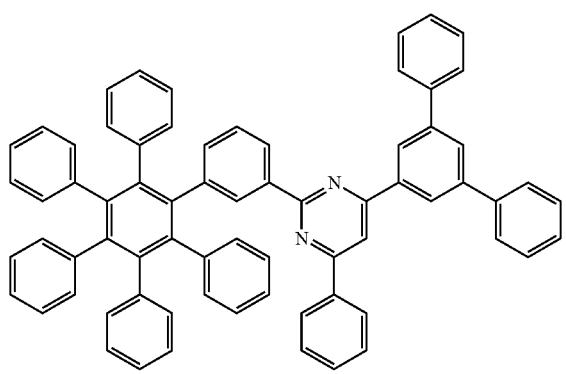
54
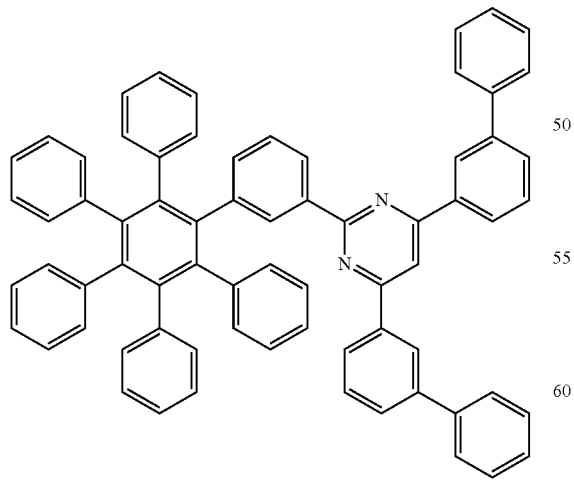
55
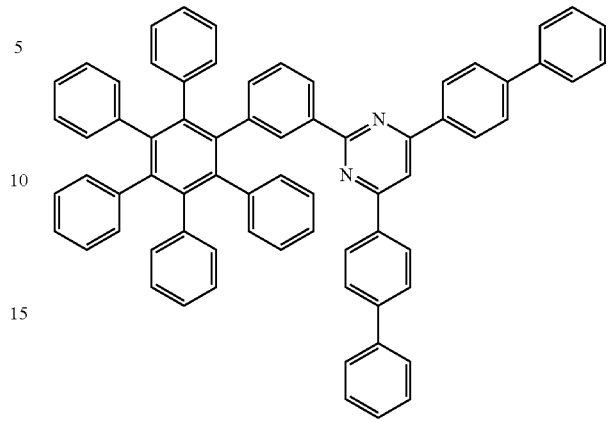
56
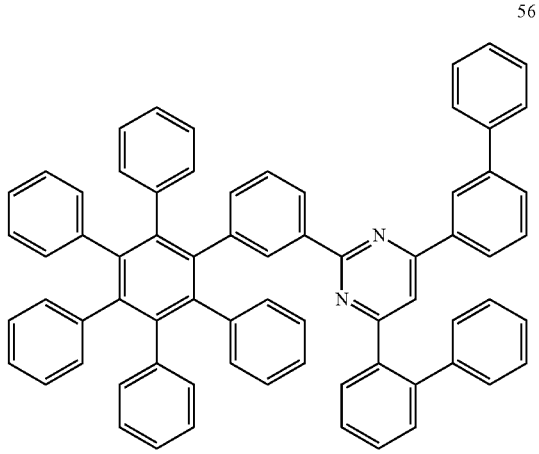
57
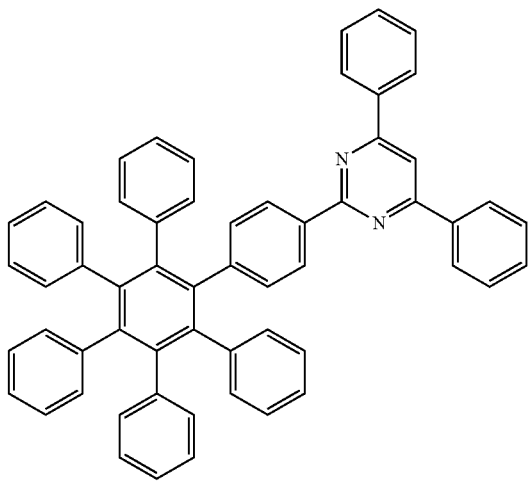

58
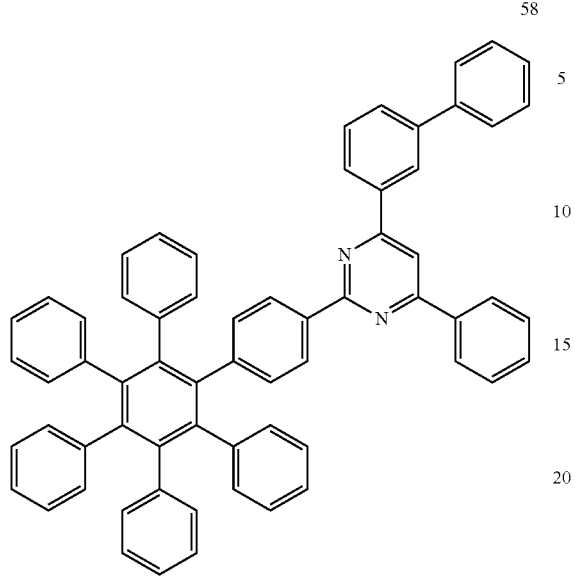
60
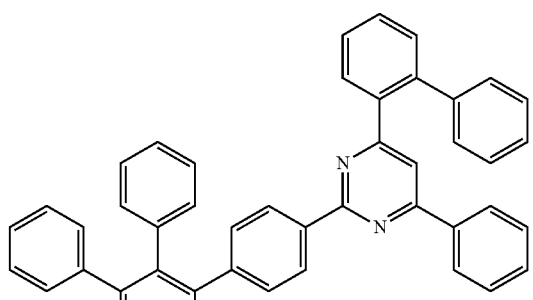
61
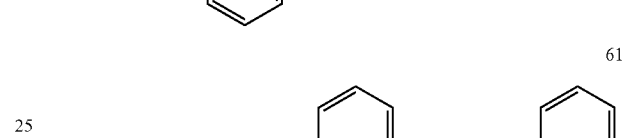
59
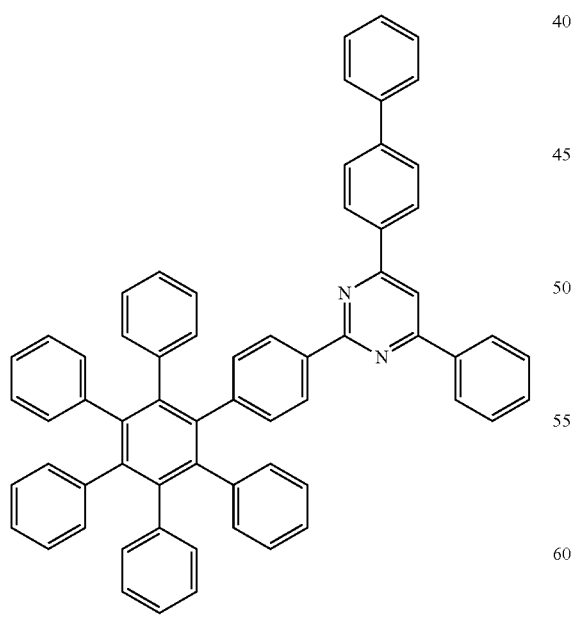
62
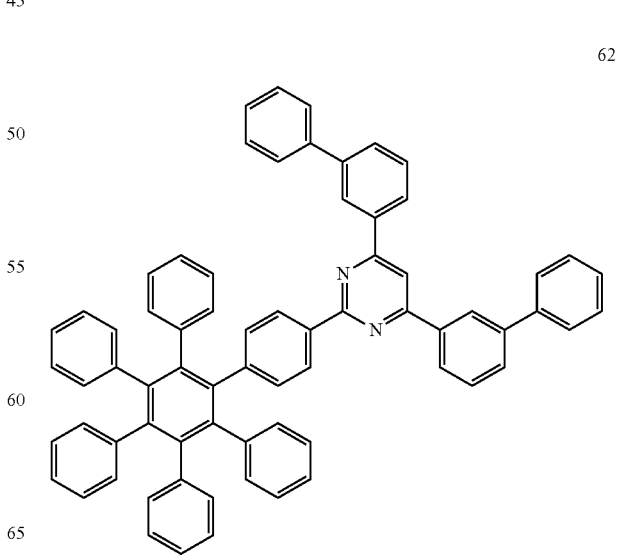

63
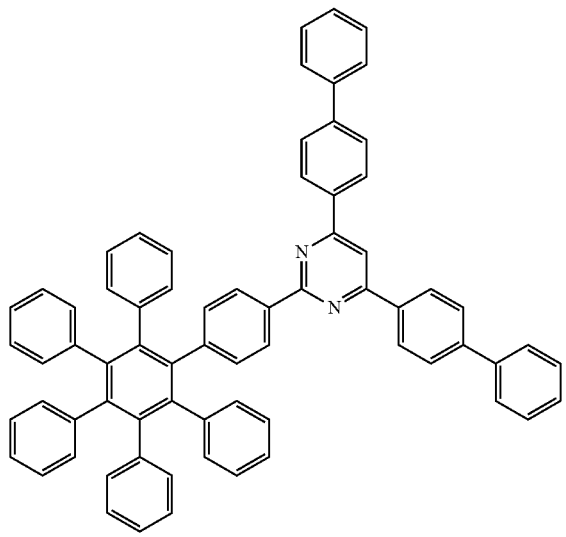
64
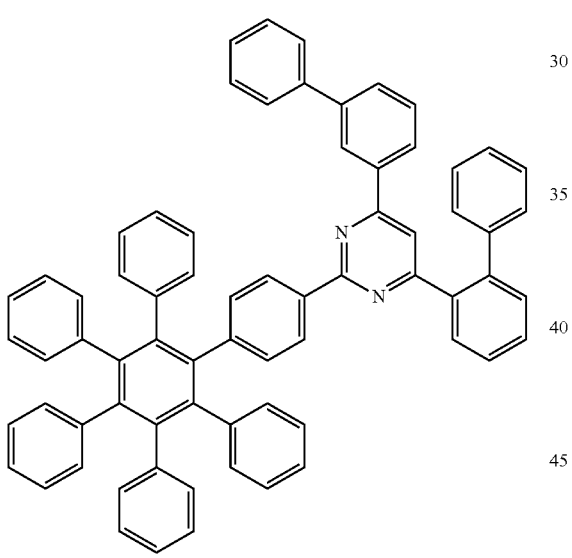
65
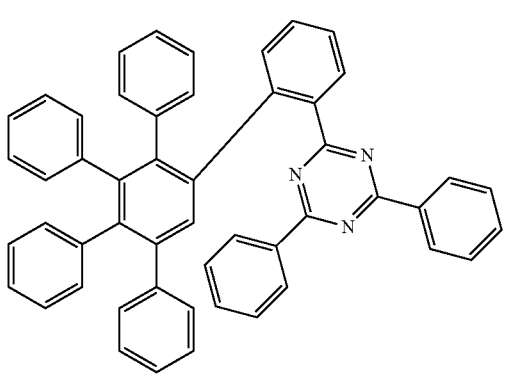
66
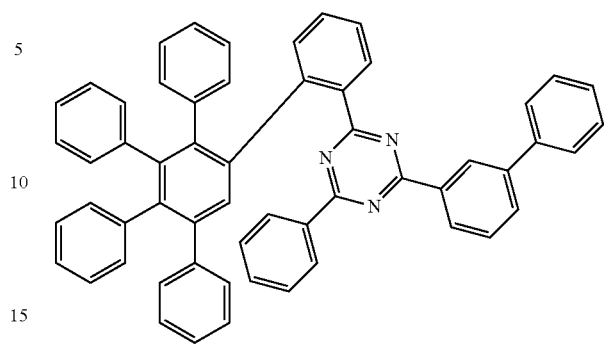
67
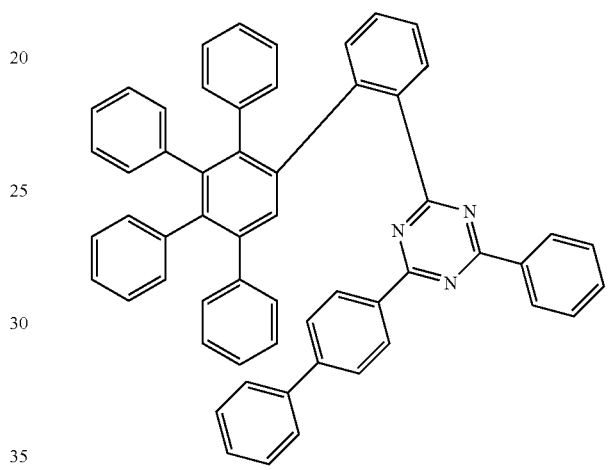
68
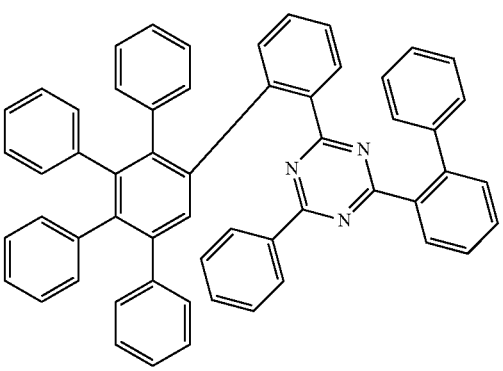
69
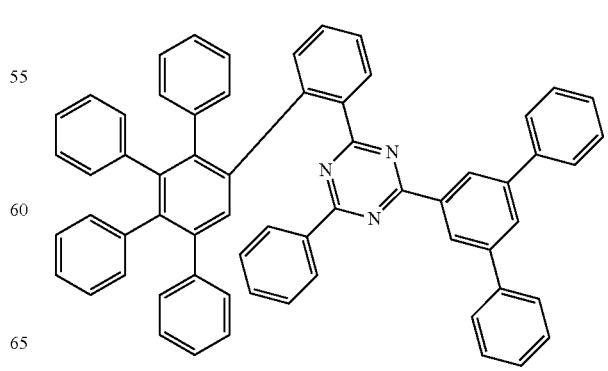

70
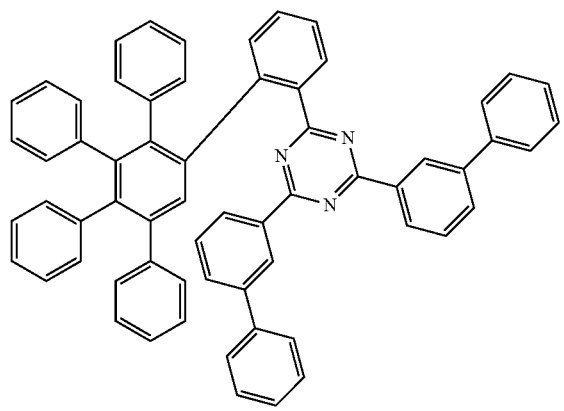
71
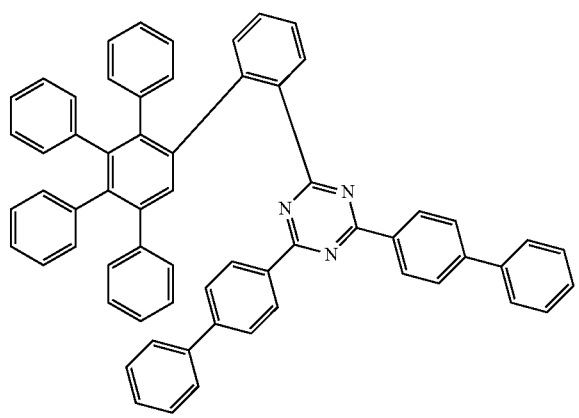
72
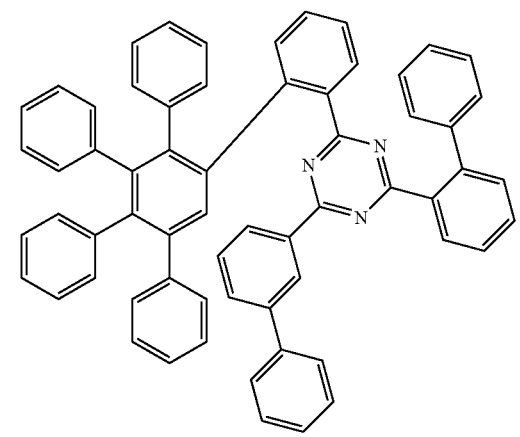
73
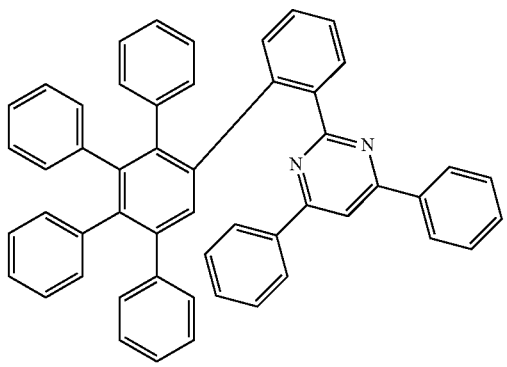
74
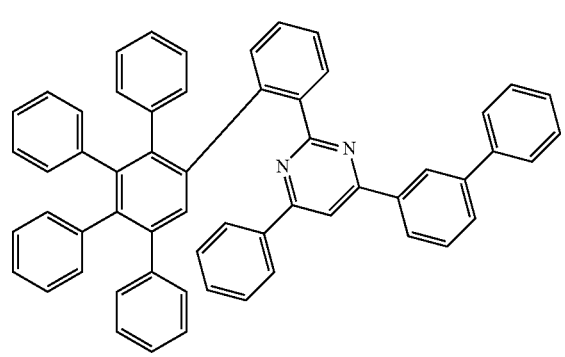
75
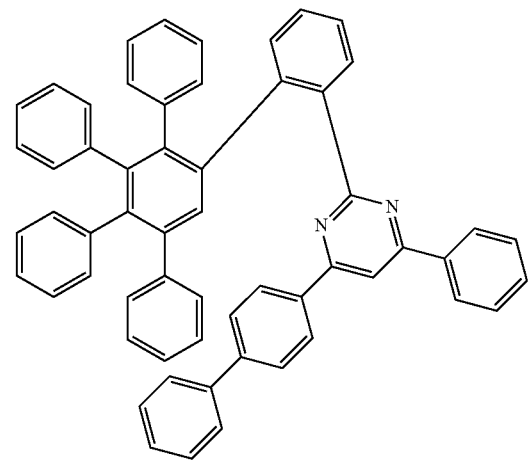
76
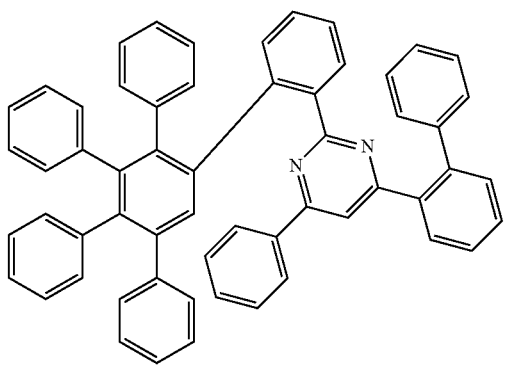

77
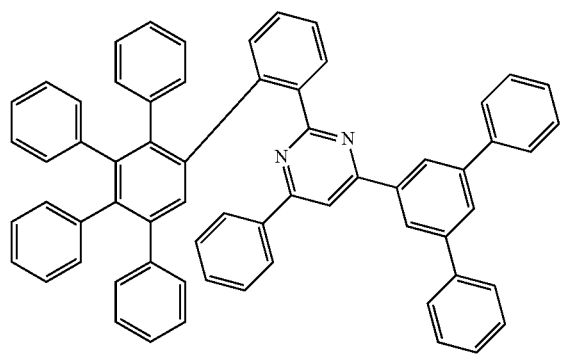
78
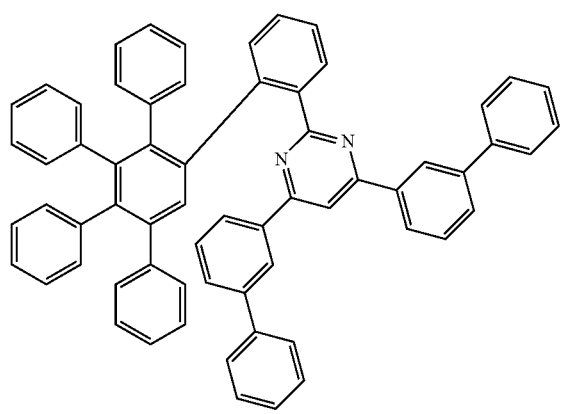
79
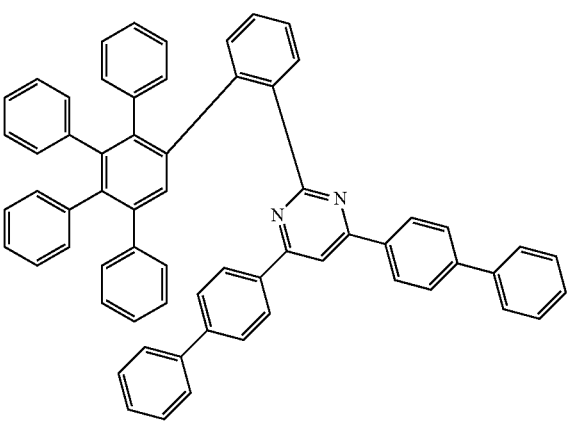
80
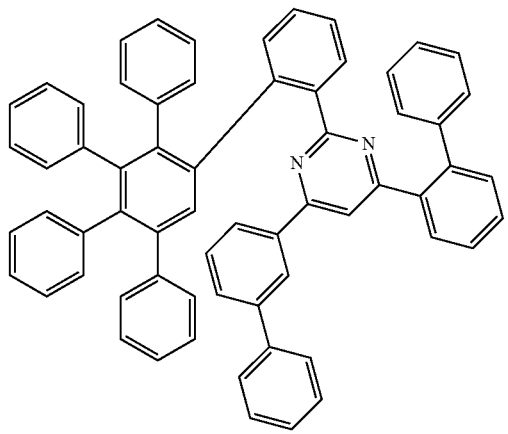
81
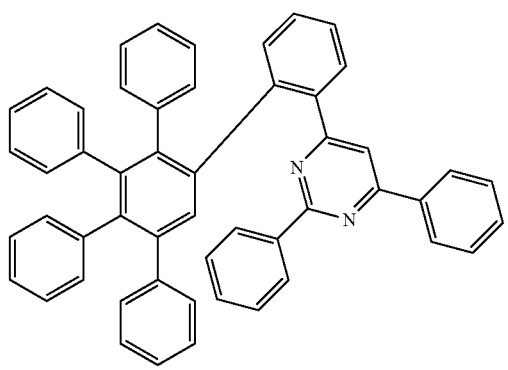
82
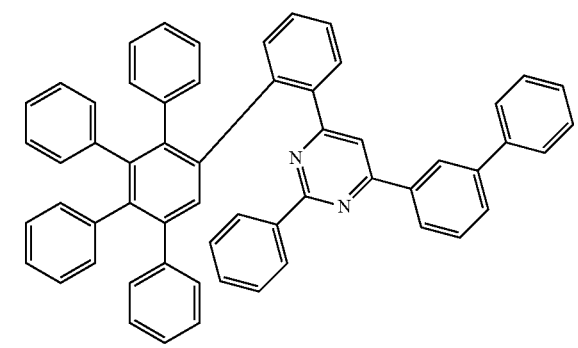

83
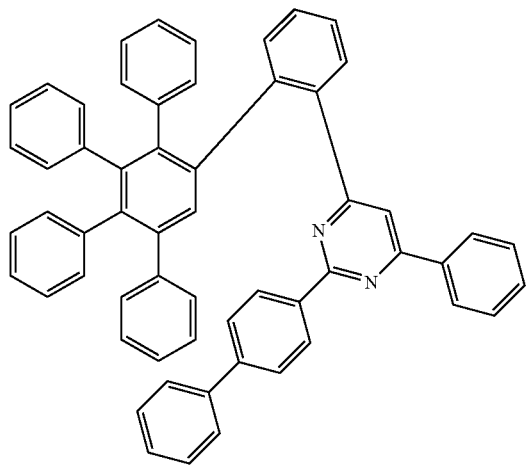
86
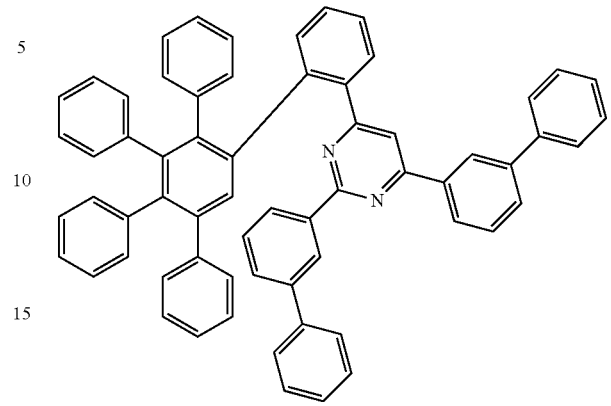
84
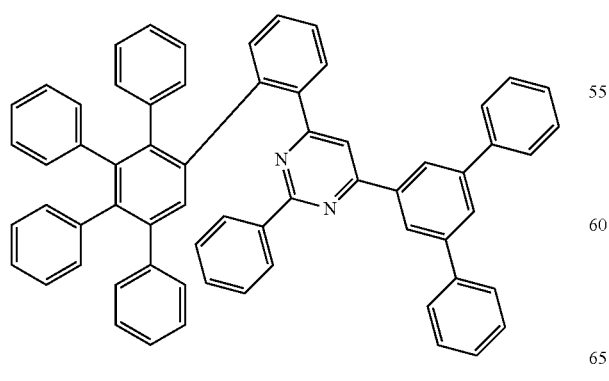
87
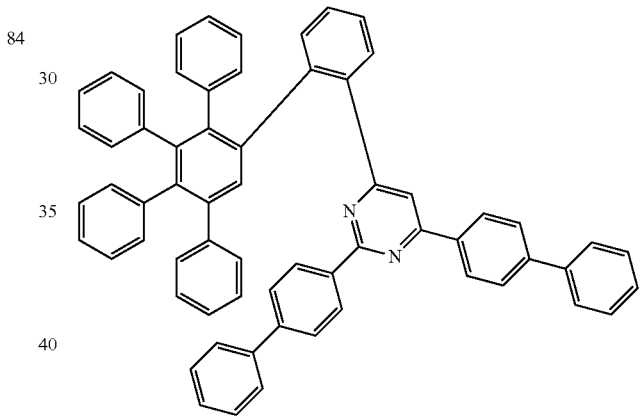
85
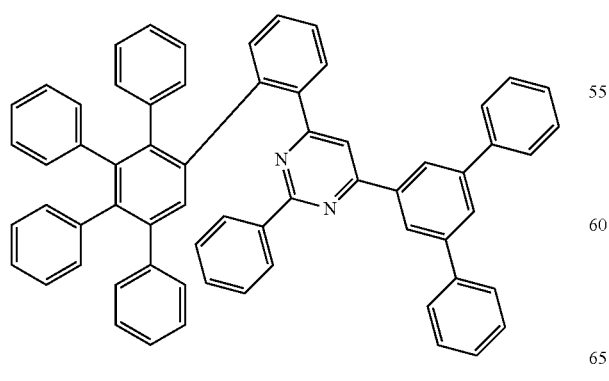
88
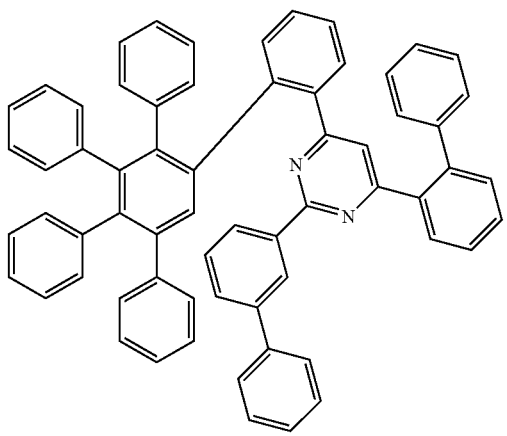

89
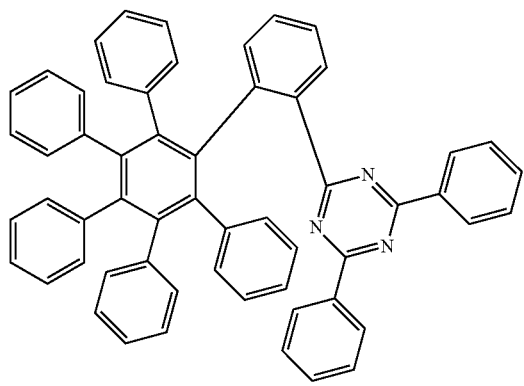
92
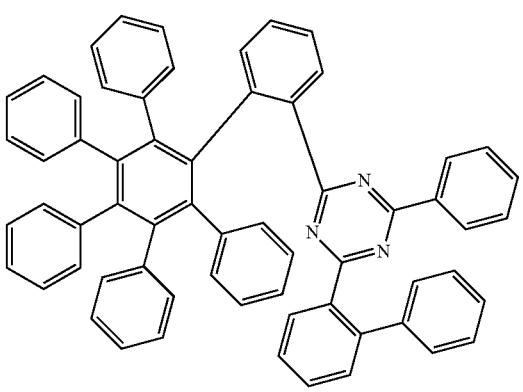
90
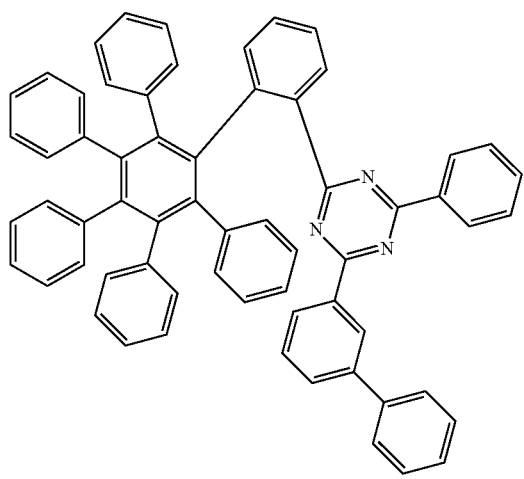
93
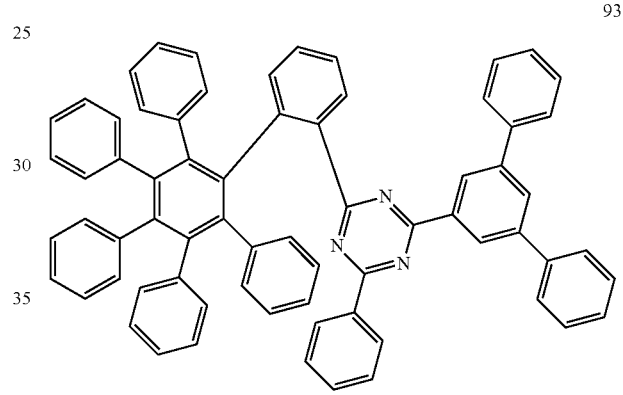
91
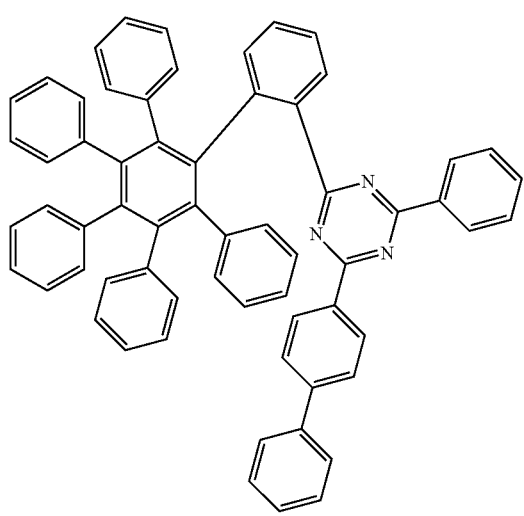
94
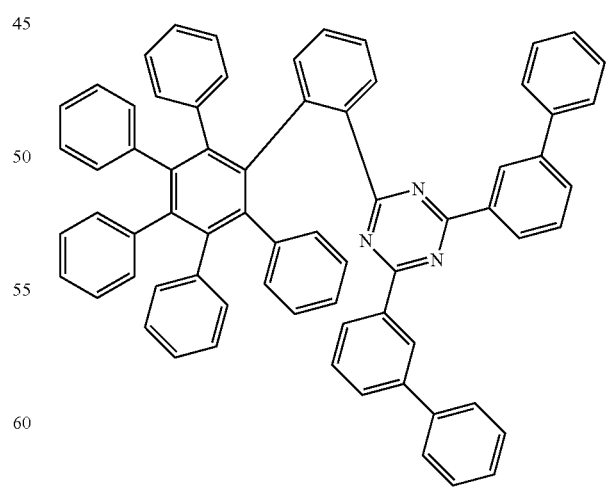

-continued
95
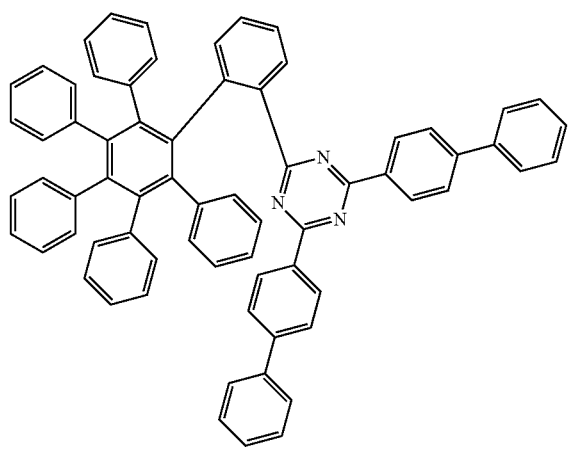
96
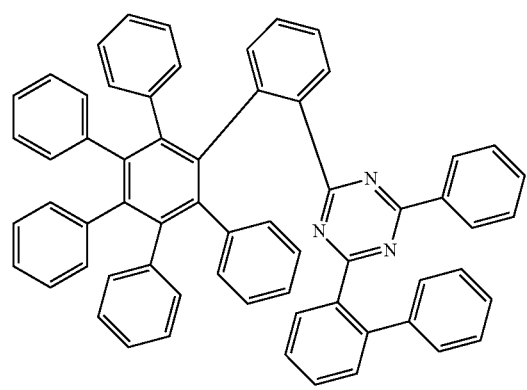
97
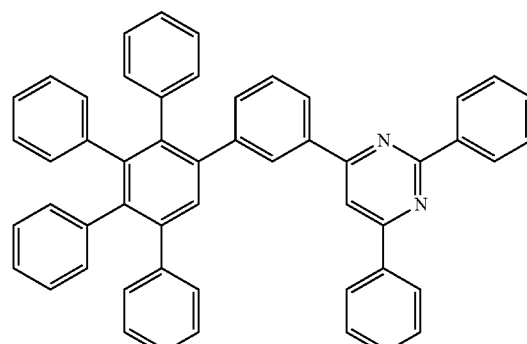
98
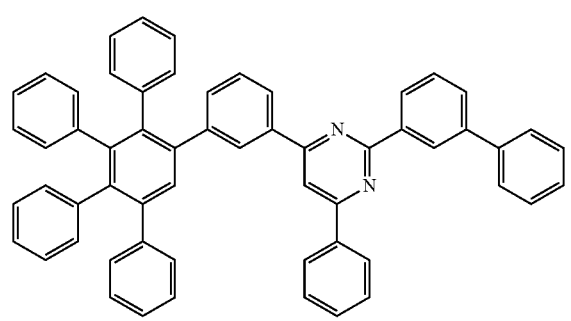
-continued
99
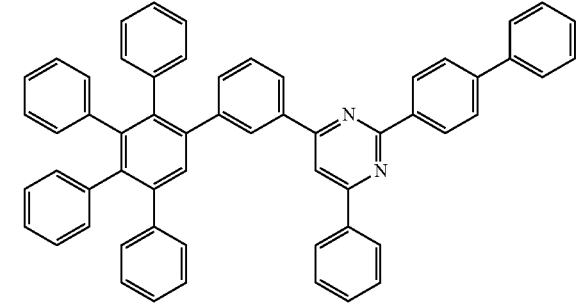
100
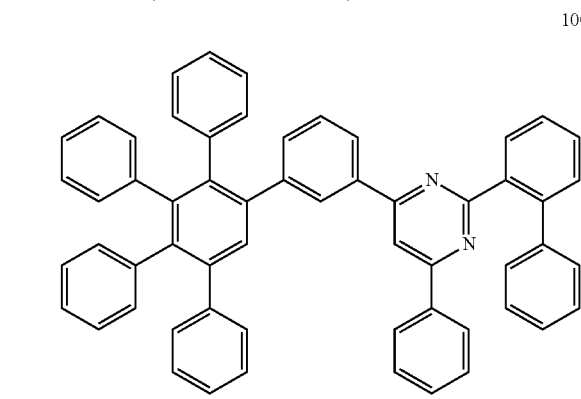
101
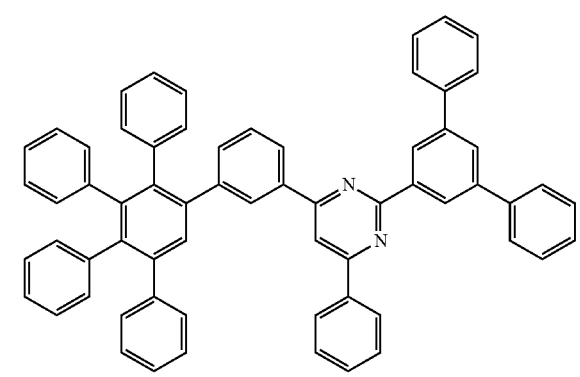
102
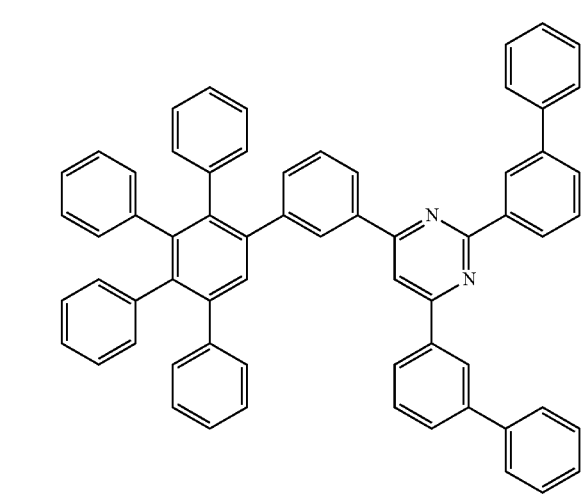

103
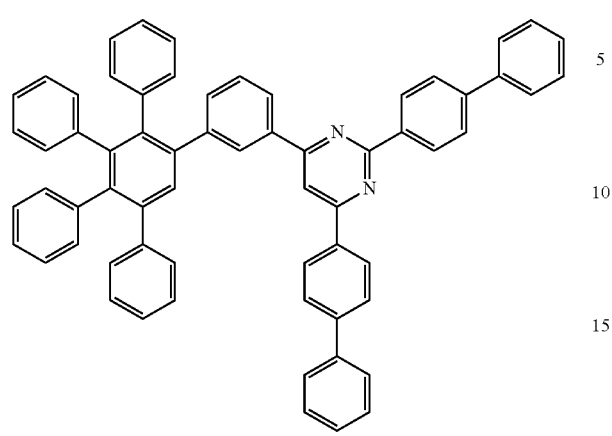
104
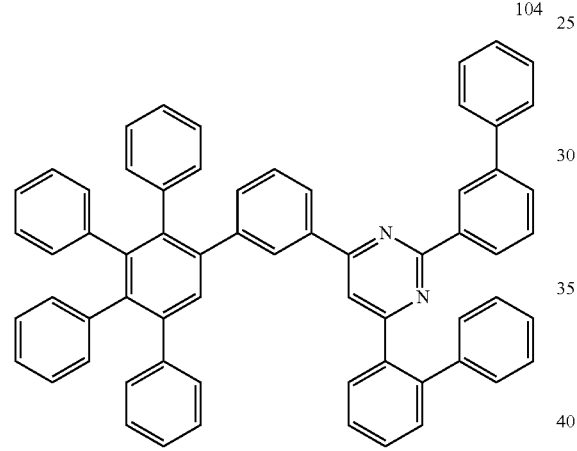
105
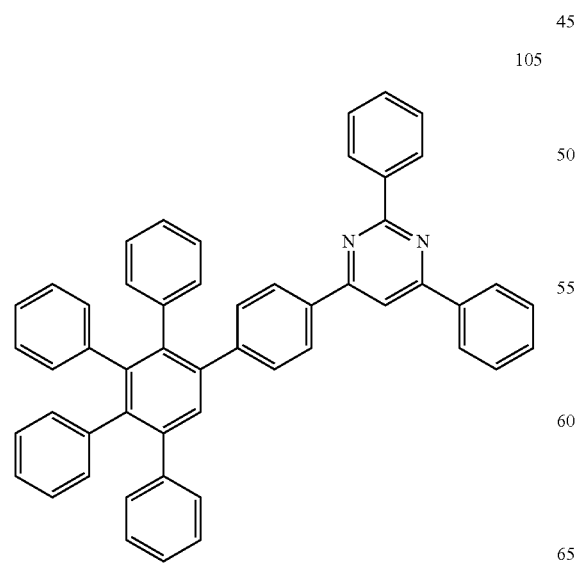
106
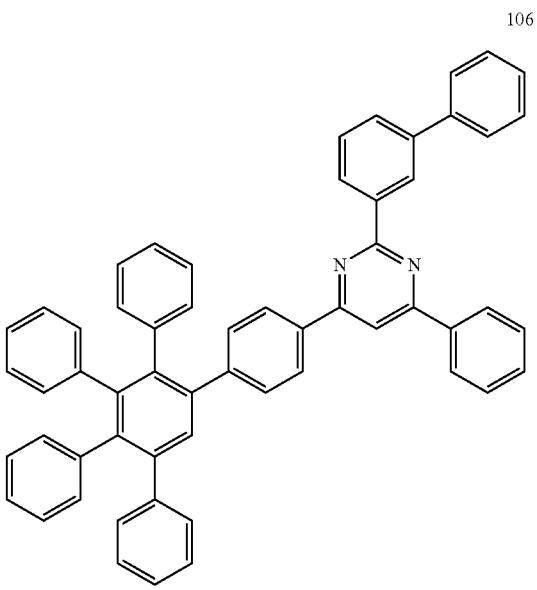
107
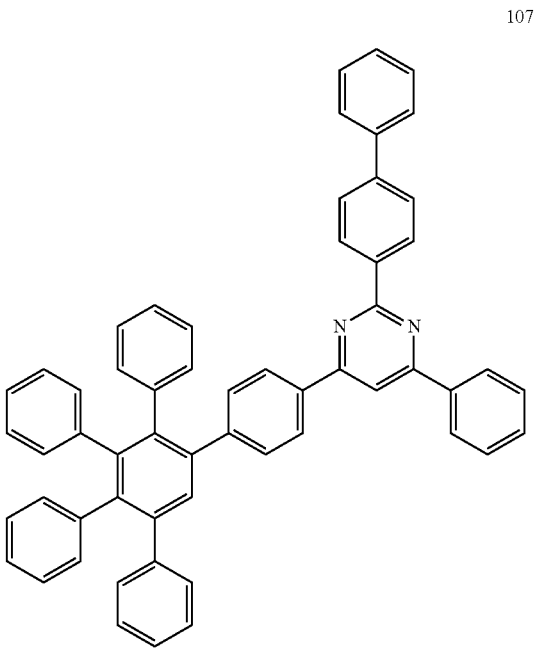

108
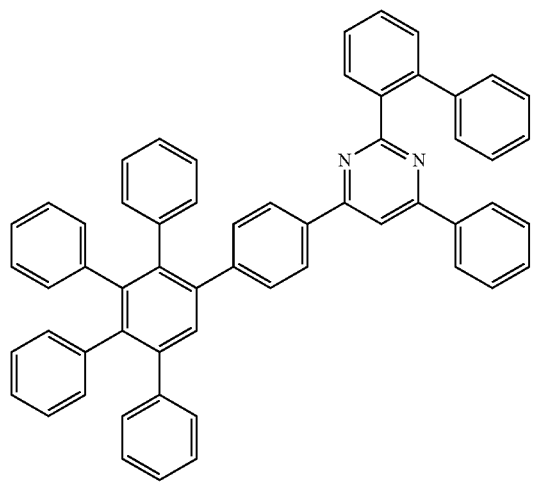
109
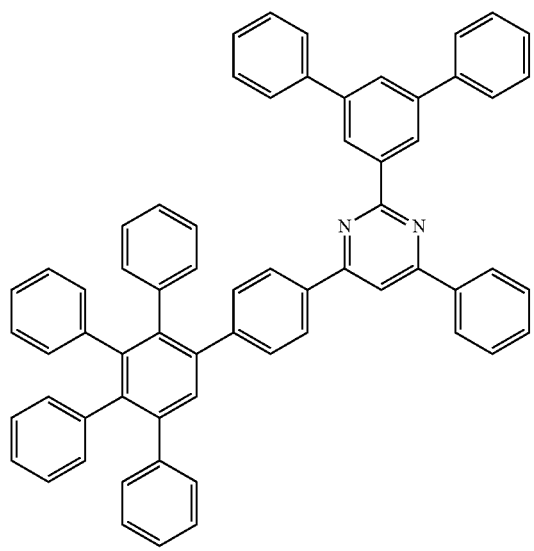
110
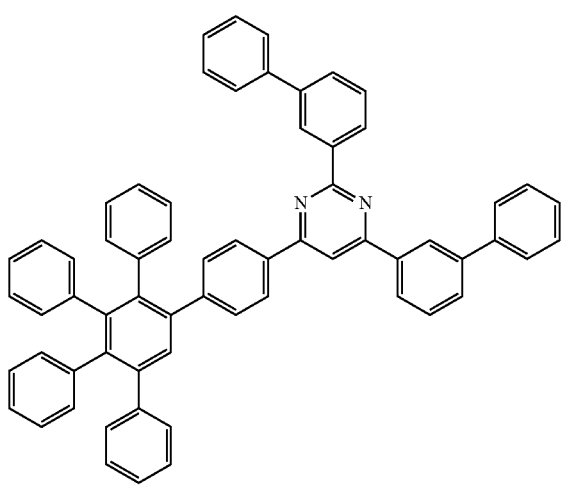
111
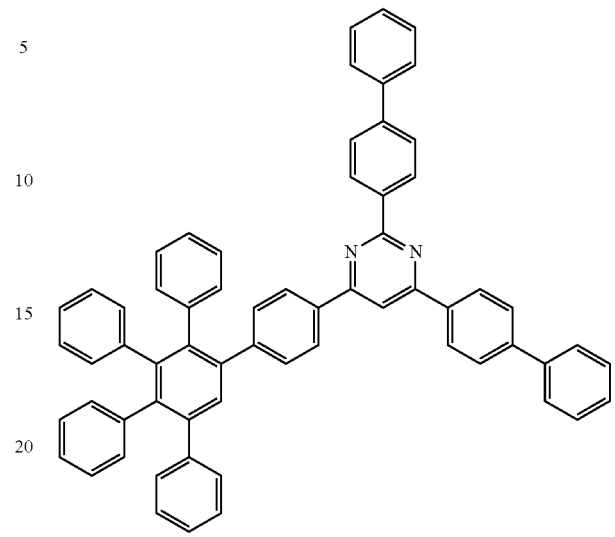
112
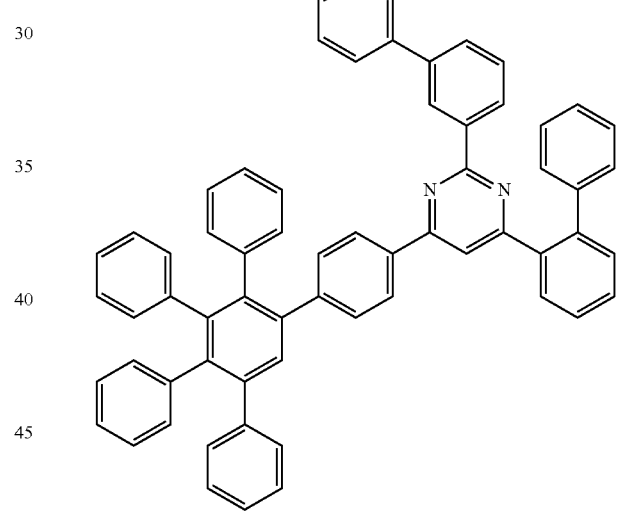
113
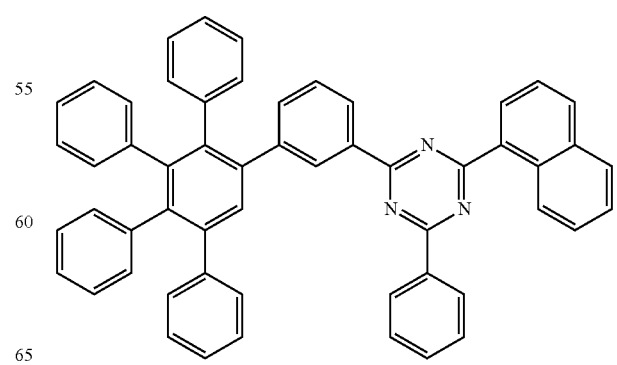

114
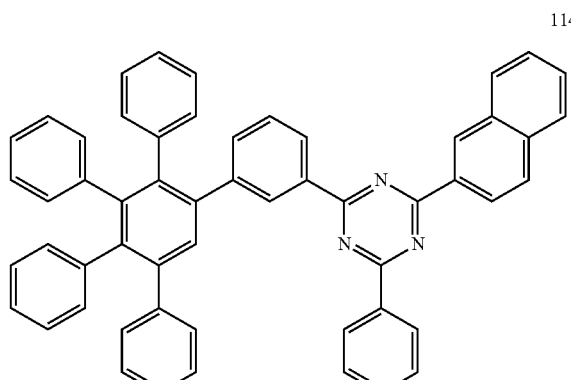
118
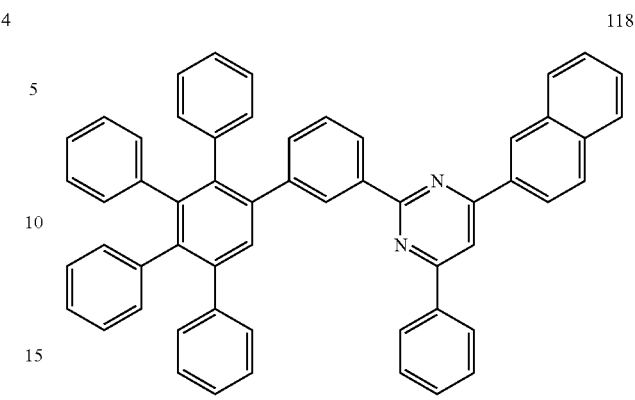
115
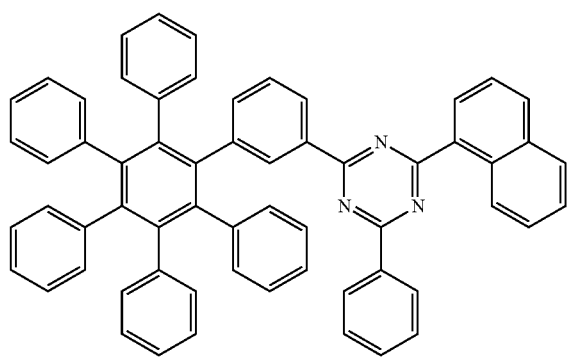
119
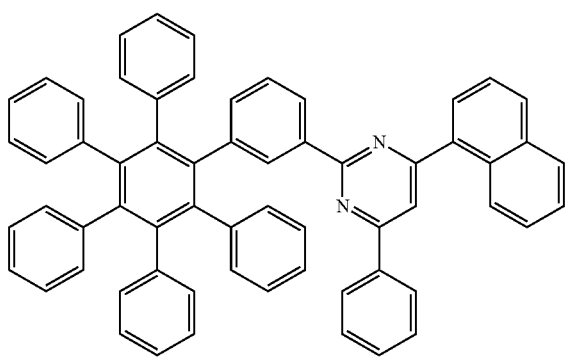
116
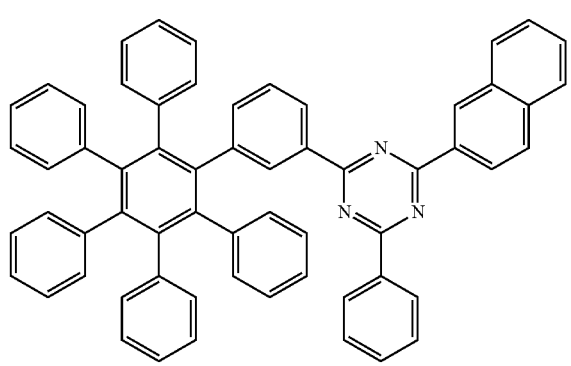
120
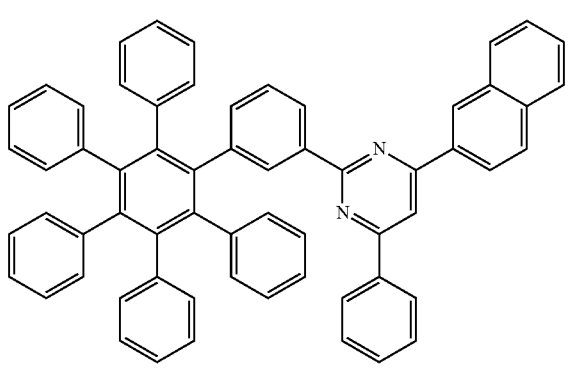
117
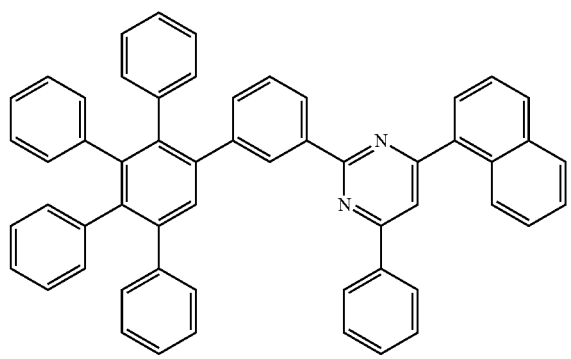
121
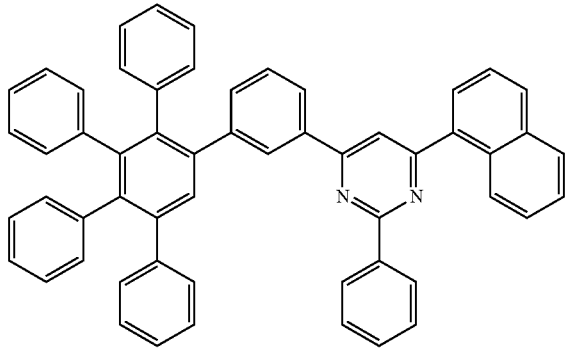

122
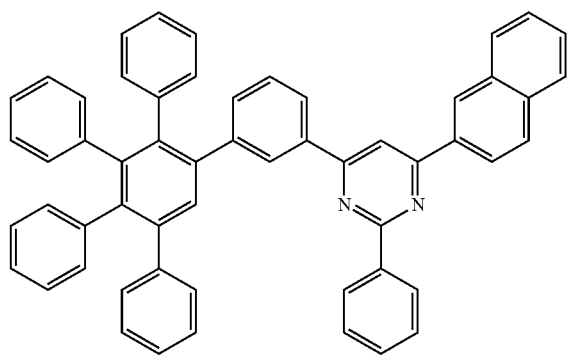
123
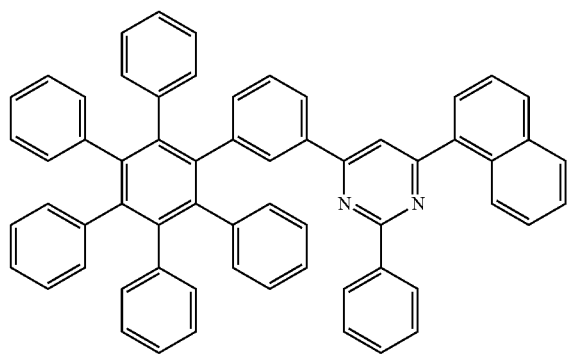
124
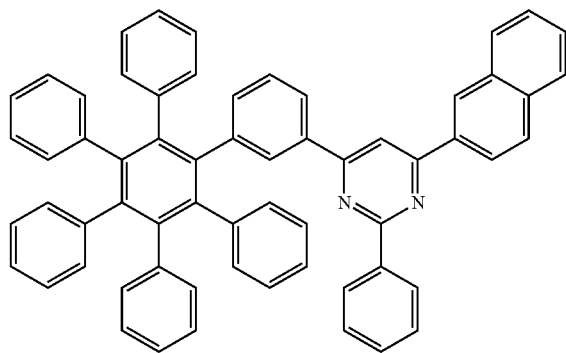
125
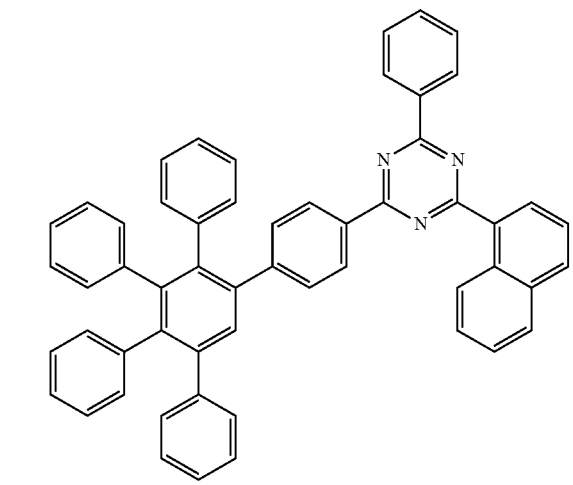
126
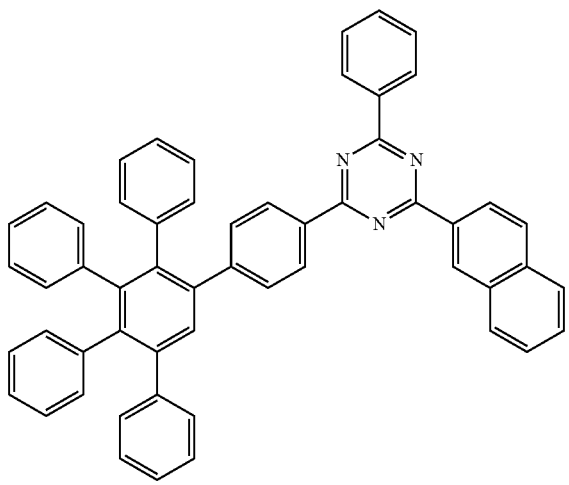
127
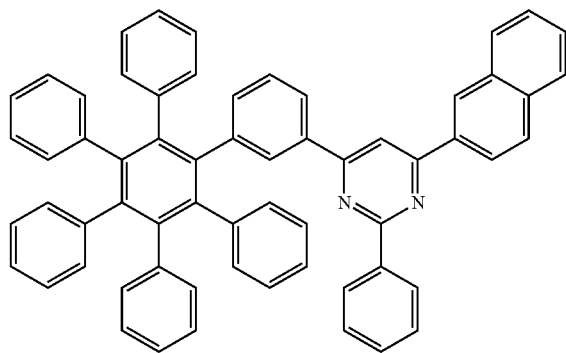
128
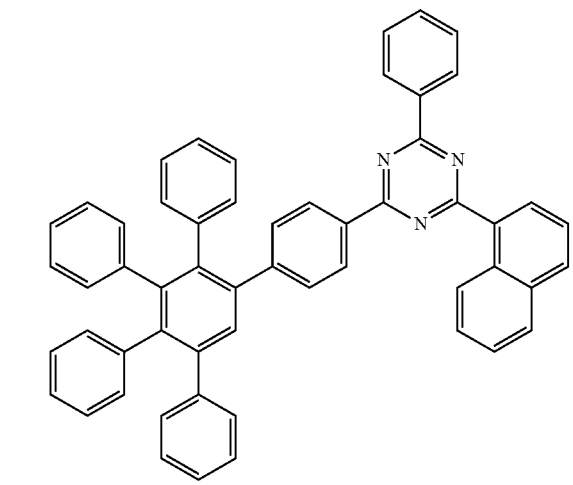

129
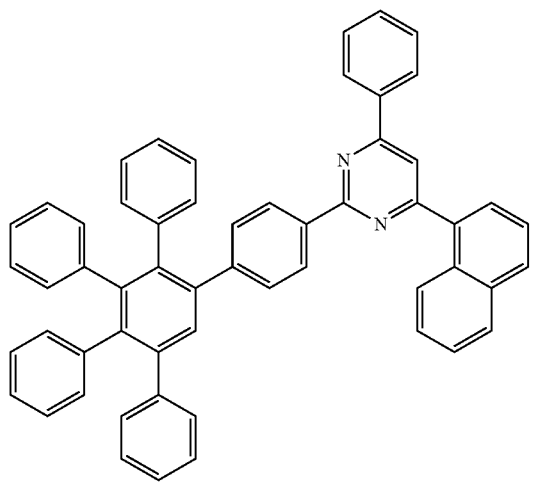
130
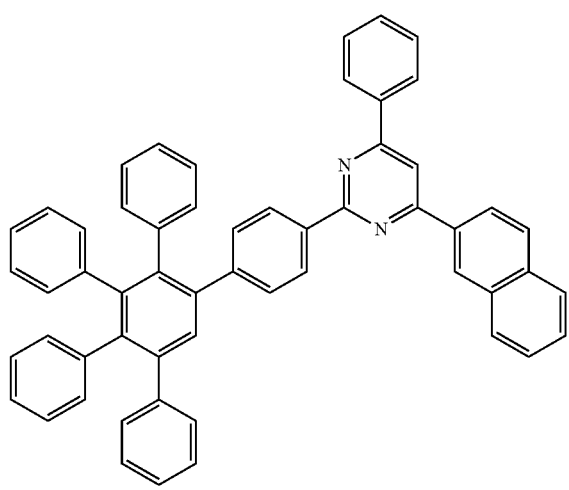
131
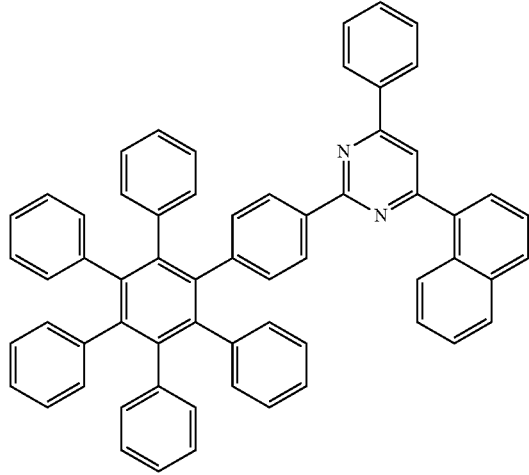
132
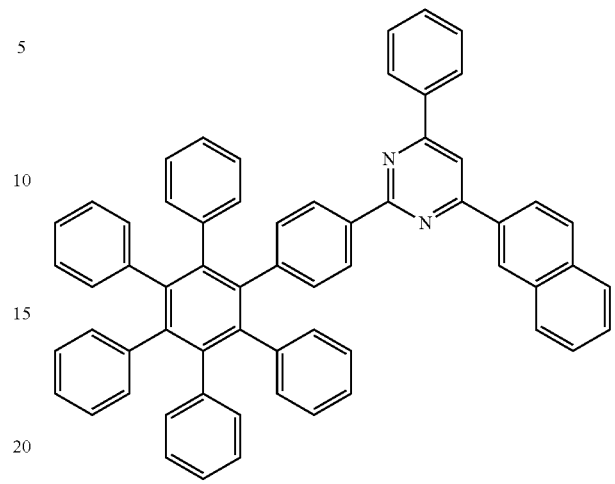
133
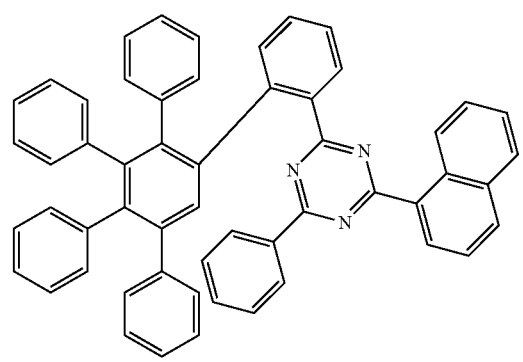
134
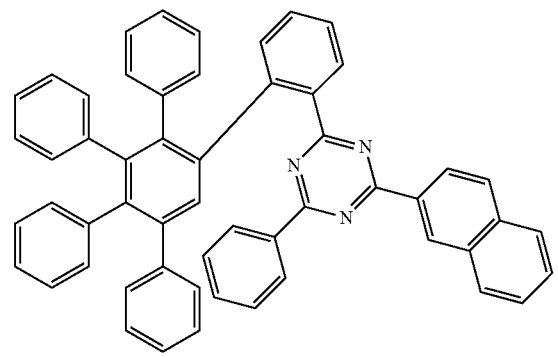

135
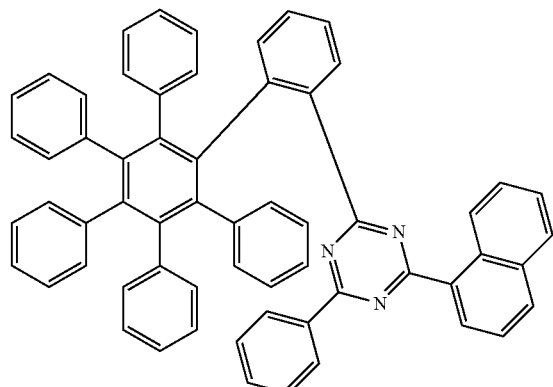
136
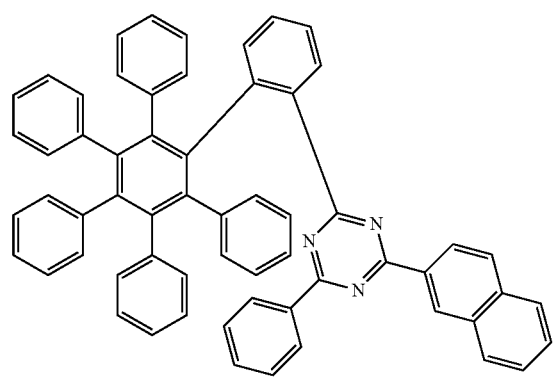
137
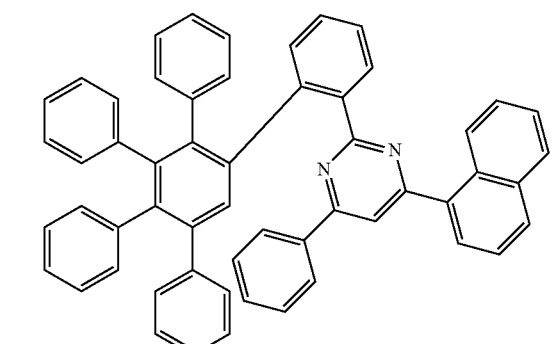
138
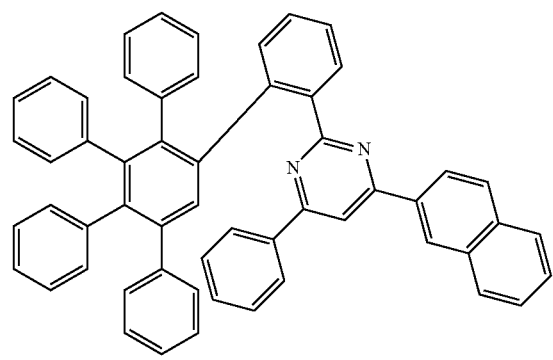
139
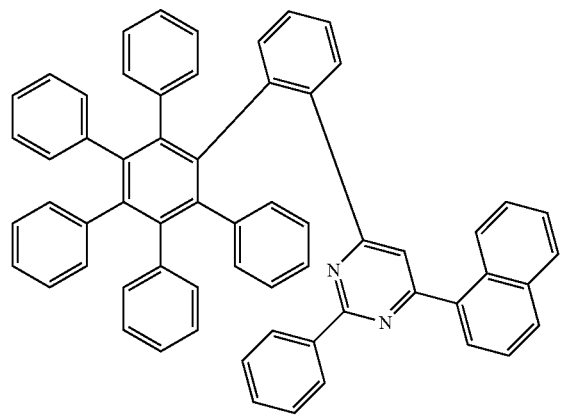
140
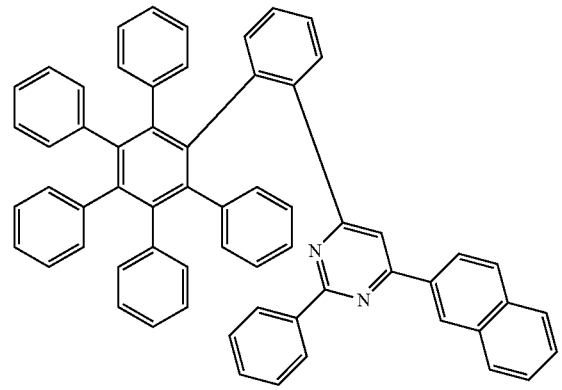
141
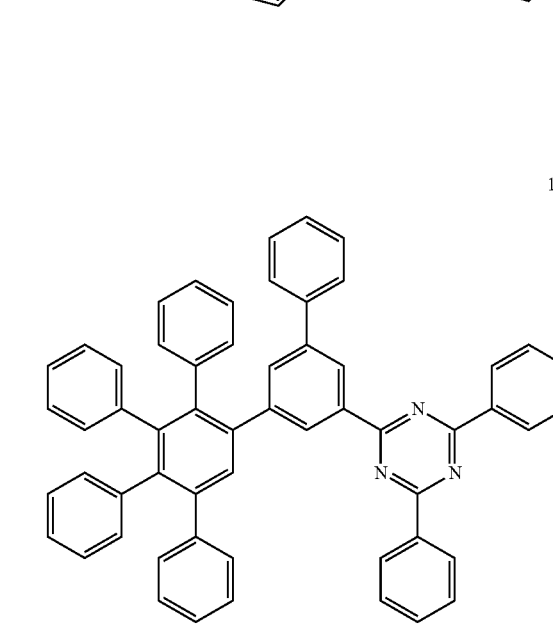

142
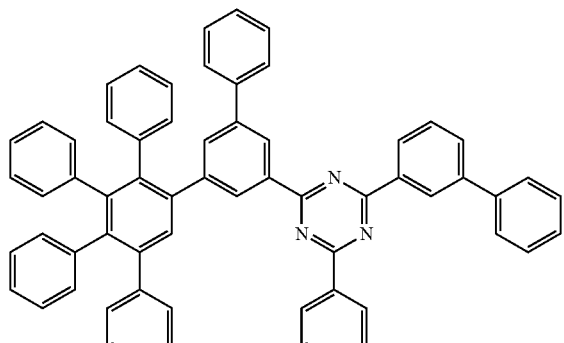
143
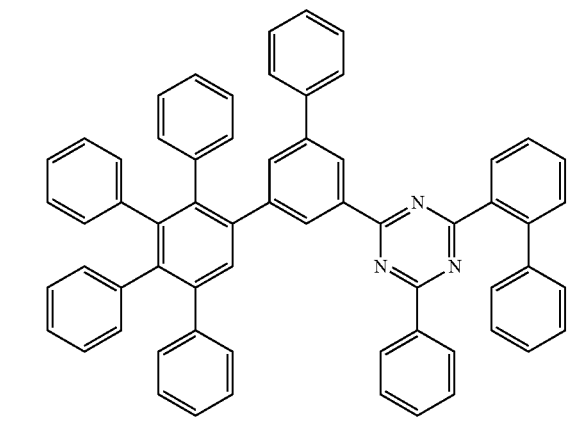
144
145
146
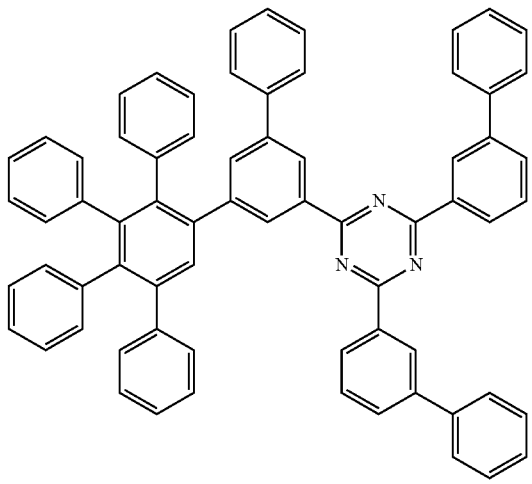
147
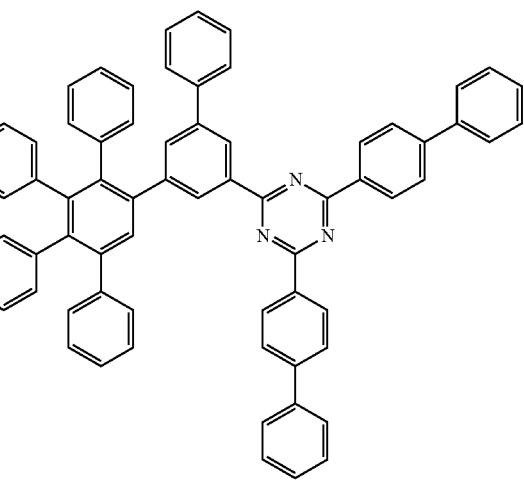
148
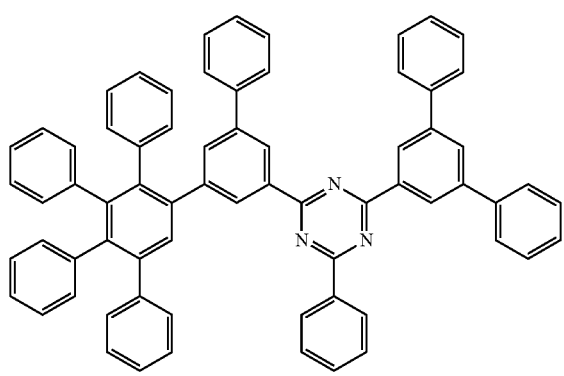
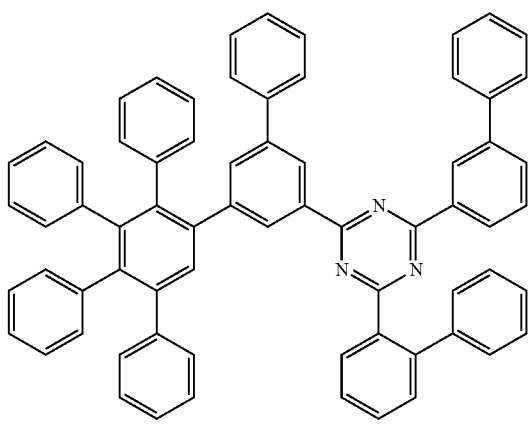

149

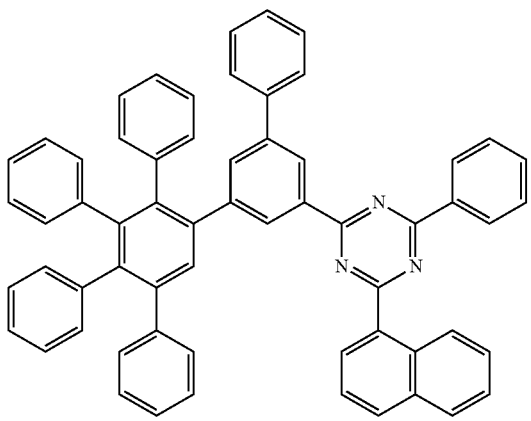

150

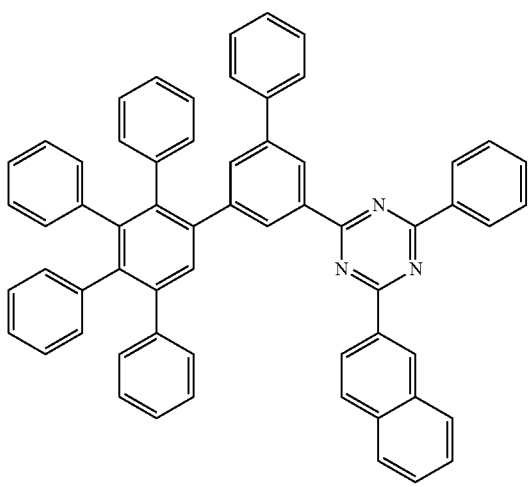

151

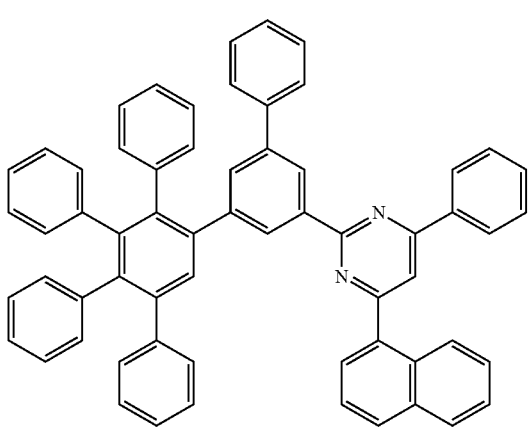

152

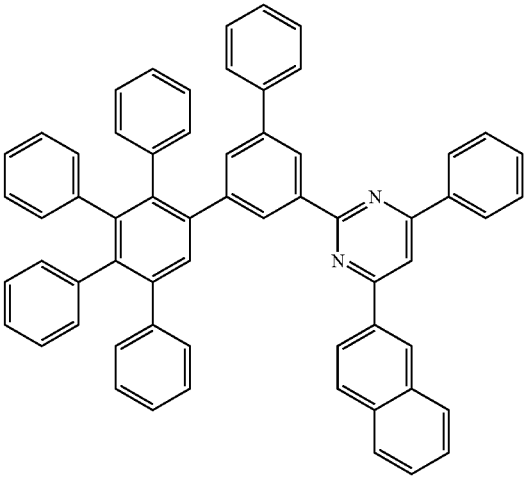

Hereinafter, an organic optoelectronic device according to another embodiment is described.

An organic optoelectronic device according to another embodiment includes an anode and a cathode facing each other and at least one organic layer between the anode and the cathode and the organic layer includes the compound for an organic optoelectronic device.

More specifically, the organic layer may include an emission layer, an electron transport layer, and a hole transport layer, and the electron transport layer or the emission layer includes the compound for an organic optoelectronic device represented by Chemical Formula 1.

In addition, the electron transport layer may further include an electron transport auxiliary layer being adjacent to the emission layer, and the compound for an organic optoelectronic device may be included in the electron transport auxiliary layer.

The organic optoelectronic device may realize a low driving voltage, high efficiency, high luminance and long life-span by including the organic layer including the compound for an organic optoelectronic device.

FIGS. 1 to 4 are schematic cross-sectional views of organic light emitting diodes 100, 200, 300, and 400 according to an embodiment of the present invention. Hereinafter, referring to FIG. 1, a structure of an organic light emitting diode according to an embodiment of the present invention and a method of manufacturing the same are as follows.

The organic light emitting diode 100 has a structure where a cathode 110, an emission layer 130, and an anode 120 that are sequentially stacked.

A substrate may be further disposed under the cathode 110 or on the anode 120. The substrate may be a substrate that used in a general organic light emitting diode and may be a glass substrate or a transparent plastic substrate with strong mechanical strength, thermal stability, transparency, surface smoothness, ease of handling, and water resistance.

The anode 120 may be formed by depositing or sputtering an anode material on a substrate. The anode material may be selected from materials having a high work function that makes hole injection easy. The anode 120 may be a reflective electrode, a transflective electrode, or a transmissive electrode. The anode material may use indium tin oxide (ITO), indium zinc oxide (IZO), tin oxide ($SnO_2$), zinc oxide (ZnO), and the like. Or, it may be a metal such as magnesium (Mg), aluminum (Al), aluminum-lithium (Al—Li), calcium (Ca), magnesium-indium (Mg—In), or magnesium-silver (Mg—Ag).

The anode 120 may have a monolayer or a multi-layer structure of two or more layers.

An organic layer 105 is disposed on the anode 120.

The organic layer 105 may include a hole transport region; an emission layer; and an electron transport region. For example, referring to FIG. 2, an organic light emitting diode according to an embodiment of the present invention is described.

The organic layer 105 further includes a hole auxiliary layer 140 between the anode 120 and the emission layer 130.

Referring to FIG. 3, the hole transport region may include at least two layered hole auxiliary layer, and in this case, a hole auxiliary layer contacting the emission layer is defined as a hole transport auxiliary layer 33 and a hole auxiliary layer contacting an anode is defined as a hole transport layer 31.

The hole transport region may include at least one of a hole injection layer, a hole transport layer, an electron blocking layer, and a buffer layer.

The hole transport region may include only hole injection layer or only hole transport layer. Or, the hole transport region may have a structure where a hole injection layer 37/hole transport layer 31 or hole injection layer 37/hole transport layer 31/electron blocking layer is sequentially stacked from the anode 120.

For example, the hole injection layer 37 and the electron injection layer 36 are additionally included and as shown in FIG. 4, anode 120/hole injection layer 37/hole transport layer 31/hole transport auxiliary layer 33/emission layer 130/electron transport auxiliary layer 35/electron transport layer 34/electron injection layer 36/cathode 110 are sequentially stacked.

The hole injection layer 37 may improve interface properties between ITO as an anode and an organic material used for the hole transport layer 31, and is applied on a non-planarized ITO and thus planarizes the surface of the ITO. For example, the hole injection layer 37 may include a material having a median value, particularly desirable conductivity between a work function of ITO and HOMO of the hole transport layer 31, in order to adjust a difference a work function of ITO as an anode and HOMO of the hole transport layer 31. In connection with the present invention, the hole injection layer 37 may include N4,N4'-diphenyl-N4,N4'-bis(9-phenyl-9H-carbazol-3-yl)biphenyl-4,4'-diamine), but is not limited thereto. In addition, the hole injection layer 37 may further include a conventional material, for example, copper phthlalocyanine (CuPc), aromatic amines such as N,N'-dinaphthyl-N,N'-phenyl-(1,1'-biphenyl)-4,4'-diamine (NPD), 4,4',4''-tris[methylphenyl(phenyl)amino] triphenyl amine (m-MTDATA), 4,4',4''-tris[1-naphthyl(phenyl) amino] triphenyl amine (1-TNATA), 4,4',4''-tris[2-naphthyl (phenyl)amino]triphenyl amine (2-TNATA), 1,3,5-tris[N-(4-diphenylaminophenyl)phenylamino] benzene (p-DPA-TDAB), and the like, compounds such as 4,4'-bis[N-[4-{N, N-bis(3-methylphenyl)amino}phenyl]-N-phenylamino] biphenyl (DNTPD), hexaazatriphenylene-hexacarbonitirile (HAT-CN), and the like, a polythiophene derivative such as poly(3,4-ethylenedioxythiophene)-poly(styrnesulfonate) (PEDOT) as a conductive polymer. The hole injection layer 37 may be, for example coated on ITO as an anode in a thickness of 10 to 300 Å.

When the hole transport region includes a hole injection layer 37, the hole injection layer may be formed on the anode 120 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-8}$ torr to about $10^{-3}$ torr, and a deposition rate of about 0.01 to about 100 Å/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

A thickness of the hole transport region may be from about 100 Å to about 10000 Å, for example, about 100 Å to about 1000 Å. When the hole transport region includes the hole injection layer and the hole transport layer, a thickness of the hole injection layer may be from about 100 Å to about 10,000 Å, for example about 100 Å to about 1000 Å and a thickness of the hole transport layer may be from about 50 Å to about 2,000 Å, for example about 100 Å to about 1500 Å. When the thicknesses of the hole transport region, the HIL, and the HTL are within these ranges, satisfactory hole transport characteristics may be obtained without a substantial increase in a driving voltage.

The hole transport region may further include a charge-generating material to improve conductivity, in addition to the materials as described above. The charge-generating material may be homogeneously or non-homogeneously dispersed in the hole transport region.

The charge-generating material may be, for example, a p-dopant. The p-dopant may be one of a quinine derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as compound HT-D1 below.

<Compound HT-D1>

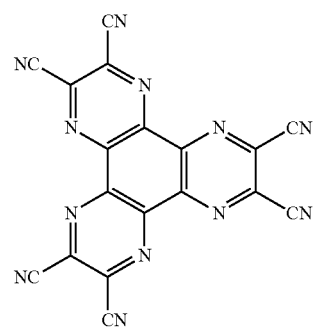

<F4-TCNQ>

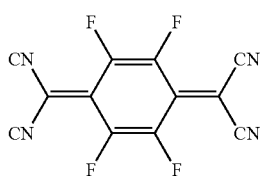

The hole transport region may further include a buffer layer.

The buffer layer may compensate for an optical resonance distance of light according to a wavelength of the light emitted from the emission layer, and thus may increase efficiency.

The emission layer (EML) may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer.

The emission layer may include a host and a dopant.

An organic optoelectronic device according to an embodiment of the present invention includes the compound for an organic optoelectronic device represented by Chemical Formula 1 alone, or the compound for an organic optoelectronic device represented by Chemical Formula 1 as a first host and a carbazole-based compound as a second host.

The carbazole-based compound may specifically be represented by Chemical Formula 2 or may consist of a combination of a moiety represented by Chemical Formula 3 and a moiety represented by Chemical Formula 4.

[Chemical Formula 2]

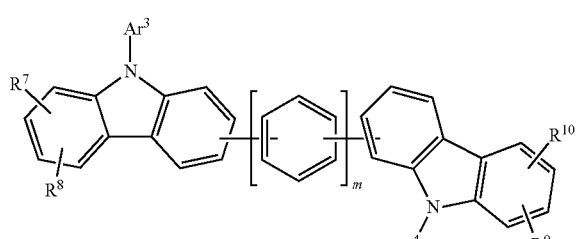

[Chemical Formula 3]

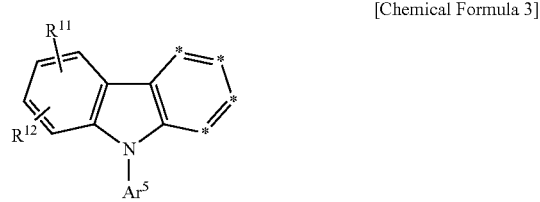

[Chemical Formula 4]

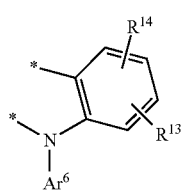

In Chemical Formulae 2 to 4, $Ar^3$ to $Ar^6$ are independently a substituted or unsubstituted C6 to C30 aryl group, or a substituted or unsubstituted C2 to C30 heteroaryl group, m is an integer of 0 or 1, adjacent two *'s of Chemical Formula 3 are combined with two *'s of Chemical Formula 4 to form a fused ring and * that does not form the fused ring of Chemical Formula 3 is independently $CR^b$, and $R^b$ and $R^7$ to $R^{14}$ are independently hydrogen, a deuterium, a substituted or unsubstituted C1 to C10 alkyl group, C6 to C30 aryl group, or a substituted or unsubstituted C2 to C30 heteroaryl group.

In one example of the present invention, in Chemical Formulae 2 to 4, the substituted or unsubstituted C6 to C30 aryl group, or the substituted or unsubstituted C2 to C30 heteroaryl group are a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, or a substituted or unsubstituted quinazolyl group, wherein in the "substituted or unsubstituted," the "substituted" refers to replacement of at least one hydrogen by deuterium, a C1 to C10 alkyl group, a C6 to C18 aryl group, or a C3 to C20 heteroaryl group.

In one example of the present invention, in Chemical Formulae 2 to 4, the substituted or unsubstituted C6 to C30 aryl group, or the substituted or unsubstituted C2 to C30 heteroaryl group refers to a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, or a substituted or unsubstituted quinazolyl group, wherein in the "substituted or unsubstituted," the "substituted" refers to replacement of at least one hydrogen by deuterium, a C1 to C4 alkyl group, a C6 to C12 aryl group, or a C3 to C15 heteroaryl group.

The bicarbazole represented by Chemical Formula 2 may be, for example selected from compounds of Group B, The indolocarbazole consisting of the combination of the moiety represented by Chemical Formula 3 and the moiety represented by Chemical Formula 4 may be for example selected from compounds of Group C.

[Group B]
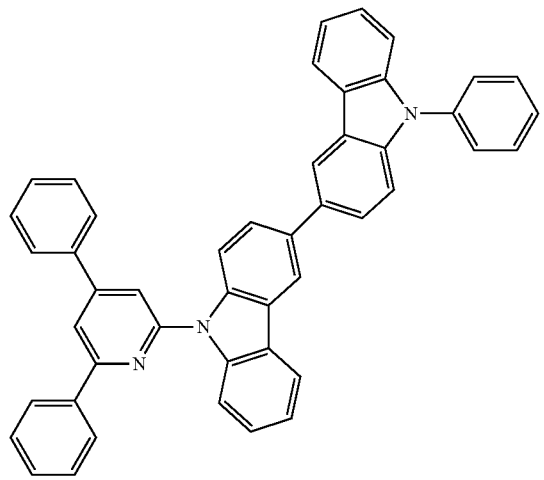
[B-1]
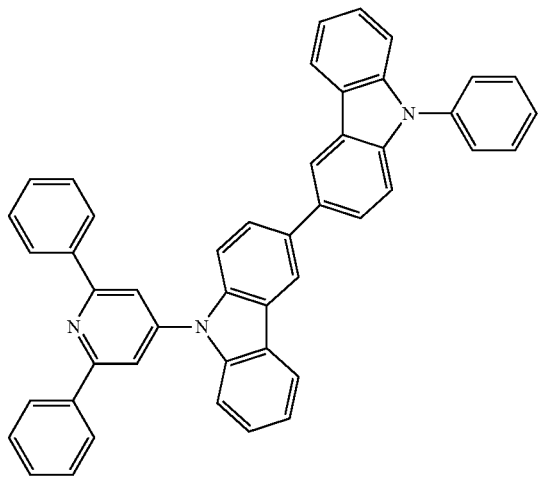
[B-2]
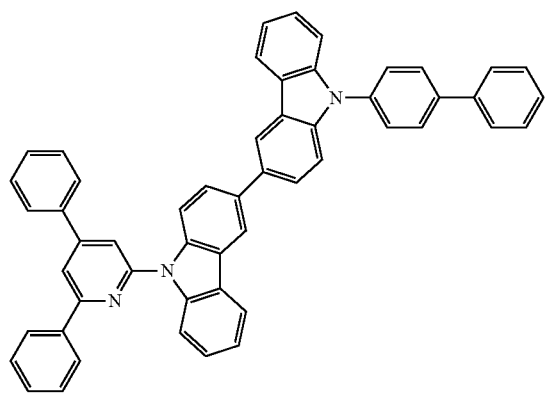
[B-3]
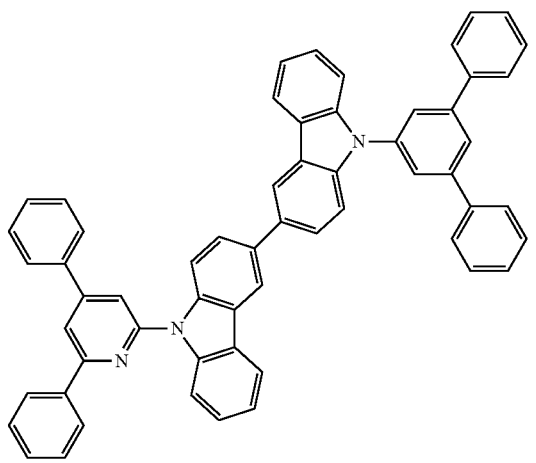
[B-4]
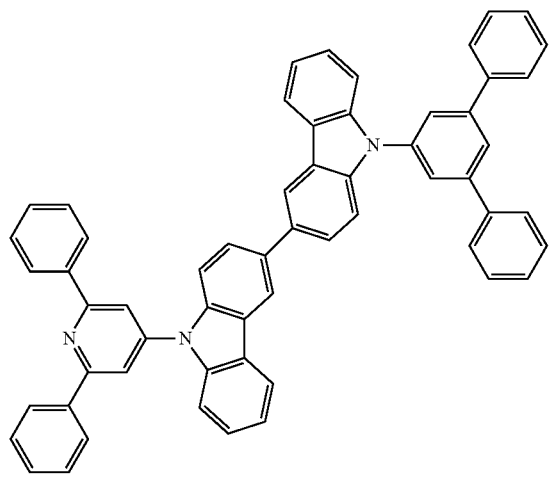
[B-5]
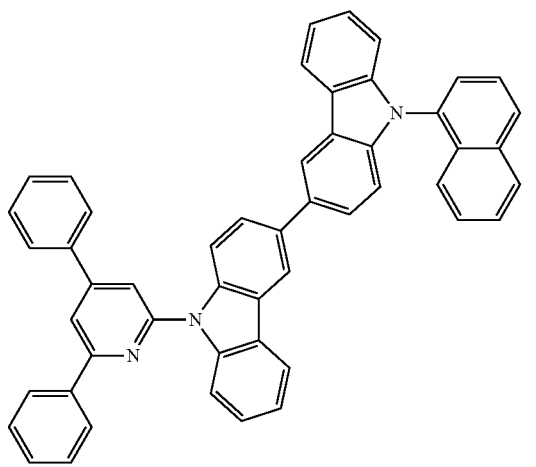
[B-6]

-continued
[B-7]
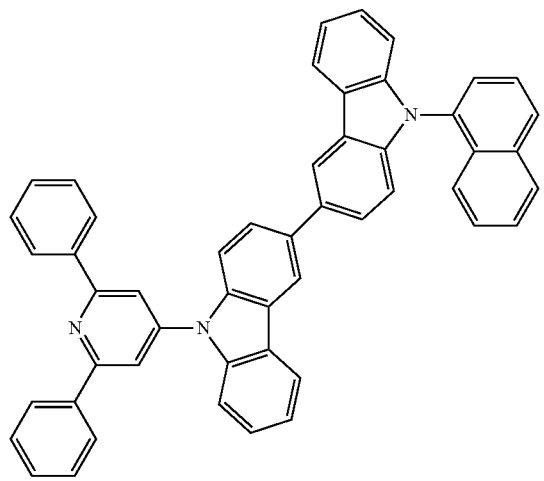
[B-8]
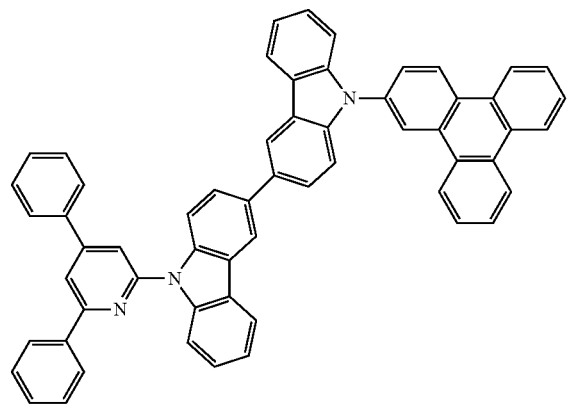
[B-9]
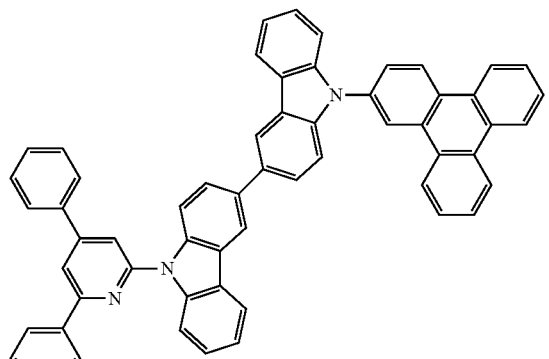
[B-10]
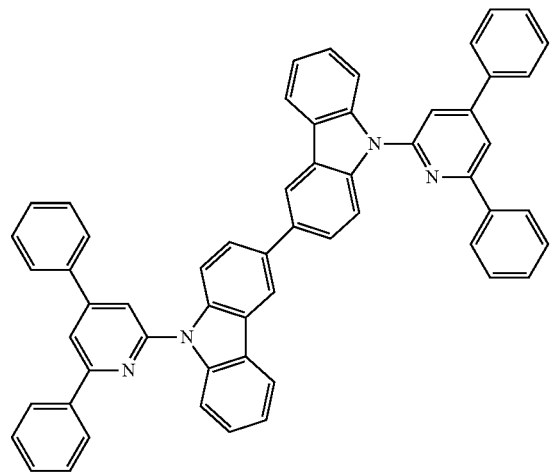
[B-11]
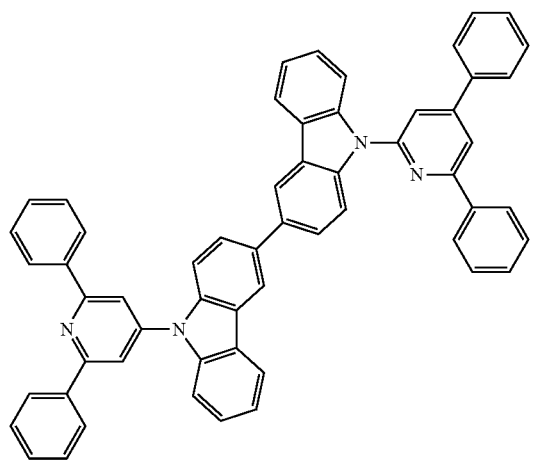
[B-12]
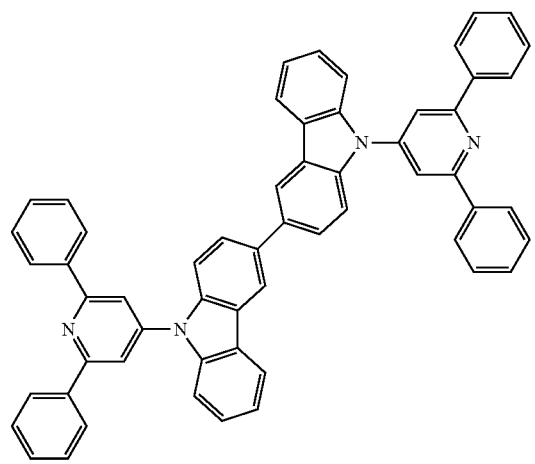

-continued
[B-13]
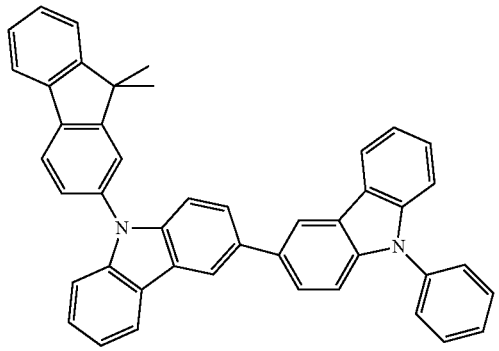
[B-14]
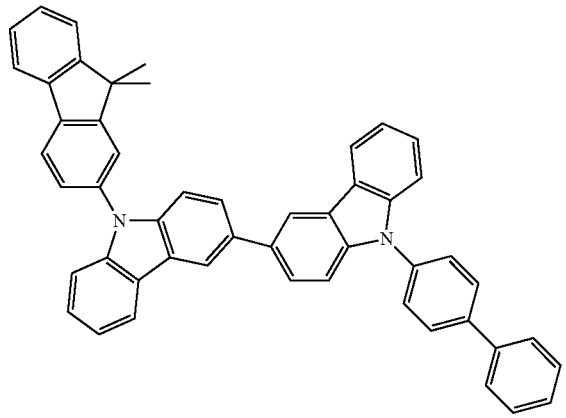
[B-15]
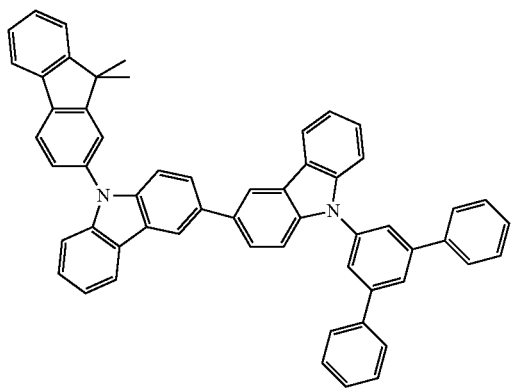
[B-16]
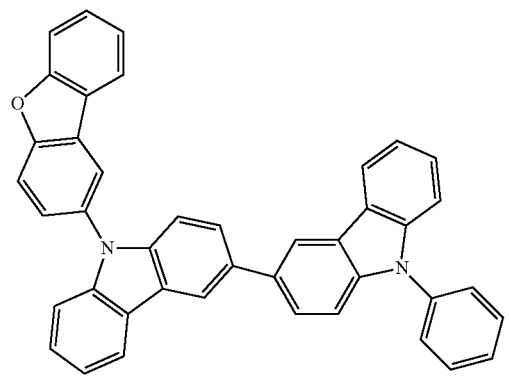
[B-17]
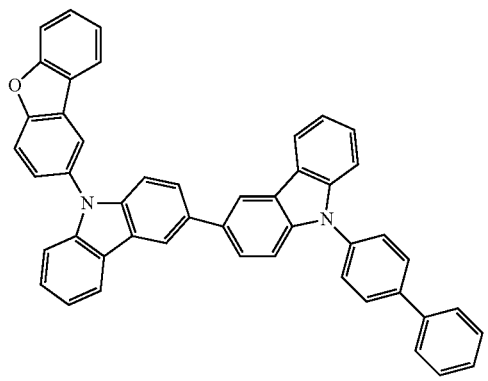
[B-18]
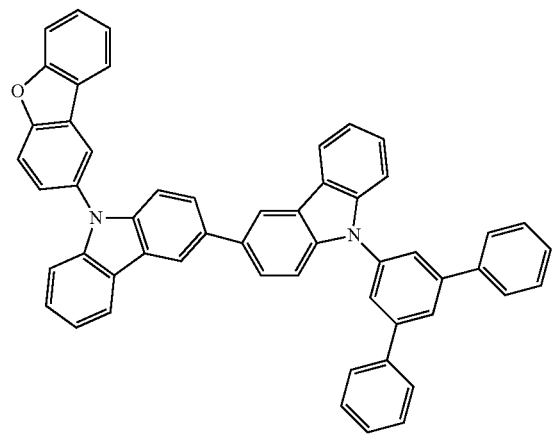

-continued
[B-19]
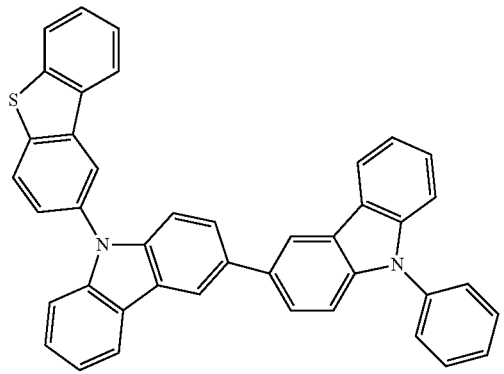
[B-20]
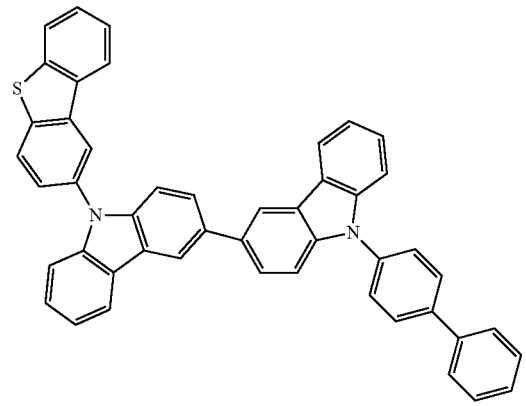
[B-21]
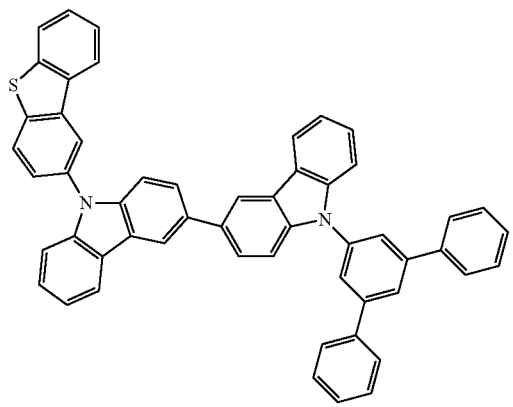
[B-22]
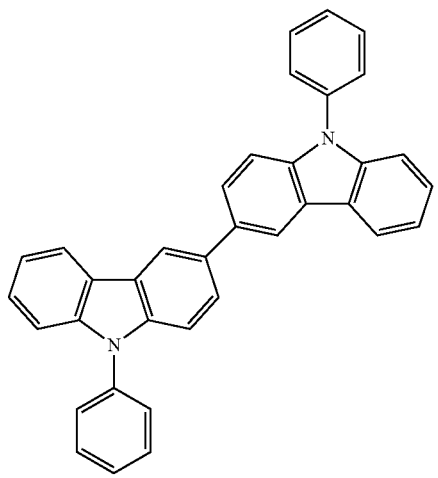
[B-23]
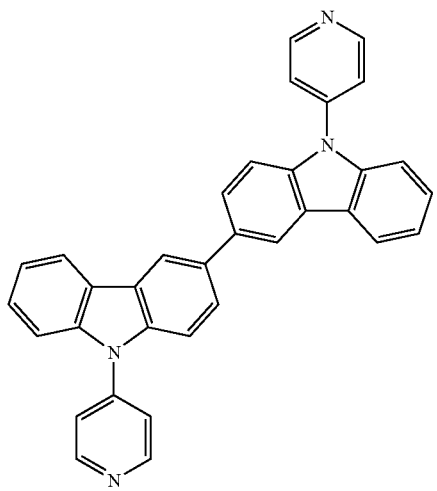
[B-24]
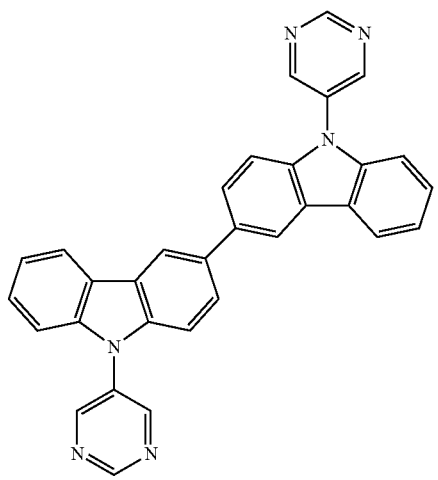

-continued
[B-25]
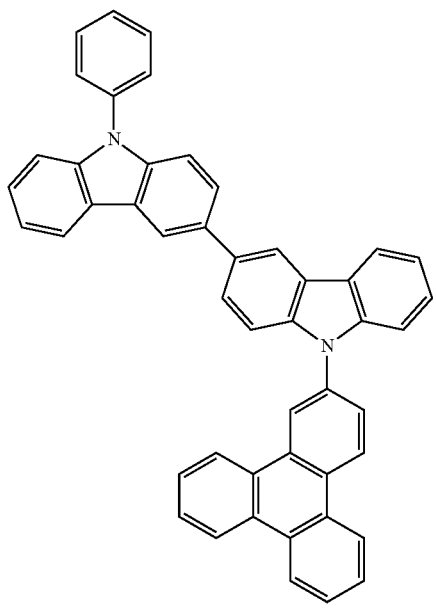
[B-26]
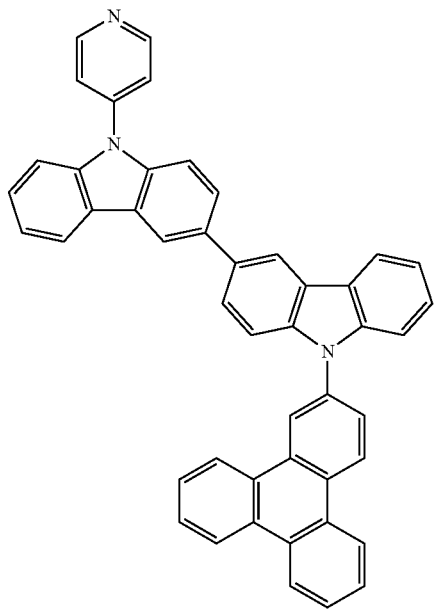
[B-27]
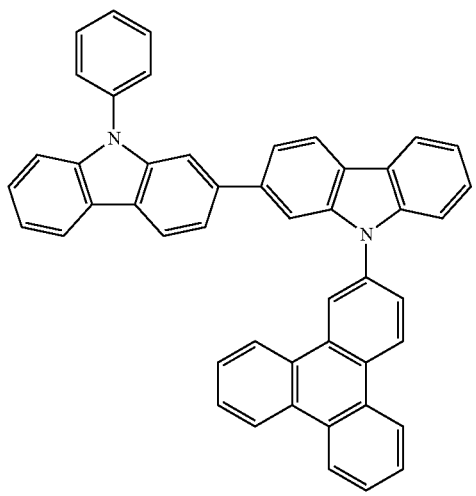
[B-28]
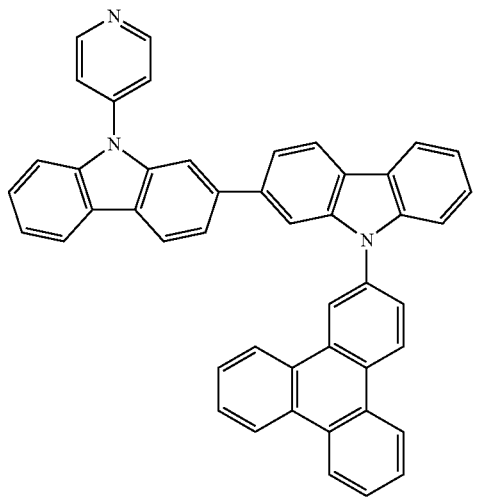
[B-29]
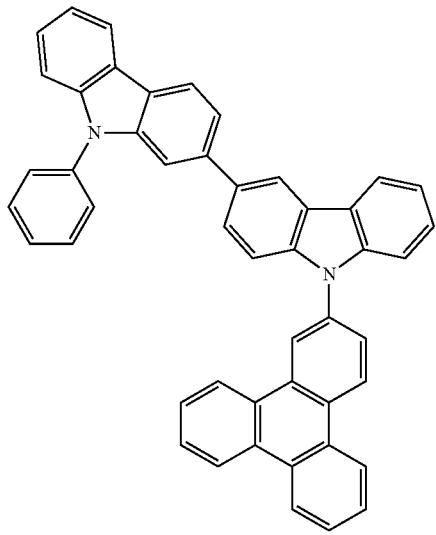
[B-30]
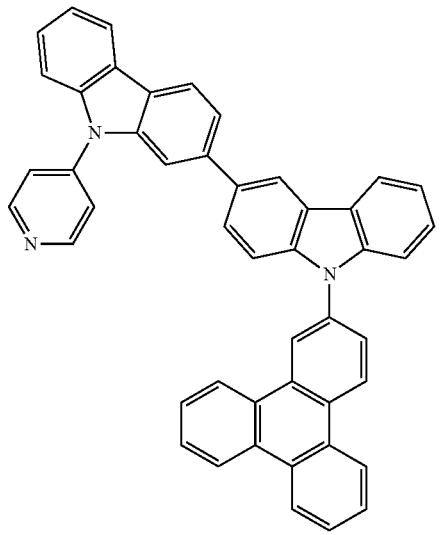

-continued
[B-31]
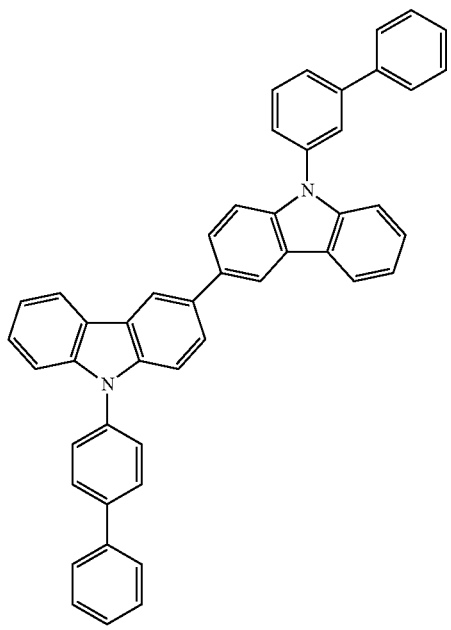
[B-32]
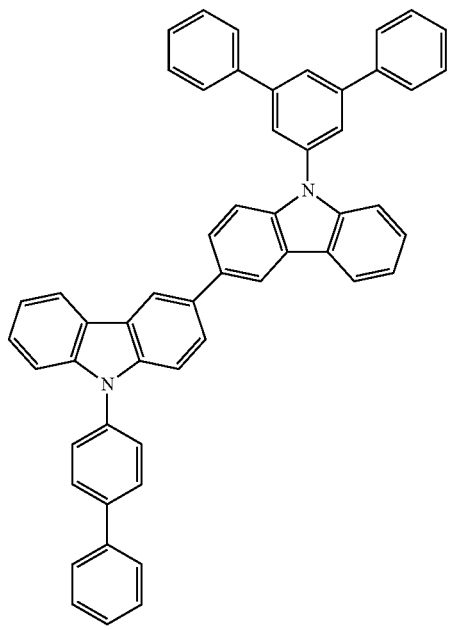
[B-33]
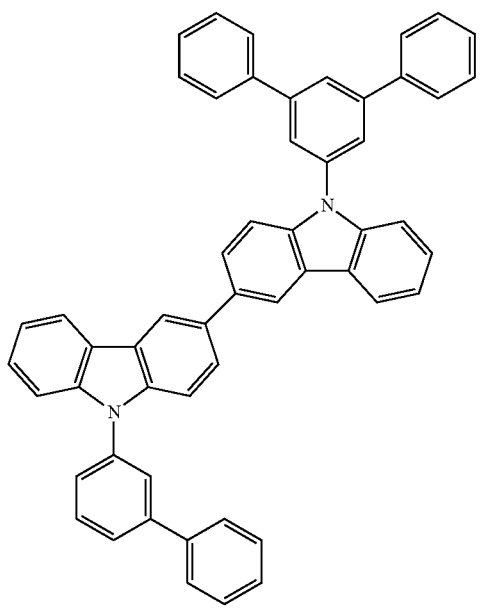
[B-34]
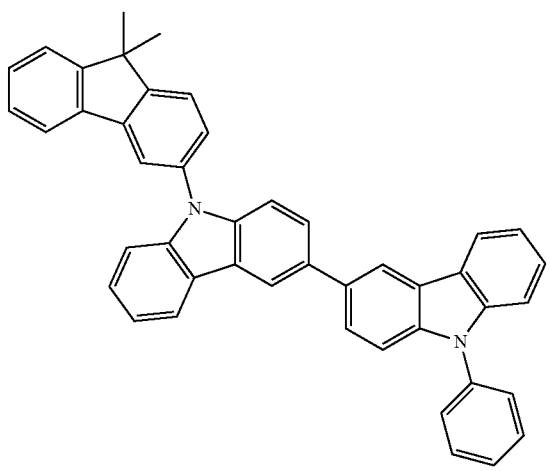

-continued
[B-35]
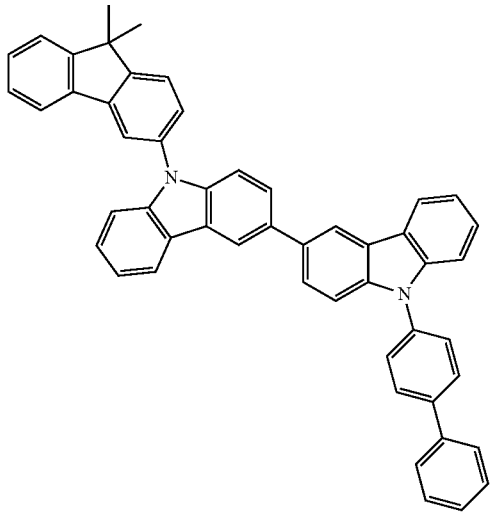
[B-36]
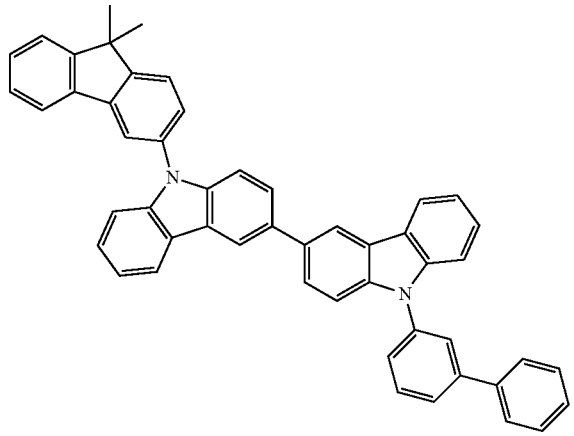
[B-37]
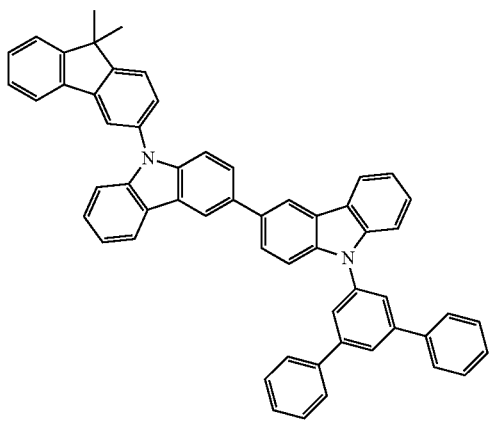
[B-38]
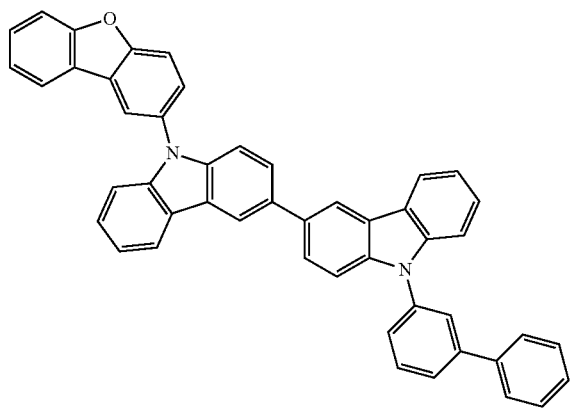
[B-39]
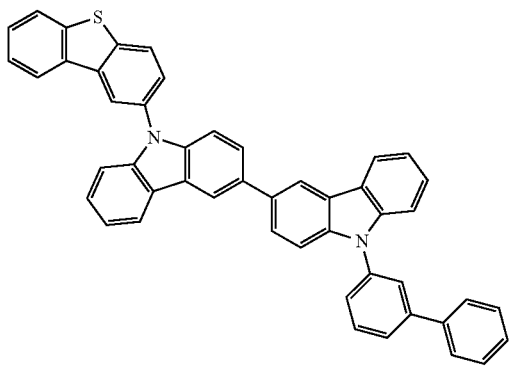
[B-40]
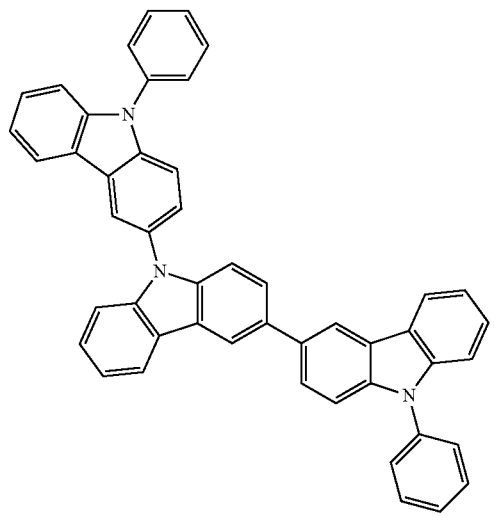

-continued
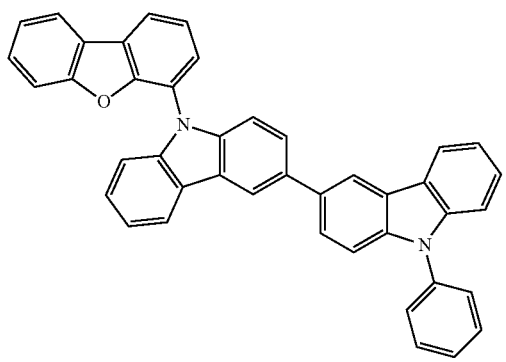
[B-41]
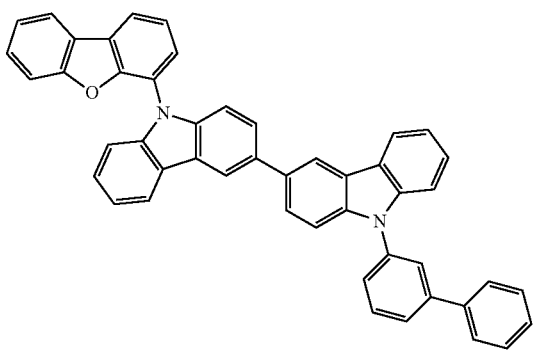
[B-42]
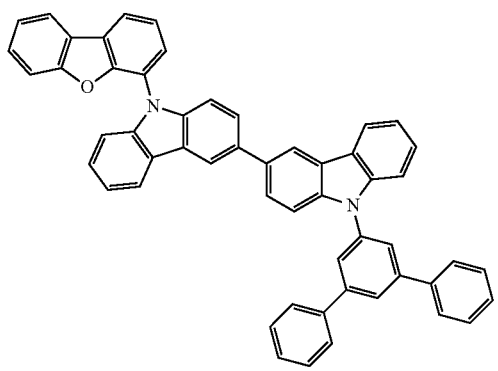
[B-43]
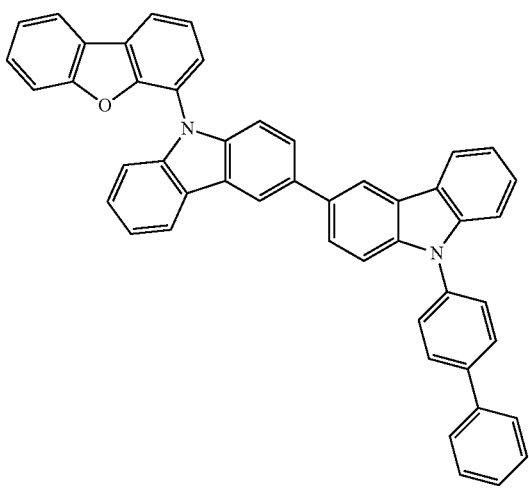
[B-44]
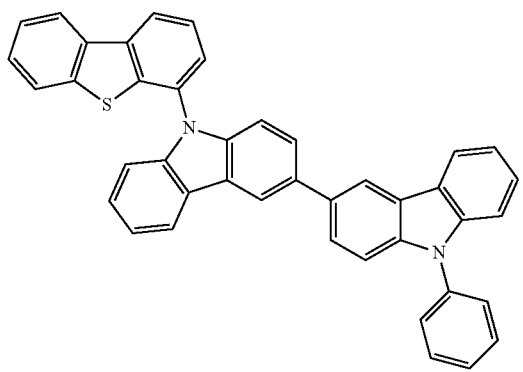
[B-45]
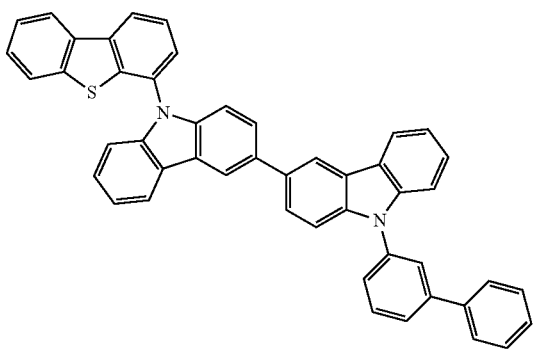
[B-46]

[B-47]
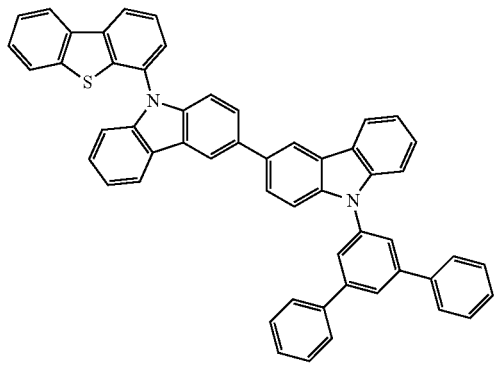
[B-48]
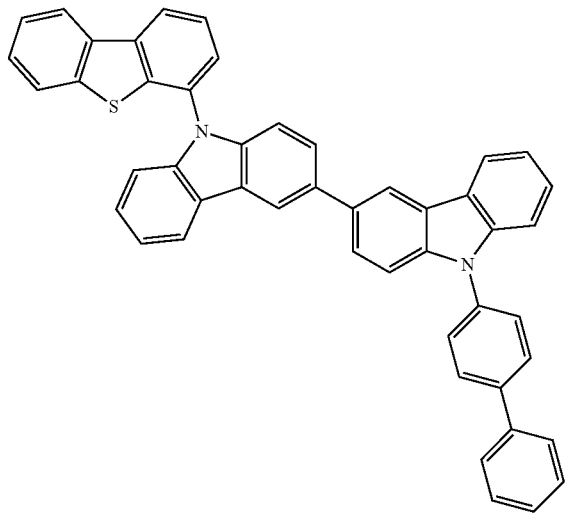
[B-49]
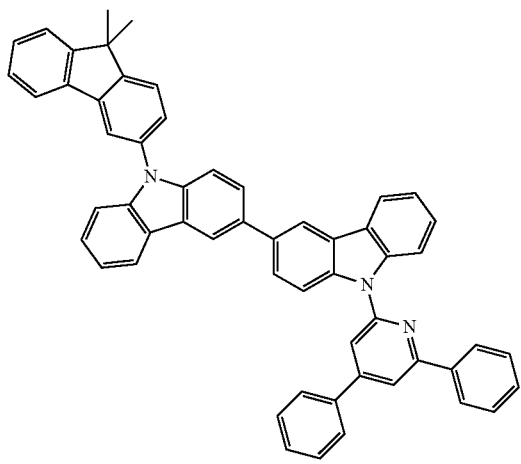
[B-50]
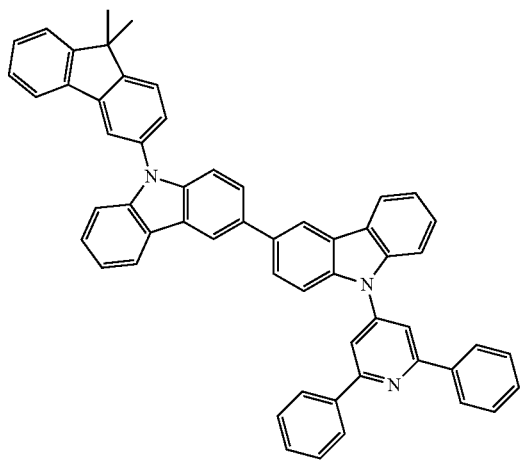
[B-51]
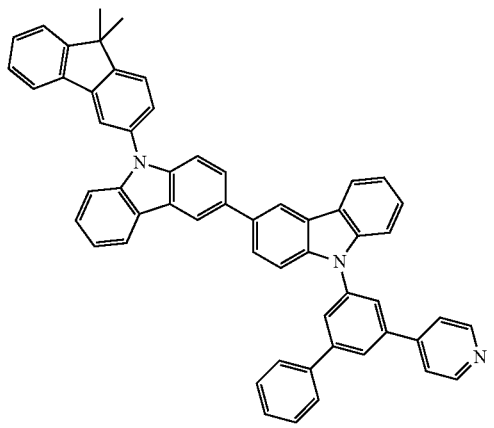
[B-52]
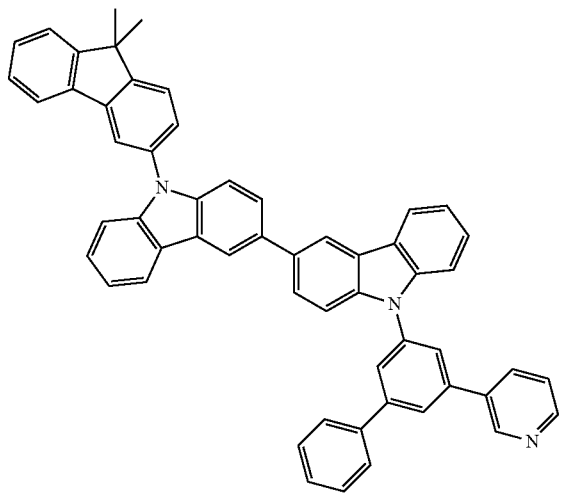

[B-53]
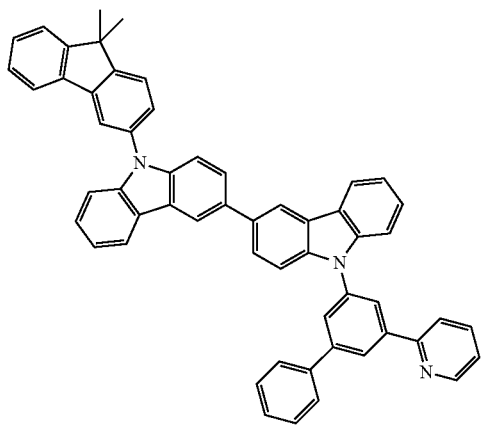
[B-54]
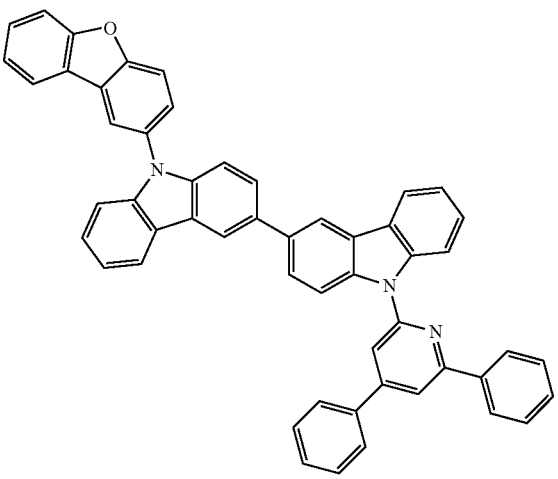
[B-55]
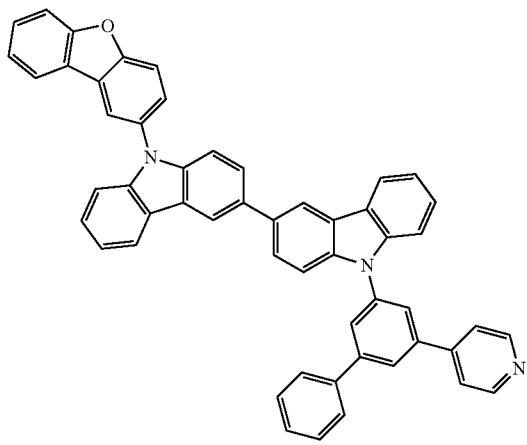
[B-56]
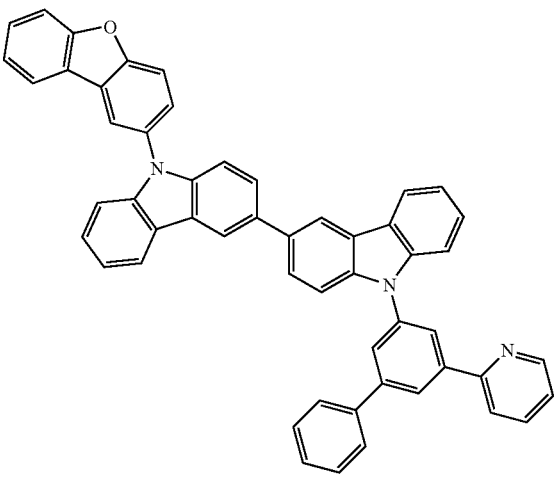
[B-57]
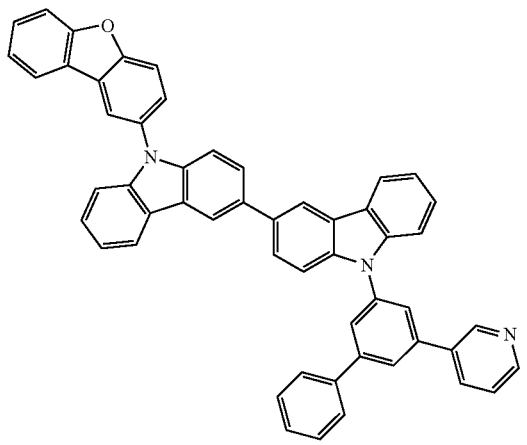
[B-58]
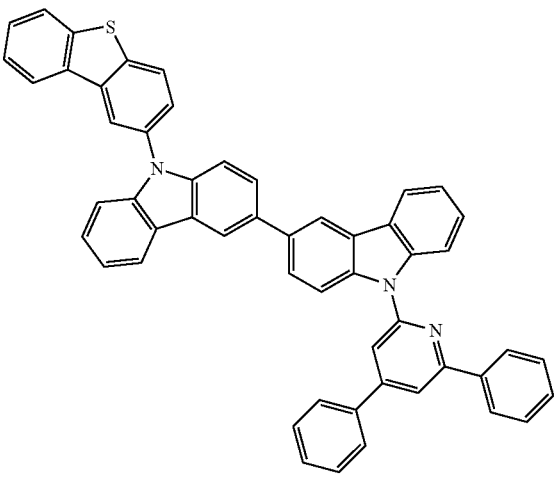

-continued
[B-59]
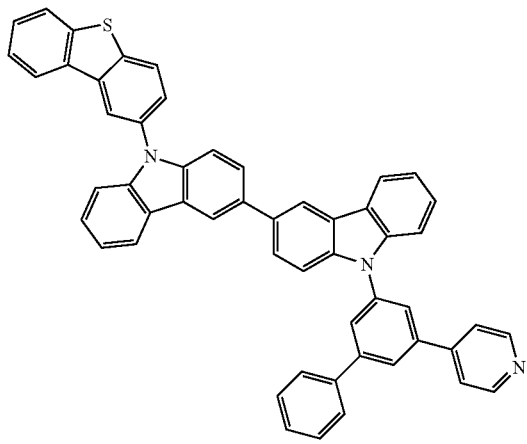
[B-60]
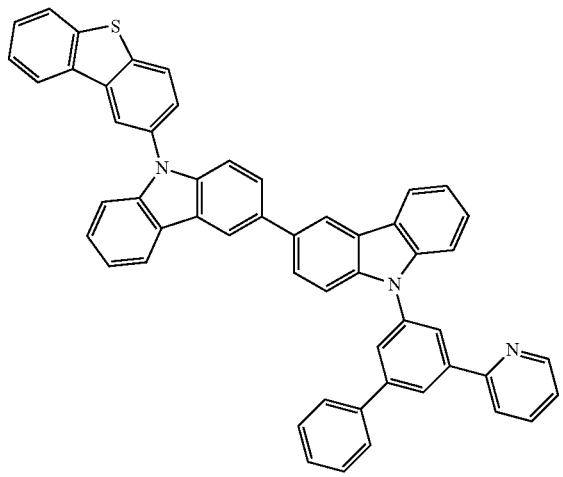
[B-61]
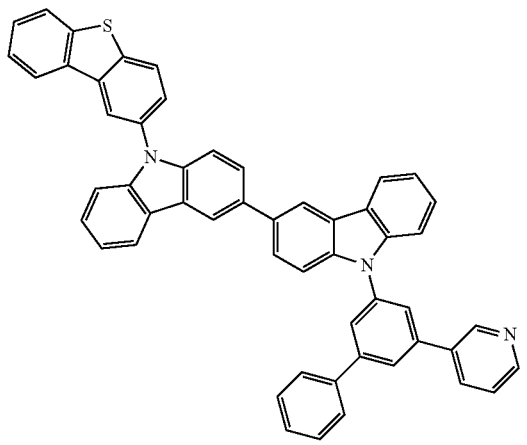
[B-62]
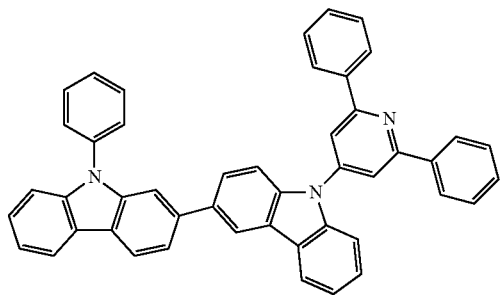
[B-63]
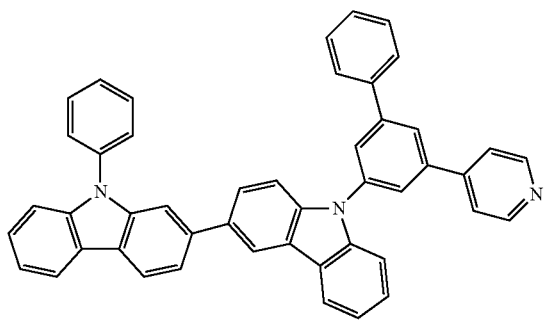
[B-64]
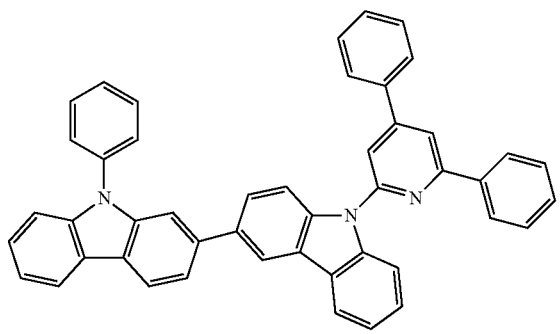

-continued
[B-65]
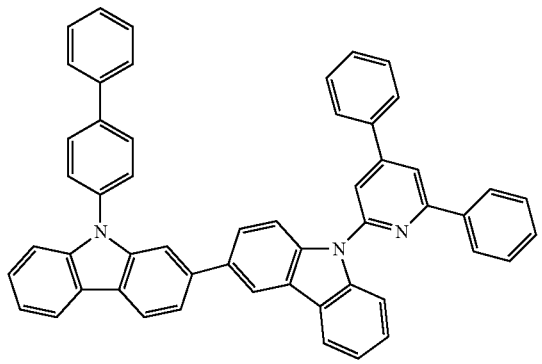
[B-66]
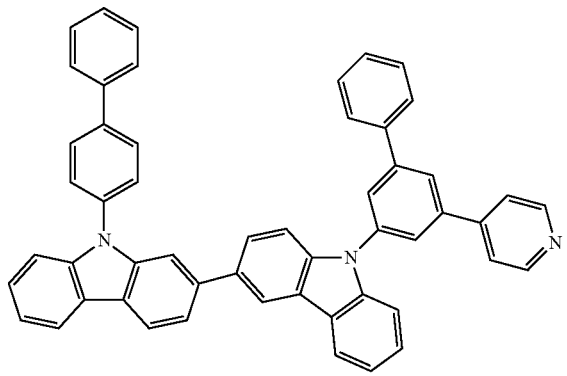
[B-67]
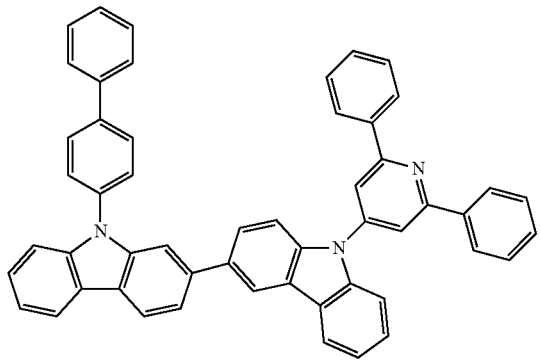
[B-68]
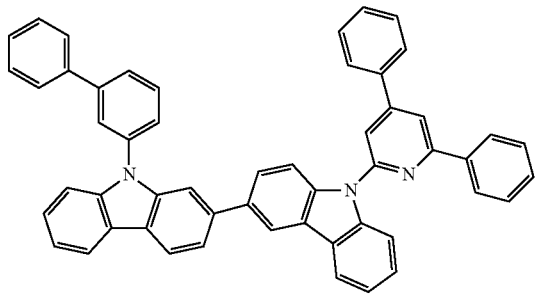
[B-69]
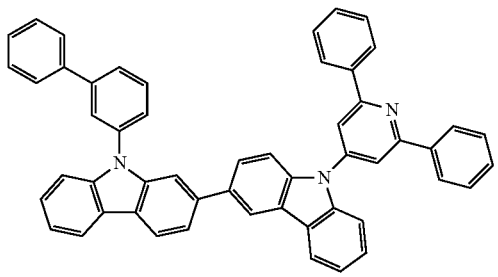
[B-70]
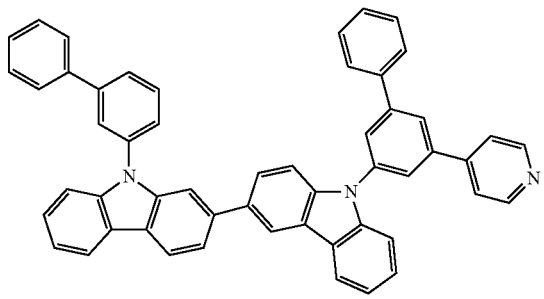
[B-71]
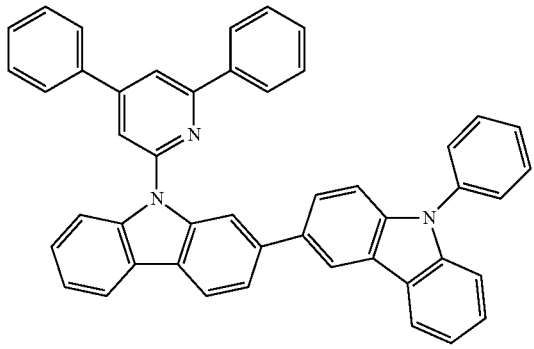
[B-72]
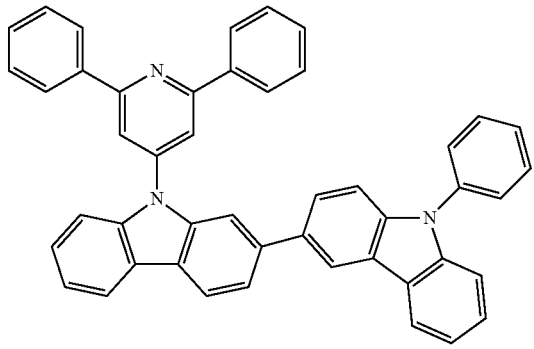

-continued
[B-73]
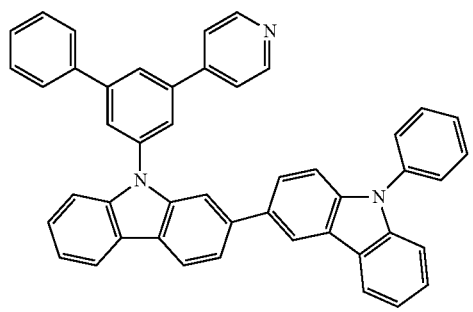
[B-74]
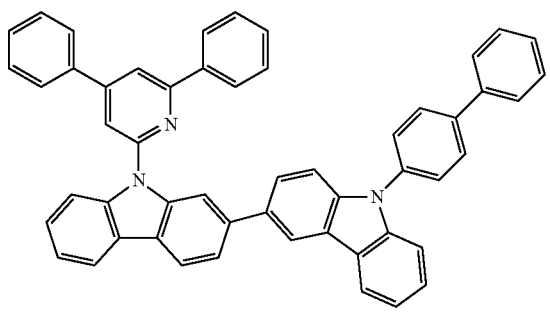
[B-75]
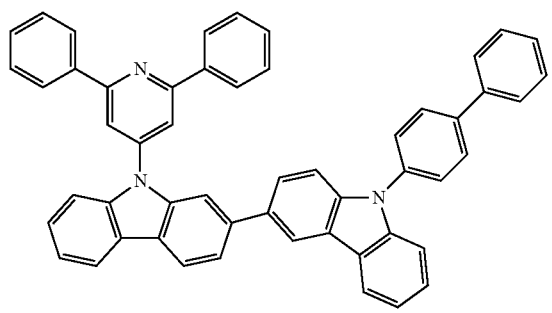
[B-76]
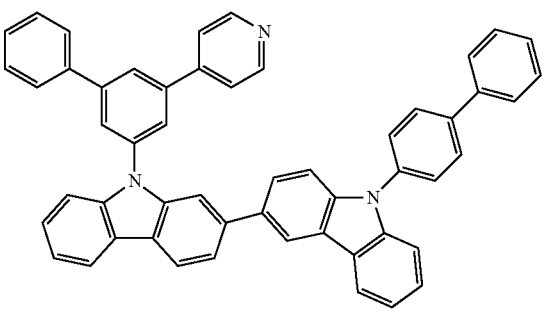
[B-77]
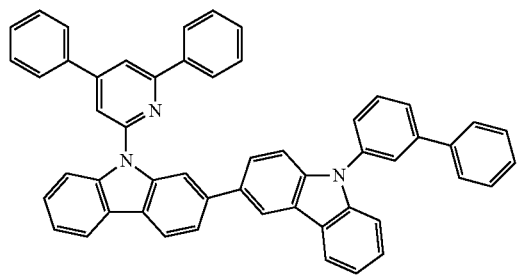
[B-78]
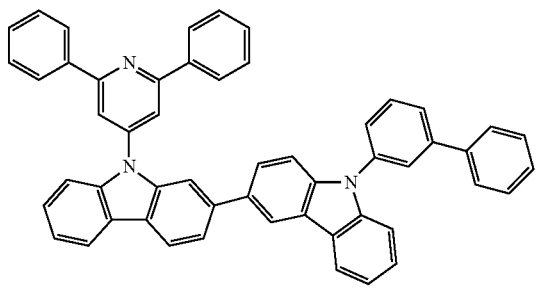
[B-79]
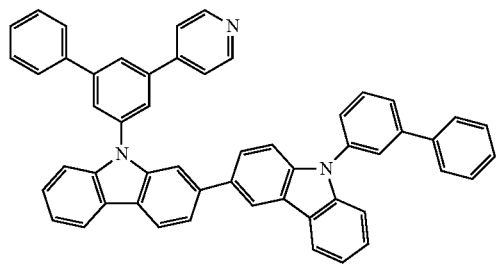
[B-80]
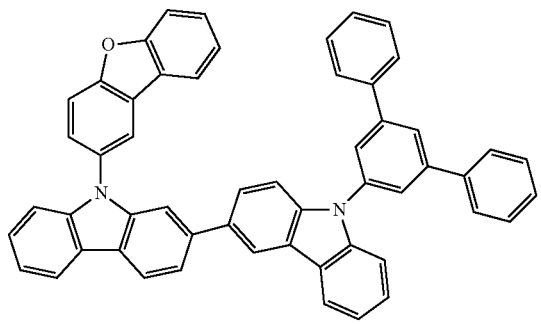

[B-81]
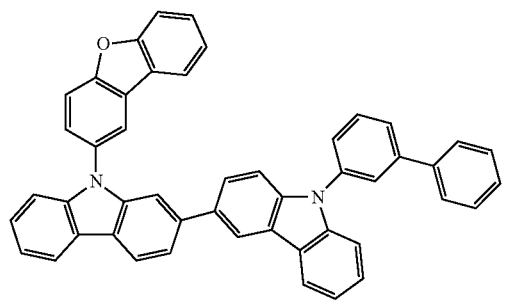
[B-82]
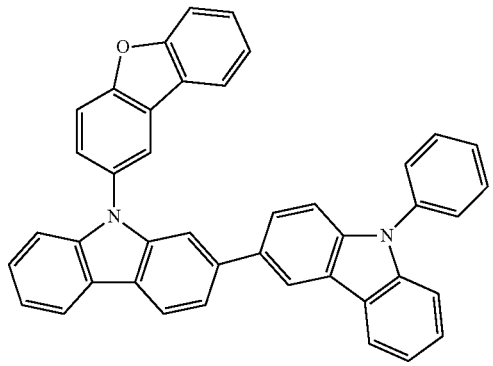
[B-83]
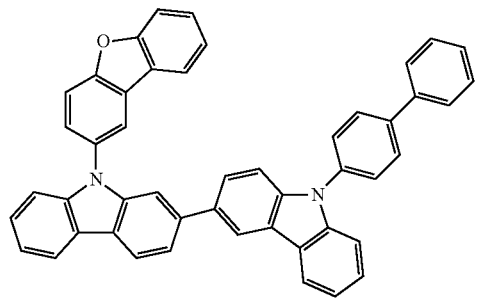
[B-84]
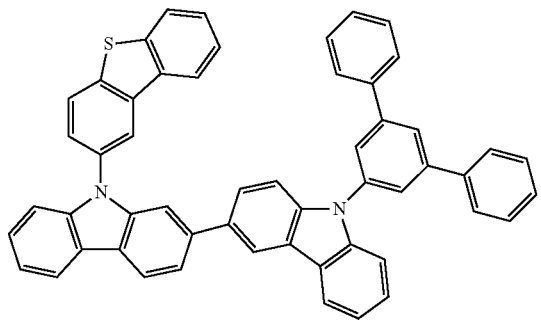
[B-85]
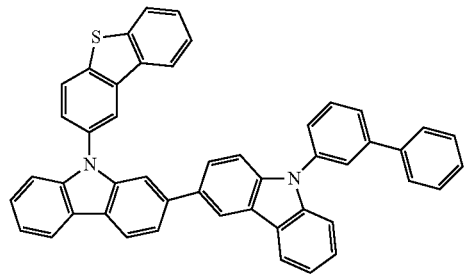
[B-86]
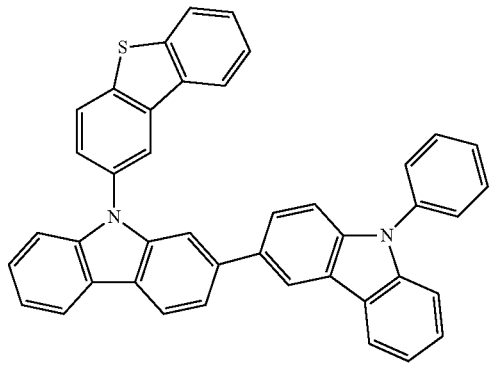
[B-87]
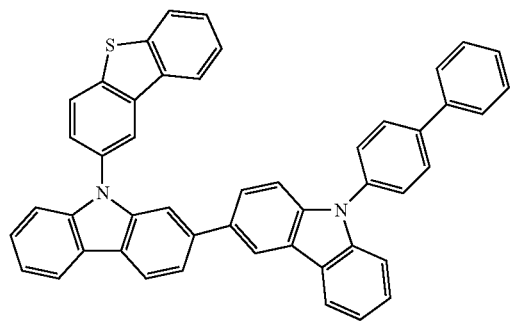
[B-88]
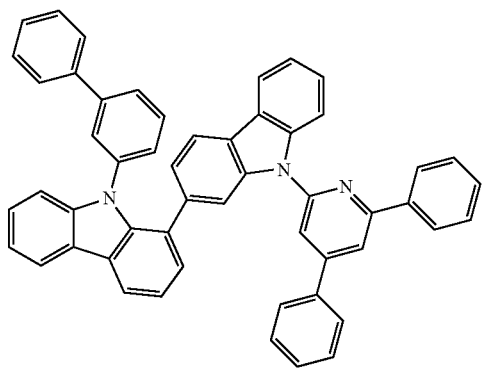

-continued
[B-89]
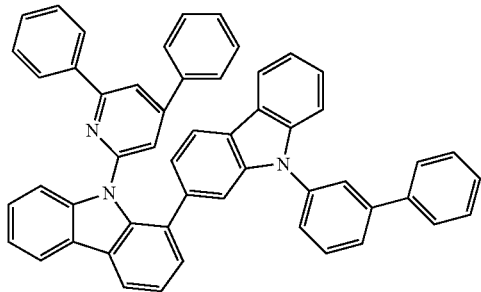
[B-90]
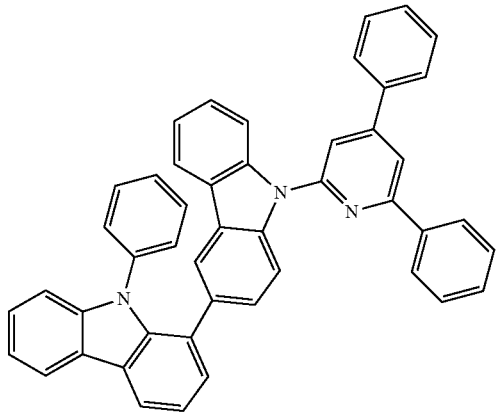
[B-91]
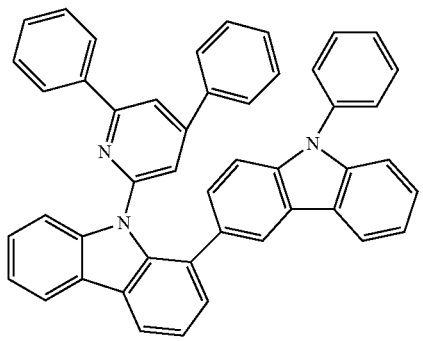
[B-92]
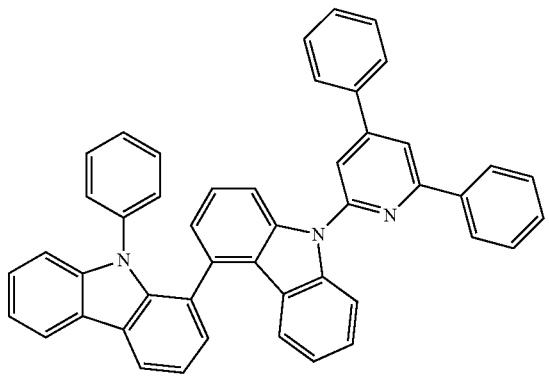
[B-93]
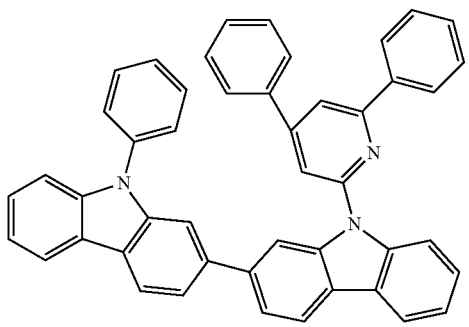
[B-94]
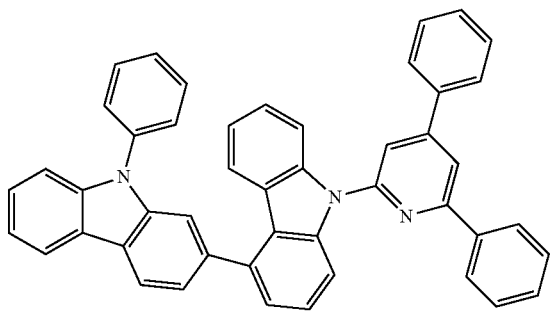
[B-95]
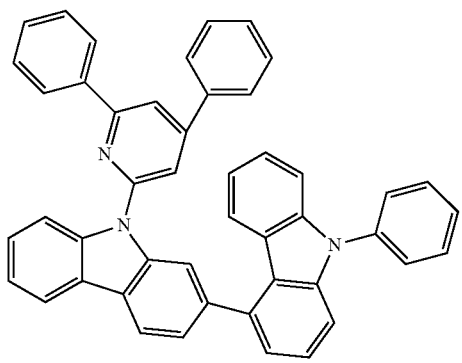
[B-96]
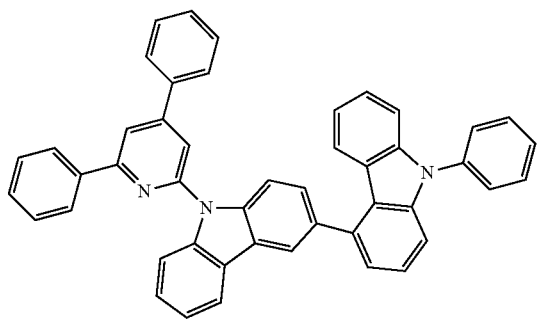

-continued
[B-97]
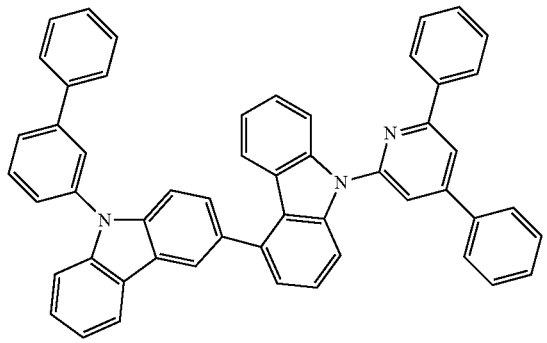
[B-98]
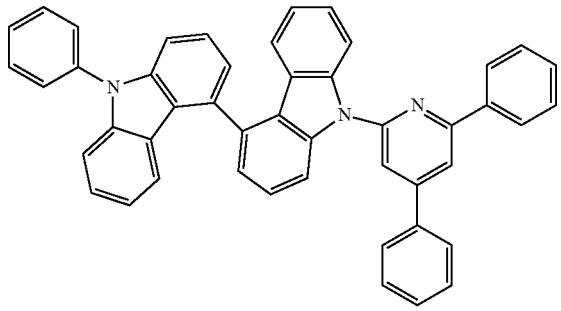
[B-99]
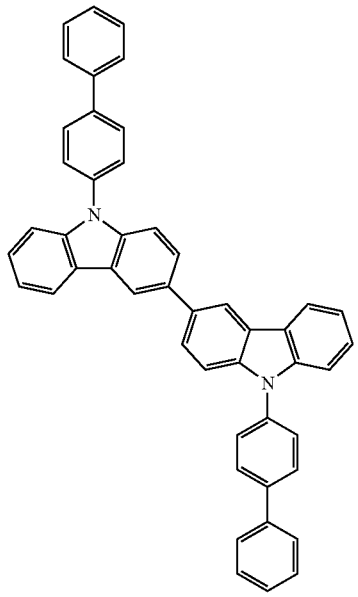
[B-100]
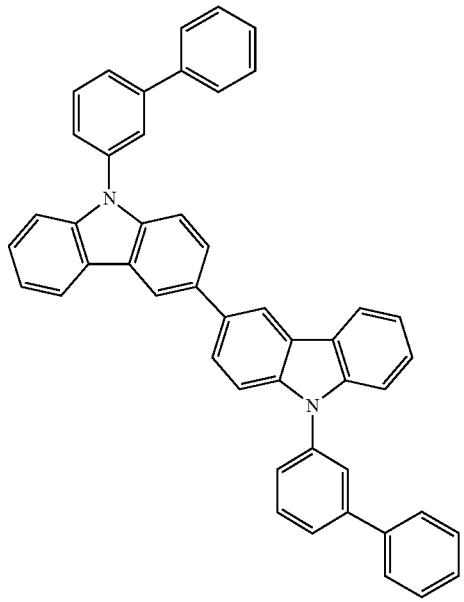
[B-101]
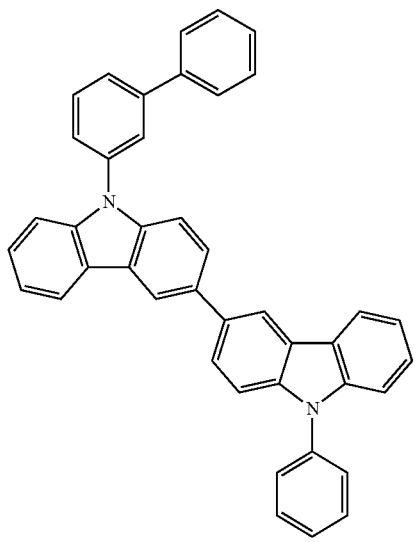
[B-102]
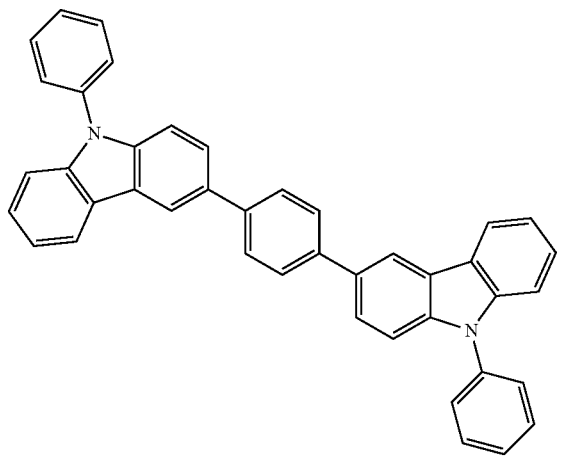

-continued
[B-103]
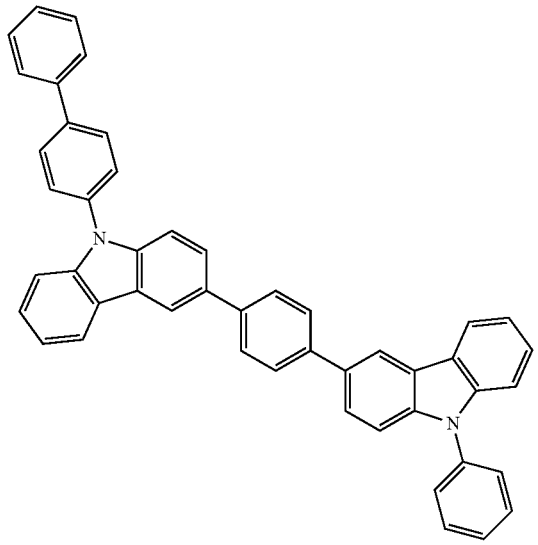
[B-104]
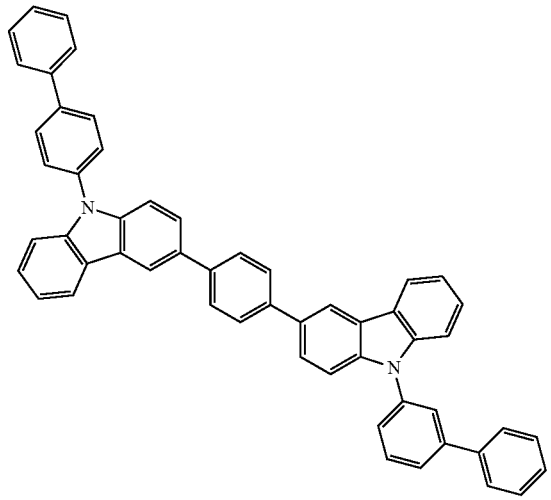
[B-105]
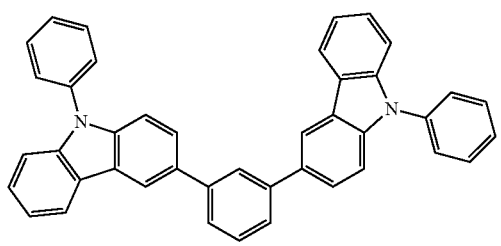
[B-106]
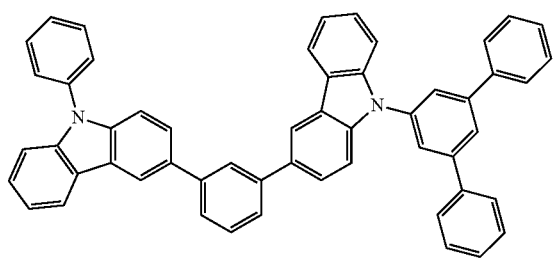
[B-107]
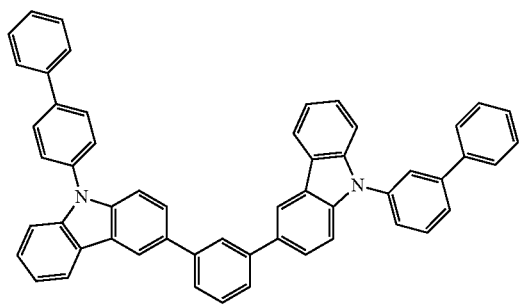
[B-108]
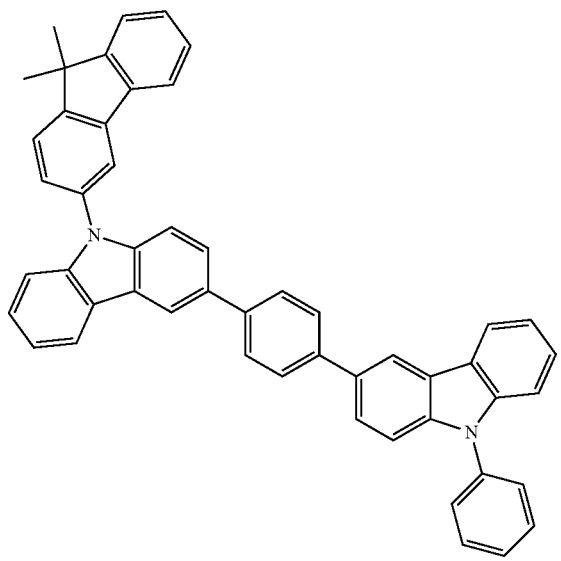

-continued
[B-109]
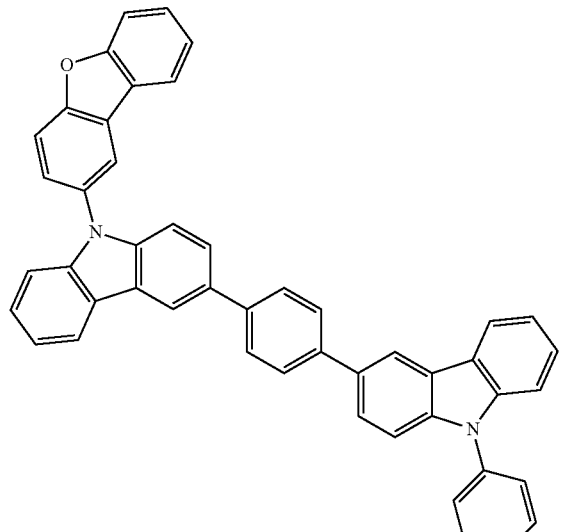
[B-110]
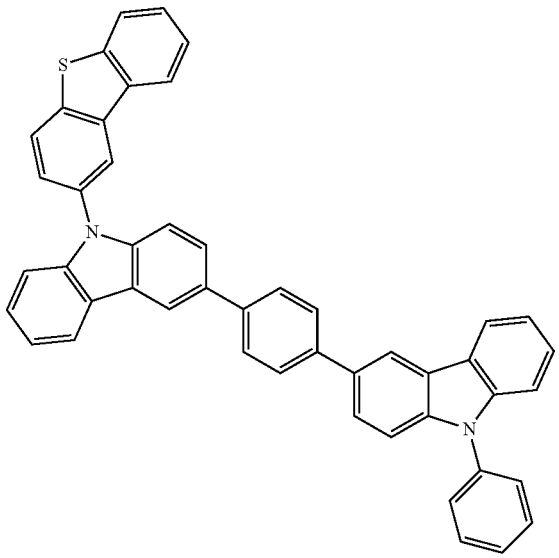
[B-111]
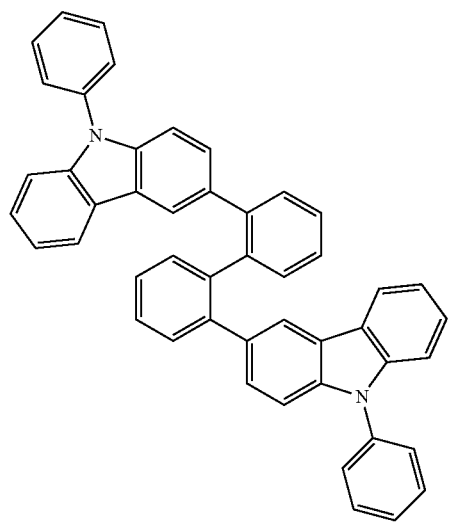
[B-112]
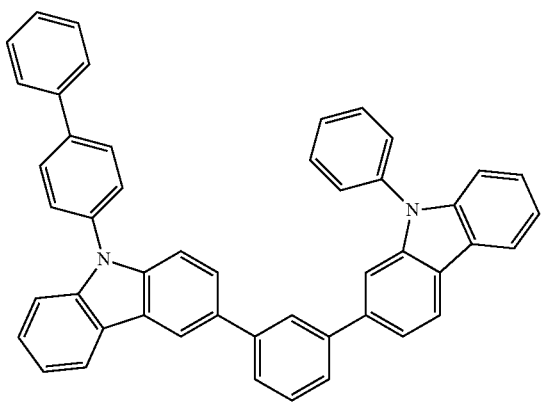
[B-113]
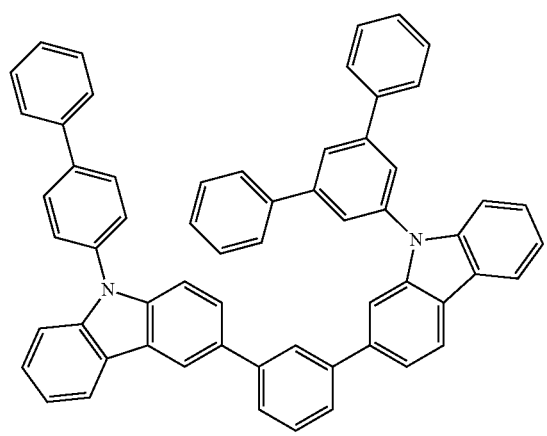
[B-114]
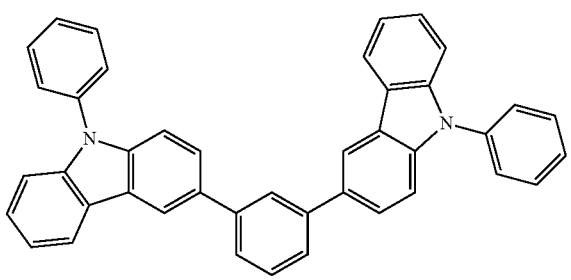

-continued
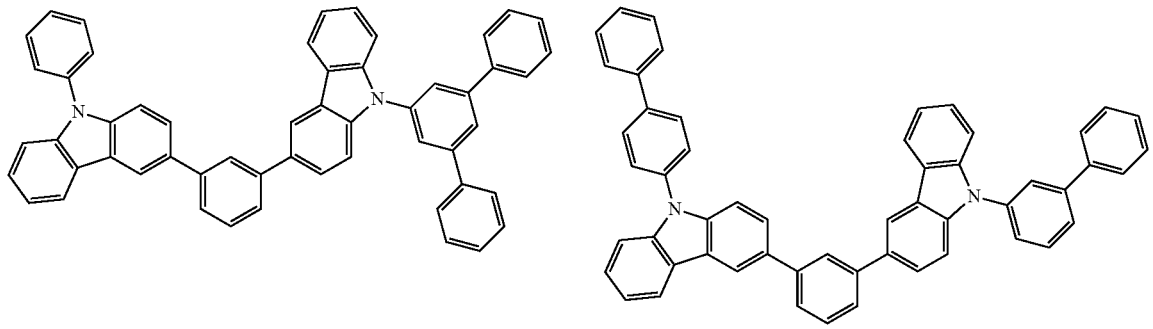
[B-115]
[B-116]
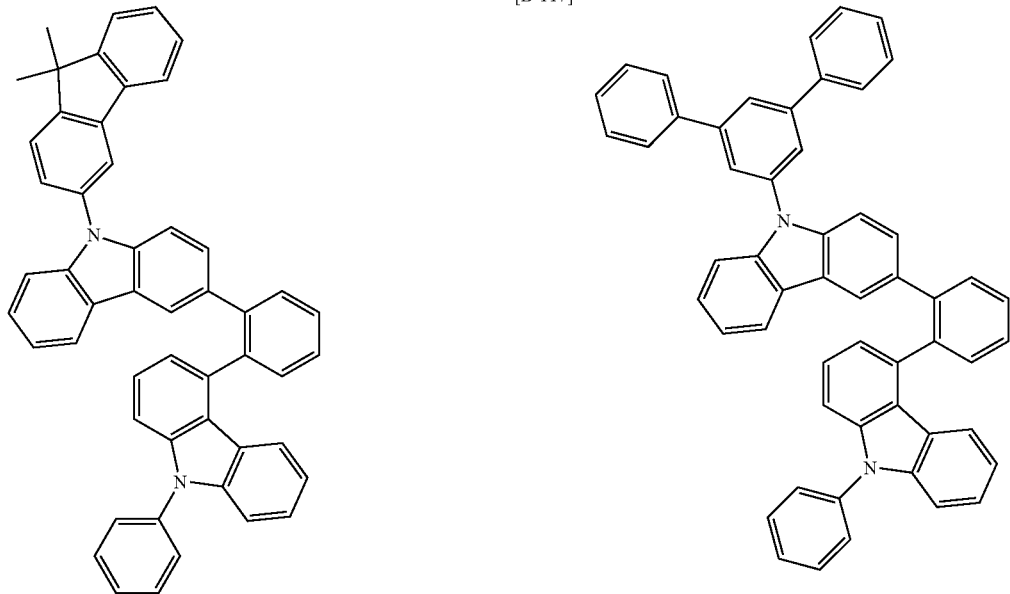
[B-117]
[B-118]
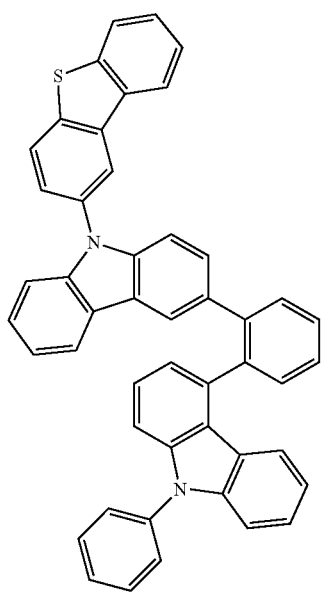
[B-119]

-continued
[B-120]
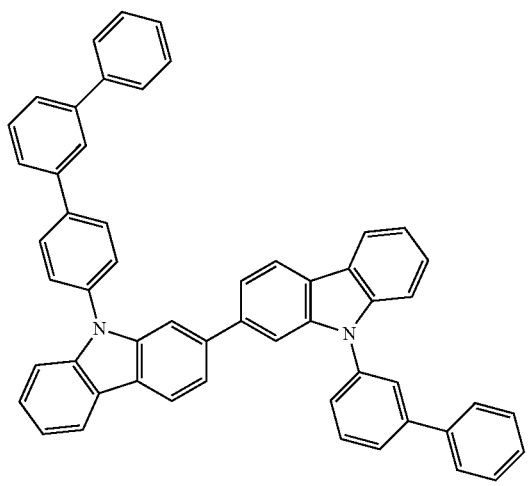
[B-121]
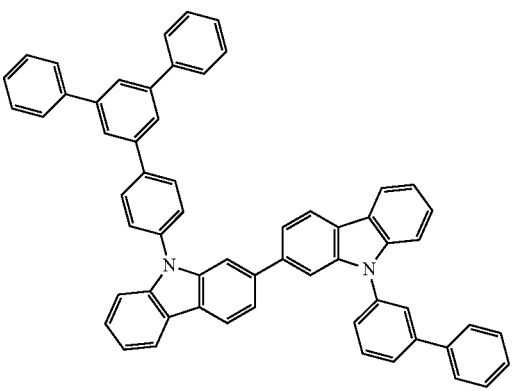
[B-122]
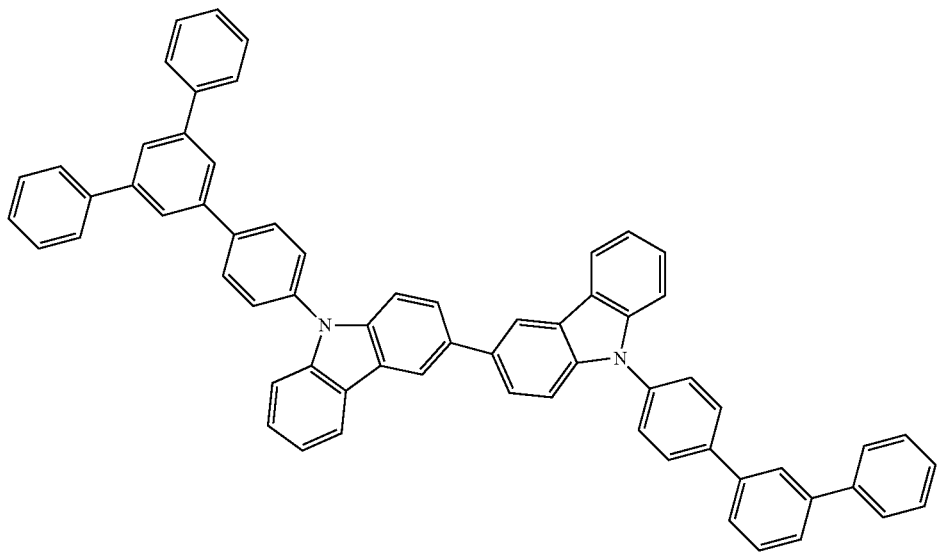
[B-123]
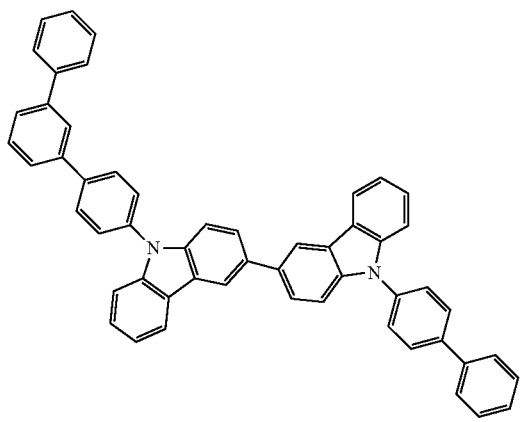
[B124]
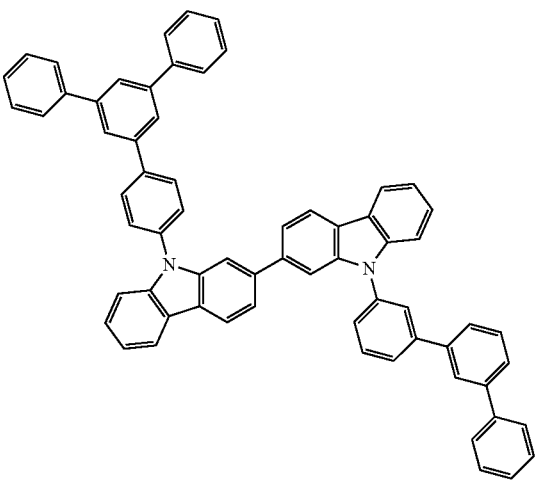

[B-125]
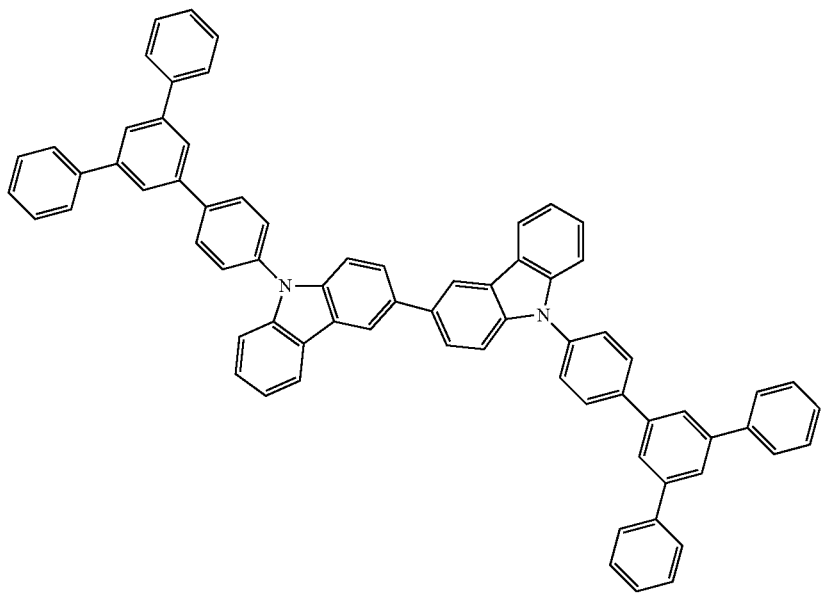
[B-126]
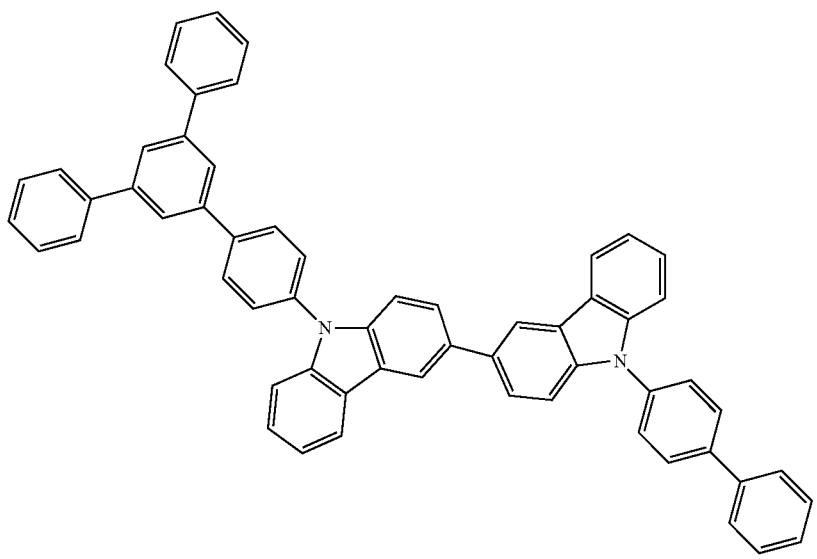
[B-127]
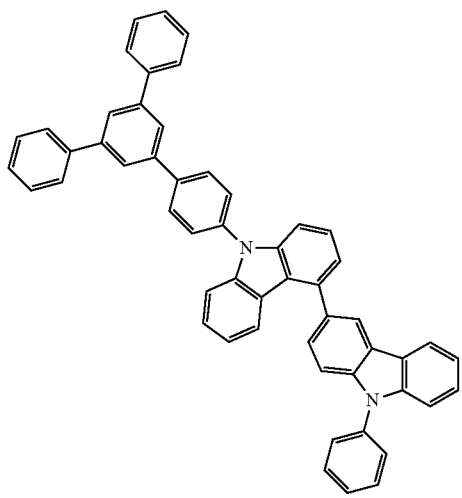
[B-128]
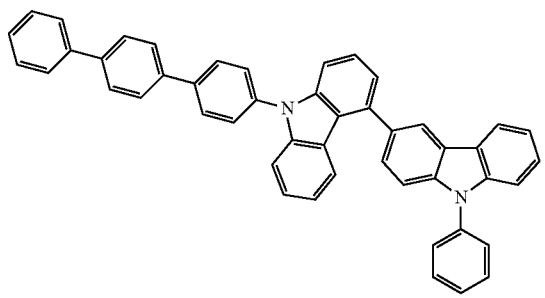

-continued
[B-129]
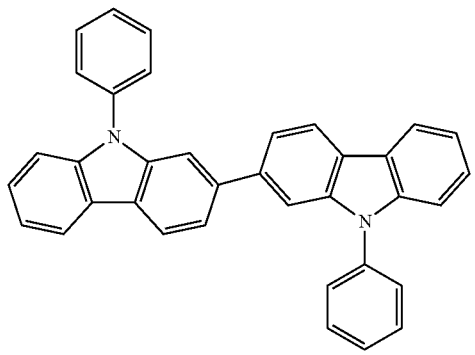
[B-130]
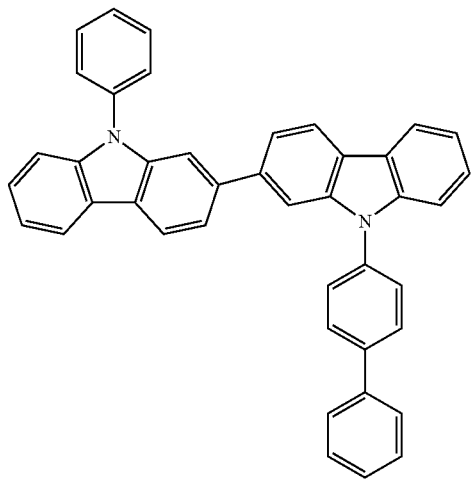
[B-131]
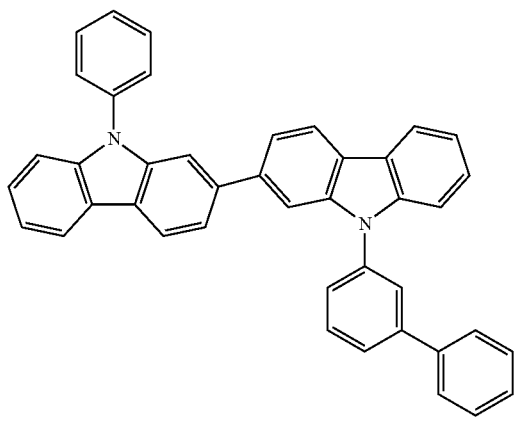
[B-131]
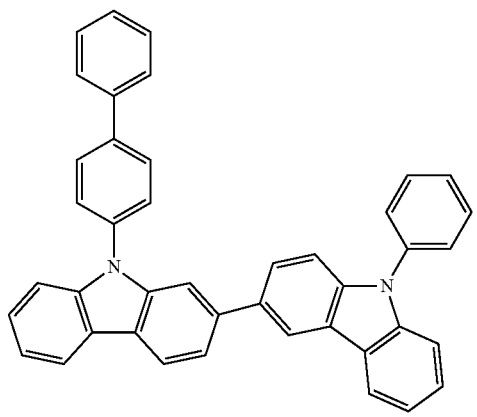
[B-133]
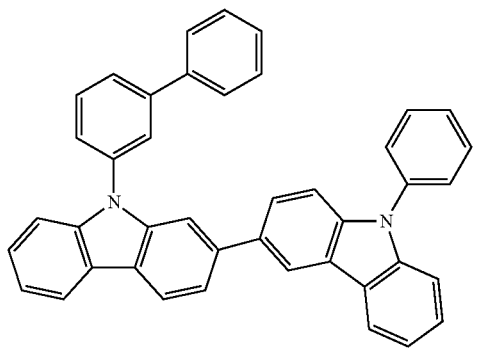
[B-134]
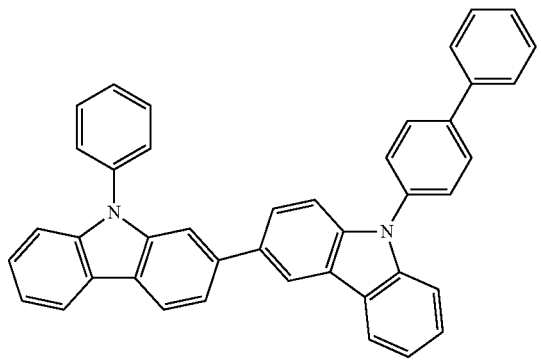

-continued
[B-135]
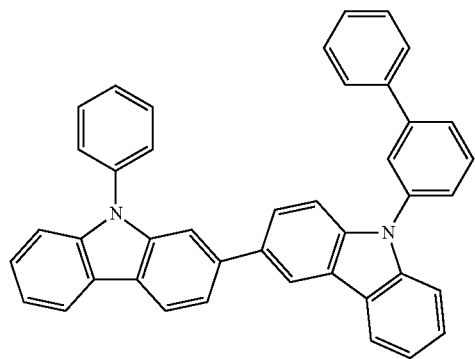
[B-136]
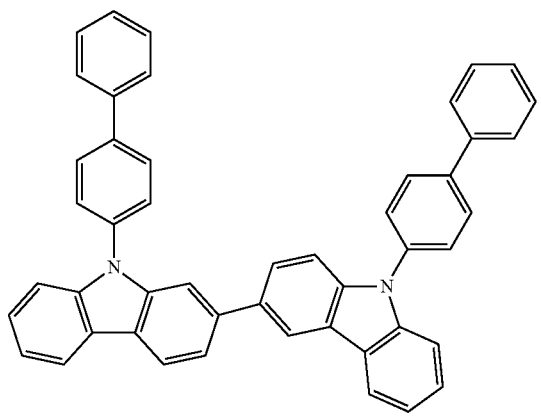
[B137]
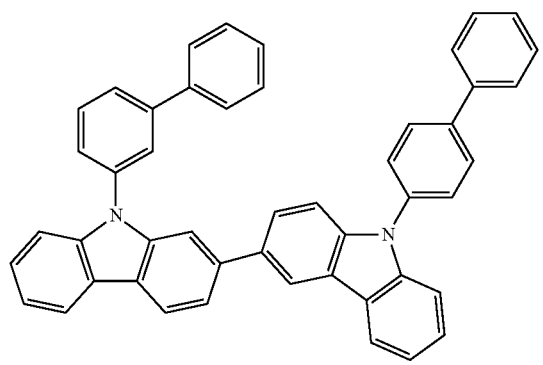
[B-138]
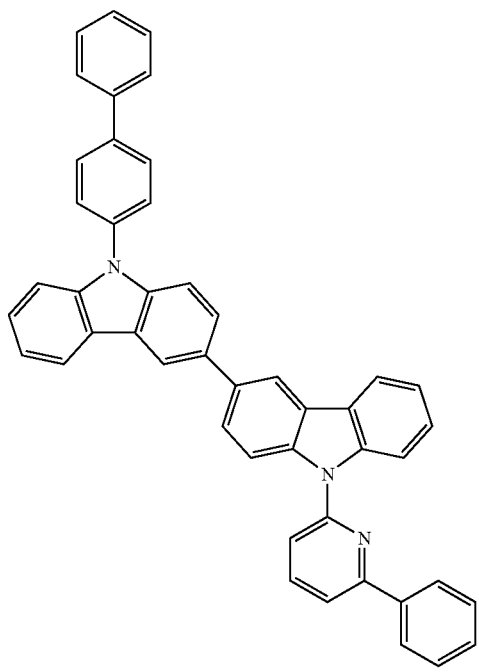

-continued
[B-139]
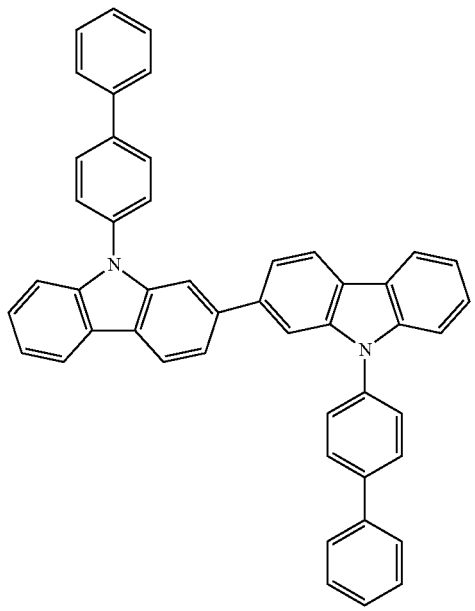
[B-140]
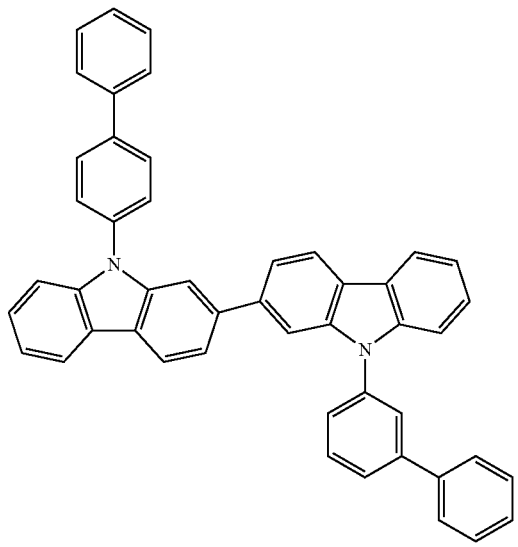
[B-141]
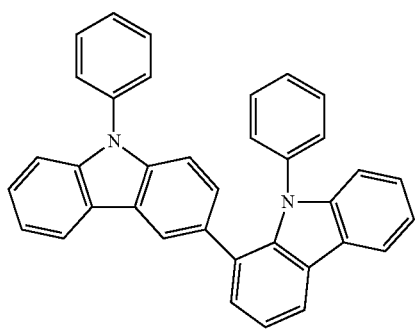
[B-142]
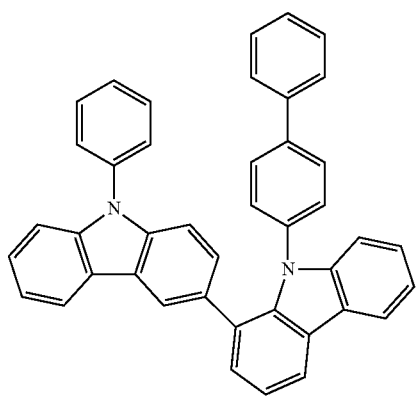
[B-143]
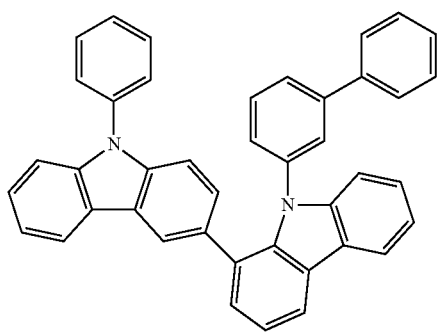
[B144]
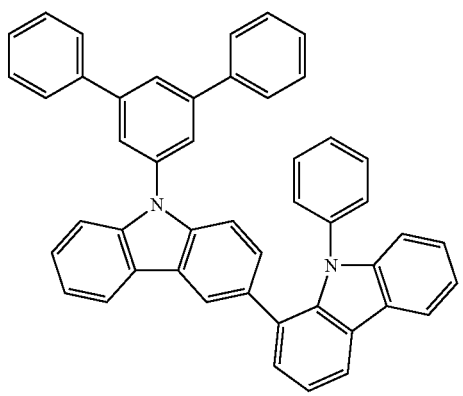

-continued
[B-145]
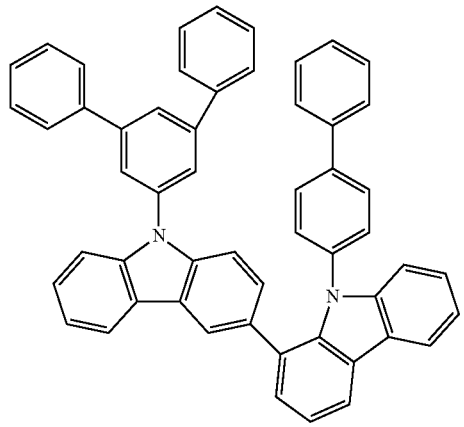
[B-146]
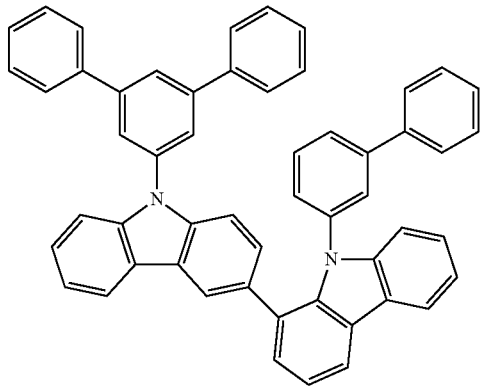
[B-147]
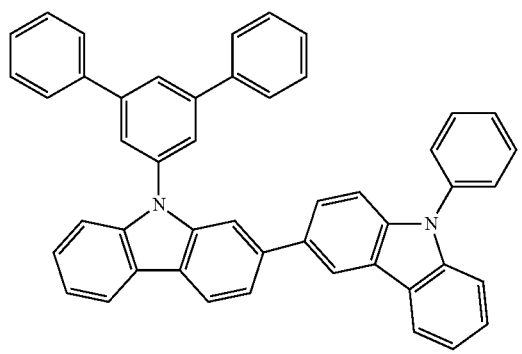
[B-148]
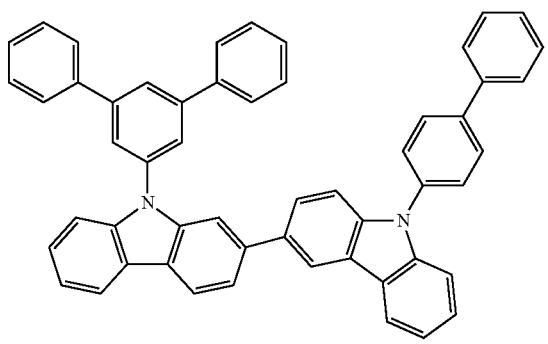
[B-149]
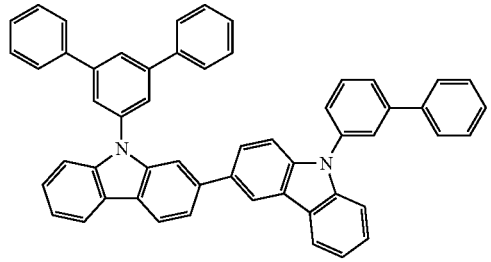
[B-150]
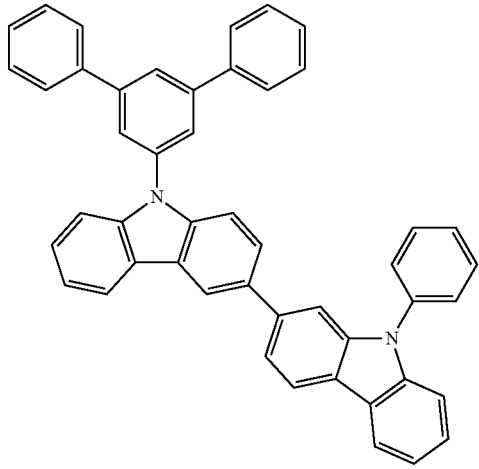

-continued
[B-151]
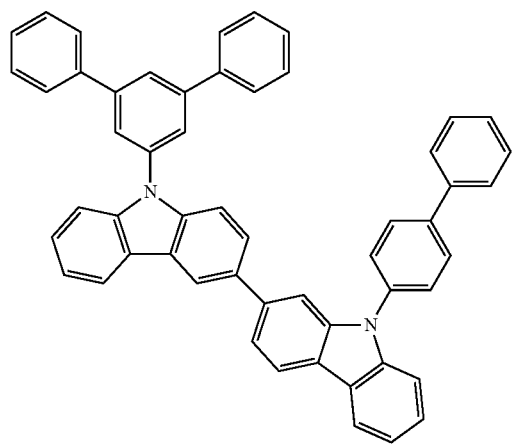
[B-152]
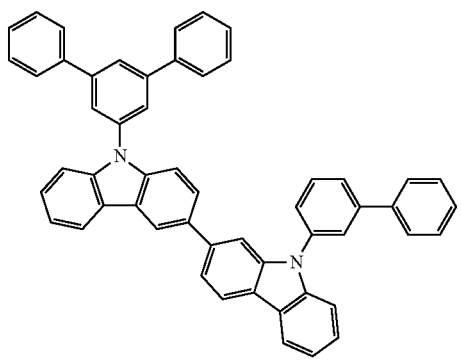
[B-153]
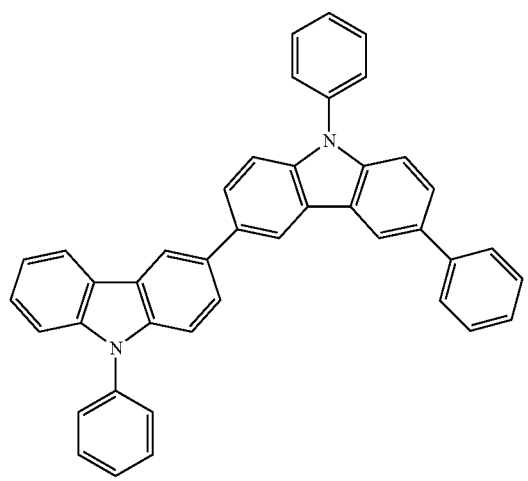
[B-154]
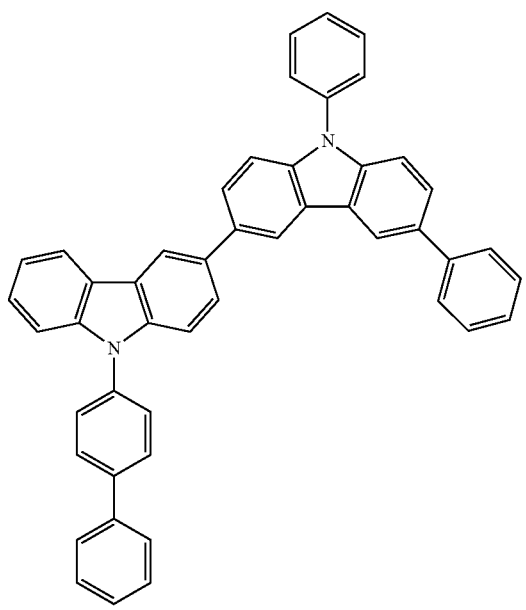

-continued
[B-155]
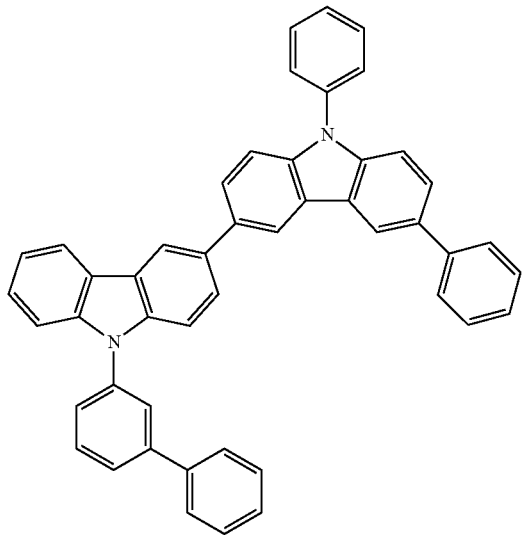
[B-156]
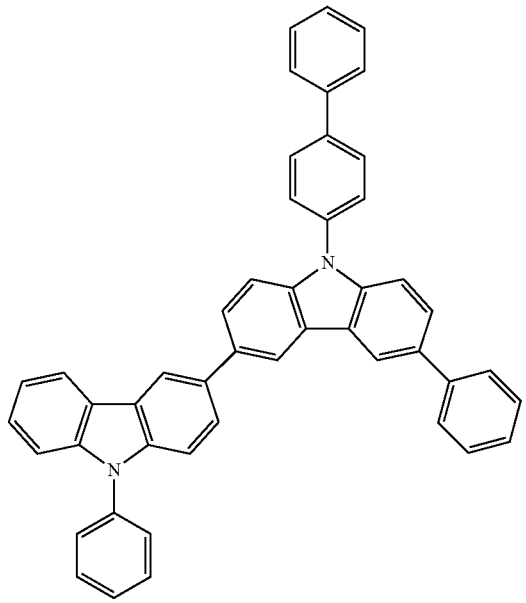
[B-157]
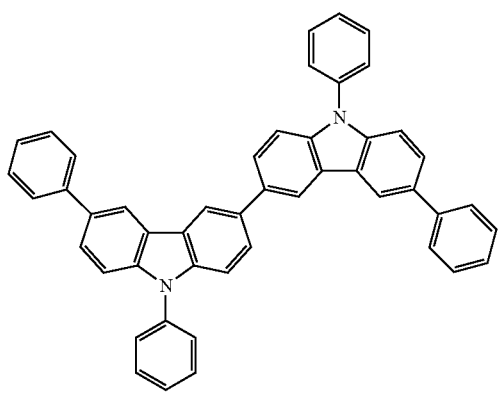
[B-158]
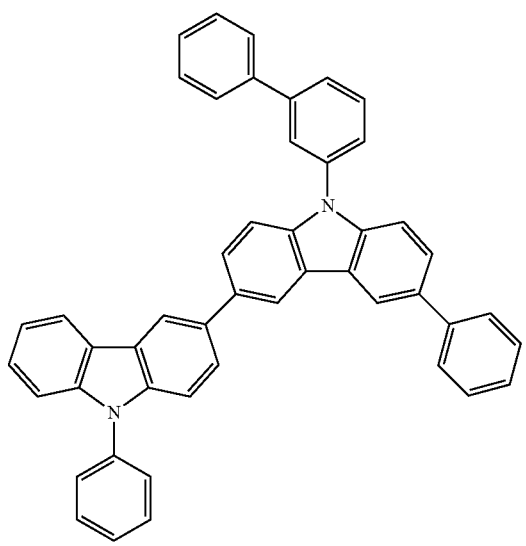

-continued
[B-159]
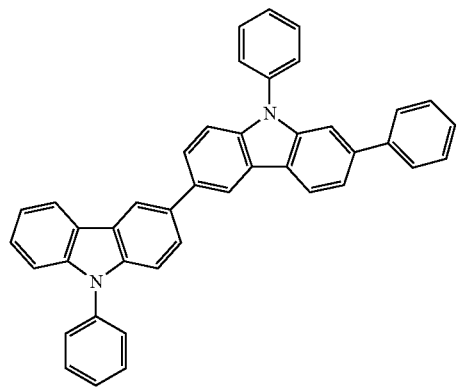
[B-160]
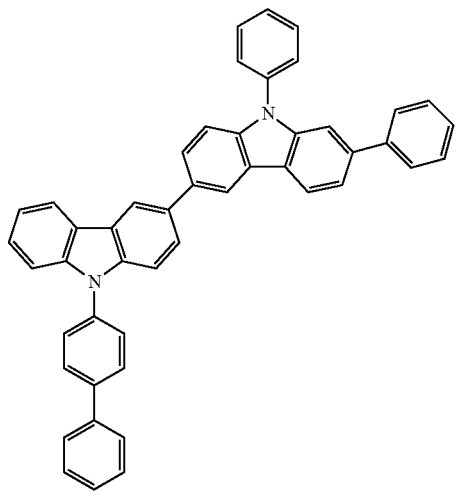
[B-161]
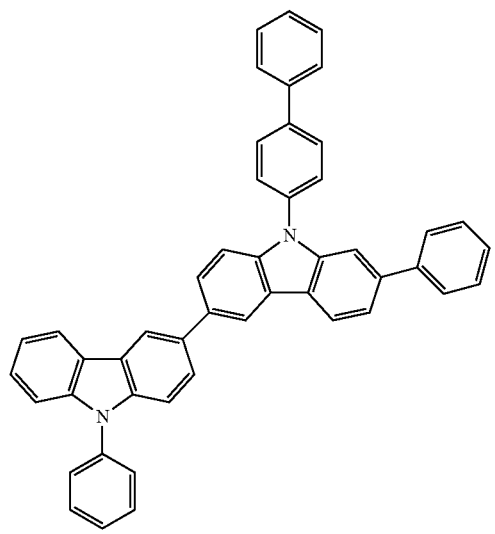
[B-162]
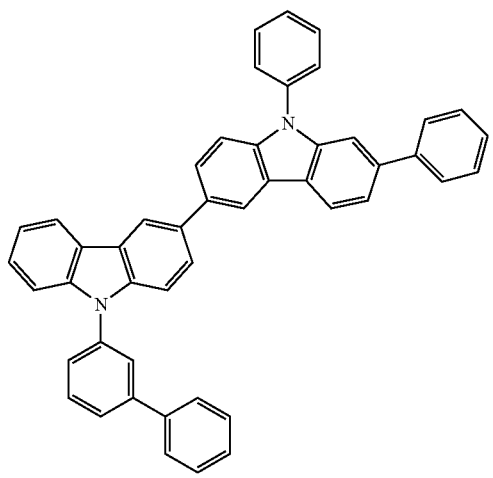
[B-163]
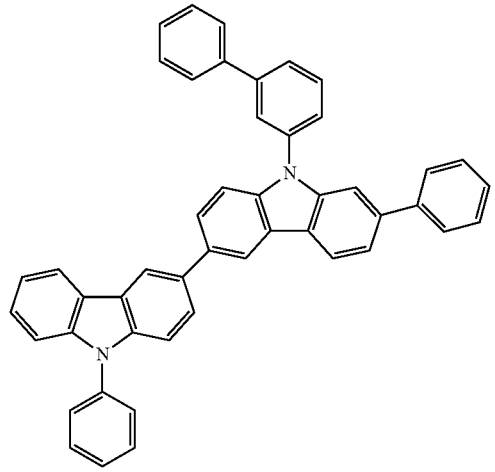
[B-164]
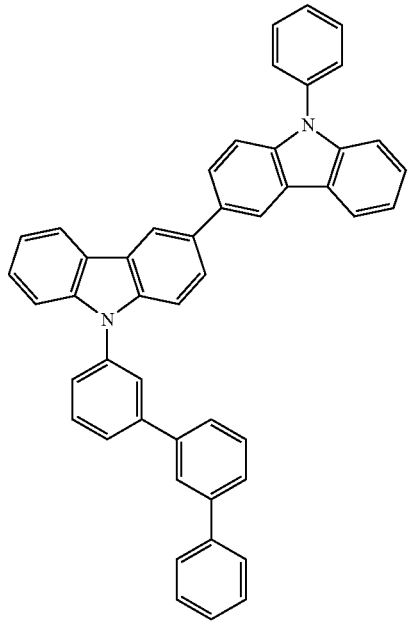

[B-165]
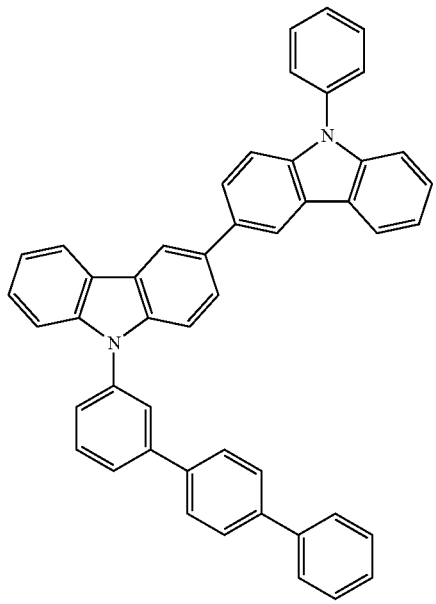
[B-166]
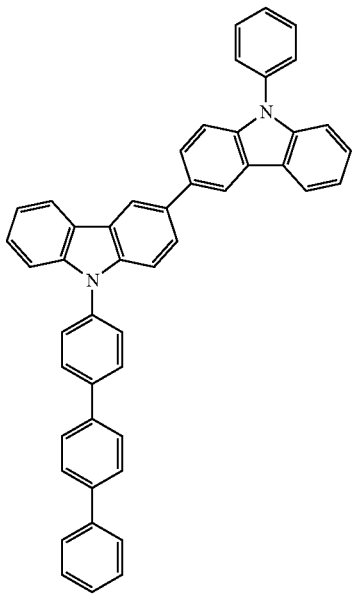
[group C]
[C-1]
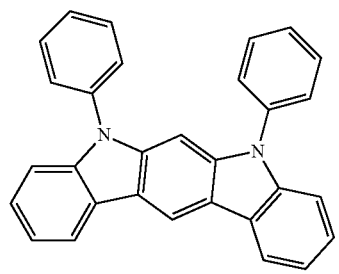
[C-2]
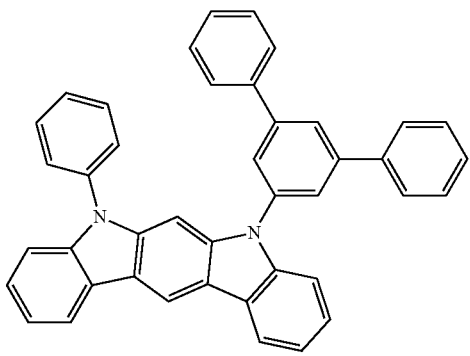
[C-3]
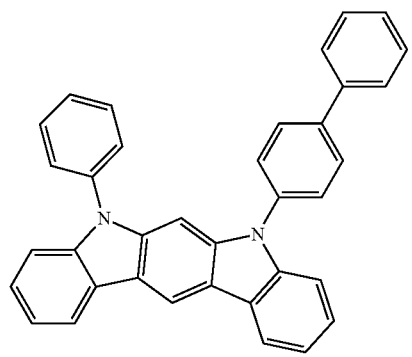
[C-4]
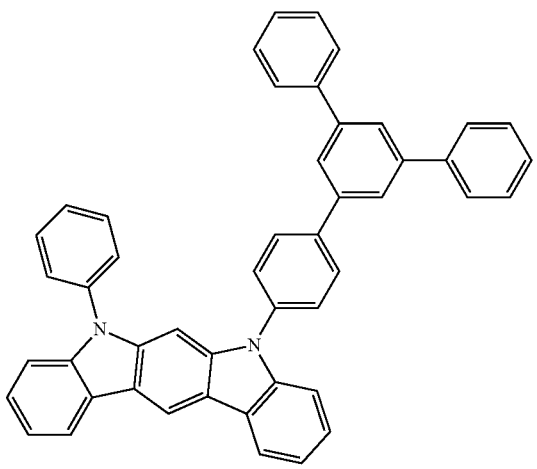

-continued
[C-5]
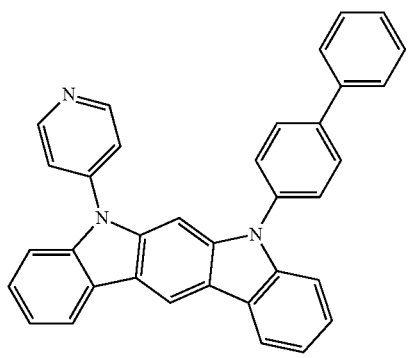
[C-6]
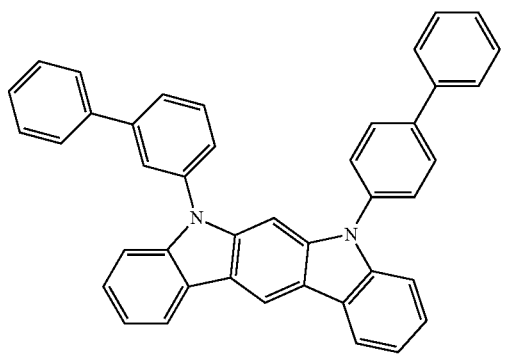
[C-7]
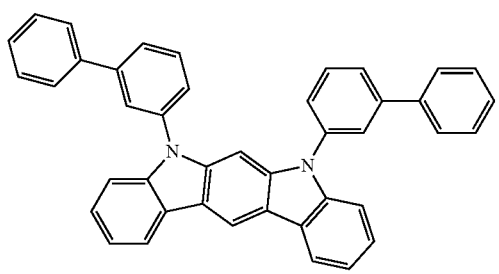
[C-8]
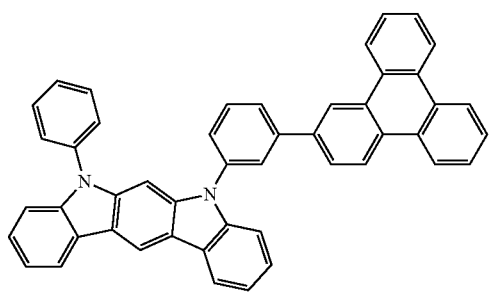
[C-9]
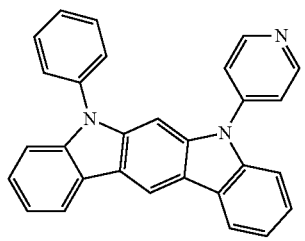
[C-10]
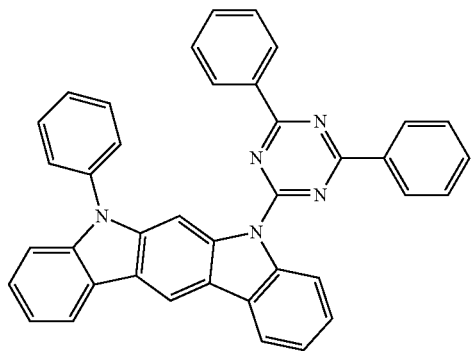
[C-11]
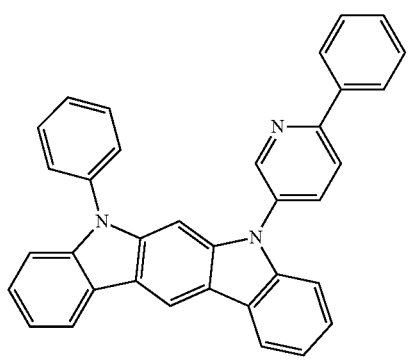
[C-12]
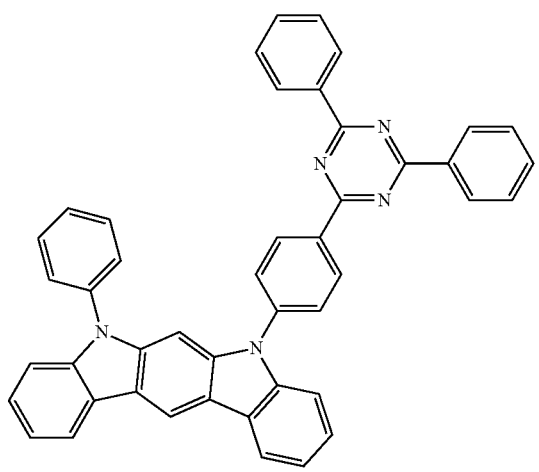

-continued
[C-13]
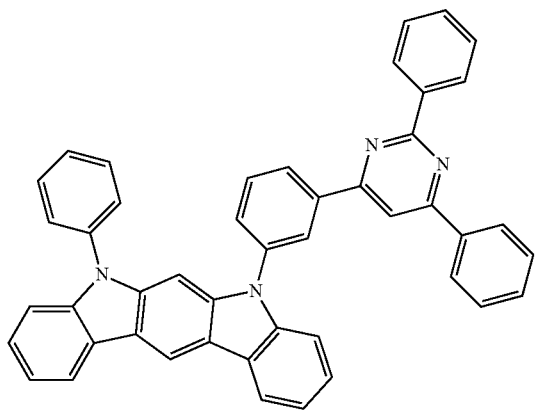
[C-14]
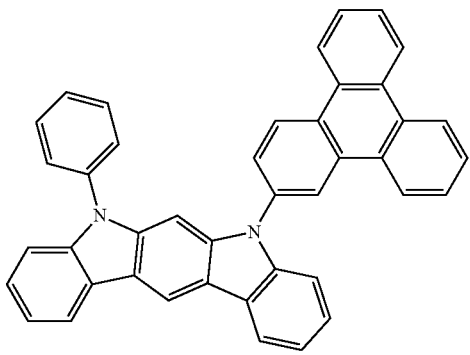
[C-15]
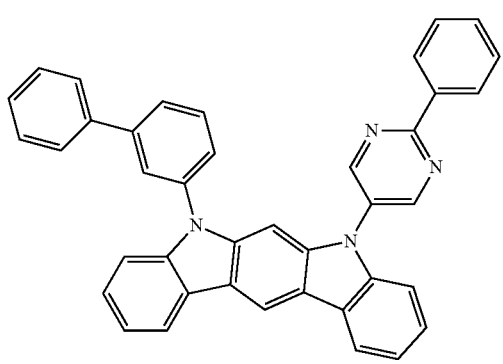
[C-16]
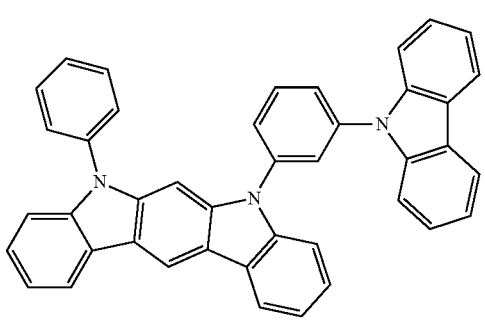
[C-17]
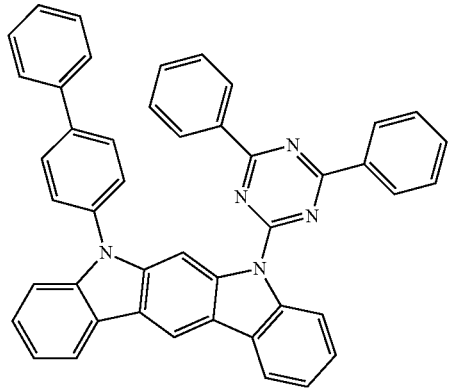
[C-18]
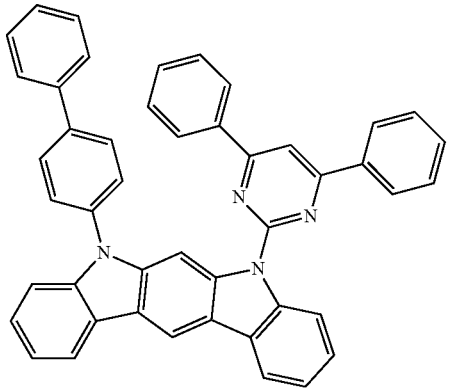
[C-19]
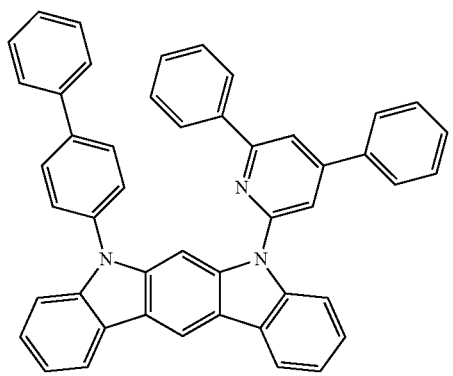
[C-20]
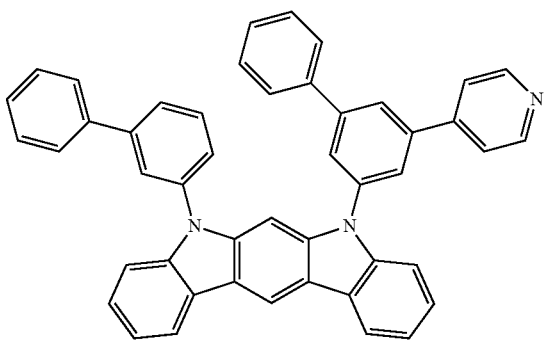

-continued
[C-21]
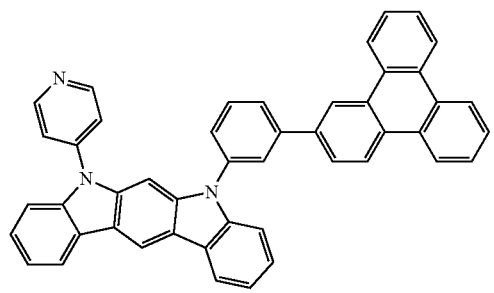
[C-22]
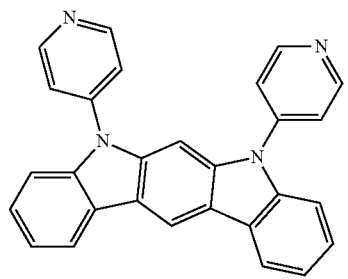
[C-23]
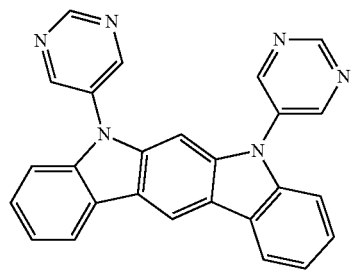
[C-24]
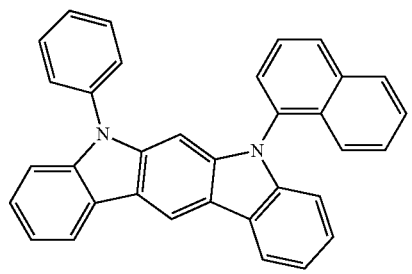
[C-25]
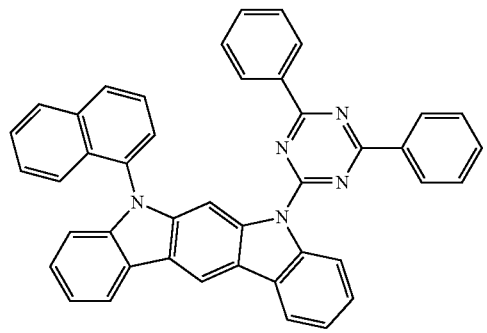
[C-26]
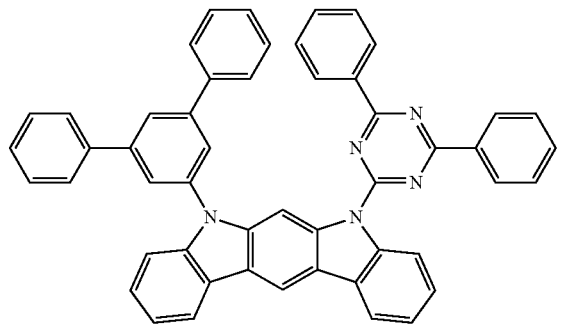
[C-27]
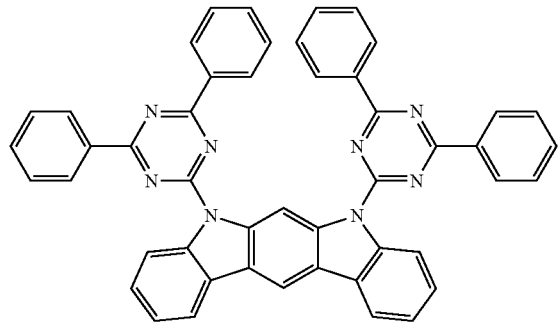
[C-28]
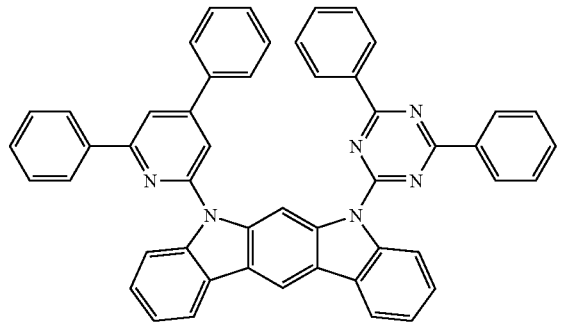

[C-29]
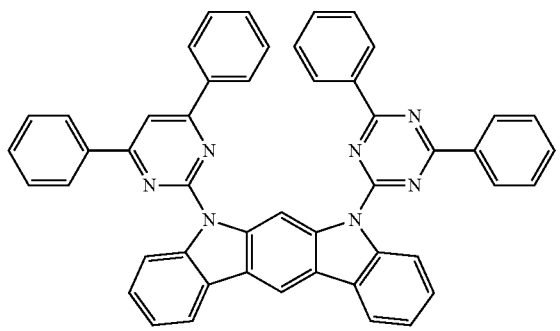
[C-30]
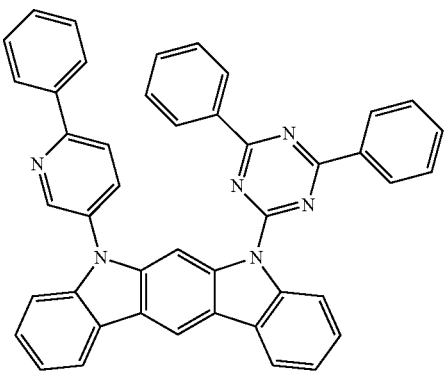
[C-31]
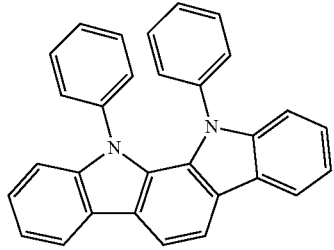
[C-32]
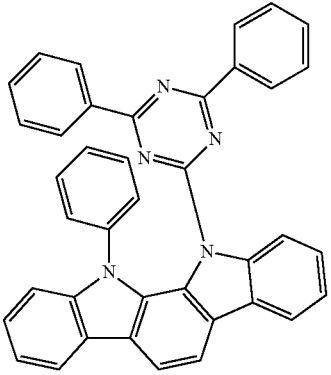
[C-33]
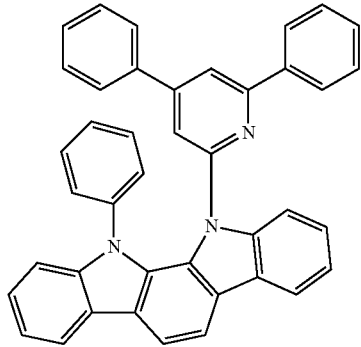
[C-34]
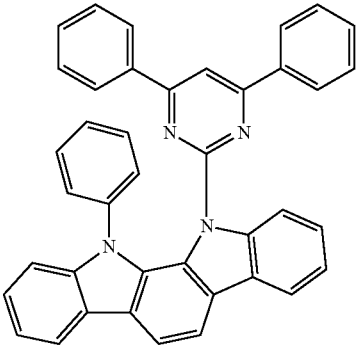
[C-35]
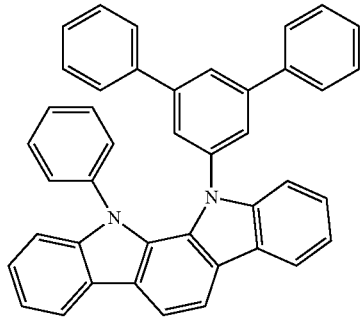
[C-36]
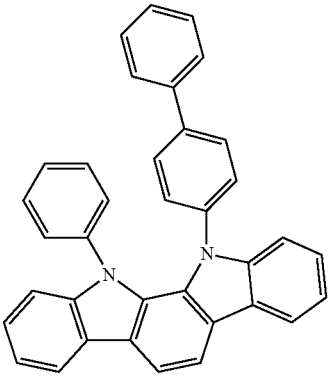

[C-37]

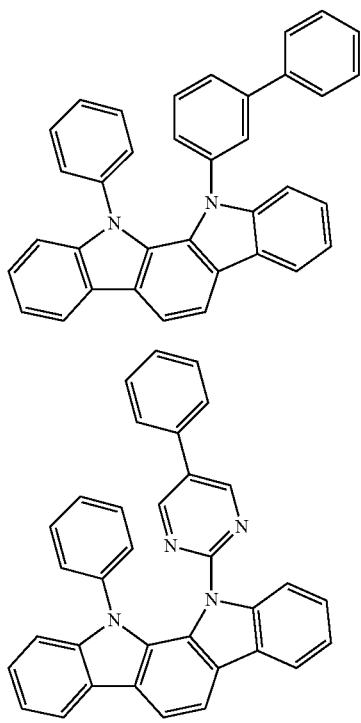

[C-38]

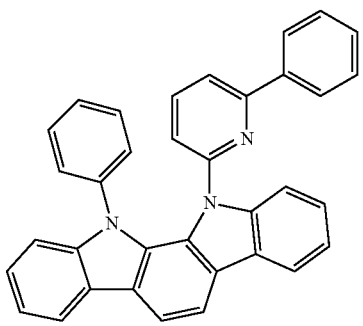

[C-39]

[C-40]

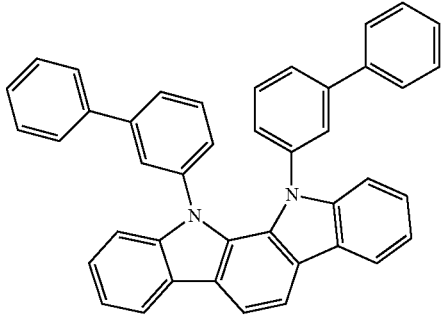

The aforementioned first and second hosts may be used in various ratios to prepare various compositions. For example, the first host and the second host may be used in a weight ratio ranging from 1:99 to 99:1, for example, 10:90 to 90:10. For example, the weight ratio may be 2:8 to 8:2, 3:7 to 7:3, 4:6 to 6:4, and 5:5. When the first and second hosts satisfy the weight ratio range, electron transport characteristics by the first host and hole transport characteristics by the second host may be balanced and thus improve luminance efficiency and life-span of an organic light emitting diode.

For example, the composition may be used as a light-emitting material for an organic optoelectronic device. Herein, the light-emitting material may be the organic compound as a host, and may further include at least one dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be a phosphorescent dopant, and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$$L_2MX \quad \text{[Chemical Formula Z]}$$

In Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidendate ligand.

A thickness of the emission layer may be about 100 Å to about 1000 Å, for example about 200 Å to about 600 Å. When the thickness of the emission layer is within these ranges, the emission layer may have improved emission characteristics without a substantial increase in a driving voltage.

Next, an electron transport region is disposed on the emission layer.

The electron transport region may include at least one of a hole blocking layer, an electron transport layer, and an electron injection layer.

For example, the electron transport region may have a structure of a hole blocking layer/electron transport layer/electron injection layer or electron transport layer/electron injection layer, but is not limited thereto. For example, an organic light emitting diode according to an embodiment of the present invention includes at least two electron transport layers in the electron transport region, and in this case, an electron transport layer contacting the emission layer is defined as an electron transport auxiliary layer 35.

The electron transport layer may have a monolayer or multi-layer structure including two or more different materials.

The electron transport region may include the compound for an organic optoelectronic device represented by Chemical Formula 1. For example, the electron transport region may include an electron transport layer, and the electron transport layer may include the compound for an organic optoelectronic device represented by Chemical Formula 1. More specifically, the electron transport auxiliary layer may include the compound for an organic optoelectronic device represented by Chemical Formula 1.

The formation conditions of the hole blocking layer, electron transport layer, and electron injection layer of the electron transport region refers to the formation condition of the hole injection layer.

When the electron transport region includes the hole blocking layer, the hole blocking layer may include at least one of BCP, Bphen, and BAlq, but is not limited thereto.

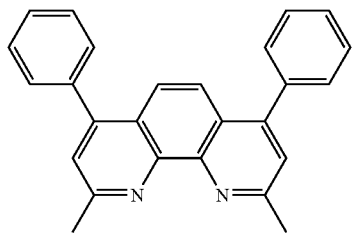

BCP

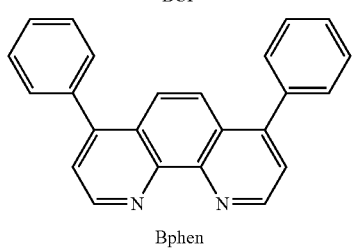

Bphen

A thickness of the hole blocking layer may be from about 20 Å to about 1000 Å, for example about 30 Å to about 300 Å. When the thickness of the hole blocking layer is within these ranges, the hole blocking layer may have improved hole blocking ability without a substantial increase in driving voltage.

The electron transport layer may further include at least one of the BCP, Bphen and the following $Alq_3$, Balq, TAZ, and NTAZ.

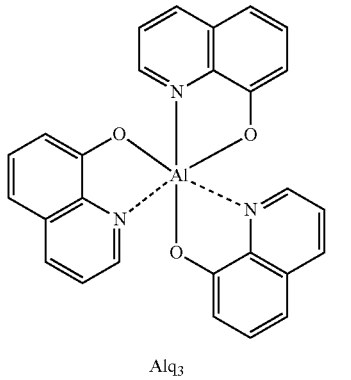

$Alq_3$

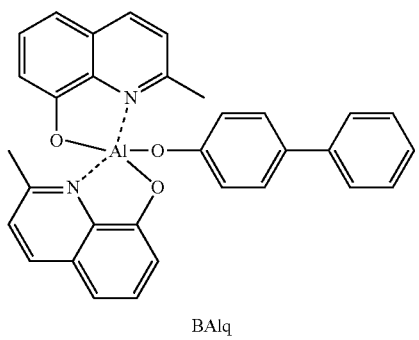

BAlq

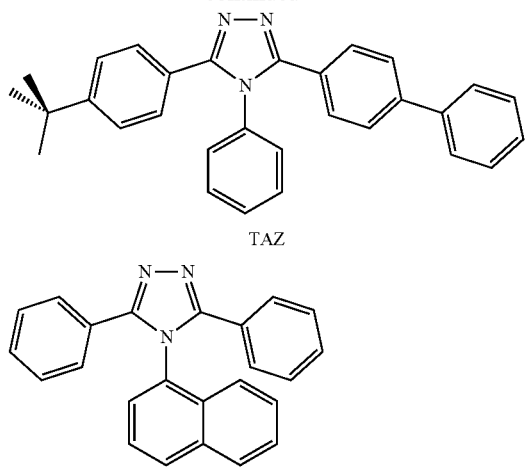

TAZ

NTAZ

Or, the electron transport layer may include at least one of Compounds ET1 and ET2, but is not limited thereto.

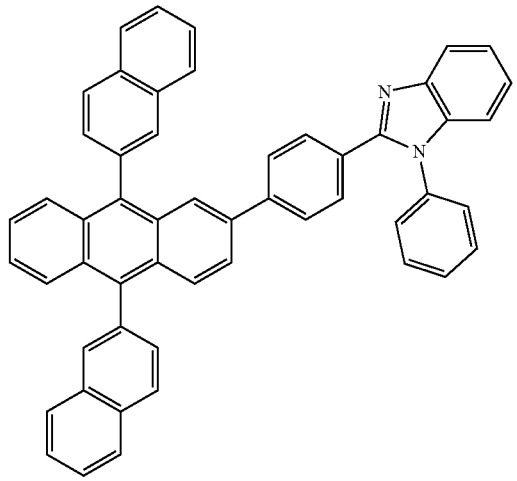

ET1

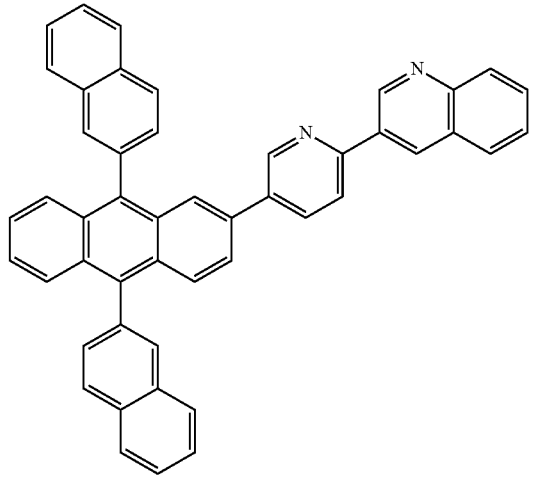

ET2

A thickness of the electron transport layer may be about 100 Å to about 1000 Å, for example about 150 Å to about 500 Å. When the thickness of the electron transport layer is within these ranges, the electron transport layer may have satisfactory electron transporting ability without a substantial increase in driving voltage.

The electron transport layer may further include a metal-containing material, in addition to the above-described materials.

The metal-containing material may include a lithium (Li) complex. The Li complex may include, for example, Compound ET-D1 (lithium quinolate, LiQ) or ET-D2.

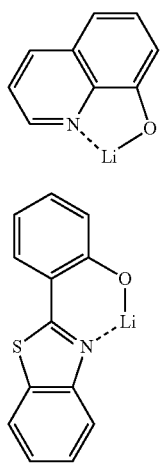

ET-D1

ET-D2

In addition, the electron transport region may include an electron injection layer (EIL) that may facilitate injection of electrons from the cathode 110.

The electron injection layer 36 is disposed on an electron transport layer and may play a role of facilitating an electron injection from a cathode and ultimately improving power efficiency and be formed by using any material used in a related art without a particular limit, for example, LiF, Liq, NaCl, CsF, Li$_2$O, BaO, and the like.

The electron injection layer may include at least one selected from LiF, NaCl, CsF, Li$_2$O, and BaO.

A thickness of the EIL may be from about 1 Å to about 100 Å, or about 3 Å to about 90 Å. When the thickness of the electron injection layer is within these ranges, the electron injection layer may have satisfactory electron injection ability without a substantial increase in driving voltage.

The cathode 110 is disposed on the organic layer 105. A material for the cathode 110 may be a metal, an alloy, or an electrically conductive compound that have a low work function, or a combination thereof. Specific examples of the material for the cathode 110 may be lithium (Li), magnesium (Mg), aluminum (Al), aluminum-lithium (Al—Li), calcium (Ca), magnesium-indium (Mg—In), magnesium-silver (Mg—Ag), etc. In order to manufacture a top-emission light-emitting device, the cathode 110 may be formed as a transmissive electrode from, for example, indium tin oxide (ITO) or indium zinc oxide (IZO).

The aforementioned organic light emitting diode may be applied to an organic light emitting diode (OLED) display.

Hereinafter, the embodiments are illustrated in more detail with reference to examples. These examples, however, are not in any sense to be interpreted as limiting the scope of the invention.

(Synthesis of Compound for Organic Optoelectronic Device)

Hereinafter, a starting material and a reactant used in Examples and Synthesis Examples were purchased from Sigma-Aldrich Co. Ltd. or TCI Inc. as far as there in no particular comment and may be easily synthesized as a publicly known material.

In the following Synthesis Examples, when "'B' is used instead of 'A'", the amounts of 'A' and 'B' are the same as based on a mole equivalent.

As specific examples of the compound for an organic optoelectronic device of the present invention, the compound of Chemical Formula 1 is synthesized by the following reaction schemes.

Synthesis Example 1: Synthesis of Compound 1

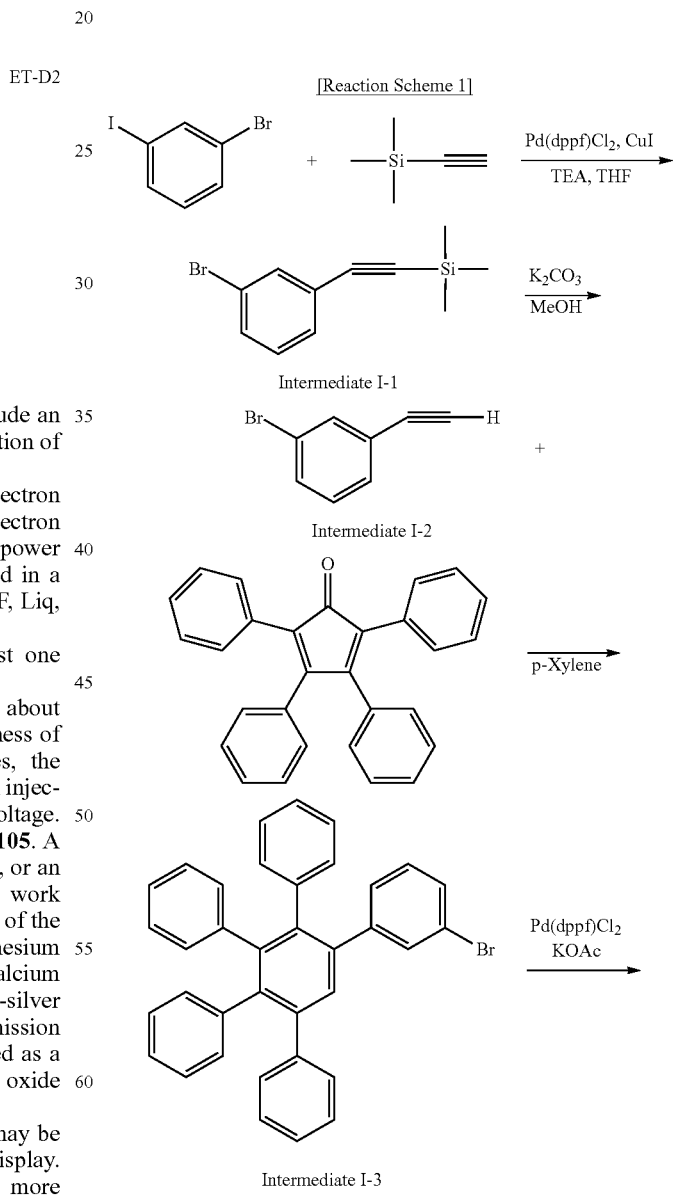

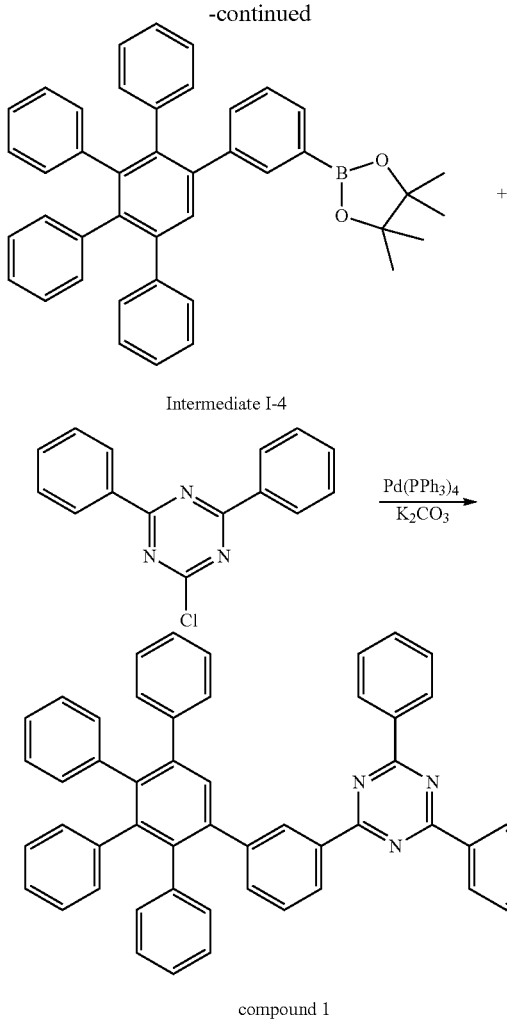

Intermediate I-4 compound 1

First Step: Synthesis of Intermediate I-1

1-bromo-3-iodobenzene (200.0 g, 704.8 mmol) and (1,1'-bis(diphenylphosphine)ferrocene)dichloropalladium (II) (25.8 g, 35.4 mmol), copper iodide (4.04 g, 21.2 mmol), triethylamine (295.6 ml, 2120 mmol), and tetrahydrofuran (1700 mL) were put in a 3 L round-bottomed flask under a nitrogen atmosphere. Then, trimethyl silylacetylene (107.6 ml, 776.6 mmol) was added thereto in a dropwise fashion, and the mixture was stirred at room temperature for 3 hours. The reactant was filtered, and a solvent was removed therefrom. A compound obtained therefrom was purified to through column chromatography to obtain an intermediate I-1 (166.0 g, 93%).

Second Step: Synthesis of Intermediate I-2

The intermediate I-1 (166 g, 655.6 mmol) was put and dissolved in methanol (1000 mL) in a reactor, and potassium carbonate (90.6 g, 655.6 mmol) was slowly added thereto in a dropwise fashion. The mixture is stirred for about 30 minutes and filtered. After removing all the solvents, the reactant was dissolved in ethylacetate and twice washed with distilled water. Then, an intermediate I-2 (116 g, 98%) was obtained by removing the solvent again.

Third Step: Synthesis of Intermediate I-3

The intermediate I-2 (113.0 g, 624.2 mmol) and tetraphenylcyclopentadione (120.0 g, 312.1 mmol) were put and dissolved in 700 mL of xylene and then, heated and refluxed for 3 hours. The reactant was poured into methanol (2000 mL) to complete the reaction. Then, a solid was filtered therefrom to obtain an intermediate I-3 (124.1 g, 74%).

Fourth Step: Synthesis of Intermediate I-4

The intermediate I-3 (52.0 g, 96.75 mmol) was dissolved in dimethyl formamide (DMF, 350 ml) under a nitrogen atmosphere, bis(pinacolato)sdiboron (29.5 g, 116.1 mmol), (1,1'-bis(diphenylphosphine)ferrocene)dichloropalladium (II) (4.74 g, 5.8 mmol), and potassium acetate (28.5 g, 290.2 mmol) were added thereto, and the mixture was heated and refluxed at 150° C. for 24 hours. When the reaction was complete, water was added to the reaction solution, and the obtained mixture was filtered and dried in a vacuum oven. The obtained residue was separated and purified through column chromatography to obtain an intermediate I-4 (35 g, 62%).

Fifth Step: Synthesis of Compound 1

The intermediate I-4 (5.0 g, 8.6 mmol), 2-chloro-4,6-diphenyl-1,3,5-triazine (2.8 g, 10.3 mmol), potassium carbonate (3.0 g, 21.4 mmol), and tetrakis(triphenylphosphine) palladium (0) (0.3 g, 0.3 mmol) were added to 1,4-dioxane (30 mL) and water (15 mL) in a 100 mL flask, and the mixture was heated at 60° C. for 12 hours under a nitrogen flow. The obtained mixture was added to 150 mL of methanol, a solid crystallized therein was filtered, dissolved in toluene, filtered through silica gel/Celite, and then, recrystallized with methanol after removing an appropriate amount of an organic solvent, obtaining a compound 1 (3.78 g, a yield: 64%).

calcd. C51H35N3: C, 88.79; H, 5.11; N, 6.09; found: C, 88.78; H, 5.10; N, 6.10

Synthesis Example 2: Synthesis of Compound 2

[Reaction Scheme 2]

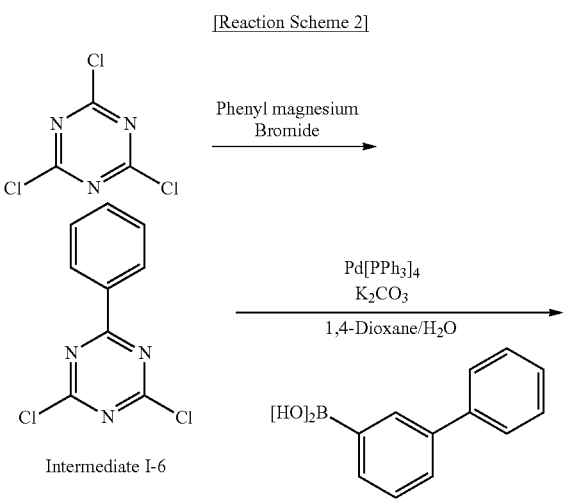

Intermediate I-6

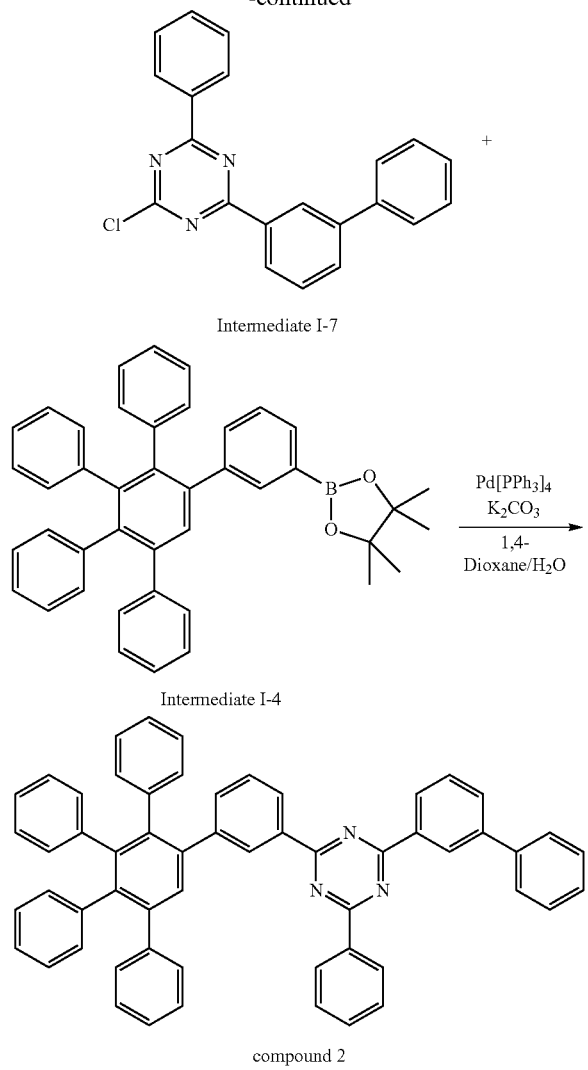

First Step: Synthesis of Intermediate I-6

Cyanuric chloride (200.0 g, 1.085 mmol) and anhydrous THF (1.4 L) were put in a 3 L flask, and phenyl magnesium bromide (3 M, 361.4 mL) was slowly added in a dropwise fashion at 0° C. When the reaction was complete, water was poured into the reaction, the mixture was stirred for 30 minutes, an organic layer therefrom was separated, concentrated after removing moisture therefrom by using magnesium sulfate, and purified with methanol and hexane to obtain an intermediate I-6 as a white solid (127.4 g, a yield: 52%).

Second Step: Synthesis of Intermediate I-7

The intermediate I-6 (60.0 g, 265.4 mmol), 3-biphenyl boronic acid (50.0 g, 252.0 mmol), potassium carbonate (91.6 g, 660.0 mmol), and tetrakis(triphenylphosphine) palladium (0) (8.0 g, 9.2 mmol) were put in 1,4-dioxane (880 mL) and water (440 mL) in a 2 L round flask, and the mixture was heated and refluxed under a nitrogen flow for 16 hours. The obtained mixture was added to methanol (3000 L), a solid crystallized therein was filtered, dissolved in toluene, filtered through silica gel/Celite, and then, recrystallized with methanol after removing an appropriate amount of an organic solvent to obtain an intermediate I-7 (63.6 g, a yield: 70%).

Third Step: Synthesis of Compound 2

The intermediate I-7 (3.0 g, 8.7 mmol), the intermediate I-4 (6.1 g, 10.5 mmol), potassium carbonate (3.0 g, 21.8 mmol), and tetrakis(triphenylphosphine) palladium (0) (0.3 g, 0.3 mmol) were put in 1,4-dioxane (30 mL) and water (15 mL) in a 100 mL flask, and the mixture was heated at 60° C. for 12 hours under a nitrogen flow. The obtained mixture was added to methanol (150 mL), a solid crystallized therein was filtered, dissolved in toluene, filtered through silica gel/Celite, and then, recrystallized by using methanol after removing an appropriate amount of an organic solvent to obtain a compound 2 (4.13 g, 62% of a yield).

calcd. C57H39N3: C, 89.38; H, 5.13; N, 5.49; found: C, 89.38; H, 5.13; N, 5.49

Synthesis Example 3: Synthesis of Compound 3

[Reaction Scheme 3]

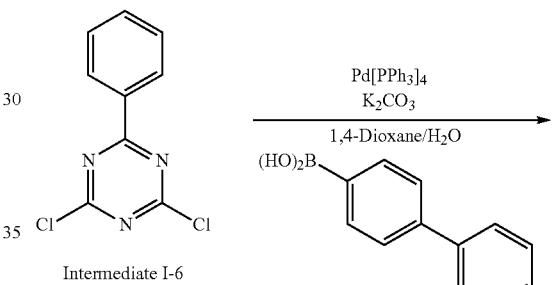

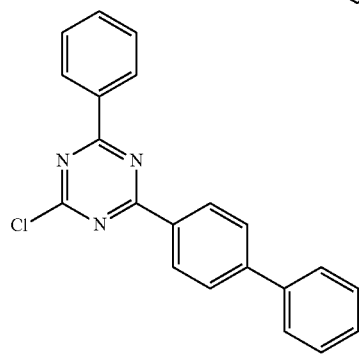

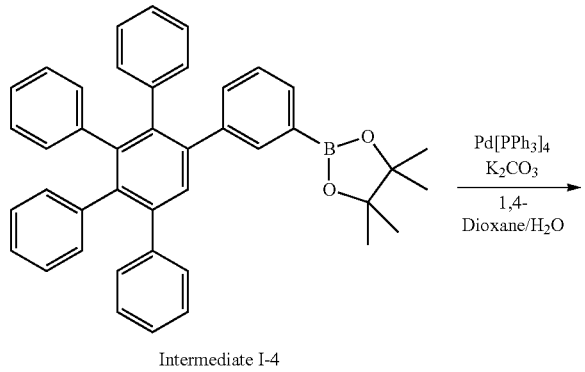

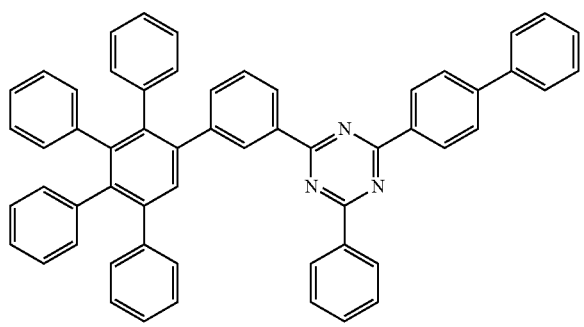

compound 3

First Step: Synthesis of Intermediate I-8

The intermediate I-6 (60.0 g, 265.4 mmol), 4-biphenyl boronic acid (50.0 g, 252.0 mmol), potassium carbonate (91.6 g, 660.0 mmol), and tetrakis(triphenylphosphine) palladium (0) (8.0 g, 9.2 mmol) were put in 1,4-dioxane (880 mL) and water (440 mL) in a 2 L round flask, and the mixture was heated and refluxed under a nitrogen flow for 16 hours. The obtained mixture was added to methanol (3000 L), a solid crystallized therein was filtered, dissolved in monochlorobenzene, filtered through silica gel/Celite, and then, recrystallized with methanol after removing an appropriate amount of an organic solvent to obtain an intermediate I-8 (60.2 g, a yield: 66%).

Second Step: Synthesis of Compound 3

The intermediate I-8 (3.0 g, 8.7 mmol), the intermediate I-4 (6.1 g, 10.5 mmol), potassium carbonate (3.0 g, 21.8 mmol), and tetrakis(triphenylphosphine) palladium (0) (0.3 g, 0.3 mmol) were added to 1,4-dioxane (30 mL) and water (15 mL) in a 100 mL flask, and the mixture was heated at 60° C. under a nitrogen flow for 12 hours. The obtained mixture was added to methanol (150 mL), a solid crystallized therein was filtered, dissolved in monochlorobenzene, filtered through silica gel/Celite, and then, recrystallized with methanol after removing an appropriate amount of an organic solvent to obtain a compound 3 (4.39 g, 66% of a yield).

calcd. C57H39N3: C, 89.38; H, 5.13; N, 5.49; found: C, 89.37; H, 5.13; N, 5.49

Synthesis Example 4: Synthesis of Compound 6

[Reaction Scheme 4]

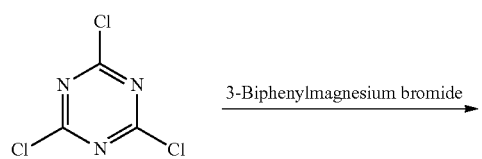

3-Biphenylmagnesium bromide →

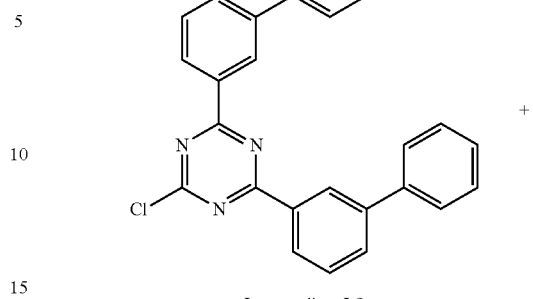

Intermediate I-9

+

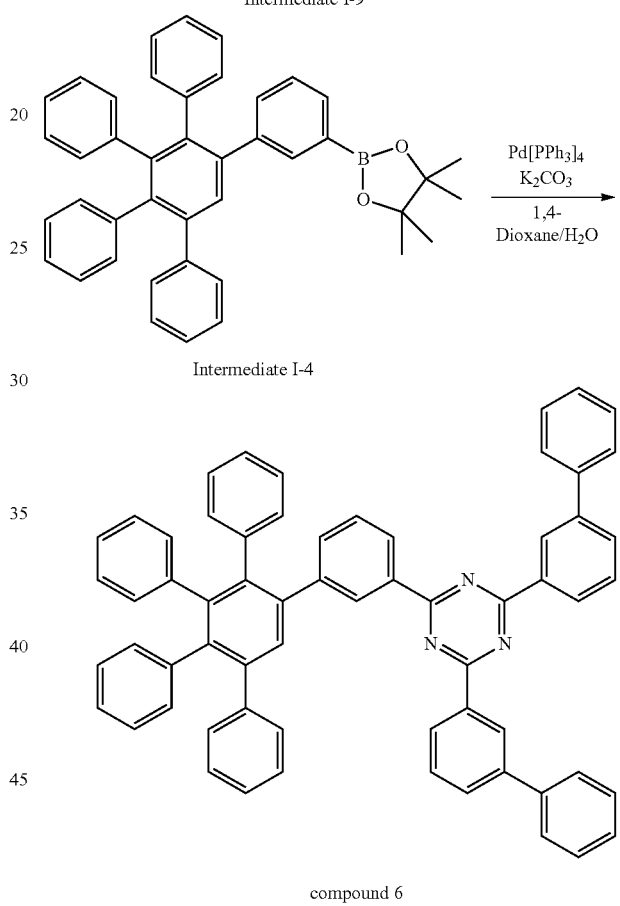

compound 6

First Step: Synthesis of Intermediate I-9

Cyanuric chloride (100.0 g, 542.3 mmol) and anhydrous THF (700 mL) were put in a 2 L flask, and 3-biphenyl magnesium bromide (3 M, 361.4 mL) was slowly added thereto in a dropwise fashion at 0° C. When the reaction was complete, water was poured into the reaction solution, the mixture was stirred for 30 minutes, an organic layer therein was separated, concentrated after removing moisture with magnesium sulfate, and purified with methanol and hexane to obtain an intermediate I-9 as a white solid (122.9 g, a yield: 55%).

Second Step: Synthesis of Compound 6

The intermediate I-9 (3.0 g, 7.1 mmol), the intermediate I-4 (5.0 g, 8.6 mmol), potassium carbonate (2.5 g, 17.9 mmol), and tetrakis(triphenylphosphine) palladium (0) (0.3 g, 0.2 mmol) were added to 1,4-dioxane (20 mL) and water (10 mL) in a 100 mL flask, and the mixture was heated at 60° C. under a nitrogen flow for 12 hours. The obtained mixture was added to methanol (100 mL), a solid crystallized therein was filtered, dissolved in toluene, filtered through silica gel/Celite, and then, recrystallized with methanol after removing an appropriate amount of an organic solvent to obtain a compound 6 (4.07 g, a yield: 68%).

calcd. C63H43N3: C, 89.86; H, 5.15; N, 4.99; found: C, 89.86; H, 5.15; N, 4.98

Synthesis Example 5: Synthesis of Compound 7

[Reaction Scheme 5]

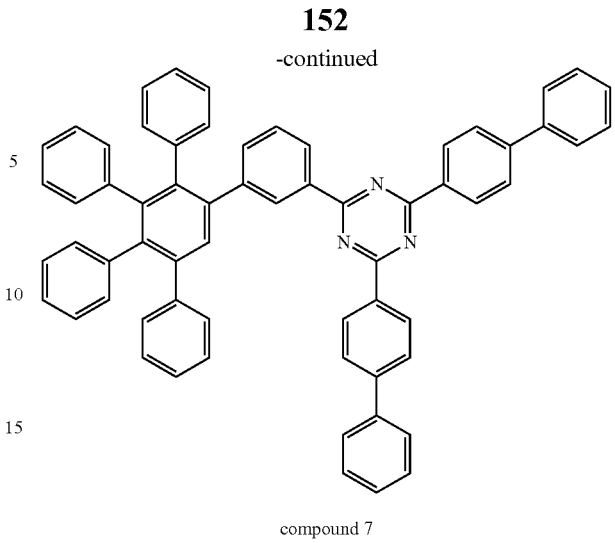

compound 7

First Step: Synthesis of Intermediate I-10

Cyanuric chloride (100.0 g, 542.3 mmol) and anhydrous THF (700 mL) were put in a 2 L flask, and 4-biphenylmagnesium bromide (3 M, 361.4 mL) was slowly added thereto in a dropwise fashion at 0° C. When the reaction was complete, water was poured into the reaction solution, the mixture was stirred for 30 minutes, and an organic layer therefrom was separated, concentrated after removing moisture by using magnesium sulfate, and purified with methanol and hexane to obtain an intermediate I-10 as a white solid (127.4 g, a yield: 57%).

Second Step: Synthesis of Compound 7

The intermediate I-10 (3.0 g, 7.1 mmol), the intermediate I-4 (5.0 g, 8.6 mmol), potassium carbonate (2.5 g, 17.9 mmol), and tetrakis(triphenylphosphine) palladium (0) (0.3 g, 0.2 mmol) were added to 1,4-dioxane (20 mL) and water (10 mL) in a 100 mL flask, and the mixture was heated at 60° C. under a nitrogen atmosphere for 12 hours. The obtained mixture was added to methanol (100 mL), a solid crystallized therein was filtered, dissolved in dichlorobenzene, filtered through silica gel/Celite after removing an appropriate amount of an organic solvent, and then, recrystallized with methanol to obtain a compound 7 (4.19 g, a yield: 70%).

calcd. C63H43N3: C, 89.86; H, 5.15; N, 4.99; found: C, 89.85; H, 5.16; N, 4.99

Synthesis Example 6: Synthesis of Compound 9

[Reaction Scheme 6]

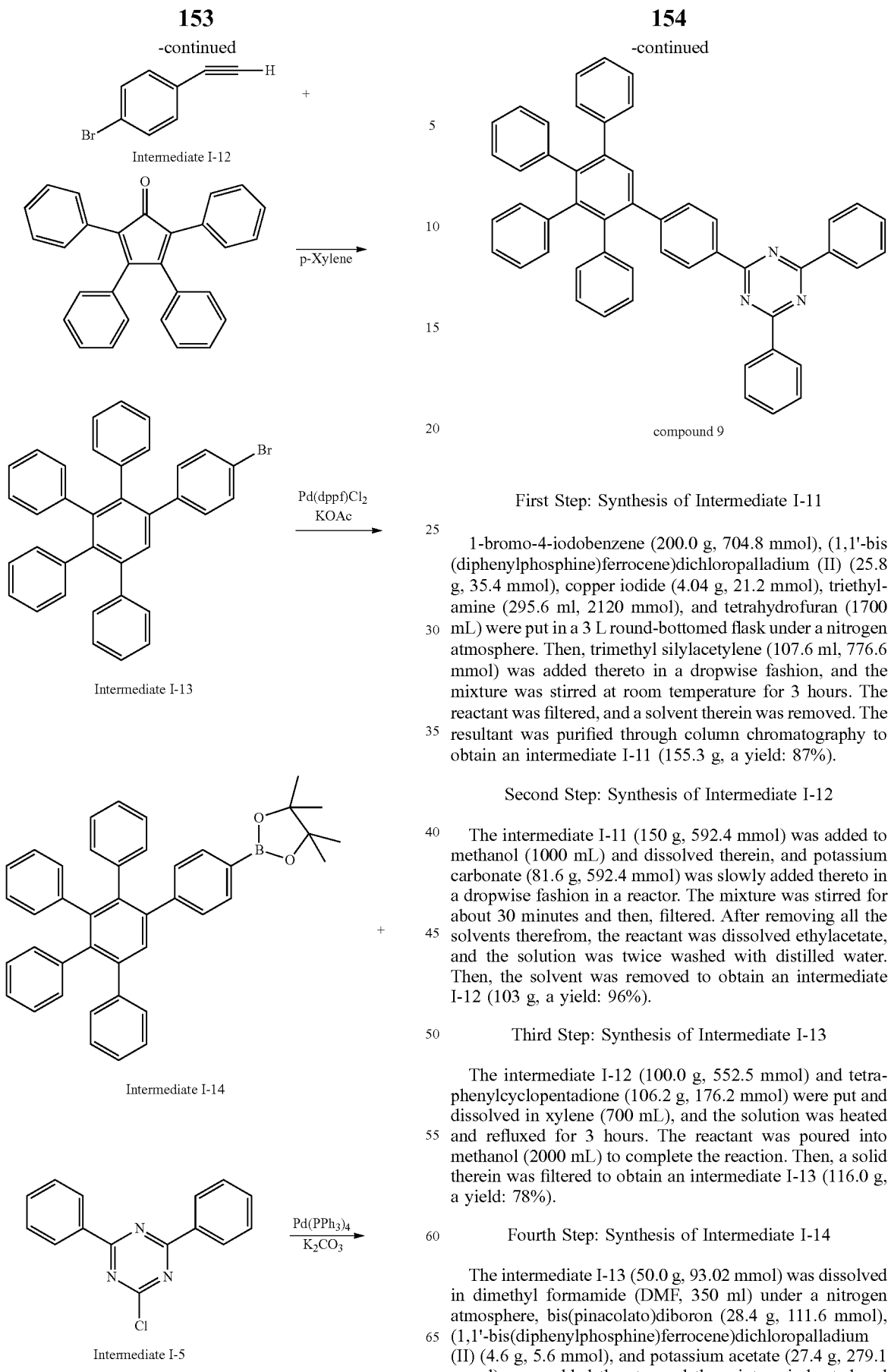

First Step: Synthesis of Intermediate I-11

1-bromo-4-iodobenzene (200.0 g, 704.8 mmol), (1,1'-bis(diphenylphosphine)ferrocene)dichloropalladium (II) (25.8 g, 35.4 mmol), copper iodide (4.04 g, 21.2 mmol), triethylamine (295.6 ml, 2120 mmol), and tetrahydrofuran (1700 mL) were put in a 3 L round-bottomed flask under a nitrogen atmosphere. Then, trimethyl silylacetylene (107.6 ml, 776.6 mmol) was added thereto in a dropwise fashion, and the mixture was stirred at room temperature for 3 hours. The reactant was filtered, and a solvent therein was removed. The resultant was purified through column chromatography to obtain an intermediate I-11 (155.3 g, a yield: 87%).

Second Step: Synthesis of Intermediate I-12

The intermediate I-11 (150 g, 592.4 mmol) was added to methanol (1000 mL) and dissolved therein, and potassium carbonate (81.6 g, 592.4 mmol) was slowly added thereto in a dropwise fashion in a reactor. The mixture was stirred for about 30 minutes and then, filtered. After removing all the solvents therefrom, the reactant was dissolved ethylacetate, and the solution was twice washed with distilled water. Then, the solvent was removed to obtain an intermediate I-12 (103 g, a yield: 96%).

Third Step: Synthesis of Intermediate I-13

The intermediate I-12 (100.0 g, 552.5 mmol) and tetraphenylcyclopentadione (106.2 g, 176.2 mmol) were put and dissolved in xylene (700 mL), and the solution was heated and refluxed for 3 hours. The reactant was poured into methanol (2000 mL) to complete the reaction. Then, a solid therein was filtered to obtain an intermediate I-13 (116.0 g, a yield: 78%).

Fourth Step: Synthesis of Intermediate I-14

The intermediate I-13 (50.0 g, 93.02 mmol) was dissolved in dimethyl formamide (DMF, 350 ml) under a nitrogen atmosphere, bis(pinacolato)diboron (28.4 g, 111.6 mmol), (1,1'-bis(diphenylphosphine)ferrocene)dichloropalladium (II) (4.6 g, 5.6 mmol), and potassium acetate (27.4 g, 279.1 mmol) were added thereto, and the mixture is heated and refluxed at 150° C. for 24 hours. When the reaction was complete, water was added to the reaction solution, and the mixture was filtered and then, dried in a vacuum oven. The obtained residue was separated and purified through column chromatography to obtain an intermediate I-14 (37 g, a yield: 68%).

Fifth Step: Synthesis of Compound 9

The intermediate I-14 (5.0 g, 8.6 mmol), 2-chloro-4,6-diphenyl-1,3,5-triazine (2.8 g, 10.3 mmol), potassium carbonate (3.0 g, 21.4 mmol), and tetrakis(triphenylphosphine) palladium (0) (0.3 g, 0.3 mmol) were added to 1,4-dioxane (30 mL) and water (15 mL) in a 100 mL flask, and the mixture was heated at 60° C. under a nitrogen flow for 12 hours. The obtained mixture was added to methanol (150 mL), a solid crystallized therein was filtered, dissolved in toluene, filtered through silica gel/Celite, and then, recrystallized with methanol after removing an appropriate amount of an organic solvent to obtain a compound 9 (3.89 g, a yield: 66%).

calcd. C51H35N3: C, 88.79; H, 5.11; N, 6.09; found: C, 88.79; H, 5.11; N, 6.10

Synthesis Example 7: Synthesis of Compound 10

[Reaction Scheme 7]

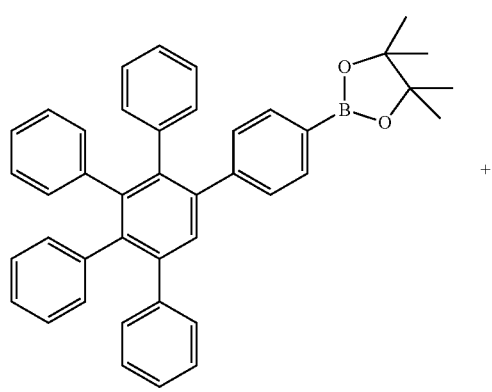

Intermediate I-14

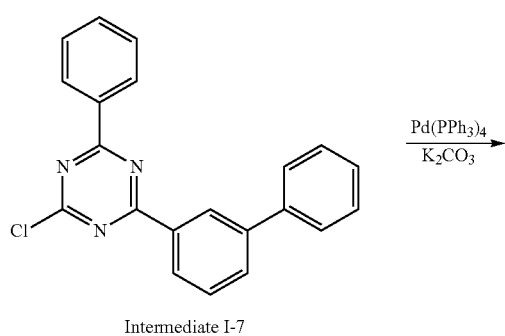

Intermediate I-7

-continued

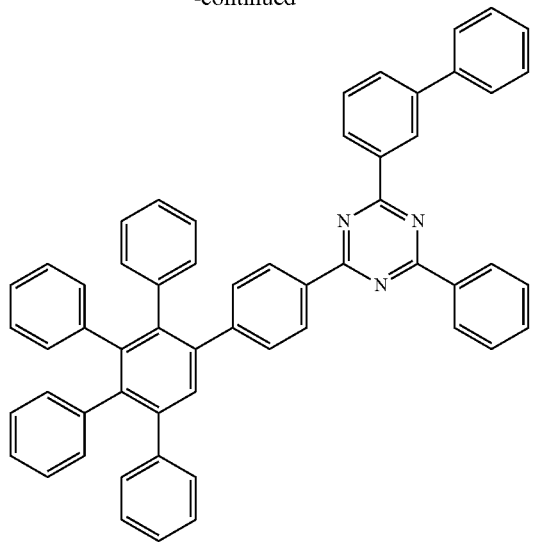

compound 10

First Step: Synthesis of Compound 10

2-chloro-4-(biphenyl-3-yl)-6-phenyl-1,3,5-triazine (3.0 g, 8.7 mmol), the intermediate I-14 (6.1 g, 10.5 mmol), potassium carbonate (3.0 g, 21.8 mmol), and tetrakis(triphenylphosphine) palladium (0) (0.3 g, 0.3 mmol) were added to 1,4-dioxane (30 mL) and water (15 mL) in a 100 mL flask, and the mixture was heated at 60° C. under a nitrogen flow for 12 hours. The obtained mixture was added to methanol (150 mL), a solid crystallized therein was filtered, dissolved in toluene, filtered through silica gel/Celite, and then, recrystallized with methanol after removing an appropriate amount of an organic solvent to obtain a compound 10 (4.59 g, a yield: 69%).

calcd. C57H39N3: C, 89.38; H, 5.13; N, 5.49; found: C, 89.38; H, 5.13; N, 5.48

Synthesis Example 8: Synthesis of Compound 11

[Reaction Scheme 8]

Intermediate I-14

Synthesis Example 9: Synthesis of Compound 14

[Reaction Scheme 9]

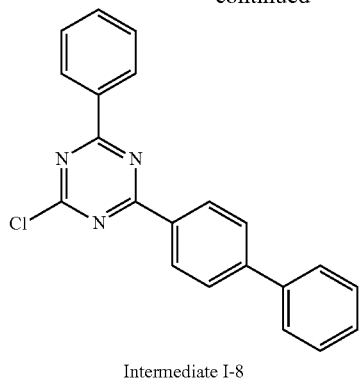

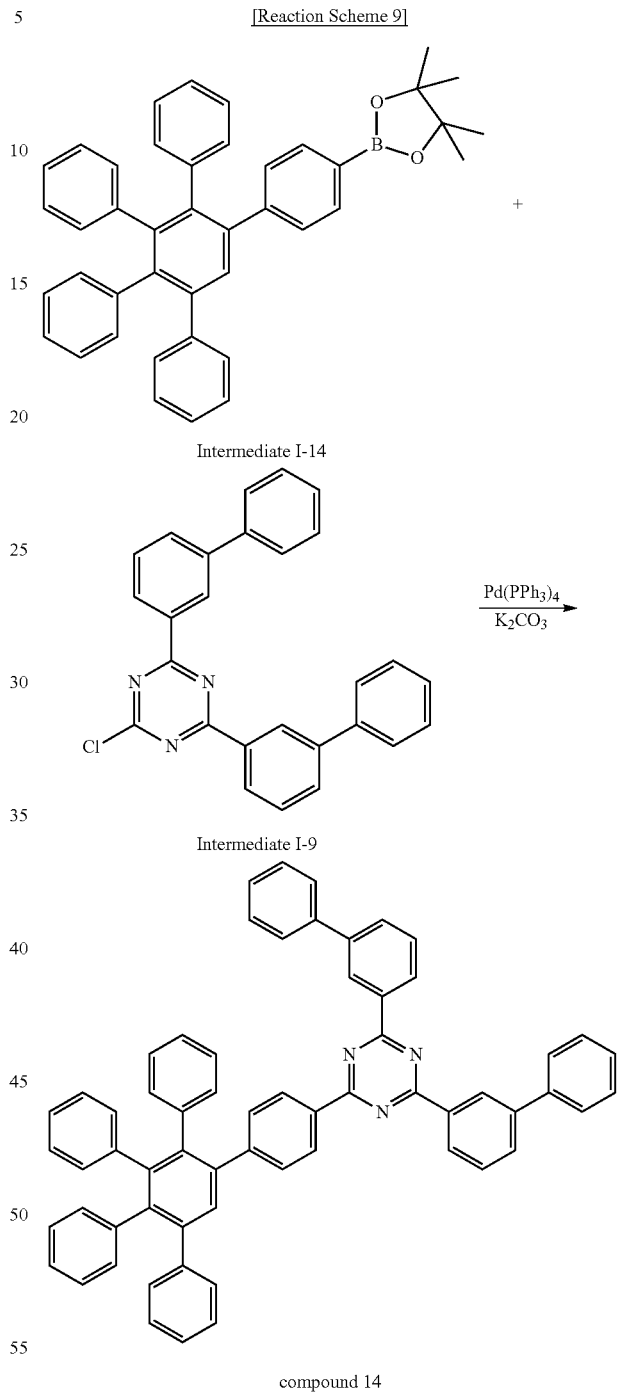

2-chloro-4-(biphenyl-4-yl)-6-phenyl-1,3,5-triazine (3.0 g, 8.7 mmol), the intermediate I-14 (6.1 g, 10.5 mmol), potassium carbonate (3.0 g, 21.8 mmol), and tetrakis(triphenylphosphine) palladium (0) (0.3 g, 0.3 mmol) were added to 1,4-dioxane (30 mL) and water (15 mL) in a 100 mL flask, and the mixture was heated at 60° C. under a nitrogen flow for 12 hours. This obtained mixture was added to methanol (150 mL), a solid crystallized therein was filtered, dissolved in monochlorobenzene, filtered through silica gel/Celite, and then, recrystallized with methanol after removing an appropriate amount of an organic solvent to obtain a compound 11 (4.06 g, a yield: 61%).

calcd. $C_{57}H_{39}N_3$: C, 89.38; H, 5.13; N, 5.49; found: C, 89.38; H, 5.12; N, 5.48

The intermediate I-9 (3.0 g, 7.1 mmol), the intermediate I-14 (5.0 g, 8.6 mmol), potassium carbonate (2.5 g, 17.9 mmol), and tetrakis(triphenylphosphine) palladium (0) (0.3 g, 0.2 mmol) were added to 1,4-dioxane (20 mL) and water (10 mL) in a 100 mL flask, and the mixture was heated at 60° C. under a nitrogen atmosphere for 12 hours. The obtained mixture was added to methanol (100 mL), a solid crystallized therein was filtered, dissolved in toluene, filtered through silica gel/Celite, and recrystallized with methanol after removing an appropriate amount of an organic solvent to obtain a compound 14 (4.19 g, a yield: 70%).

calcd. C63H43N3: C, 89.86; H, 5.15; N, 4.99; found: C, 89.84; H, 5.15; N, 4.99

Synthesis Example 10: Synthesis of Compound 15

[Reaction Scheme 10]

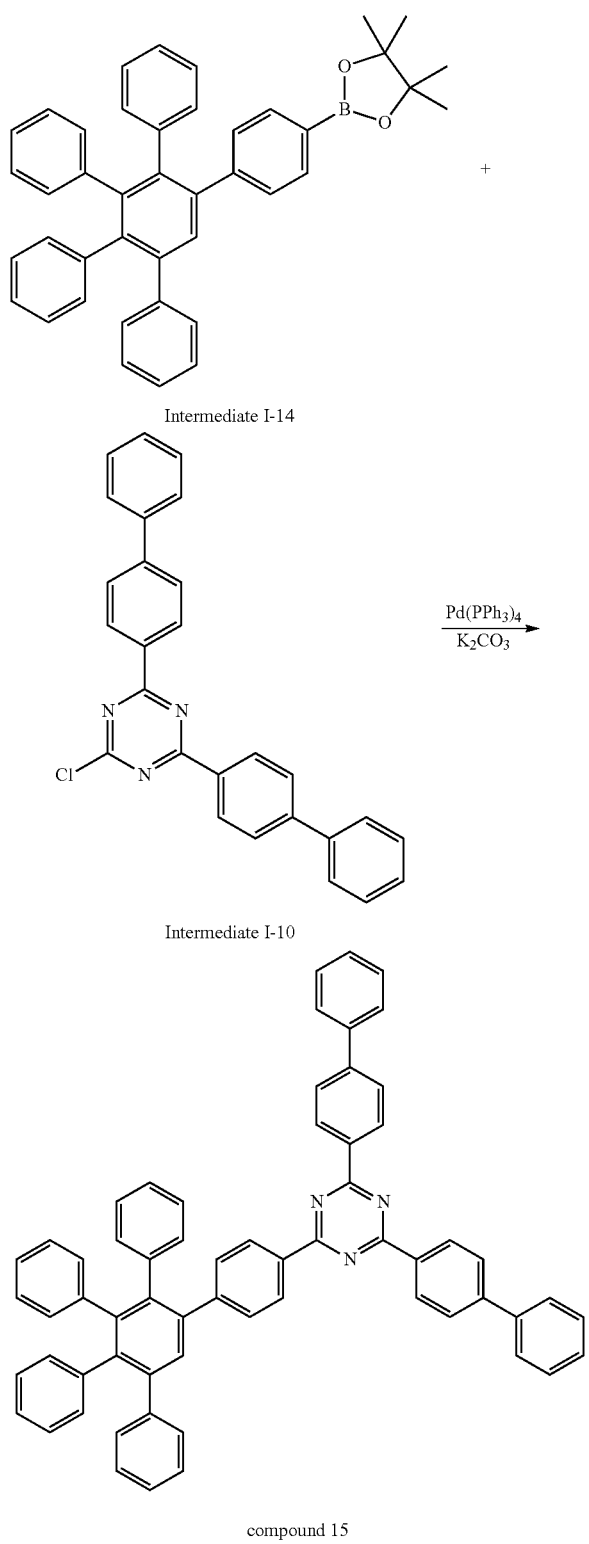

compound 15

The intermediate I-10 (3.0 g, 7.1 mmol), the intermediate I-14 (5.0 g, 8.6 mmol), potassium carbonate (2.5 g, 17.9 mmol), and tetrakis(triphenylphosphine) palladium (0) (0.3 g, 0.2 mmol) were added to 1,4-dioxane (20 mL) and water (10 mL) in a 100 mL flask, and the mixture was heated at 60° C. under a nitrogen flow for 12 hours. The obtained mixture was added to methanol (100 mL), a solid crystallized therein was filtered, dissolved in dichlorobenzene, filtered through silica gel/Celite, and then, recrystallized with methanol after removing an appropriate amount of an organic solvent to obtain a compound 15 (4.13 g, a yield: 69%).

calcd. C63H43N3: C, 89.86; H, 5.15; N, 4.99; found: C, 89.86; H, 5.16; N, 4.99

Synthesis Example 11: Synthesis of Compound 18

[Reaction Scheme 11]

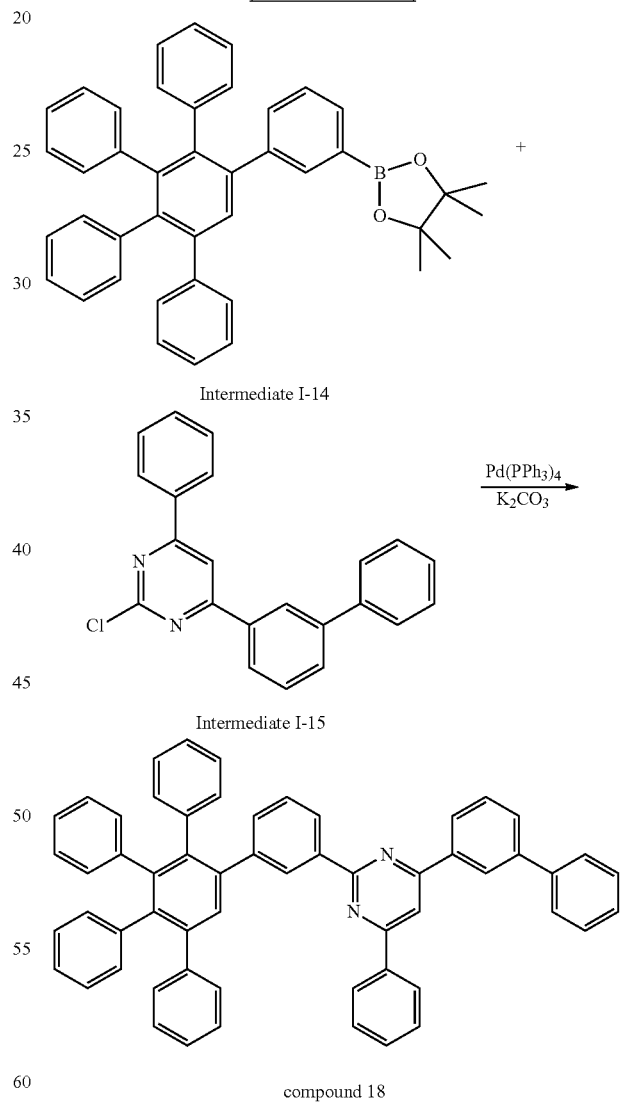

compound 18

The intermediate I-4 (5.0 g, 8.6 mmol), the intermediate I-15 (3.5 g, 10.3 mmol), potassium carbonate (3.0 g, 21.4 mmol), and tetrakis(triphenylphosphine) palladium (0) (0.3 g, 0.3 mmol) were added to 1,4-dioxane (30 mL) and water (15 mL) in a 100 mL flask, and the mixture was heated at 60°

C. under a nitrogen flow for 12 hours. The obtained mixture was added to methanol (100 mL), and a solid crystallized therein was filtered, dissolved in toluene, filtered through silica gel/Celite, and then, recrystallized with methanol after removing an appropriate amount of an organic solvent to obtain a compound 18 (4.39 g, a yield: 67%).

calcd. C58H40N2: C, 91.07; H, 5.27; N, 3.66; found: C, 91.08; H, 5.26; N, 3.65

Synthesis Example 12: Synthesis of Compound 26

The intermediate I-14 (5.0 g, 8.6 mmol), the intermediate I-15 (3.5 g, 10.3 mmol), potassium carbonate (3.0 g, 21.4 mmol), and tetrakis(triphenylphosphine) palladium (0) (0.3 g, 0.3 mmol) were added to 1,4-dioxane (30 mL) and water (15 mL) in a 100 mL flask, and the mixture was heated at 60° C. under a nitrogen flow for 12 hours. The obtained mixture was added to methanol (100 mL), and a solid crystallized therein was filtered, dissolved in toluene, filtered through silica gel/Celite, and then, recrystallized with methanol after removing an appropriate amount of an organic solvent to obtain a compound 26 (4.19 g, a yield: 64%).

calcd. C58H40N2: C, 91.07; H, 5.27; N, 3.66; found: C, 91.07; H, 5.26; N, 3.67

Synthesis Example 13: Synthesis of Compound 33

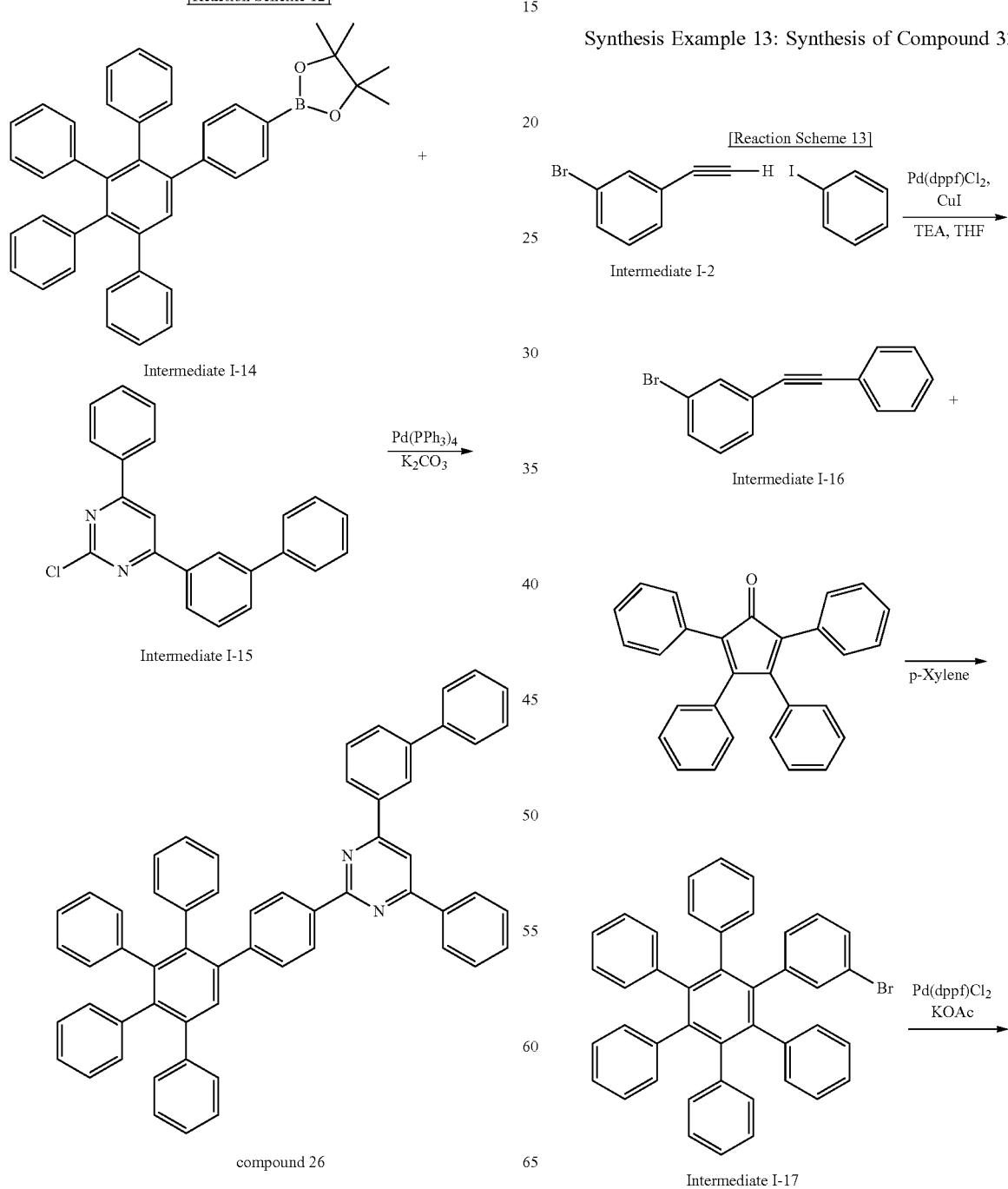

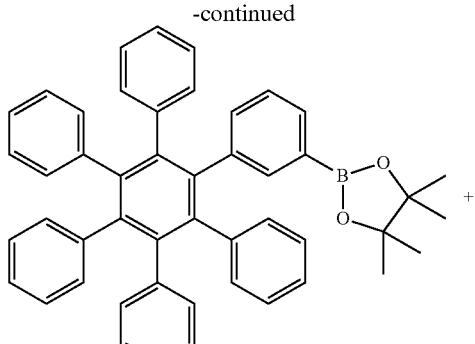

Intermediate I-18

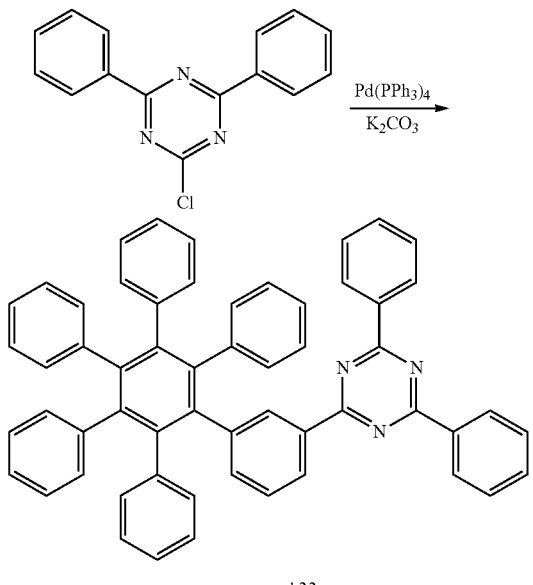

compound 33

First Step: Synthesis of Intermediate I-16

An intermediate I-16 (100 g, a yield: 79%) was obtained according to the same method as the synthesis method of the intermediate I-1 by using the intermediate I-2 (100 g, 549.0 mmol) and iodobenzene (120 g, 488.18 mmol) under a nitrogen atmosphere.

Second Step: Synthesis of Intermediate I-17

An intermediate I-17 (186 g, a yield: 74%) was obtained according to the same method as the synthesis method of the intermediate I-3 by using the intermediate I-16 (93.0 g, 514.98 mmol) and tetraphenylcyclopentadione (180 g, 468.18 mmol) under a nitrogen atmosphere.

Third Step: Synthesis of Intermediate I-18

An intermediate I-18 (72 g, a yield: 75%) was obtained according to the same method as the synthesis method of the intermediate I-4 by using the intermediate I-17 (90.0 g, 146.71 mmol) under a nitrogen atmosphere.

Fourth Step: Synthesis of Compound 33

The intermediate I-18 5.0 g (7.6 mmol), 2-chloro-4,6-diphenyl-1,3,5-triazine (2.4 g, 9.1 mmol), potassium carbonate (2.6 g, 18.9 mmol), and tetrakis(triphenylphosphine) palladium (0) (0.26 g, 0.23 mmol) were added to 1,4-dioxane (30 mL) and water (15 mL) in a 100 mL flask, and the mixture was heated at 60° C. under a nitrogen flow for 12 hours. The obtained mixture was added to methanol (100 mL), and a solid crystallized therein was dissolved in toluene, filtered through silica gel/Celite, and recrystallized with methanol after removing an appropriate amount of an organic solvent to obtain a compound 33 (4.18 g, a yield: 72%).

calcd. C57H39N3: C, 89.38; H, 5.13; N, 5.49 found: C, 89.37; H, 5.13; N, 5.48

Synthesis Example 14: Synthesis of Compound 34

[Reaction Scheme 14]

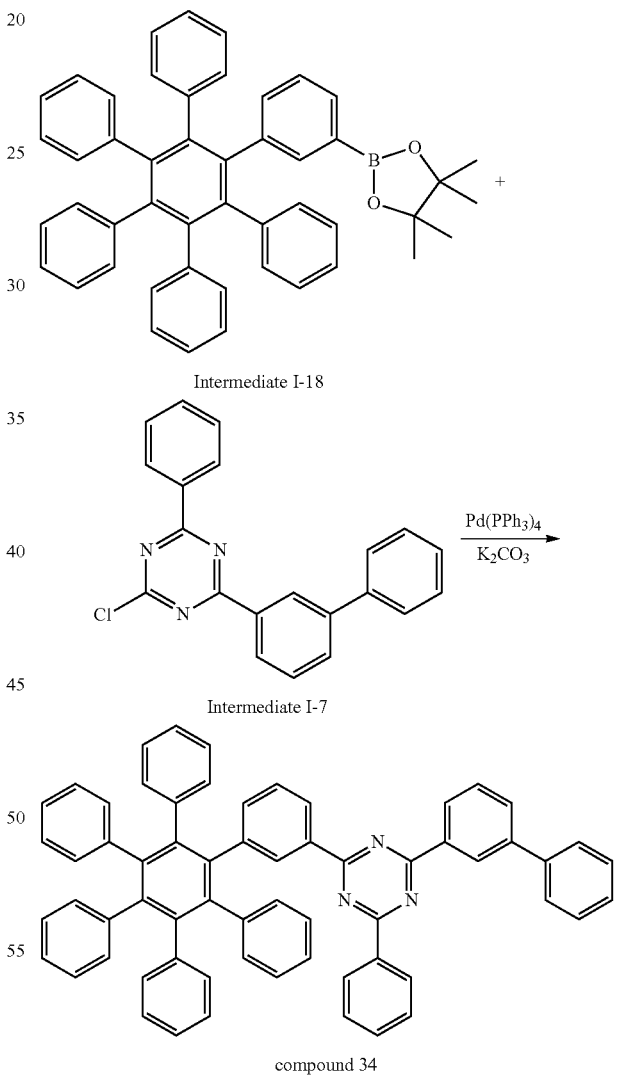

compound 34

The intermediate I-18 (5.0 g, 7.6 mmol), the intermediate I-7 (3.1 g, 9.1 mmol), potassium carbonate (2.6 g, 18.9 mmol), and tetrakis(triphenylphosphine) palladium (0) (0.26 g, 0.23 mmol) were added to 1,4-dioxane (30 mL) and water (15 mL) in a 100 mL flask, and the mixture was heated at 60° C. under a nitrogen flow for 12 hours. The obtained mixture was added to methanol (100 mL), and a solid crystallized therein was filtered, dissolved in toluene, filtered through silica gel/Celite, and recrystallized with methanol after removing an appropriate amount of an organic solvent to obtain a compound 34 (3.83 g, a yield: 60%).

calcd. C63H43N3: C, 89.86; H, 5.15; N, 4.99 found: C, 89.85; H, 5.15; N, 4.99

Synthesis Example 15: Synthesis of Compound 35

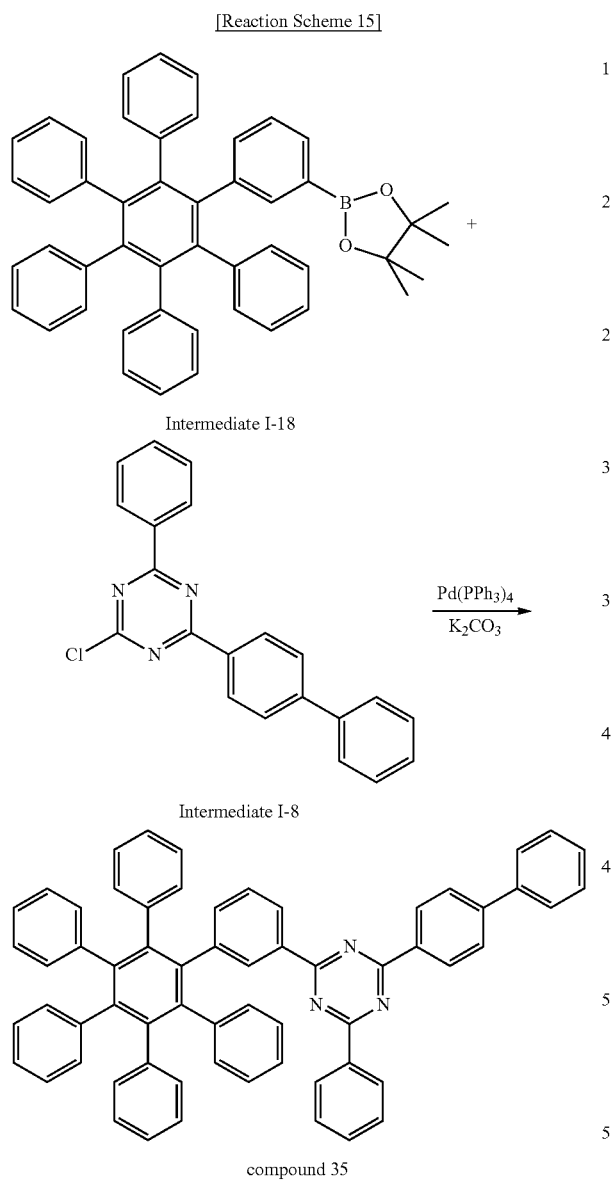

Intermediate I-18

Intermediate I-8 compound 35

The intermediate I-18 (5.0 g, 7.6 mmol), the intermediate I-8 (3.1 g, 9.1 mmol), potassium carbonate (2.6 g, 18.9 mmol), and tetrakis(triphenylphosphine) palladium (0) (0.26 g, 0.23 mmol) were added to 1,4-dioxane (30 mL) and water (15 mL) in a 100 mL flask, and the mixture was heated at 60° C. under a nitrogen flow for 12 hours. The obtained mixture was added to methanol (100 mL), and a solid crystallized therein was filtered, dissolved in monochlorobenzene, filtered through silica gel/Celite, and recrystallized with methanol after removing an appropriate amount of an organic solvent to obtain a compound 35 (4.01 g, a yield: 63%).

calcd. C63H43N3: C, 89.86; H, 5.15; N, 4.99 found: C, 89.86; H, 5.15; N, 4.99

Synthesis Example 16: Synthesis of Compound 41

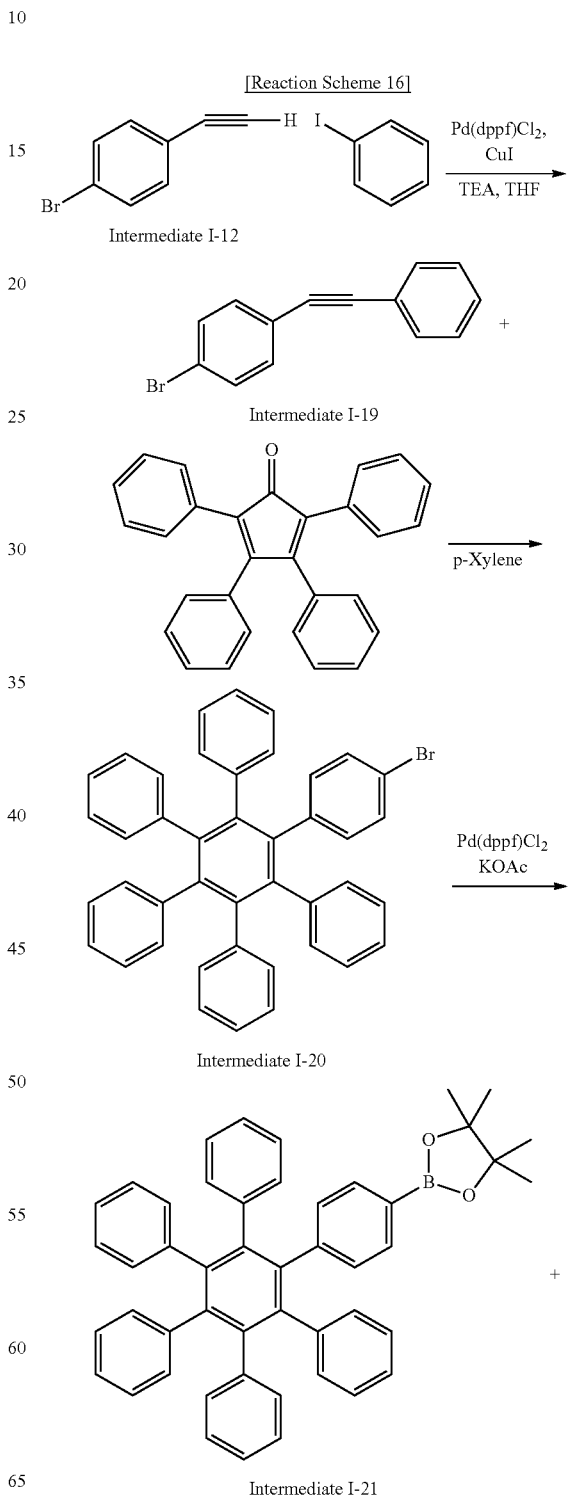

Intermediate I-12

Intermediate I-19

Intermediate I-20

Intermediate I-21

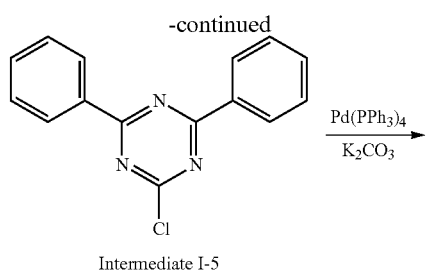

Intermediate I-5

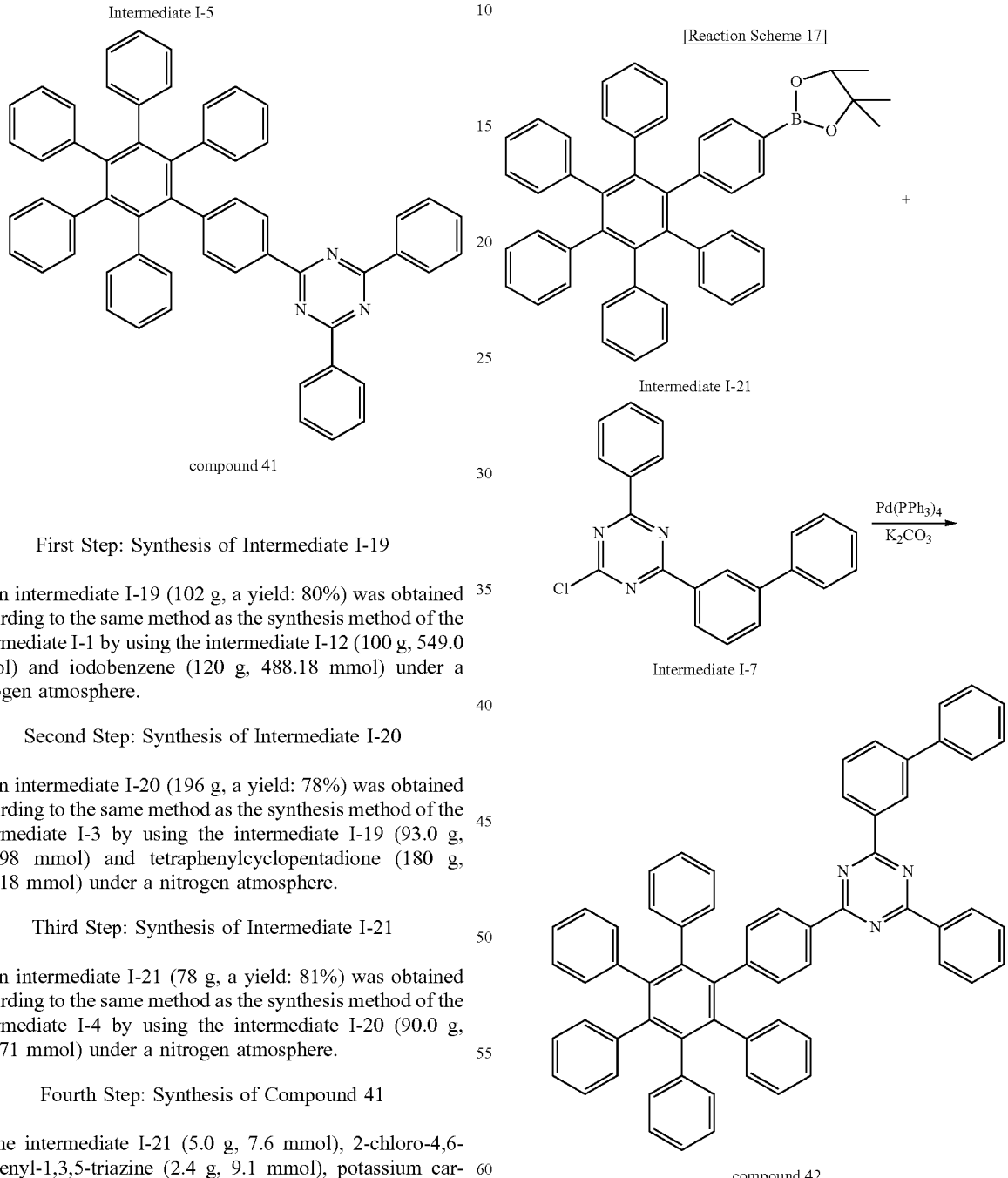

compound 41

First Step: Synthesis of Intermediate I-19

An intermediate I-19 (102 g, a yield: 80%) was obtained according to the same method as the synthesis method of the intermediate I-1 by using the intermediate I-12 (100 g, 549.0 mmol) and iodobenzene (120 g, 488.18 mmol) under a nitrogen atmosphere.

Second Step: Synthesis of Intermediate I-20

An intermediate I-20 (196 g, a yield: 78%) was obtained according to the same method as the synthesis method of the intermediate I-3 by using the intermediate I-19 (93.0 g, 514.98 mmol) and tetraphenylcyclopentadione (180 g, 468.18 mmol) under a nitrogen atmosphere.

Third Step: Synthesis of Intermediate I-21

An intermediate I-21 (78 g, a yield: 81%) was obtained according to the same method as the synthesis method of the intermediate I-4 by using the intermediate I-20 (90.0 g, 146.71 mmol) under a nitrogen atmosphere.

Fourth Step: Synthesis of Compound 41

The intermediate I-21 (5.0 g, 7.6 mmol), 2-chloro-4,6-diphenyl-1,3,5-triazine (2.4 g, 9.1 mmol), potassium carbonate (2.6 g, 18.9 mmol), and tetrakis(triphenylphosphine) palladium (0) (0.26 g, 0.23 mmol) were added to 1,4-dioxane (30 mL) and water (15 mL) in a 100 mL flask, and the mixture was heated at 60° C. under a nitrogen flow for 12 hours. The obtained mixture was added to methanol (100 mL), and a solid crystallized therein was filtered, dissolved in toluene, filtered through silica gel/Celite, and then, recrystallized with methanol after removing an appropriate amount of an organic solvent to obtain a compound 41 (3.88 g, a yield: 67%).

calcd. C57H39N3: C, 89.38; H, 5.13; N, 5.49 found: C, 89.38; H, 5.13; N, 5.49

Synthesis Example 17: Synthesis of Compound 42

[Reaction Scheme 17]

The intermediate I-21 (5.0 g, 7.6 mmol), the intermediate I-7 (3.1 g, 9.1 mmol), potassium carbonate (2.6 g, 18.9 mmol), and tetrakis(triphenylphosphine) palladium (0) (0.26 g, 0.23 mmol) were added to 1,4-dioxane (30 mL) and water (15 mL) in a 100 mL flask, and the mixture was heated at 60°

C. under a nitrogen flow for 12 hours. The obtained mixture was added to methanol (100 mL), and a solid crystallized therein was filtered, dissolved in toluene, filtered through silica gel/Celite, and then, recrystallized with methanol after removing an appropriate amount of an organic solvent to obtain a compound 42 (4.08 g, a yield: 64%).

calcd. C63H43N3: C, 89.86; H, 5.15; N, 4.99 found: C, 89.86; H, 5.15; N, 4.98

Synthesis Example 18: Synthesis of Compound 43

(15 mL) in a 100 mL flask, and the mixture was heated at 60° C. under a nitrogen flow for 12 hours. The obtained mixture was added to methanol (100 mL), and a solid crystallized therein was filtered, dissolved in monochlorobenzene, filtered through silica gel/Celite, and then, recrystallized with methanol after removing an appropriate amount of an organic solvent to obtain a compound 43 (4.26 g, a yield: 67%).

calcd. C63H43N3: C, 89.86; H, 5.15; N, 4.99 found: C, 89.86; H, 5.14; N, 4.99

Synthesis Example 19: Synthesis of Compound 50

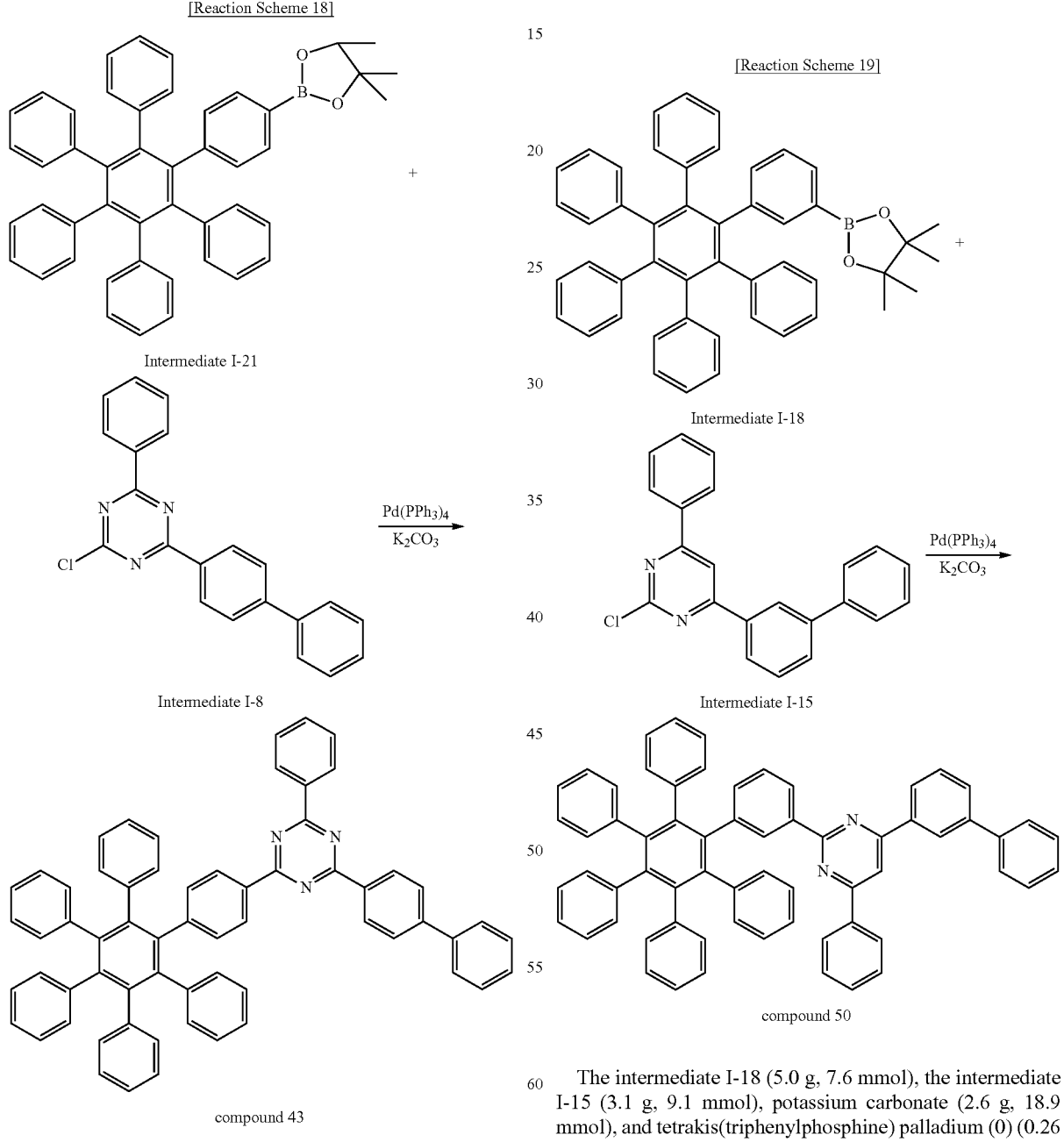

The intermediate I-21 (5.0 g, 7.6 mmol), the intermediate I-8 (3.1 g, 9.1 mmol), potassium carbonate (2.6 g, 18.9 mmol), and tetrakis(triphenylphosphine) palladium (0) (0.26 g, 0.23 mmol) were added to 1,4-dioxane (30 mL) and water The intermediate I-18 (5.0 g, 7.6 mmol), the intermediate I-15 (3.1 g, 9.1 mmol), potassium carbonate (2.6 g, 18.9 mmol), and tetrakis(triphenylphosphine) palladium (0) (0.26 g, 0.23 mmol) were added to 1,4-dioxane (30 mL) and water (15 mL) in a 100 mL flask, and the mixture was heated at 60° C. under a nitrogen flow for 12 hours. The obtained mixture was added to methanol (100 mL), and a solid crystallized therein was filtered, dissolved in toluene, filtered through silica gel/Celite, and then, recrystallized with methanol after removing an appropriate amount of an organic solvent to obtain a compound 50 (4.32 g, a yield: 68%).

calcd. C64H44N2: C, 91.40; H, 5.27; N, 3.33, found: C, 91.40; H, 5.27; N, 3.32

Synthesis Example 20: Synthesis of Compound 58

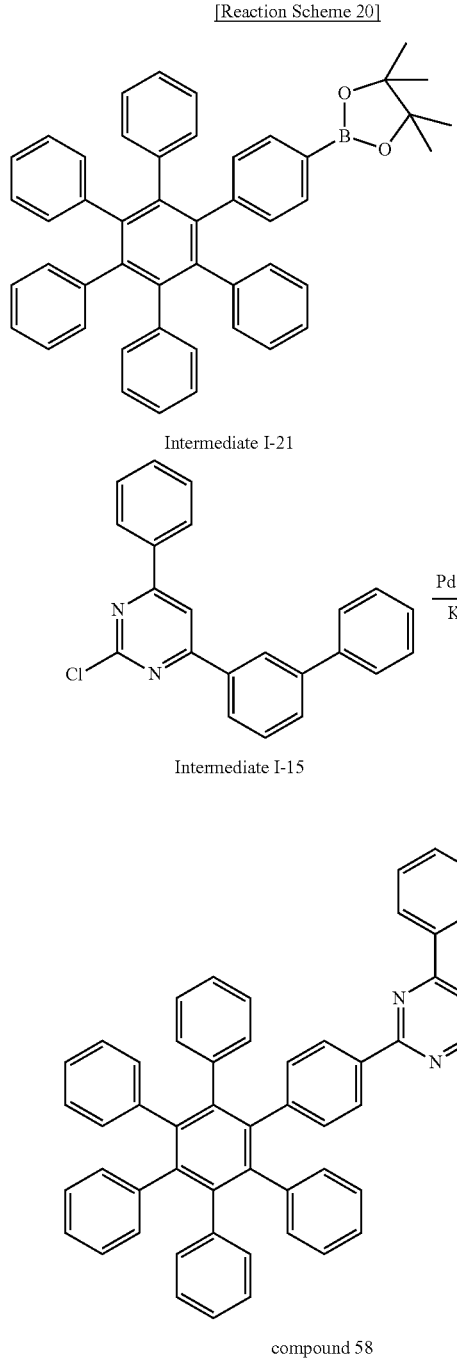

(15 mL) in a 100 mL flask, and the mixture was heated at 60° C. under a nitrogen flow for 12 hours. The obtained mixture was added to methanol (100 mL), and a solid crystallized therein was filtered, dissolved in toluene, filtered through silica gel/Celite, and then, recrystallized with methanol after removing an appropriate amount of an organic solvent to obtain a compound 58 (3.78 g, a yield: 61%).

calcd. C64H44N2: C, 91.40; H, 5.27; N, 3.33, found: C, 91.39; H, 5.27; N, 3.32

Synthesis Example 21: Synthesis of Compound 65

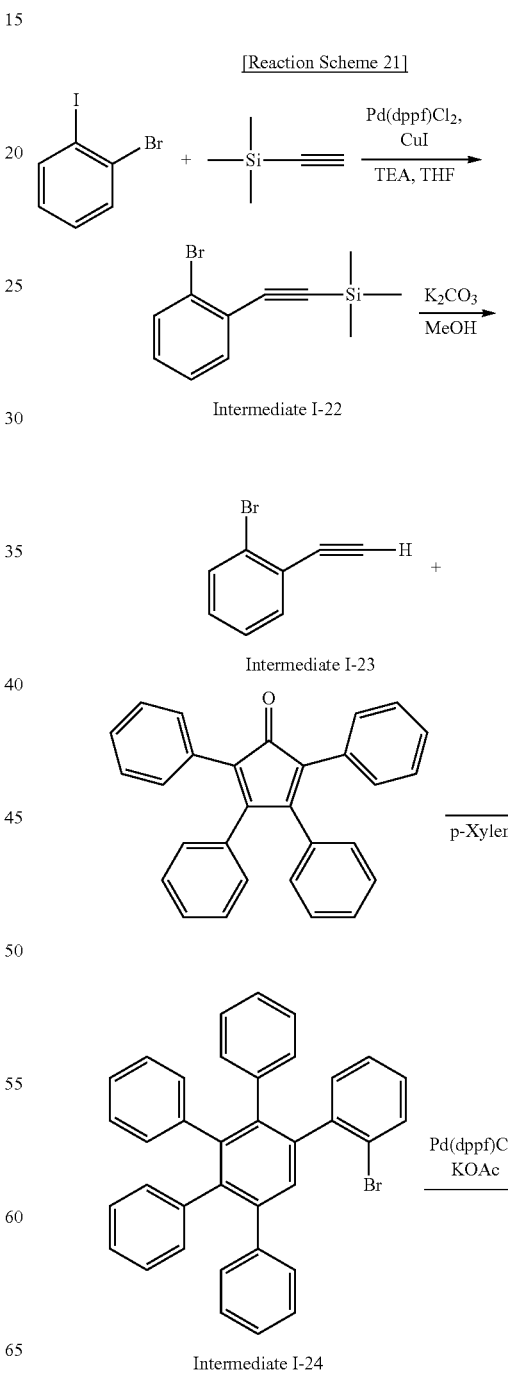

The intermediate I-21 (5.0 g, 7.6 mmol), the intermediate I-15 (3.1 g, 9.1 mmol), potassium carbonate (2.6 g, 18.9 mmol), and tetrakis(triphenylphosphine) palladium (0) (0.26 g, 0.23 mmol) were added to 1,4-dioxane (30 mL) and water 174
Synthesis Example 22: Synthesis of Compound 113

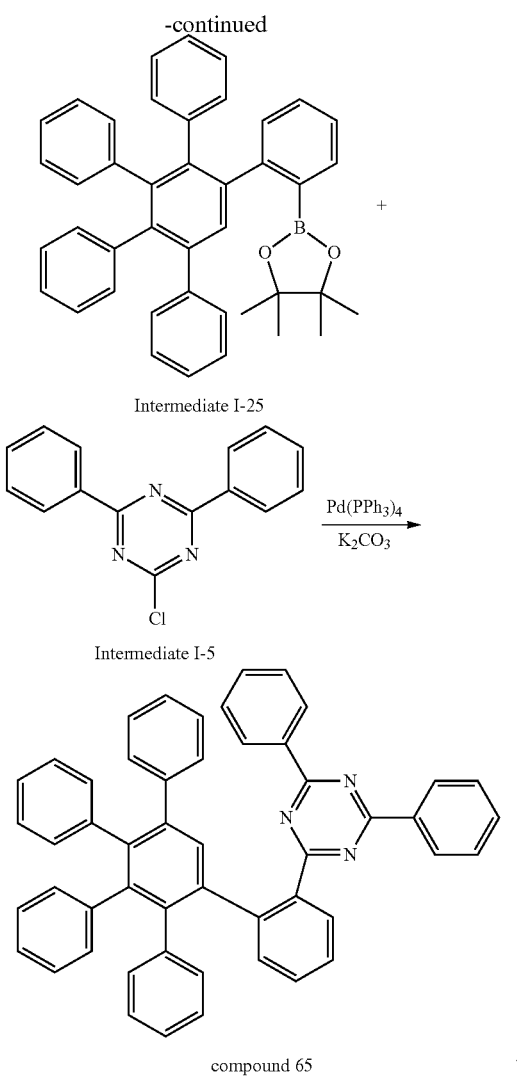

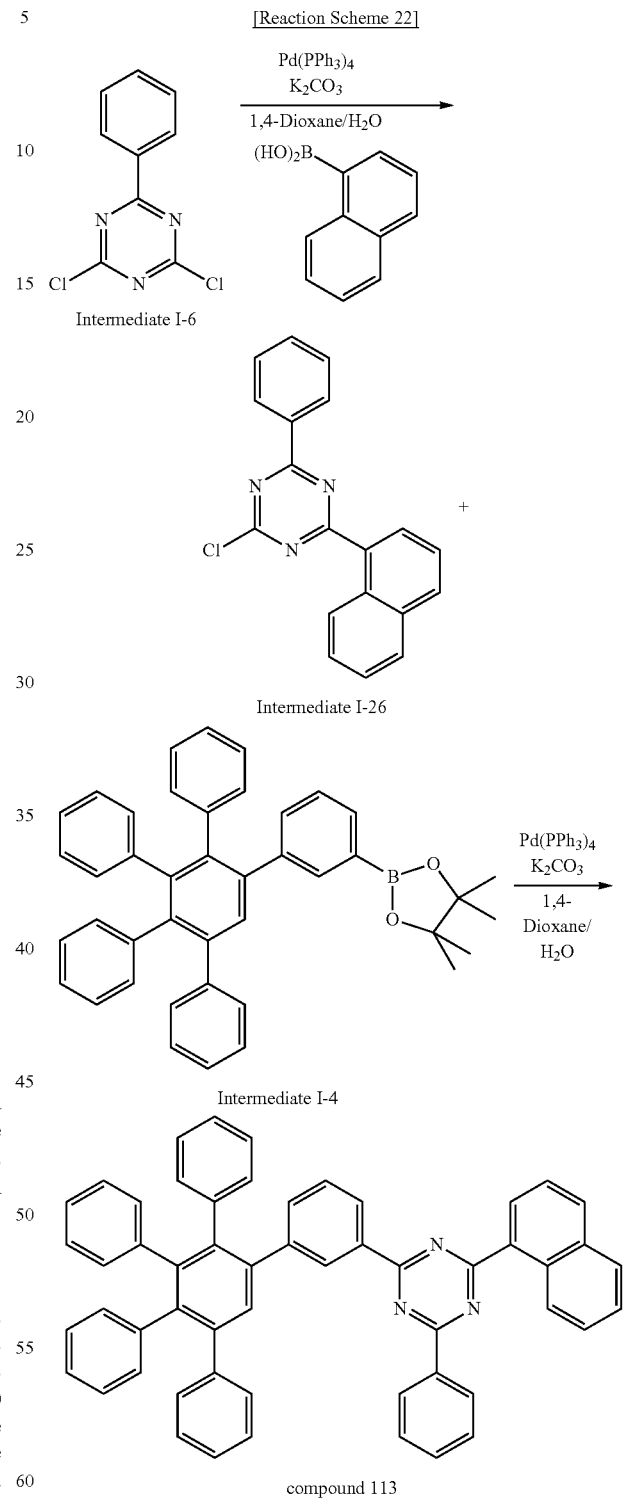

First Step: Synthesis of Intermediate I-25

An intermediate I-25 (30.2 g, a yield: 65%) was obtained according to the same method as the synthesis method of the intermediate I-4 except for using 1-bromo-2-iodobenzene as a starting material instead of the 1-bromo-3-iodobenzene in [Reaction Scheme 1] of Synthesis Example 1.

Second Step: Synthesis of Compound 65

The intermediate I-25 (5.0 g, 8.6 mmol), 2-chloro-4,6-diphenyl-1,3,5-triazine (2.8 g, 10.3 mmol), potassium carbonate (3.0 g, 21.4 mmol) tetrakis(triphenylphosphine) palladium (0) (0.3 g, 0.3 mmol) were added to 1,4-dioxane (30 mL) and water (15 mL) in a 100 mL flask, and the mixture was heated at 60° C. under a nitrogen flow for 12 hours. The obtained mixture was added to methanol (150 mL), and a solid crystallized therein was filtered, dissolved in toluene, filtered through silica gel/Celite, and then, recrystallized with methanol after removing an appropriate amount of an organic solvent to obtain a compound 65 (4.06 g, a yield: 68%).

calcd. C51H35N3: C, 88.79; H, 5.11; N, 6.09; found: C, 88.79; H, 5.11; N, 6.10

First Step: Synthesis of Intermediate I-26

An intermediate I-26 (15.2 g, a yield: 45%) was obtained according to the same method as the intermediate I-7 of Synthesis Example 2 except for using naphthylboronic acid instead of the 3-biphenyl boronic acid.

Second Step: Synthesis of Compound 113

The intermediate I-26 (3.0 g, 9.4 mmol), the intermediate I-4 (6.6 g, 11.3 mmol), potassium carbonate (3.3 g, 23.6 mmol), and tetrakis(triphenylphosphine) palladium (0) (0.3 g, 0.3 mmol) were added to 1,4-dioxane (30 mL) and water (15 mL) in a 100 mL flask, and the mixture was heated at 60° C. under a nitrogen flow for 12 hours. The obtained mixture was added to methanol (150 mL), and a solid crystallized therein was filtered, dissolved in toluene, filtered through silica gel/Celite, and then, recrystallized with methanol after removing an appropriate amount of an organic solvent to obtain a compound 113 (4.51 g, a yield: 65%).

calcd. C55H37N3: C, 89.28; H, 5.04; N, 5.68; found: C, 89.28; H, 5.03; N, 5.68

Synthesis Example 23: Synthesis of Compound 125

[Reaction Scheme 23]

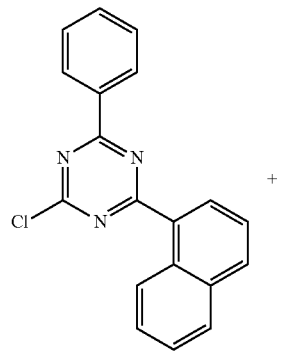

Intermediate I-26

+

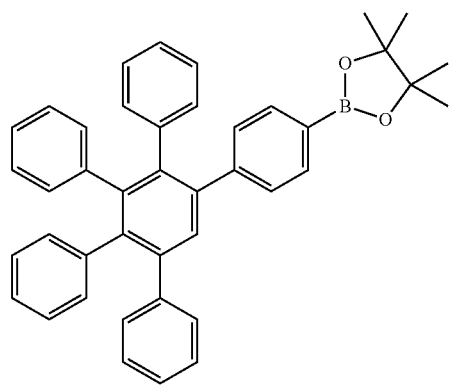

Intermediate I-14

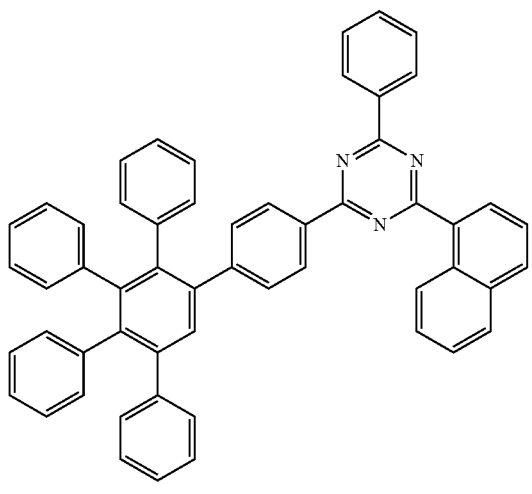

compound 125

The intermediate I-26 (3.0 g, 9.4 mmol), the intermediate I-14 (6.6 g, 11.3 mmol), potassium carbonate (3.3 g, 23.6 mmol), and tetrakis(triphenylphosphine) palladium (0) (0.3 g, 0.3 mmol) were added to 1,4-dioxane (30 mL) and water (15 mL) in a 100 mL flask, and the mixture was heated at 60° C. under a nitrogen flow for 12 hours. The obtained mixture was added to methanol (150 mL), and a solid crystallized therein was filtered, dissolved in toluene, filtered through silica gel/Celite, and then, recrystallized with methanol after removing an appropriate amount of an organic solvent to obtain a compound 125 (4.67 g, a yield: 66%).

calcd. $C_{55}H_{37}N_3$: C, 89.28; H, 5.04; N, 5.68; found: C, 89.29; H, 5.03; N, 5.67

Synthesis Example 24: Synthesis of Compound 141

[Reaction Scheme 24]

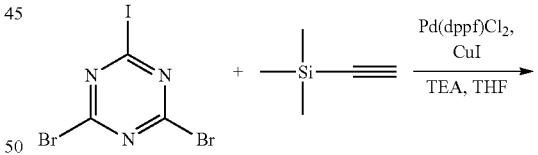

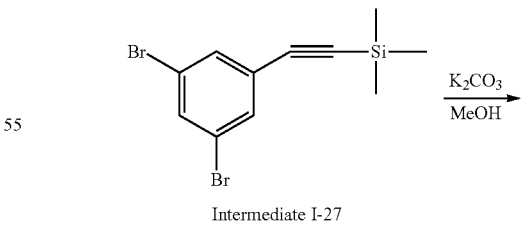

Intermediate I-27

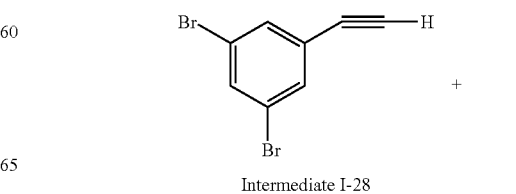

Intermediate I-28

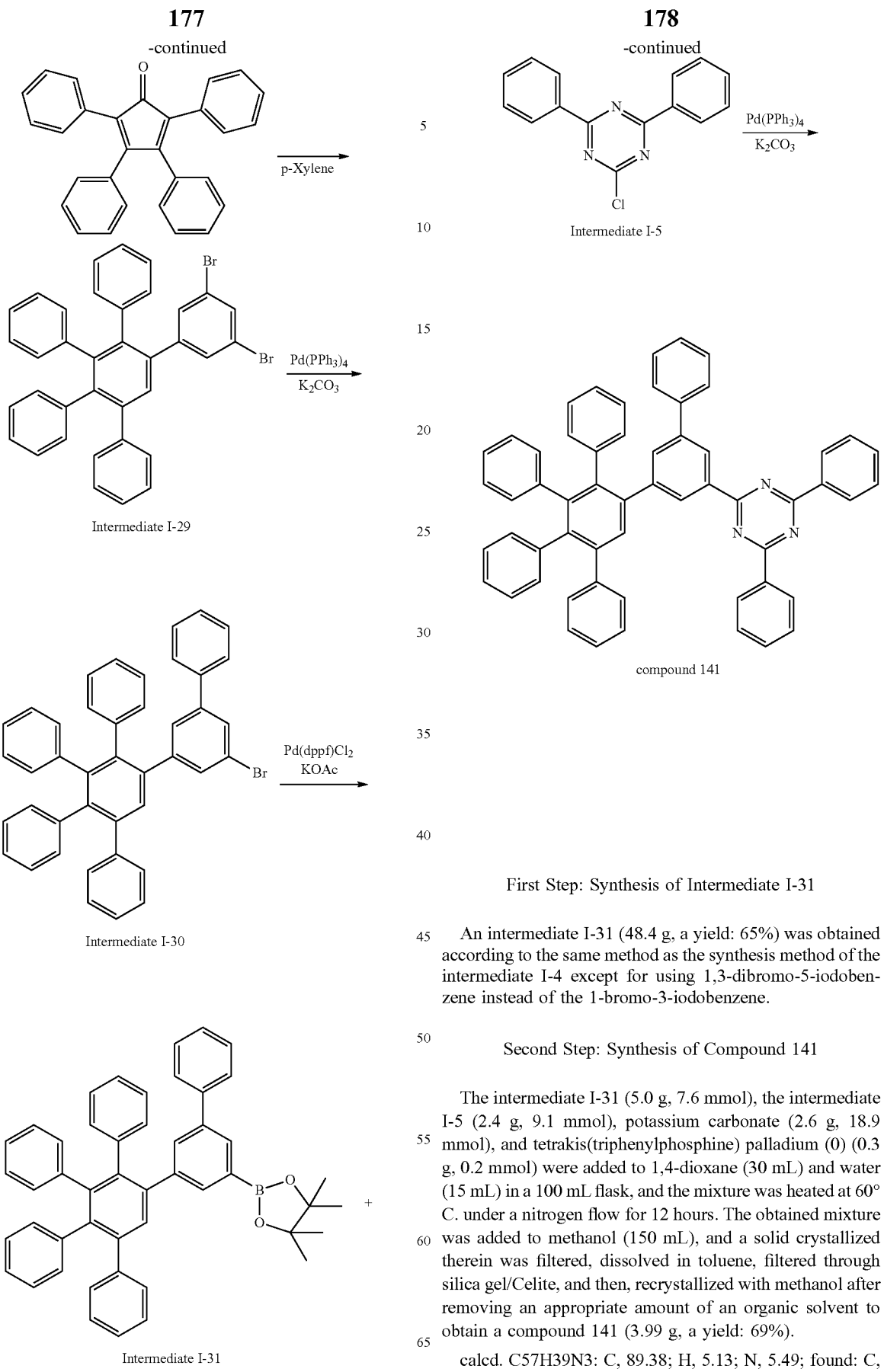

First Step: Synthesis of Intermediate I-31

An intermediate I-31 (48.4 g, a yield: 65%) was obtained according to the same method as the synthesis method of the intermediate I-4 except for using 1,3-dibromo-5-iodobenzene instead of the 1-bromo-3-iodobenzene.

Second Step: Synthesis of Compound 141

The intermediate I-31 (5.0 g, 7.6 mmol), the intermediate I-5 (2.4 g, 9.1 mmol), potassium carbonate (2.6 g, 18.9 mmol), and tetrakis(triphenylphosphine) palladium (0) (0.3 g, 0.2 mmol) were added to 1,4-dioxane (30 mL) and water (15 mL) in a 100 mL flask, and the mixture was heated at 60° C. under a nitrogen flow for 12 hours. The obtained mixture was added to methanol (150 mL), and a solid crystallized therein was filtered, dissolved in toluene, filtered through silica gel/Celite, and then, recrystallized with methanol after removing an appropriate amount of an organic solvent to obtain a compound 141 (3.99 g, a yield: 69%).

calcd. C57H39N3: C, 89.38; H, 5.13; N, 5.49; found: C, 89.38; H, 5.12; N, 5.47

Synthesis Example 25: Synthesis of Compound 142

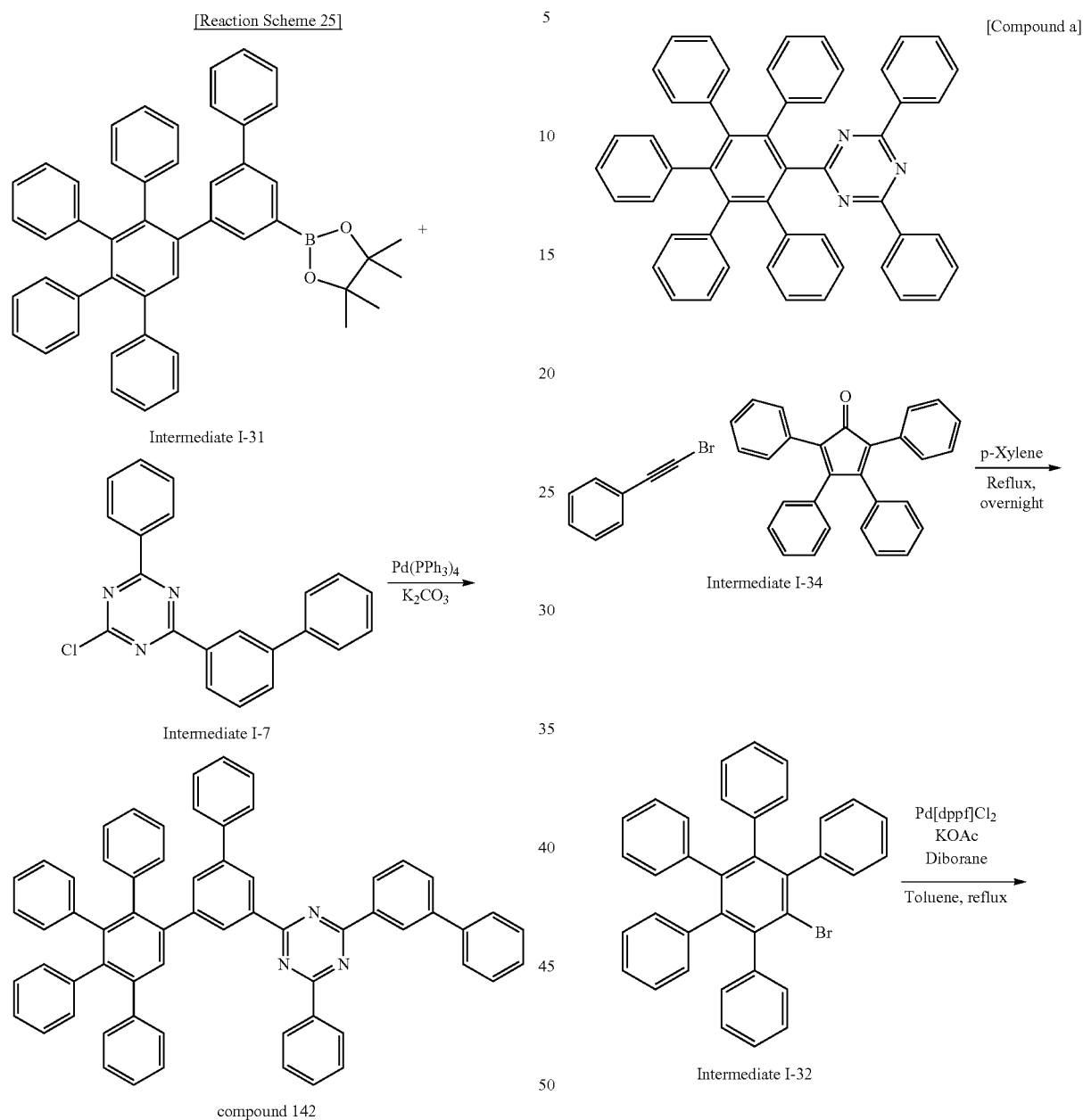

[Reaction Scheme 25]

Intermediate I-31

Intermediate I-7 compound 142

The intermediate I-31 (5.0 g, 7.6 mmol), the intermediate I-7 (3.1 g, 9.1 mmol), potassium carbonate (2.6 g, 18.9 mmol), and tetrakis(triphenylphosphine) palladium (0) (0.3 g, 0.2 mmol) were added to 1,4-dioxane (30 mL) and water (15 mL) in a 100 mL flask, and the mixture was heated at 60° C. under a nitrogen flow for 12 hours. The obtained mixture was added to methanol (150 mL), and a solid crystallized therein was filtered, dissolved in toluene, filtered through silica gel/Celite, and then, recrystallized with methanol after removing an appropriate amount of an organic solvent to obtain a compound 142 (4.22 g, a yield: 66%).

calcd. C63H43N3: C, 89.86; H, 5.15; N, 4.99; found: C, 89.86; H, 5.15; N, 4.99

Comparative Synthesis Example 1

[Compound a]

Intermediate I-34

Intermediate I-32

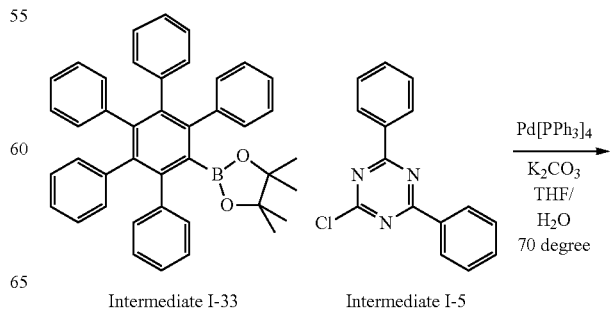

Intermediate I-33    Intermediate I-5

181
-continued

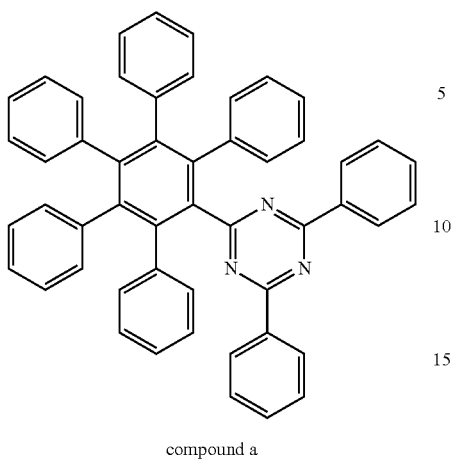

compound a

Synthesis of Compound a

A compound a (6.3 g, a yield: 51%) was obtained according to the same method as the synthesis method of the compound 1 of Synthesis Example 1 except for using the intermediate I-34 instead of the intermediate I-2.

Comparative Synthesis Example 2

[Compound b]

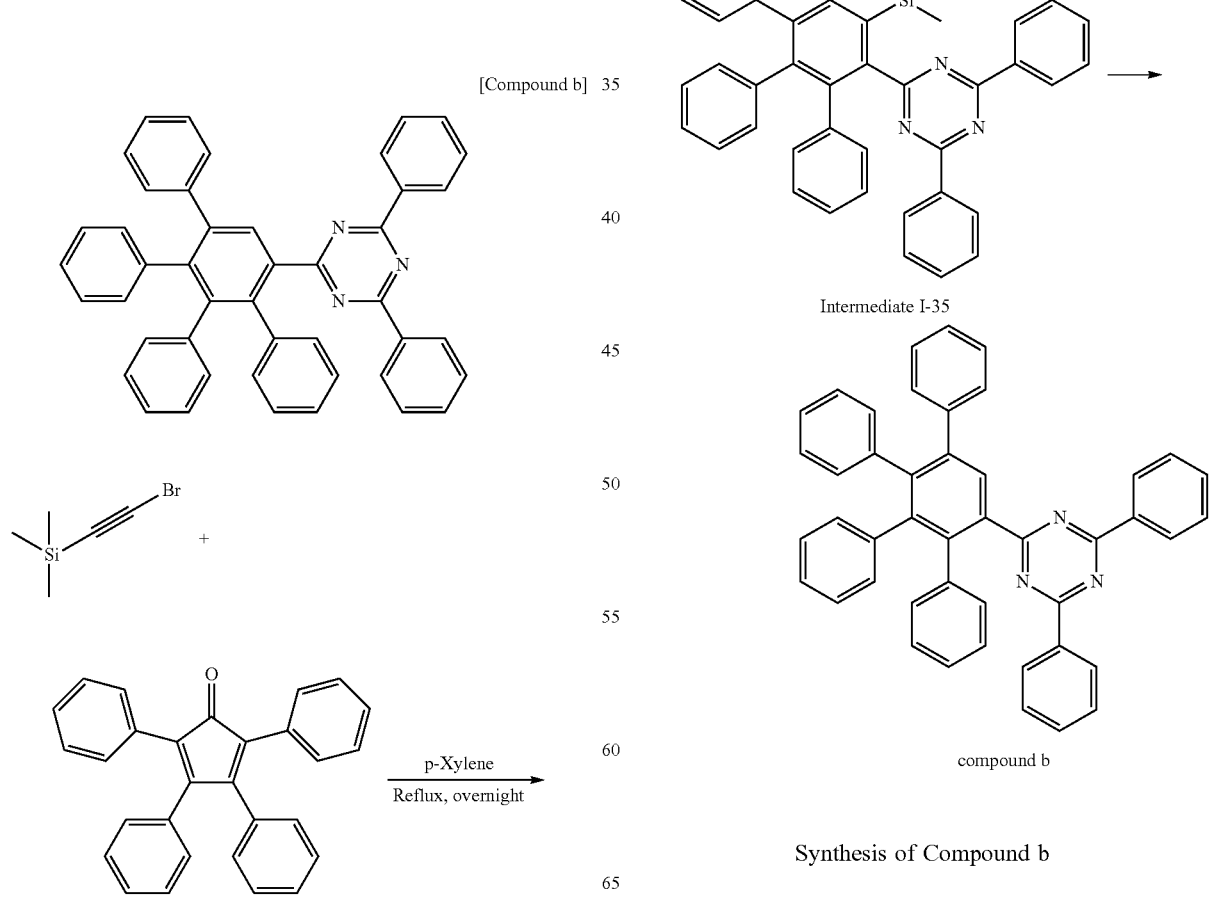

182
-continued

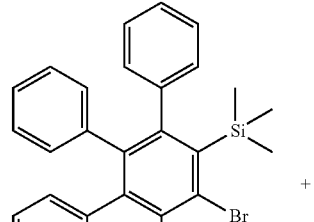

Intermediate I-34

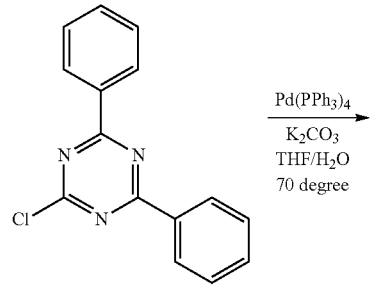

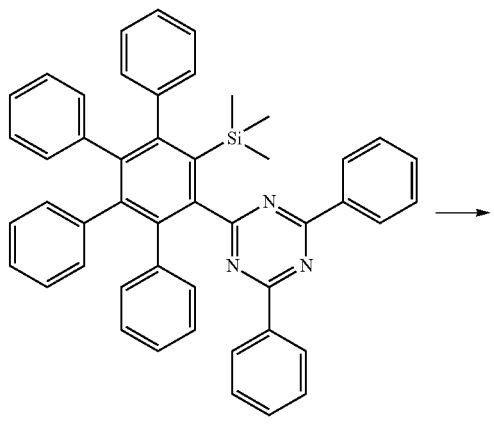

Intermediate I-35

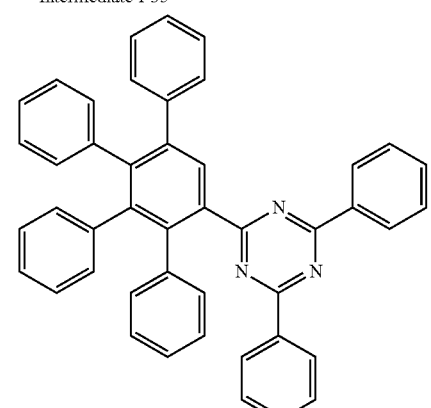

compound b

Synthesis of Compound b

A compound b (3.4 g, a yield: 41%) was obtained according to the same method as the synthesis method of the compound 1 of Synthesis Example 1 except for using (bromoethynyl)trimethylsilane instead of the intermediate I-2.

(Manufacture of Organic Light Emitting Diode: Emission Layer Device 1)

Example 1

An organic light emitting diode was manufactured by using the compound 1 according to Synthesis Example 1 as a host and Ir(PPy)$_3$ as a dopant.

A 1000 Å-thick ITO was used as an anode, and a 1000 Å-thick aluminum (Al) as a cathode. Specifically, the organic light emitting diode was manufactured in a method of cutting an ITO glass substrate having sheet resistance of 15 Ω/cm$^2$ into a size of 50 mm×50 mm×0.7 mm, ultrasonic wave-cleaning it in acetone, isopropylalcohol, and pure water respectively for 15 minutes and UV ozone-cleaning it for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of 650×10$^{-7}$ Pa at a deposition rate of 0.1 to 0.3 nm/s. Subsequently, a 300 Å-thick film as an emission layer was formed by using the compound 1 according to Synthesis Example 1 under the same vacuum deposition condition as above, and herein, Ir(PPy)$_3$ as a phosphorescent dopant was simultaneously deposited. Herein, the phosphorescent dopant was deposited in an amount of 10 wt % based on 100 wt % of the total amount of the emission layer by adjusting a deposition rate.

On the emission layer, a 50 Å-thick film as a hole blocking layer was formed by depositing bis(2-methyl-8-quinolinolate)-4-(phenylphenolato)aluminium (BAlq) under the same vacuum deposition condition as above. Subsequently, a 200 Å-thick film as an electron transport layer was formed by depositing Alq3 under the same vacuum deposition condition as above. On the electron transport layer, LiF and Al were sequentially deposited as a cathode, manufacturing the organic photoelectric device.

The organic photoelectric device had a structure of ITO/NPB (80 nm)/EML (compound 1 (90 wt %)+Ir(PPy)$_3$ (10 wt %), (30 nm))/Balq (5 nm)/Alq3 (20 nm)/LiF (1 nm)/Al (100 nm).

Examples 2 to 15

Each organic light emitting diode of Examples 2 to 15 was manufactured according to the same method as Example 1 by using the compound 2, the compound 3, the compound 6, the compound 9, the compound 10, the compound 18, the compound 26, the compound 33, the compound 34, the compound 41, compound 42, the compound 65, the compound 113, and the compound 142 according to Synthesis Example 2 to 4, Synthesis Example 6, Synthesis Example 7, Synthesis Example 11 to Synthesis Example 14, Synthesis Example 16, Synthesis Example 17, Synthesis Example 21, Synthesis Example 22, and Synthesis Example 25 instead of the compound 1 according to Synthesis Example 1.

Comparative Examples 1 to 3

Each organic light emitting diode of Comparative Examples 1 to 3 was manufactured according to the same method as Example 1 by using CBP, compound a, or compound b instead of the compound 1 according to Synthesis Example 1.

NPB, BAlq, CBP, and Ir(PPy)$_3$ used to manufacture the organic light emitting diode respectively have the following structures.

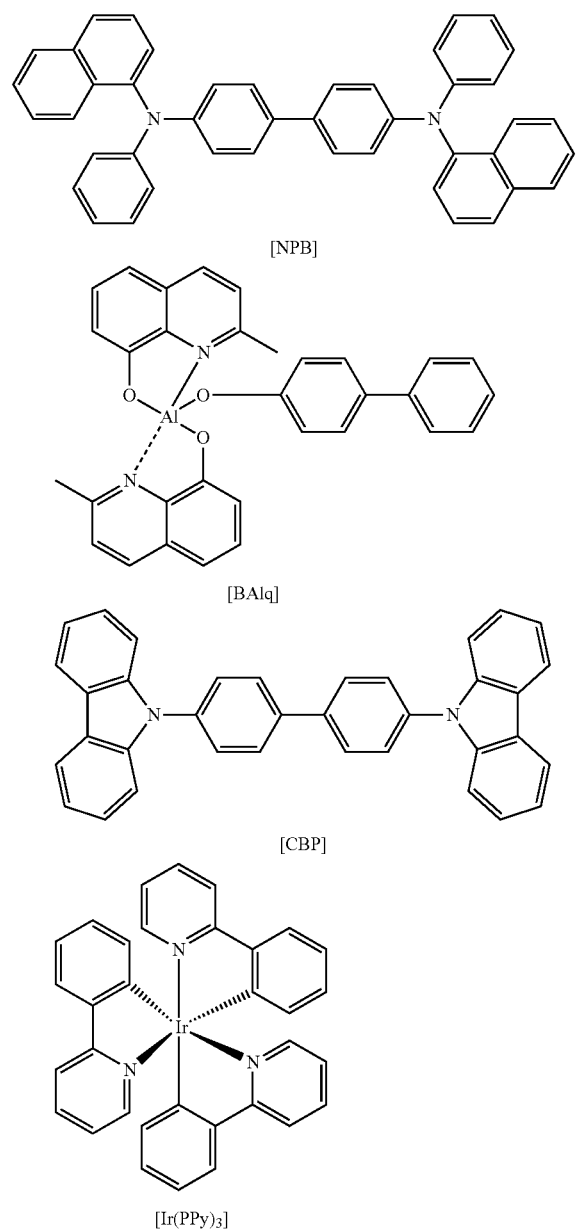

[NPB]

[BAlq]

[CBP]

[Ir(PPy)$_3$]

Evaluation

Current density change, luminance change, and luminous efficiency of each organic light emitting diode according to Examples 1 to 15 and Comparative Examples 1 to 3 were measured.

Specific measurement methods are as follows, and the results are shown in the following Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

A life span was obtained by measuring a time when current efficiency (cd/A) was decreased down to 90%, while luminance (cd/m$^2$) was maintained to be 5000 cd/m$^2$.

TABLE 1

| Nos. | Compound | Driving voltage (V) | Color (EL color) | Efficiency (cd/A) | 90% life-span (h) (@5000 cd/m$^2$) |
|---|---|---|---|---|---|
| Example 1 | compound 1 | 4.01 | Green | 39.2 | 53 |
| Example 2 | compound 2 | 3.84 | Green | 42.3 | 54 |
| Example 3 | compound 3 | 3.81 | Green | 41.7 | 48 |
| Example 4 | compound 6 | 3.78 | Green | 41.0 | 52 |
| Example 5 | compound 9 | 3.98 | Green | 38.9 | 42 |
| Example 6 | compound 10 | 3.82 | Green | 41.5 | 43 |
| Example 7 | compound 18 | 4.13 | Green | 36.2 | 46 |
| Example 8 | compound 26 | 4.09 | Green | 37.5 | 47 |
| Example 9 | compound 33 | 4.02 | Green | 39.4 | 54 |
| Example 10 | compound 34 | 3.83 | Green | 42.3 | 55 |
| Example 11 | compound 41 | 3.96 | Green | 39.0 | 51 |
| Example 12 | compound 42 | 3.81 | Green | 41.7 | 53 |
| Example 13 | compound 65 | 3.71 | Green | 40.2 | 56 |
| Example 14 | compound 113 | 4.11 | Green | 37.1 | 40 |
| Example 15 | compound 142 | 3.82 | Green | 42.3 | 48 |
| Comparative Example 1 | CBP | 4.29 | Green | 31.7 | 25 |
| Comparative Example 2 | compound a | 4.19 | Green | 35.6 | 36 |
| Comparative Example 3 | compound b | 4.14 | Green | 36.1 | 35 |

Referring to Table 1, the organic light emitting diodes according to Examples 1 to 15 showed improved life-span characteristics as well as improved driving voltage and efficiency compared with the organic light emitting diodes according to Comparative Examples 1 to 3. As described above, the driving voltage was deteriorated, since electrons were easily injected and transported by stacking a relatively-flat heterocyclic moiety by a bulky substituent. Compared with the compound according to the present invention, the compounds according to Comparative Examples had no linker and thus showed relatively insufficient packing of molecules and deteriorated a diode. On the contrary, the compound of Example 13 having an ortho bond had a kink molecular structure and thus showed stacking of heterocyclic moieties of ET characteristic substituents and resultantly the fastest driving voltage.

(Manufacture of Organic Light Emitting Diode: Emission Layer Device 2)

Example 16

A glass substrate coated with ITO (indium tin oxide) as a 1500 Å-thick thin film was ultrasonic wave-washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing the compound A, and a hole transport layer was formed on the injection layer by depositing the compound B to be 50 Å thick and the compound C to be 1020 Å thick. On the hole transport layer, a 400 Å-thick emission layer was formed by vacuum-depositing both the compound 2 according to Synthesis Example 2 and the compound B-1 as a second host compound simultaneously as a host and tris(2-phenylpyridine)iridium (III) [Ir(ppy)$_3$] as a dopant in a doping amount of 10 wt %. Herein, the compound 1 and the compound B-1 were used in a ratio of 1:1.

Subsequently, an organic light emitting diode was manufactured by simultaneously vacuum-depositing the compound D and Liq in a ratio of 1:1 to form a 300 Å-thick electron transport layer on the emission layer and sequentially vacuum-depositing Liq (15 Å) and Al (1200 Å) on the electron transport layer to form a cathode. The organic light emitting diode had the following five organic thin film-layered structure, specifically.

A structure of ITO/compound A (700 Å)/compound B (50 Å)/compound C (1020 Å)/EML [compound 1:6-1:Ir(ppy)$_3$=45 wt %:45 wt %:10 wt %] (400 Å)/compound D:Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Example 17

An organic light emitting diode was manufactured according to the same method as Example 16 except for using the compound 2 and the compound B-31 in a weight ratio of 1:1.

Example 18

An organic light emitting diode was manufactured according to the same method as Example 16 except for using the compound 2 and the compound B-154 in a weight ratio of 1:1.

Example 19

An organic light emitting diode was manufactured according to the same method as Example 16 except for using the compound 2 and the compound B-156 in a weight ratio of 1:1.

Example 20

An organic light emitting diode was manufactured according to the same method as Example 16 except for using the compound 2 and the compound C-1 in a weight ratio of 1:1.

Example 21

An organic light emitting diode was manufactured according to the same method as Example 16 except for using the compound 10 and the compound B-31 in a weight ratio of 1:1.

Example 22

An organic light emitting diode was manufactured according to the same method as Example 16 except for using the compound 34 and the compound B-31 in a weight ratio of 1:1.

Example 23

An organic light emitting diode was manufactured according to the same method as Example 16 except for using the compound 42 and the compound B-31 in a weight ratio of 1:1.

Example 24

An organic light emitting diode was manufactured according to the same method as Example 16 except for using the compound 65 and the compound B-31 in a weight ratio of 1:1.

Example 25

An organic light emitting diode was manufactured according to the same method as Example 16 except for using the compound 142 and the compound B-31 in a weight ratio of 1:1.

Comparative Examples 4 to 6

Each organic light emitting diode according to Comparative Examples 4 to 6 was manufactured according to the same method as Example 16 except for using CBP, the compound a, or the compound b alone as a host.

Evaluation

Luminous efficiency and life-span characteristics of each organic light emitting diode according to Examples 16 to 25 and Comparative Examples 4 to 6 were measured.

Specific measurement methods are as follows, and the results are shown in the following Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

A life span was obtained by measuring a time when current efficiency (cd/A) was decreased down to 97%, while luminance (cd/m$^2$) was maintained to be 6000 cd/m$^2$.

TABLE 2

| | First host | Second host | First host:Second host | Luminous efficiency (cd/A) | Life-span T 97 (h) |
|---|---|---|---|---|---|
| Example 16 | compound 2 | B-1 | 1:1 | 46.2 | 65 |
| Example 17 | compound 2 | B-31 | 1:1 | 53.5 | 71 |
| Example 18 | compound 2 | B-154 | 1:1 | 52.8 | 68 |
| Example 19 | compound 2 | B-156 | 1:1 | 52.5 | 67 |
| Example 20 | compound 2 | C-1 | 1:1 | 50.1 | 62 |
| Example 23 | compound 10 | B-31 | 1:1 | 52.5 | 70 |
| Example 24 | compound 34 | B-31 | 1:1 | 54.0 | 72 |
| Example 25 | compound 42 | B-31 | 1:1 | 52.4 | 69 |
| Example 26 | compound 65 | B-31 | 1:1 | 55.3 | 60 |
| Example 27 | compound 142 | B-31 | 1:1 | 54.4 | 69 |
| Comparative Example 4 | CBP | — | | 31.7 | 25 |
| Comparative Example 5 | compound a | — | | 35.6 | 36 |
| Comparative Example 6 | compound b | — | | 36.1 | 35 |

Referring to Table 2, the organic light emitting diodes according to Examples 16 to 25 showed remarkably improved luminous efficiency and life-span characteristics compared with the organic light emitting diodes according to Comparative Examples 3 to 6.

(Manufacture of Organic Light Emitting Diode)

Example 26

A glass substrate coated with ITO (indium tin oxide) as a 1500 Å-thick thin film was washed with a distilled water. After the washing with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, a 700 Å-thick hole injection layer was formed on the ITO substrate by vacuum-depositing the compound A, and a hole transport layer was formed on the injection layer by depositing the compound B to be 50 Å thick and the compound C to be 1020 Å thick. Then, a 200 Å-thick emission layer was formed thereon by vacuum-depositing BH113 and BD370 (dealer: SFC Inc.) as a blue fluorescent luminescent host and a dopant in a dopant concentration of 5 wt %. On the emission layer, the compound 1 was vacuum-deposited to form a 50 Å-thick electron transport auxiliary layer. The electron transport auxiliary layer may be formed by using a material represented by Chemical Formula I alone or mixing the material with the compounds B and C. On the electron transport auxiliary layer, a 300 Å-thick electron transport layer was formed by vacuum-depositing the compound D and Liq simultaneously in a weight ratio of 1:1, and on the electron transport layer, a cathode was formed by sequentially vacuum-depositing Liq to be 15 Å thick and Al to be 1200 Å thick, manufacturing an organic light emitting diode. The organic light emitting diode had a structure of 5 organic thin film layers and specifically, ITO/compound A (700 Å)/compound B (50 Å)/compound C (1020 Å)/EML [BH113:BD370=95:5 (wt:wt)] (200 Å)/compound 1 (50 Å)/compound D:Liq (300 Å)=1:1/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Examples 27 to 40

Each organic light emitting diode according to Examples 27 to 40 was manufactured according to the same method as Example 26 except for respectively using the compounds 2, 3, 6, 9, 10, 18, 26, 33, 34, 41, 42, 65, 113, and 142.

Comparative Example 7

An organic light emitting diode was manufactured according to the same method as Example 26 except for using the compound a.

Comparative Example 8

An organic light emitting diode was manufactured according to the same method as Example 26 except for using the compound b.

Comparative Example 9

An organic light emitting diode was manufactured according to the same method as Example 26 except for using no electron transport auxiliary layer.

Evaluation

Current density change, luminance change, and luminous efficiency of each organic light emitting diode according to Examples 26 to 40 and Comparative Examples 7 to 9 were measured.

Specific measurement methods are as follows, and the results are shown in Table 3.

(1) Measurement of Current Density Change Depending on Voltage Change

The obtained organic light emitting diodes were measured regarding current value flowing in the unit device while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-span

T97 life-spans of the organic light emitting diodes according to Examples 26 to 40 and Comparative Examples 7 to 9 were measured as a time when their luminance decreased down to 97% relative to the initial luminance (cd/m$^2$) after emitting light with 750 cd/m$^2$ as the initial luminance (cd/m$^2$) and measuring their luminance decrease depending on a time with a Polanonix life-span measurement system.

TABLE 3

| Devices | Electron transport auxiliary layer (weight ratio) | Luminous efficiency (cd/A) | Color coordinate (x, y) | T97 (h) @750 nit |
|---|---|---|---|---|
| Example 26 | compound 1 | 8.5 | (0.132, 0.149) | 66 |
| Example 27 | compound 2 | 8.8 | (0.133, 0.148) | 69 |
| Example 28 | compound 3 | 8.5 | (0.132, 0.149) | 66 |
| Example 29 | compound 6 | 8.5 | (0.132, 0.150) | 65 |
| Example 30 | compound 9 | 8.4 | (0.132, 0.149) | 65 |
| Example 31 | compound 10 | 8.6 | (0.133, 0.148) | 67 |
| Example 32 | compound 18 | 7.9 | (0.132, 0.149) | 62 |
| Example 33 | compound 26 | 7.7 | (0.132, 0.159) | 61 |
| Example 34 | compound 33 | 8.3 | (0.133, 0.149) | 65 |
| Example 35 | compound 34 | 8.5 | (0.133, 0.148) | 68 |
| Example 36 | compound 41 | 8.2 | (0.132, 0.149) | 64 |
| Example 37 | compound 42 | 8.5 | (0.133, 0.149) | 66 |
| Example 38 | compound 65 | 8.7 | (0.132, 0.149) | 62 |
| Example 39 | compound 113 | 8.1 | (0.133, 0.148) | 63 |
| Example 40 | compound 142 | 8.8 | (0.132, 0.149) | 69 |
| Comparative Example 7 | compound a | 7.5 | (0.132, 0.149) | 58 |
| Comparative Example 8 | compound b | 7.5 | (0.132, 0.149) | 57 |
| Comparative Example 9 | Not used | 5.8 | (0.135, 0.147) | 25 |

Referring to Table 3, the organic light emitting diodes according to Examples 26 to 40 showed simultaneously improved luminous efficiency and life-span characteristics compared with the organic light emitting diodes according to Comparative Examples 7 to 9.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectronic device represented by Chemical Formula 1:

[Chemical Formula 1]

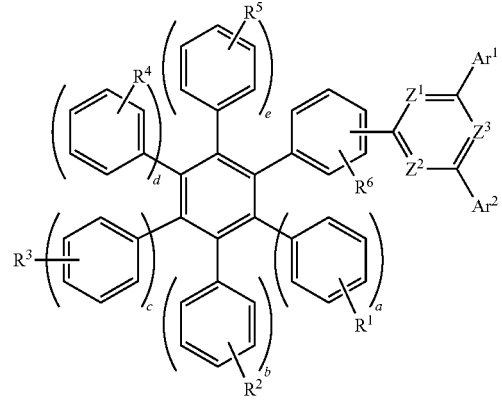

wherein, in Chemical Formula 1,
R$^1$ to R$^5$ are independently hydrogen, a deuterium, a substituted or unsubstituted C1 to C4 alkyl group, or a phenyl group,
Z$^1$ to Z$^3$ are independently CR$^a$ or N,
at least two of Z$^1$ to Z$^3$ are N, $R^a$ and $R^6$ are hydrogen, a deuterium, a substituted or unsubstituted C1 to C10 alkyl group, or a substituted or unsubstituted C6 to C12 aryl group, $Ar^1$ and $Ar^2$ are independently hydrogen, a deuterium, a substituted or unsubstituted C1 to C10 alkyl group, or a substituted or unsubstituted C6 to C18 aryl group, a, b, c, d, and e are independently an integer of 0 or 1, $4 \leq a+b+c+d+e \leq 5$, and the "substituted" refers to replacement of at least one hydrogen by deuterium, a C1 to C4 alkyl group, or a C6 to C12 aryl group.

2. The compound of claim 1, wherein the Chemical Formula 1 is represented by Chemical Formula 1-I or 1-II:

[Chemical Formula 1-I]

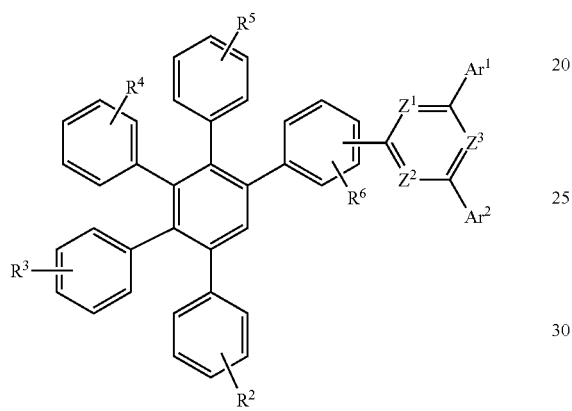

[Chemical Formula 1-II]

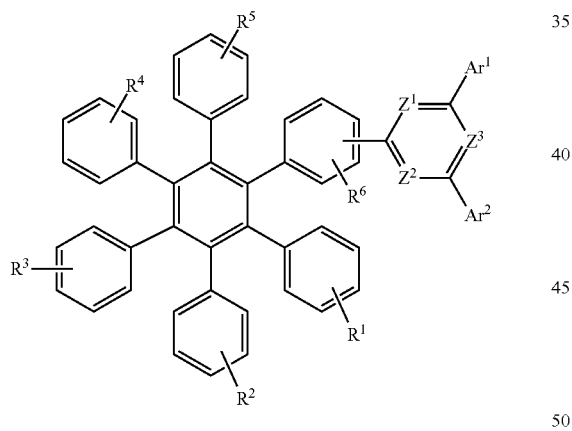

wherein, in Chemical Formulae 1-I and 1-II, $R^1$ to $R^5$ are independently hydrogen, a deuterium, a substituted or unsubstituted C1 to C4 alkyl group, or a phenyl group, $Z^1$ to $Z^3$ are independently $CR^a$ or N, at least two of $Z^1$ to $Z^3$ are N, $R^a$ and $R^6$ are hydrogen, a deuterium, a substituted or unsubstituted C1 to C10 alkyl group, or a substituted or unsubstituted C6 to C12 aryl group, and $Ar^1$ and $Ar^2$ are independently hydrogen, a deuterium, a substituted or unsubstituted C1 to C10 alkyl group, or a substituted or unsubstituted C6 to C18 aryl group.

3. The compound of claim 2, wherein the Chemical Formula 1-I is represented by Chemical Formula 1-Ia, 1-Ib, or 1-Ic:

[Chemical Formula 1-Ia]

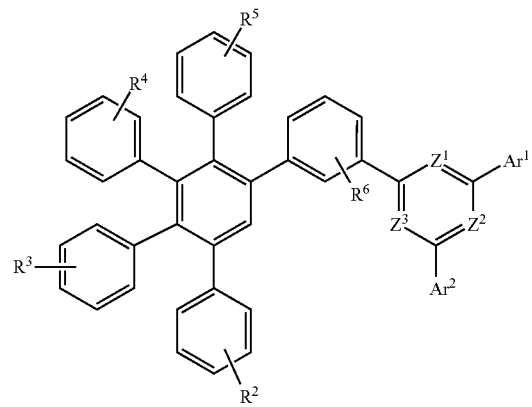

[Chemical Formula 1-Ib]

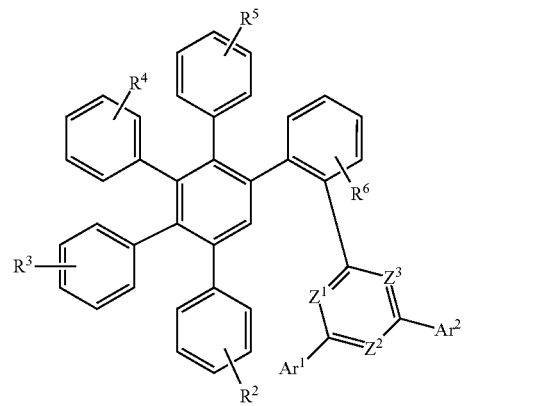

[Chemical Formula 1-Ic]

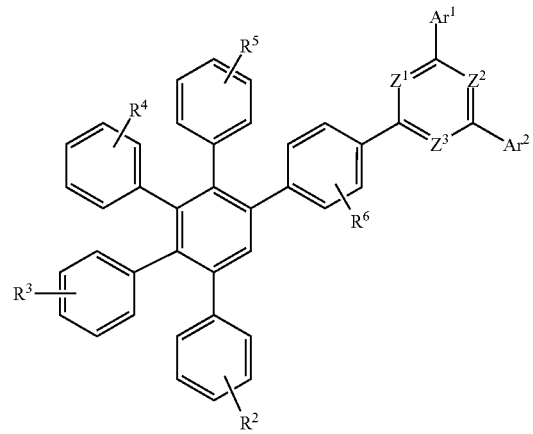

wherein, in Chemical Formulae 1-Ia to 1-Ic, $R^2$ to $R^5$ are independently hydrogen, a deuterium, a substituted or unsubstituted C1 to C4 alkyl group, or a phenyl group, $Z^1$ to $Z^3$ are independently $CR^a$ or N, at least two of $Z^1$ to $Z^3$ are N, $R^a$ and $R^6$ are hydrogen, deuterium, a substituted or unsubstituted C1 to C10 alkyl group, or a substituted or unsubstituted C6 to C12 aryl group, and $Ar^1$ and $Ar^2$ are independently hydrogen, deuterium, a substituted or unsubstituted C1 to C10 alkyl group, or a substituted or unsubstituted C6 to C18 aryl group.

4. The compound of claim 2, wherein the Chemical Formula 1-II is represented by Chemical Formula 1-IIa, 1-IIb, or 1-IIc:

[Chemical Formula 1-IIa]

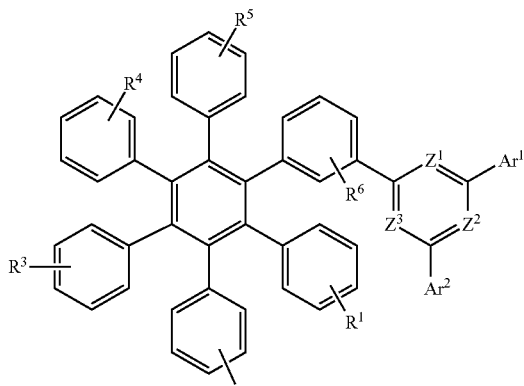

[Chemical Formula 1-IIb]

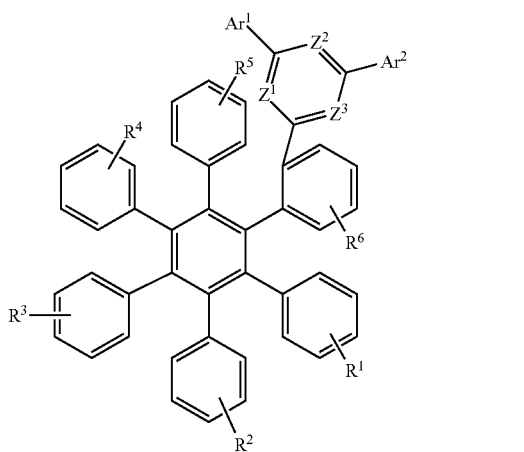

[Chemical Formula 1-IIc]

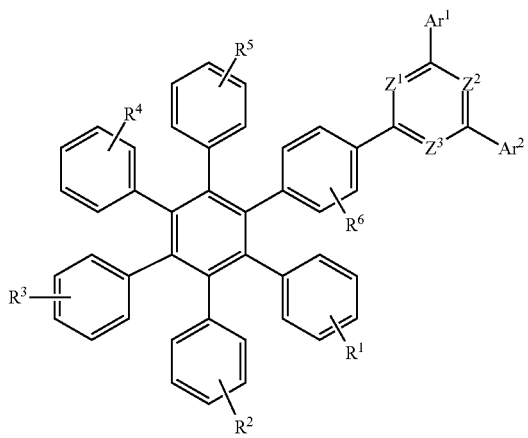

wherein, in Chemical Formulae 1-IIa to 1-IIc,
$R^1$ to $R^5$ are independently hydrogen, deuterium, a substituted or unsubstituted C1 to C4 alkyl group, or a phenyl group,
$Z^1$ to $Z^3$ are independently $CR^a$ or N,
at least two of $Z^1$ to $Z^3$ are N,
$R^a$ and $R^6$ are hydrogen, deuterium, a substituted or unsubstituted C1 to C10 alkyl group, or a substituted or unsubstituted C6 to C12 aryl group, and
$Ar^1$ and $Ar^2$ are independently hydrogen, deuterium, a substituted or unsubstituted C1 to C10 alkyl group, or a substituted or unsubstituted C6 to C18 aryl group.

5. The compound of claim 2, wherein the Chemical Formula 1-I is represented by Chemical Formula 1-Id or 1-Ie:

[Chemical Formula 1-Id]

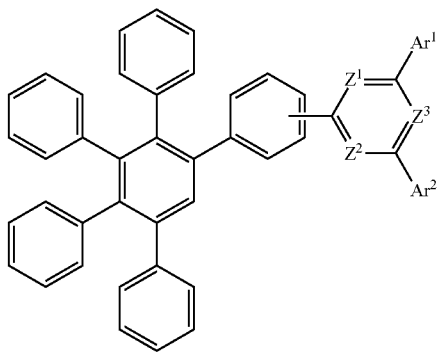

[Chemical Formula 1-Ie]

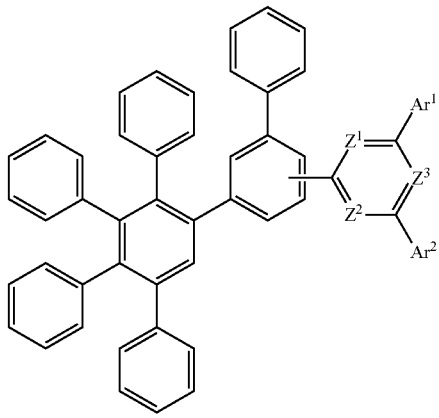

wherein, in Chemical Formulae 1-Id and 1-Ie,
$Z^1$ to $Z^3$ are independently $CR^a$ or N,
at least two of $Z^1$ to $Z^3$ are N,
$R^a$ is hydrogen, deuterium, a substituted or unsubstituted C1 to C10 alkyl group, or a substituted or unsubstituted C6 to C12 aryl group, and
$Ar^1$ and $Ar^2$ are independently hydrogen, deuterium, a substituted or unsubstituted C1 to C10 alkyl group, or a substituted or unsubstituted C6 to C18 aryl group.

6. The compound of claim 2, wherein the Chemical Formula 1-11 is represented by Chemical Formula 1-IId or 1-IIe:

[Chemical Formula 1-IId]

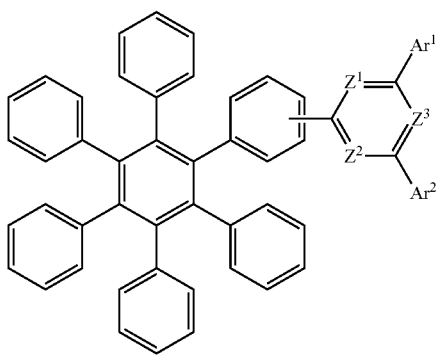

[Chemical Formula 1-IIe]

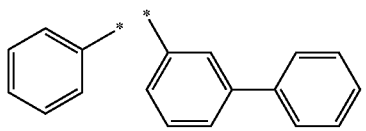

wherein, in Chemical Formulae 1-IId and 1-IIe, $Z^1$ to $Z^3$ are independently $CR^a$ or N, at least two of $Z^1$ to $Z^3$ are N, $R^a$ is hydrogen, deuterium, a substituted or unsubstituted C1 to C10 alkyl group, or a substituted or unsubstituted C6 to C12 aryl group, and $Ar^1$ and $Ar^2$ are independently hydrogen, deuterium, a substituted or unsubstituted C1 to C10 alkyl group, or a substituted or unsubstituted C6 to C18 aryl group.

7. The compound of claim 1, wherein the $Ar^1$ and $Ar^2$ are independently a substituted or unsubstituted phenyl group, a substituted or unsubstituted biphenyl group, a substituted or unsubstituted terphenyl group, or a substituted or unsubstituted naphthyl group.

8. The compound of claim 7, wherein the $Ar^1$ and $Ar^2$ are one of substituents of Group 1:

[Group 1]

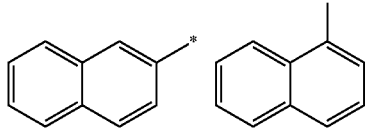

-continued

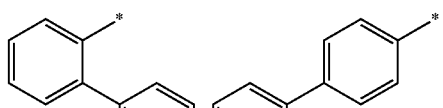

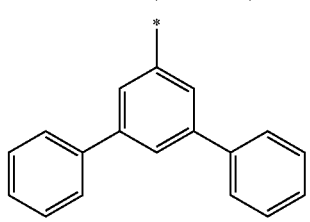

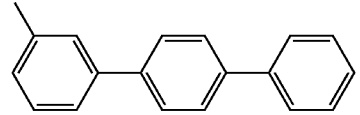

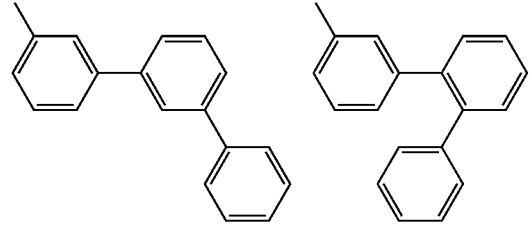

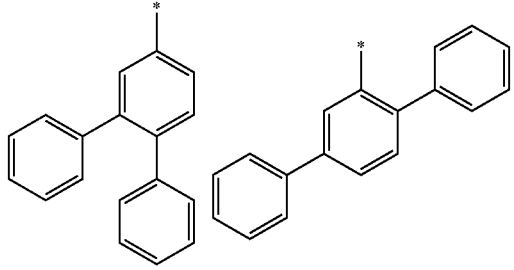

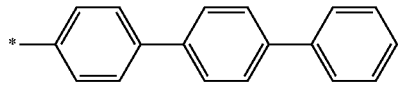

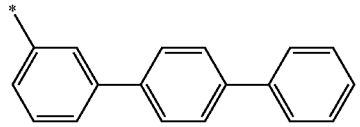

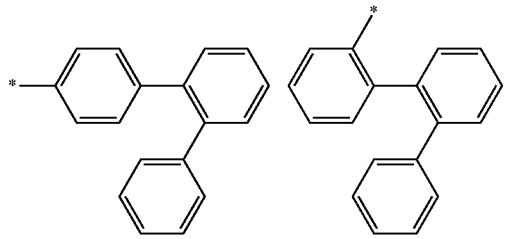

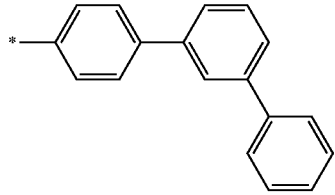

197
-continued
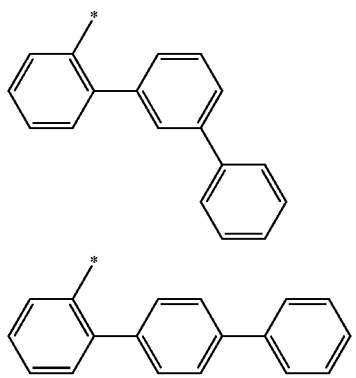
wherein, in Group 1, * is a linking point.
9. The compound of claim 1, wherein the compound is one of compounds of Group 2:
[Group 2]
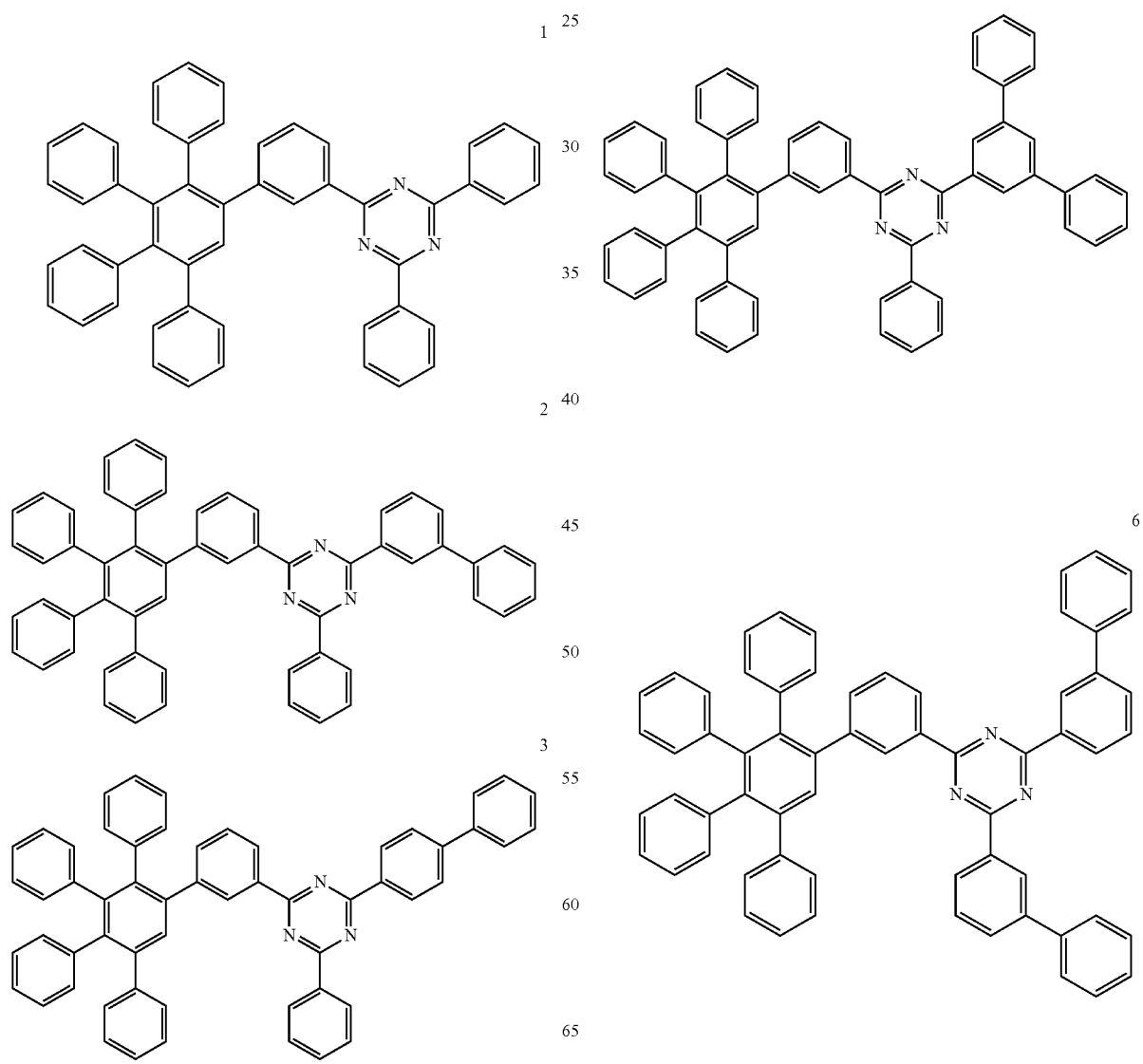
198
-continued
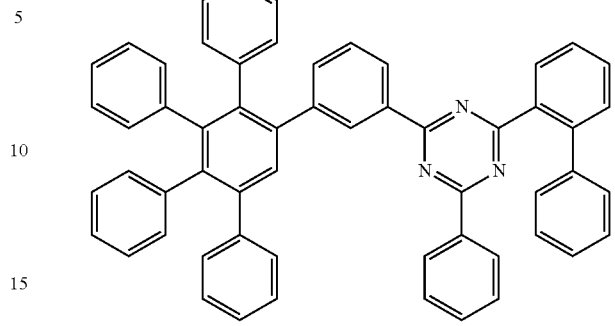

7
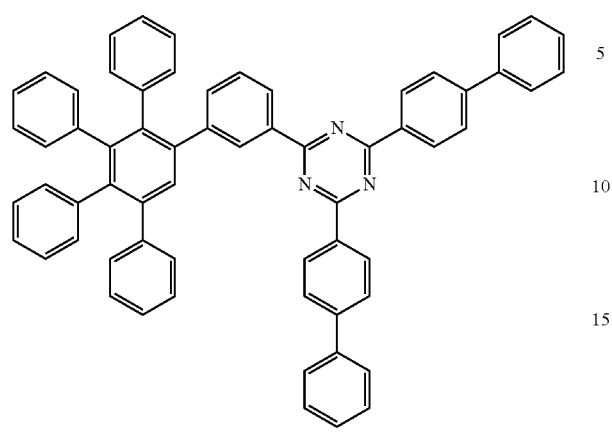
8
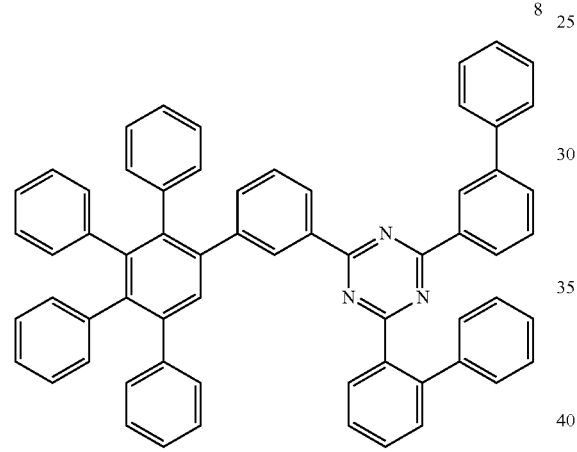
9
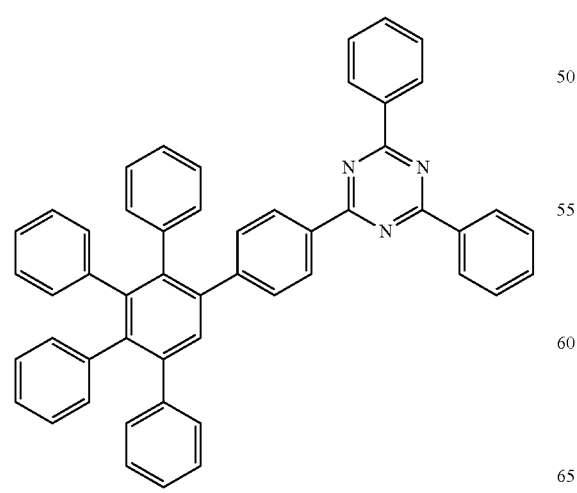
10
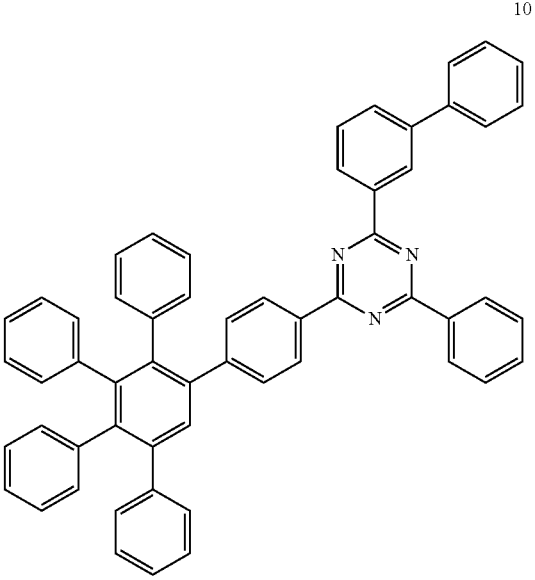
11
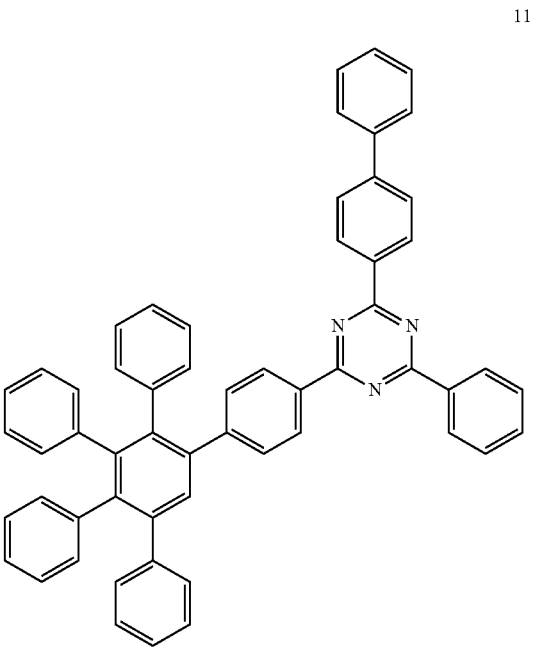

12
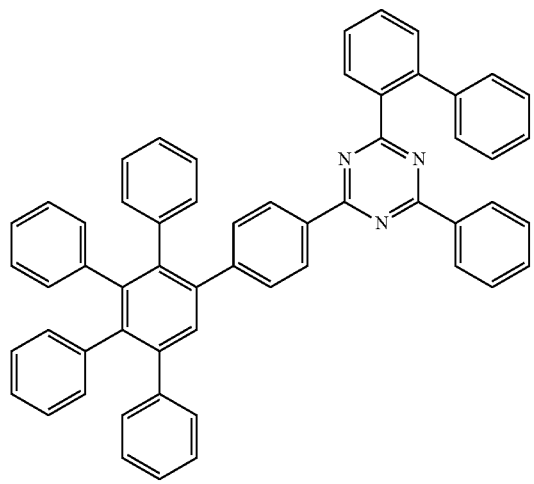
13
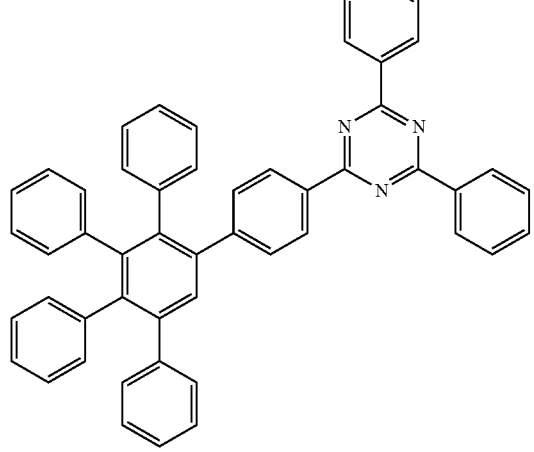
14
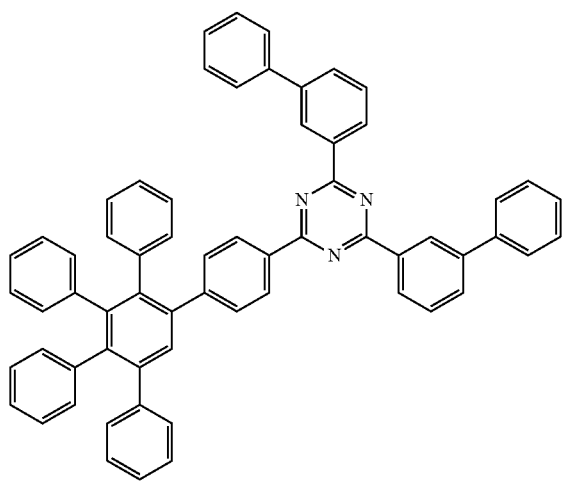
15
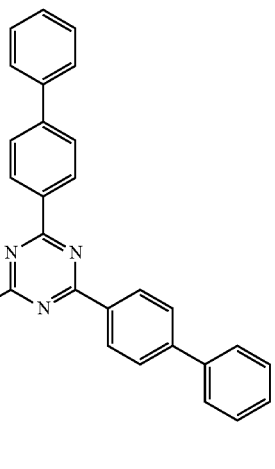
16
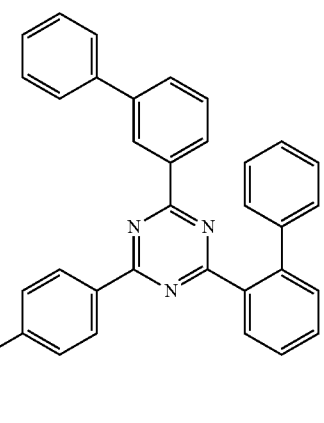
17

18
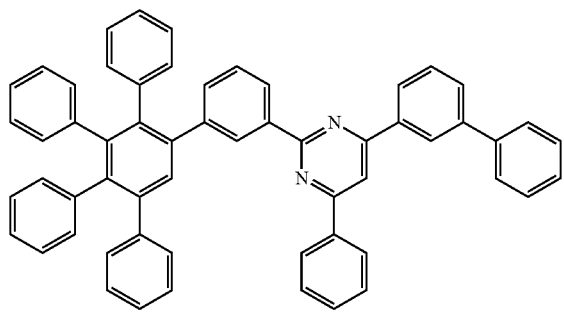
19
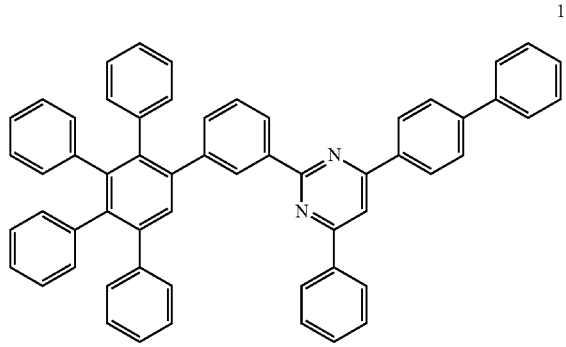
20
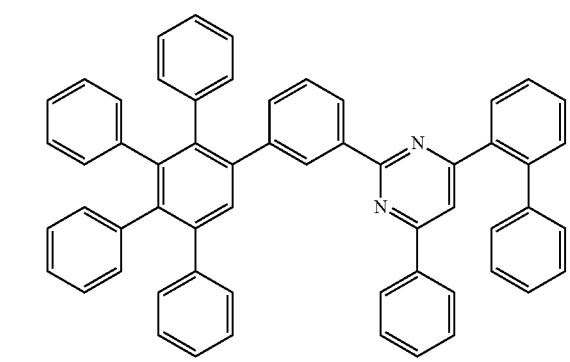
21
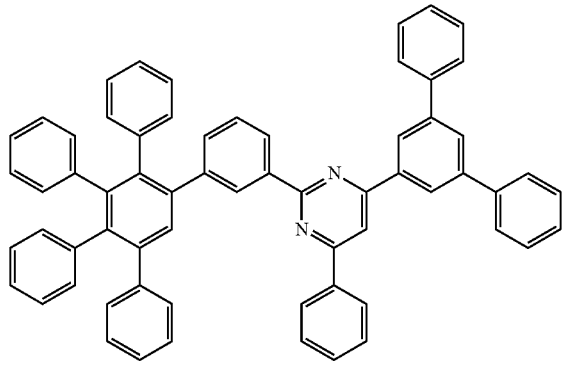
22
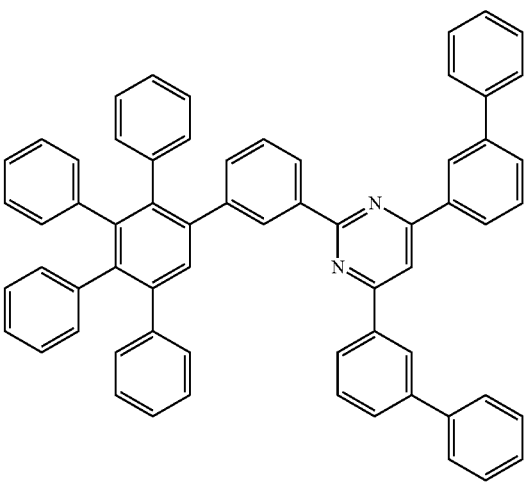
23
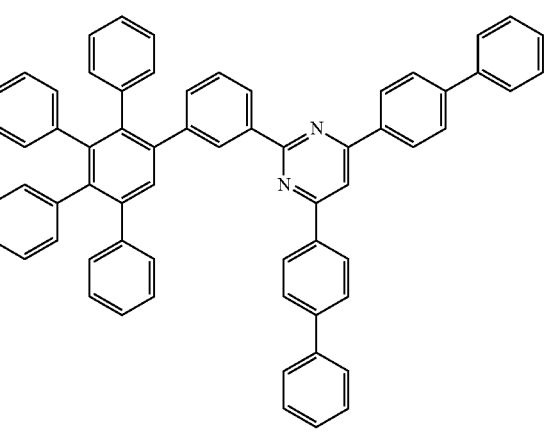
24
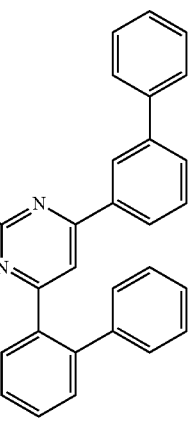

25
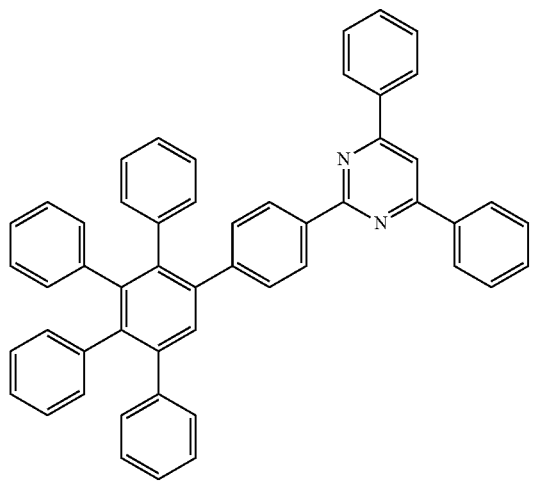
26
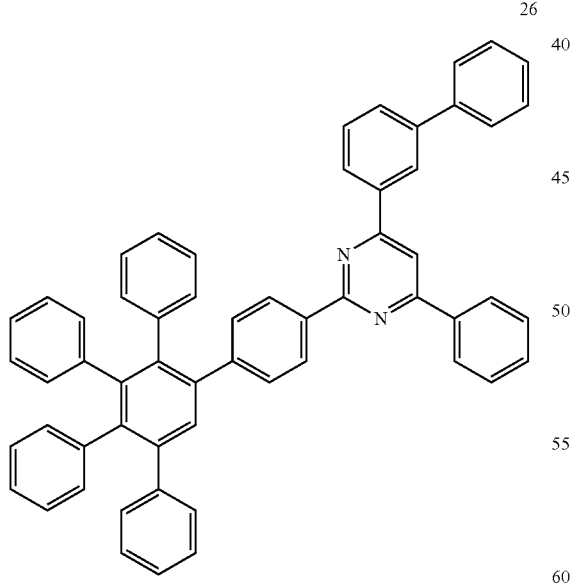
27
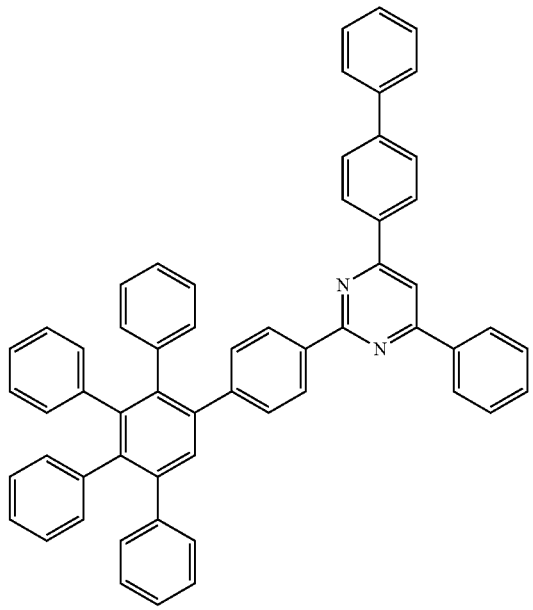
28
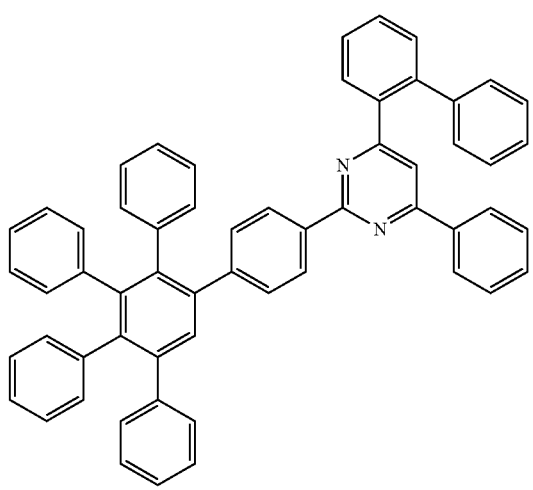

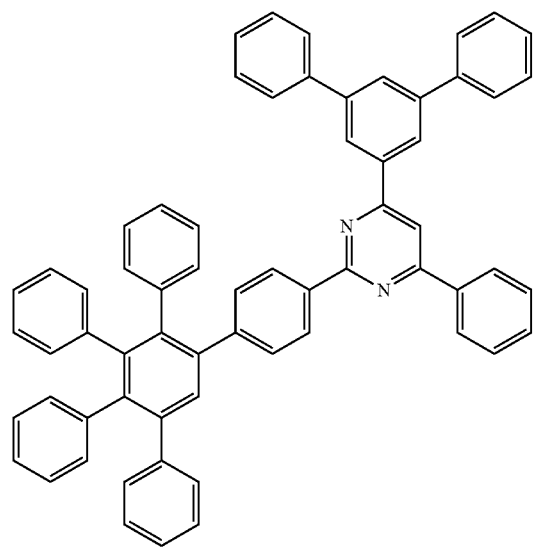
29
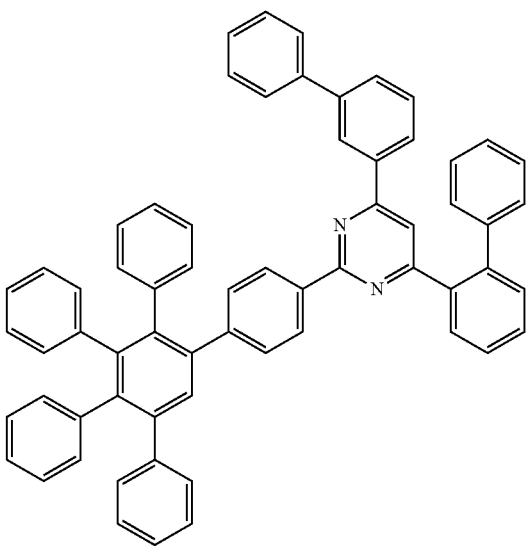
32
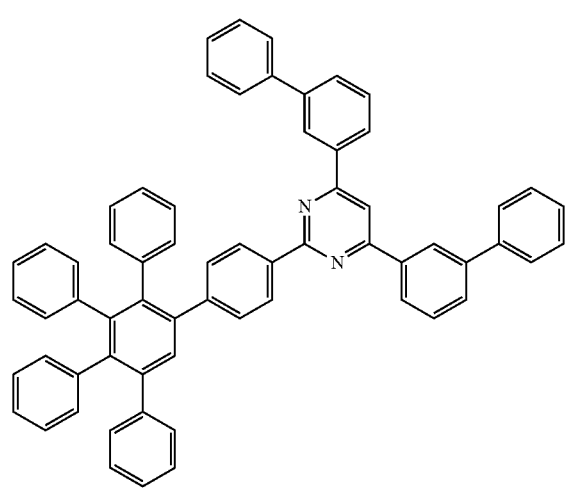
30
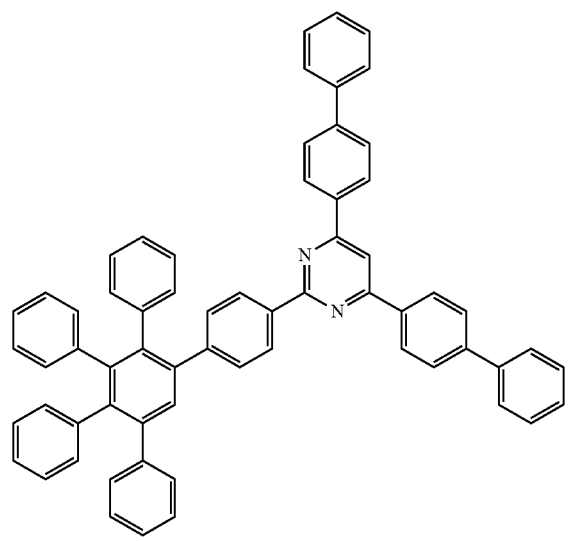
31
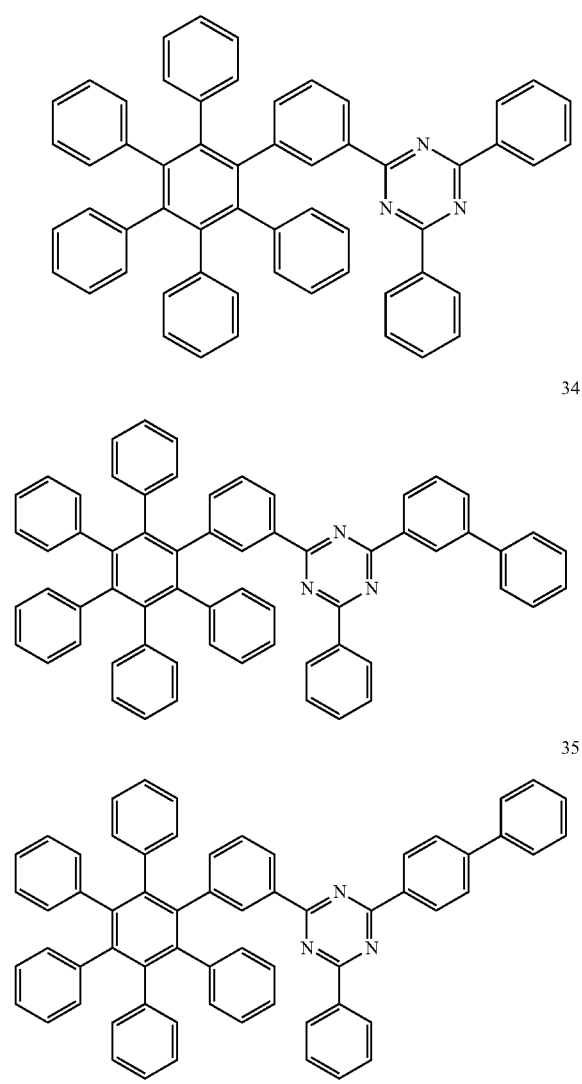
33
34
35

36
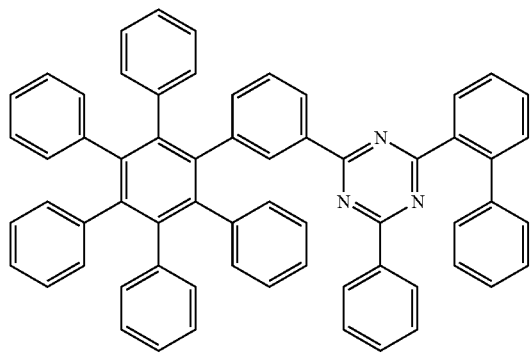
37
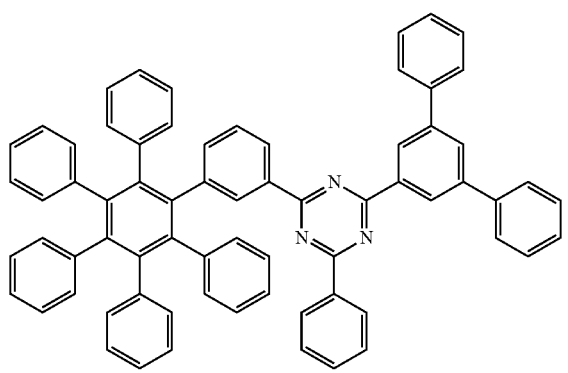
38
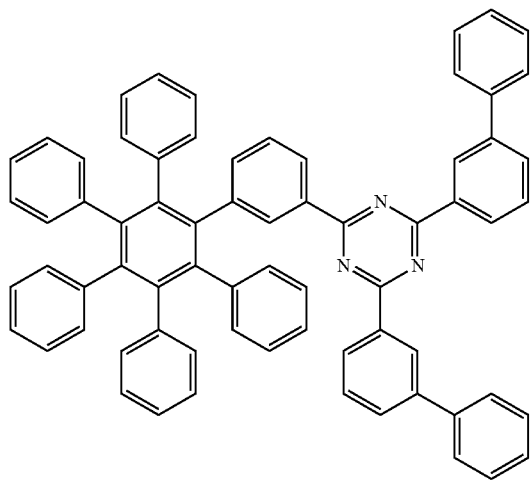
39
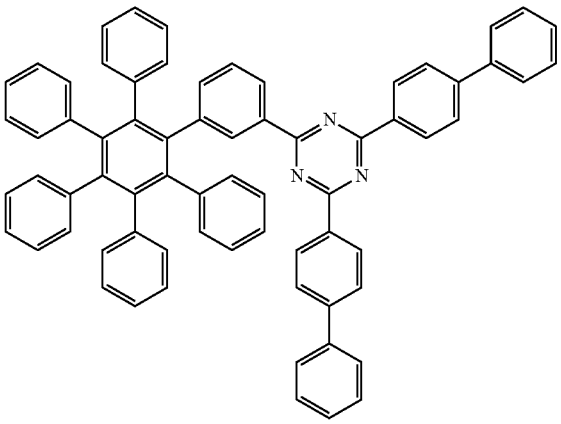
40
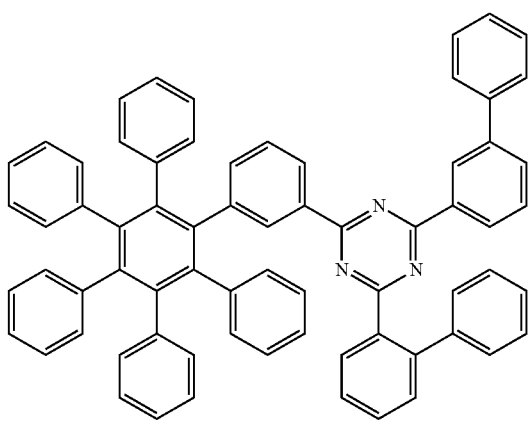
41
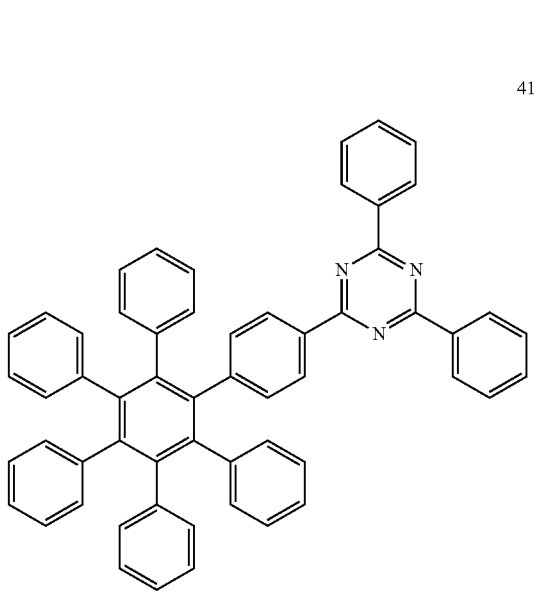

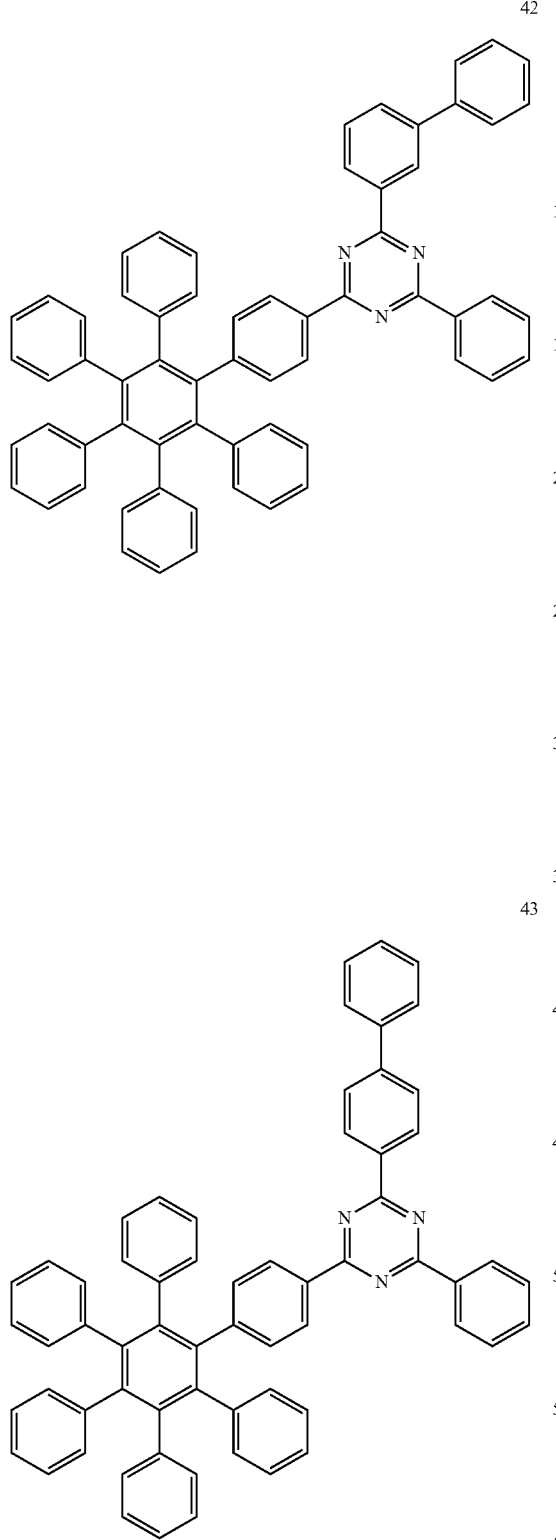
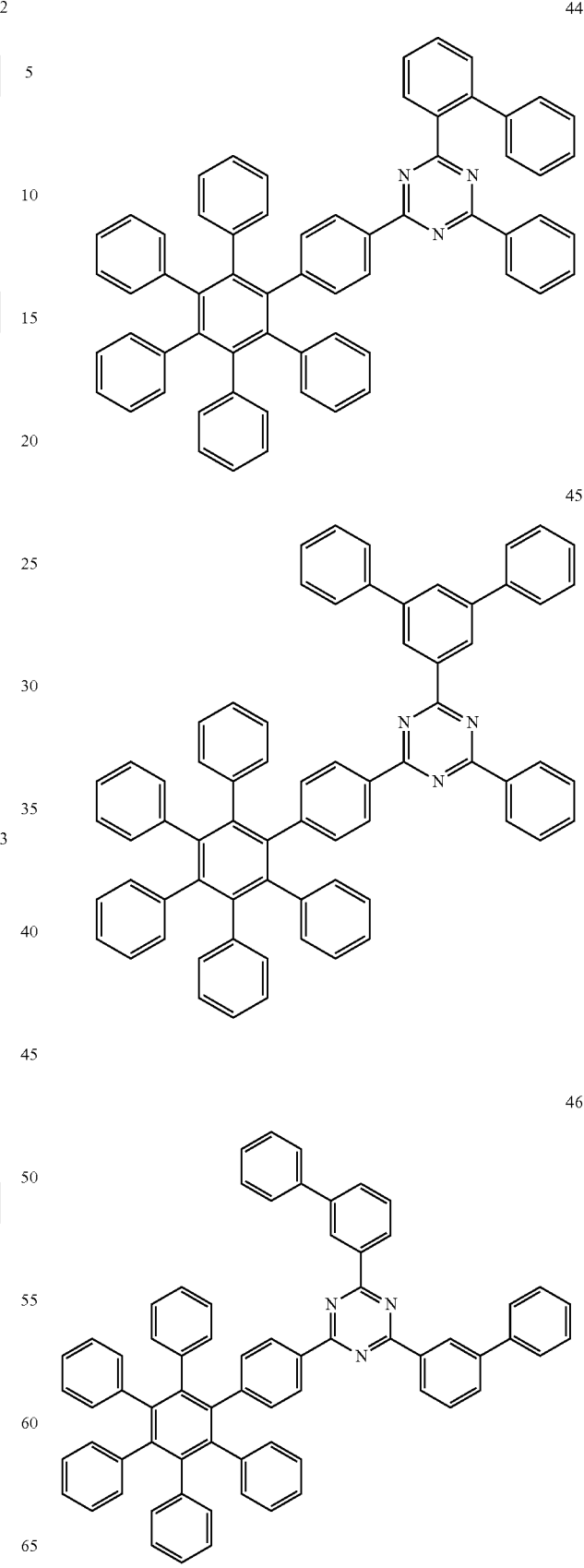

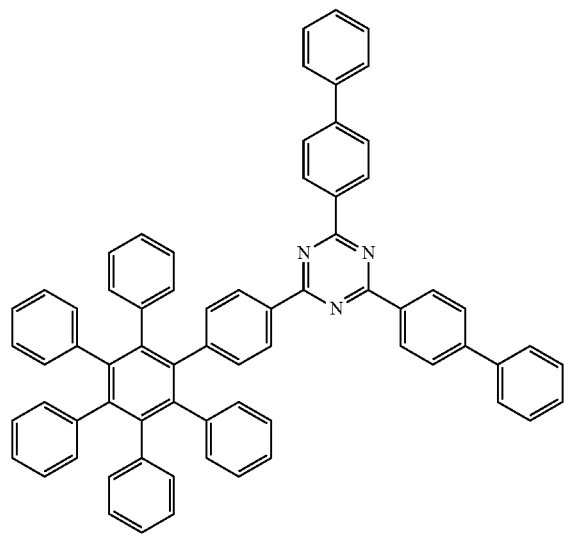
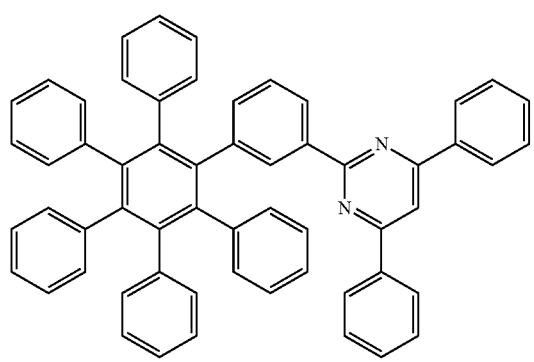
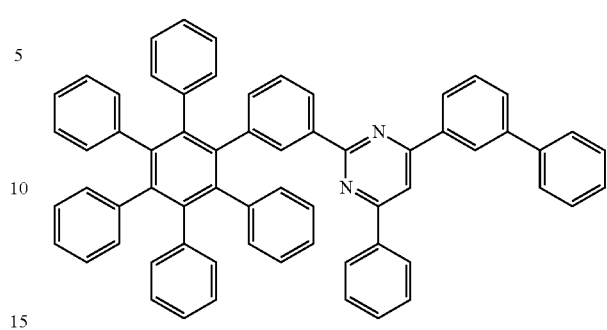
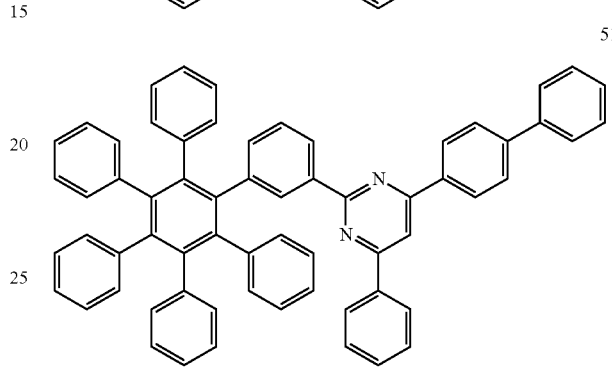
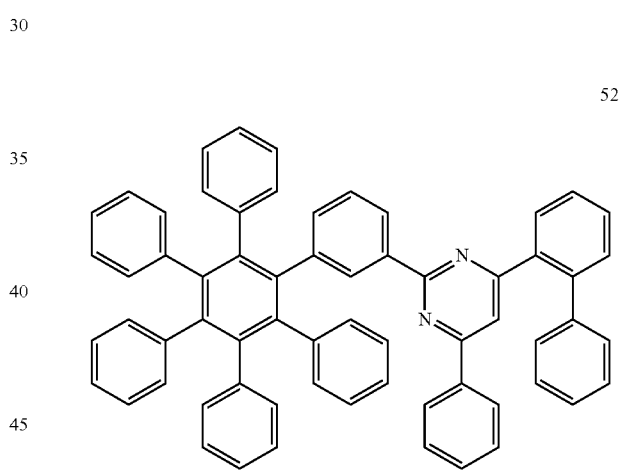
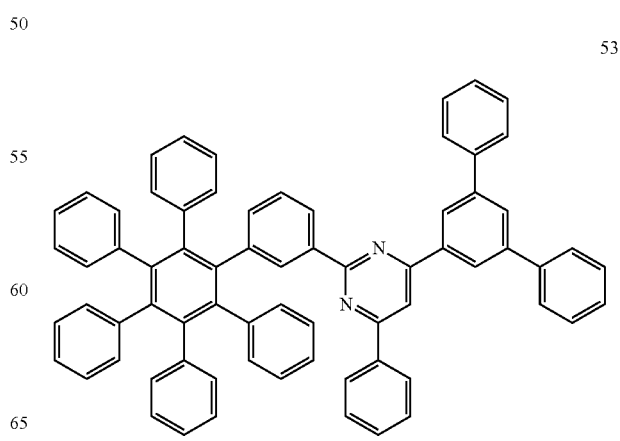

54
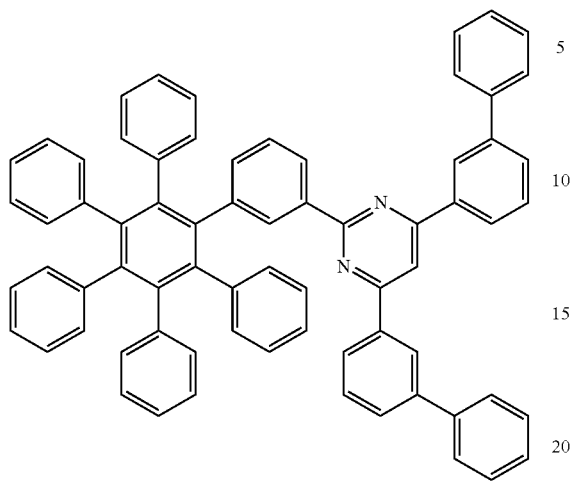
55
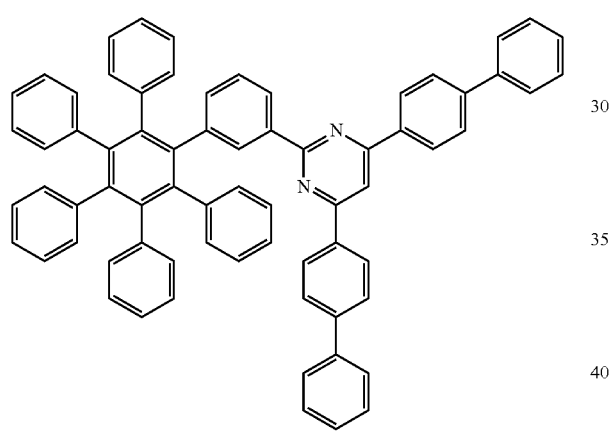
56
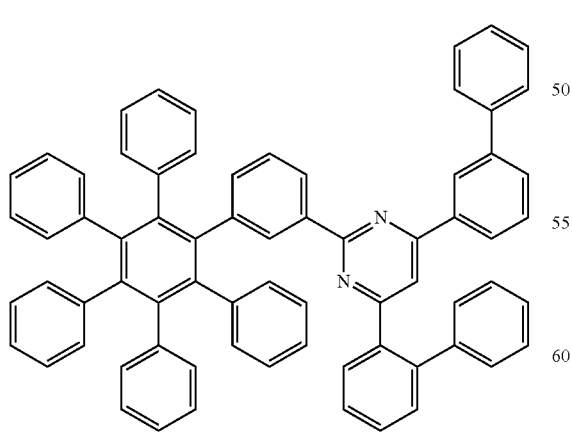
57
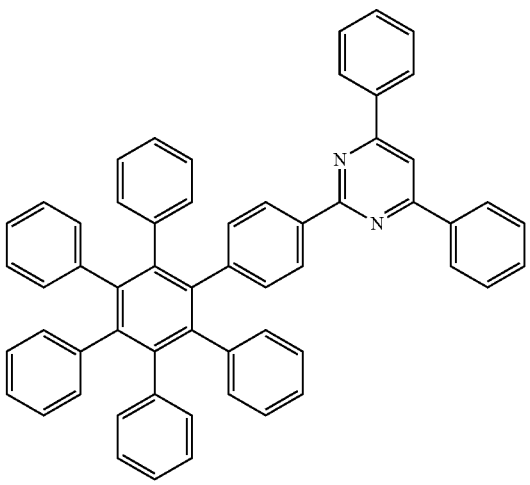
58
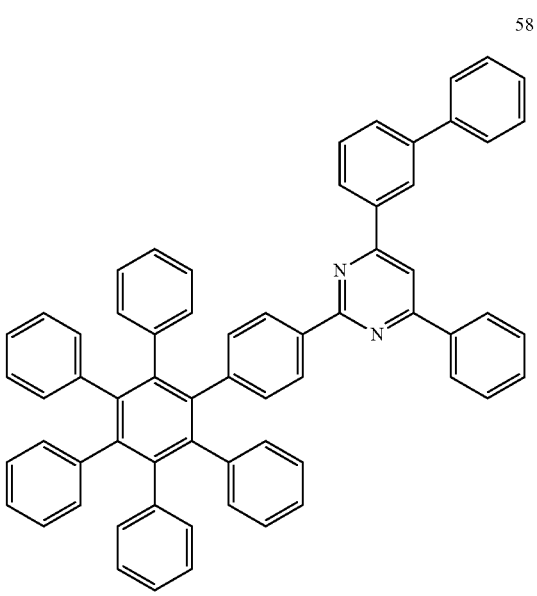

217
-continued
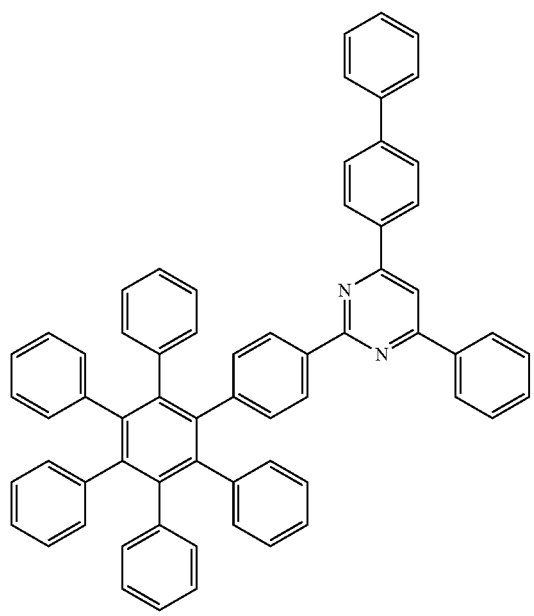
218
-continued
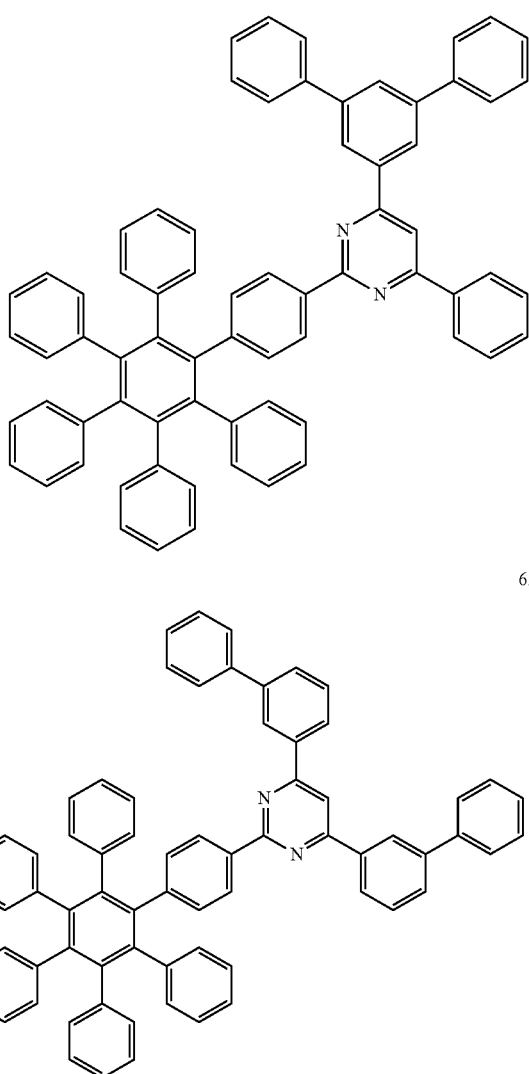
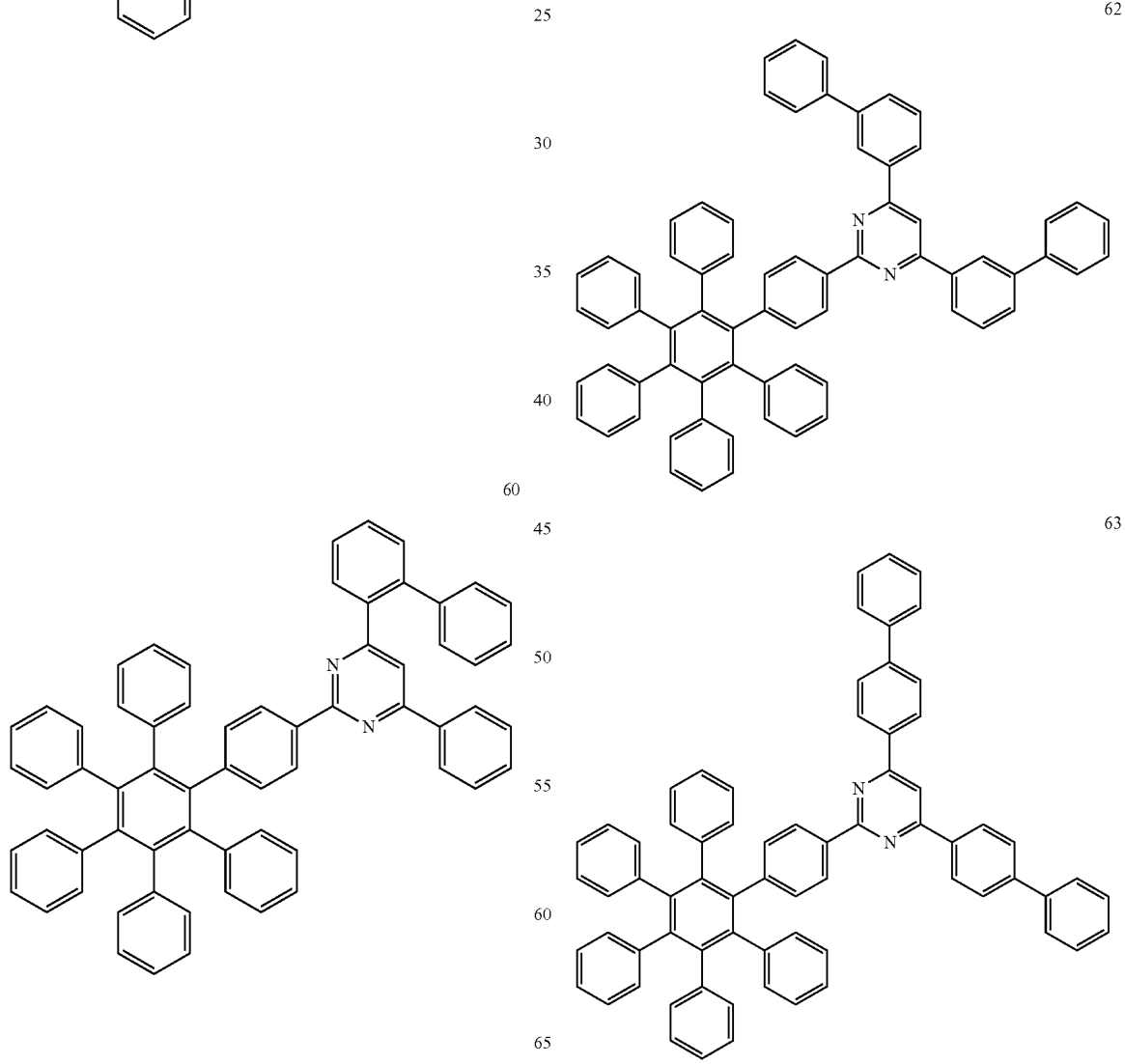

-continued
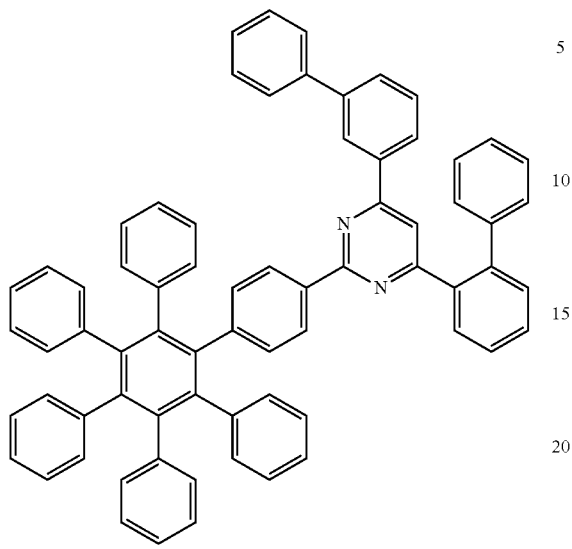
64
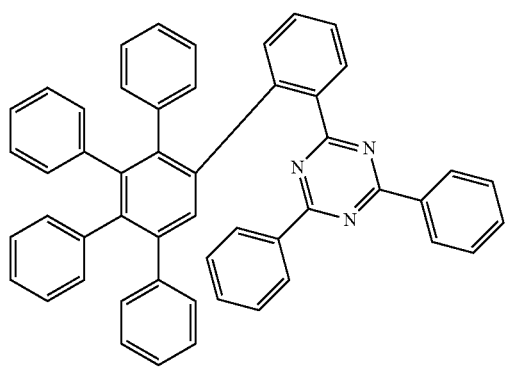
65
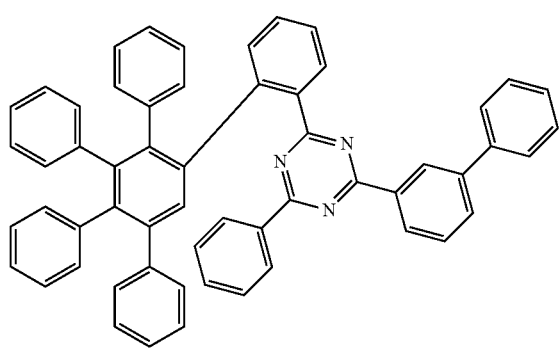
66
-continued
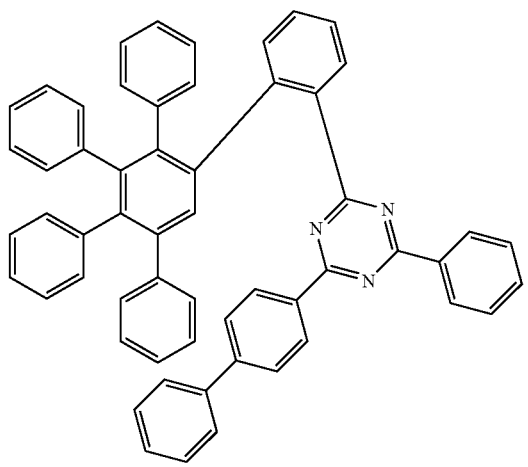
67
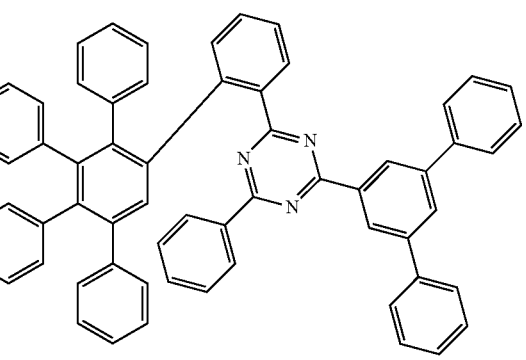
68
69

221
-continued
70
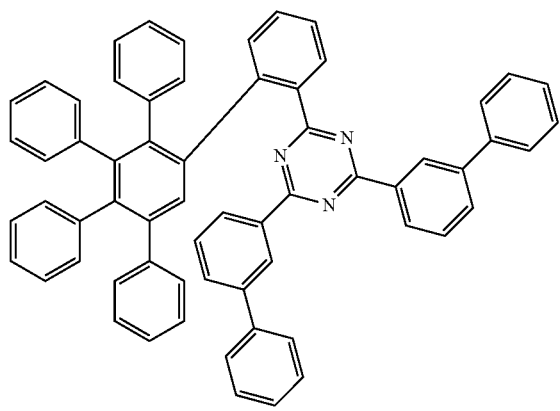
71
72
222
-continued
73
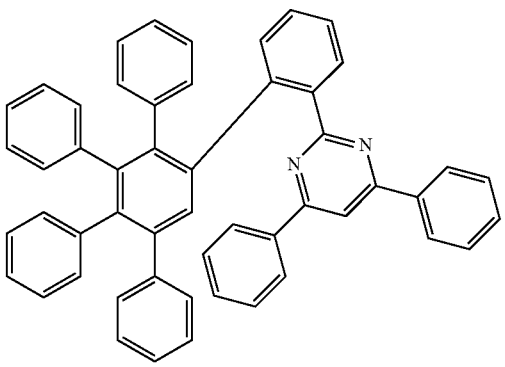
74
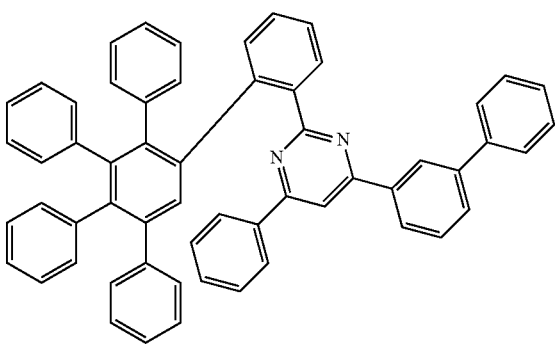
75
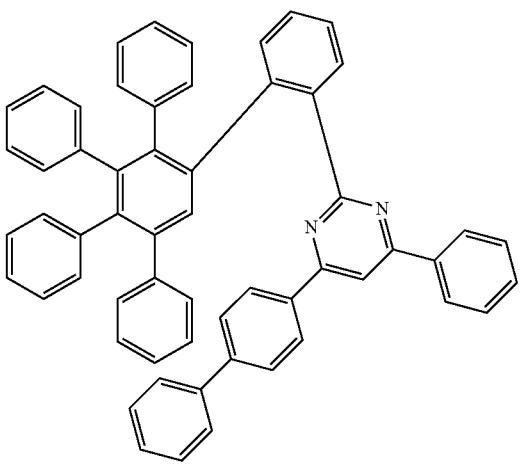
76
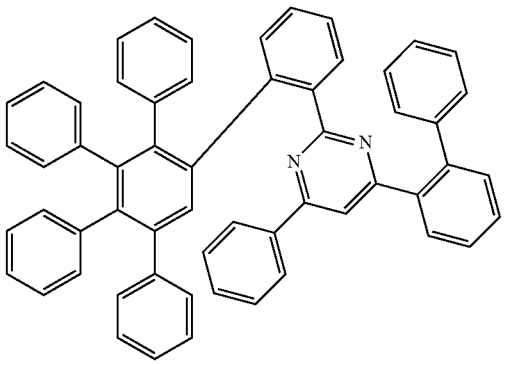

77
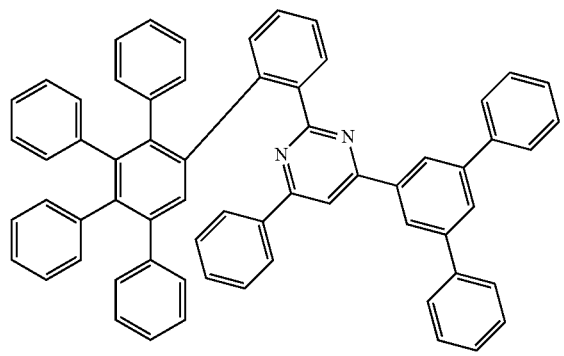
78
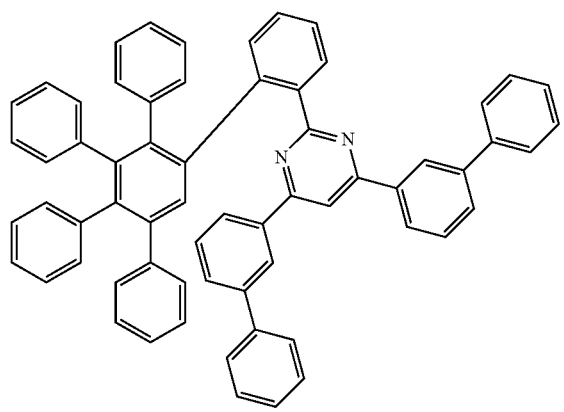
79
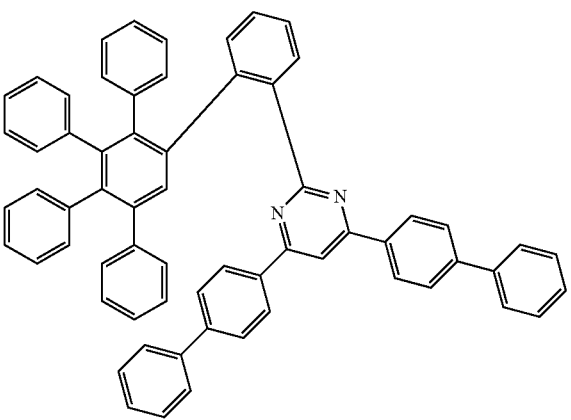
80
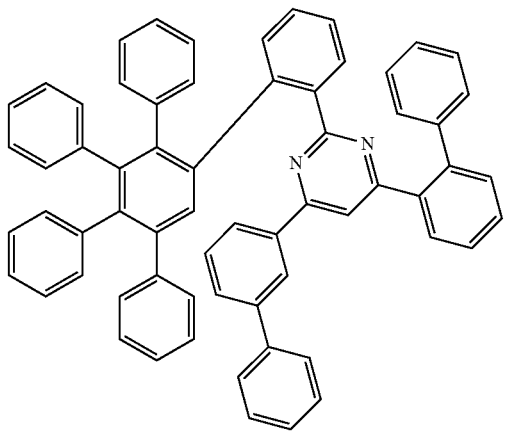
81
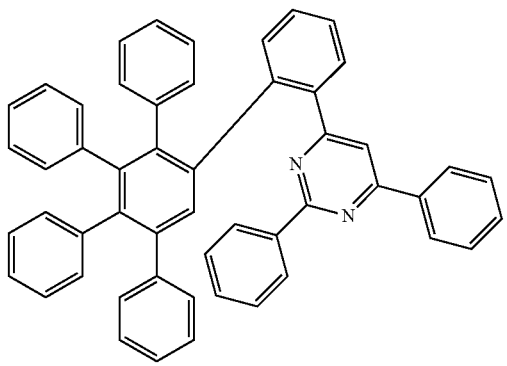
82
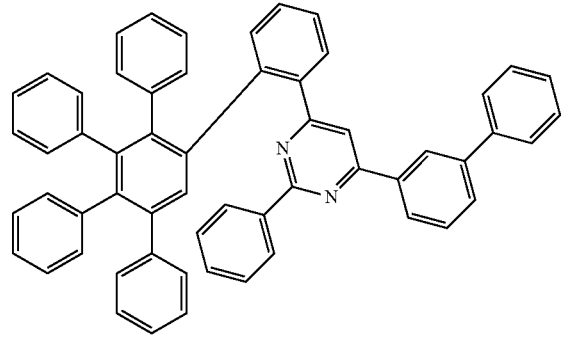

83
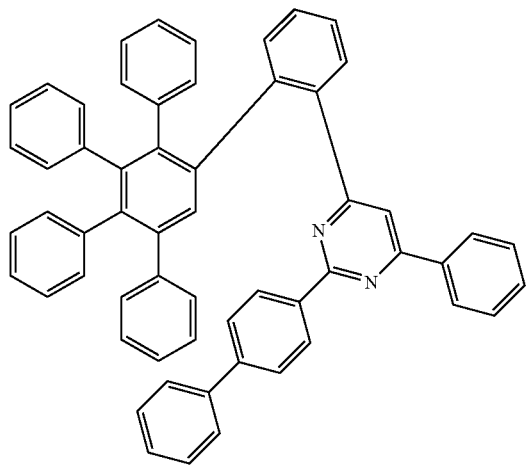
86
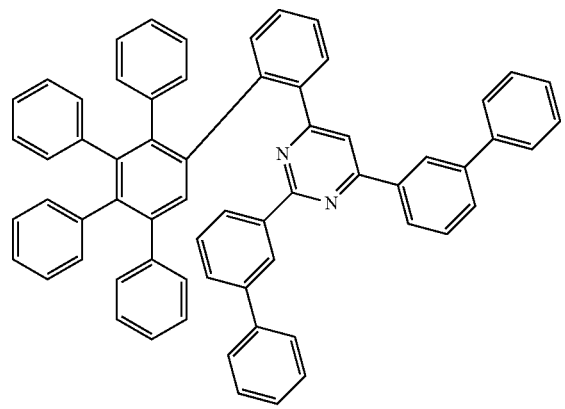
84
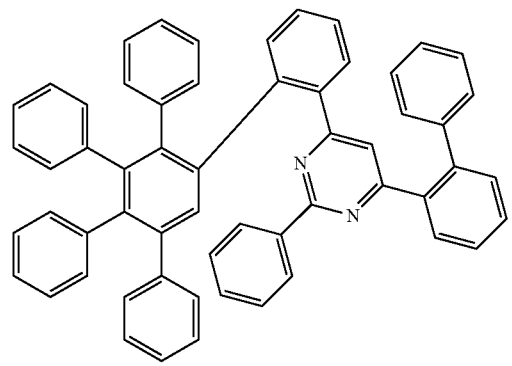
87
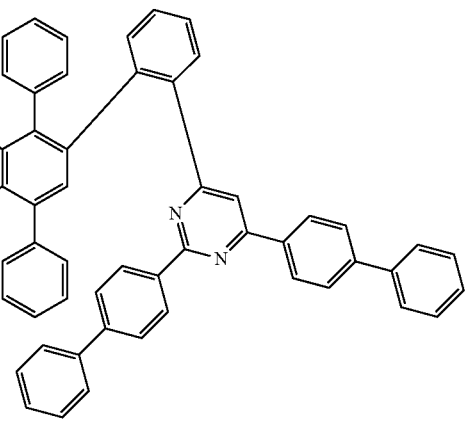
85
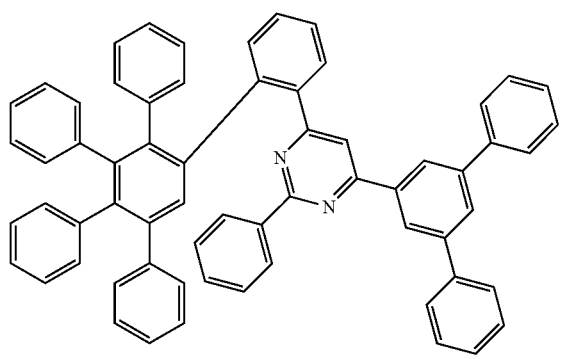
88
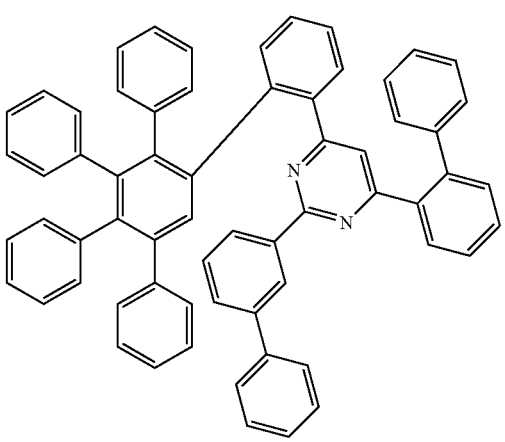

227
-continued
89
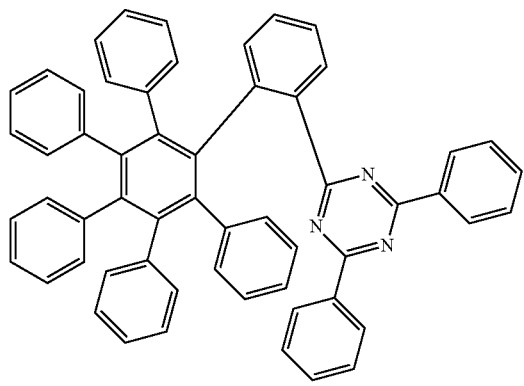
90
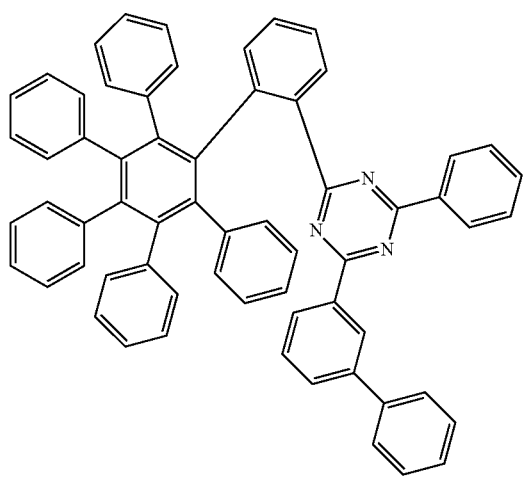
91
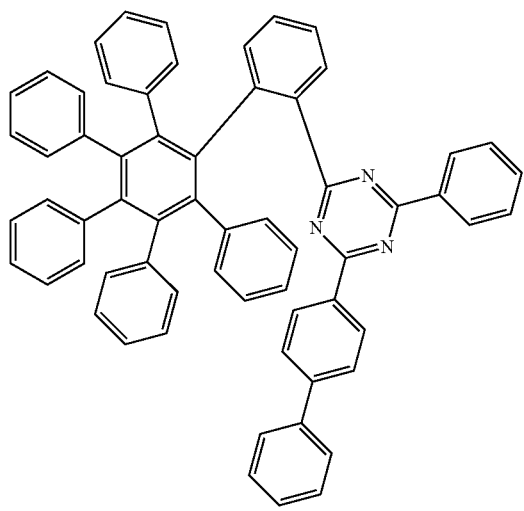
228
-continued
92
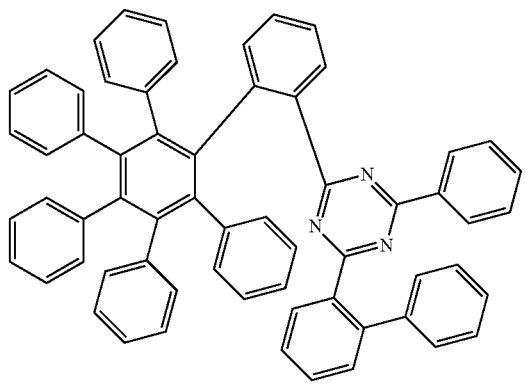
93
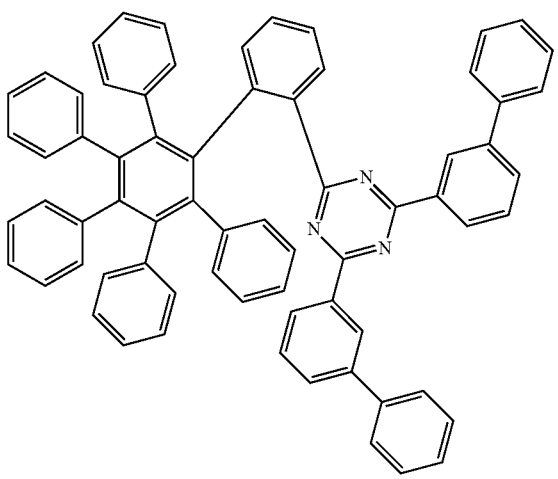
94

95
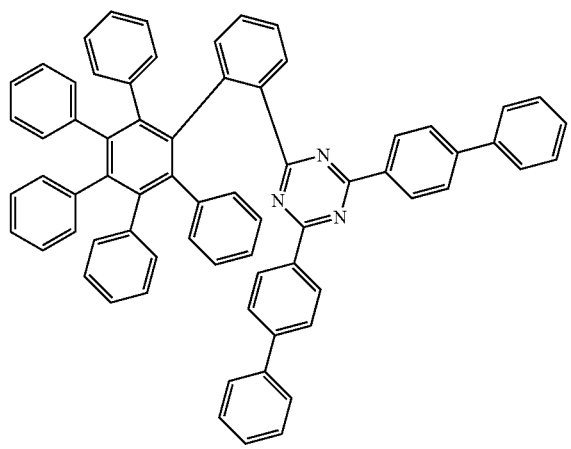
96
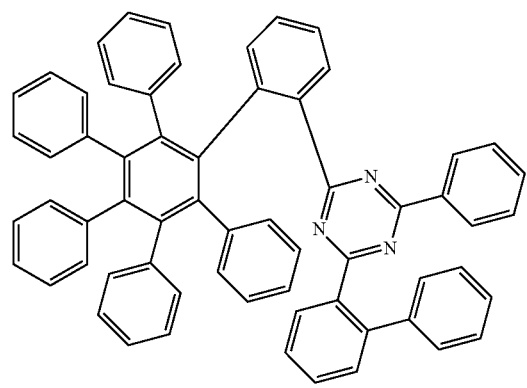
97
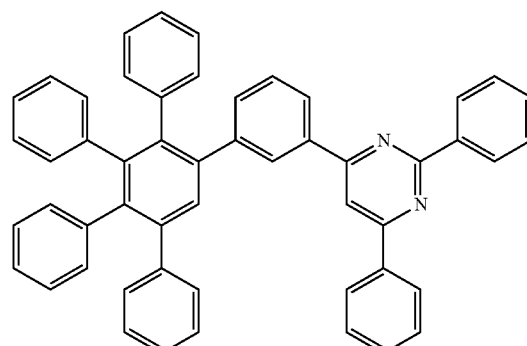
98
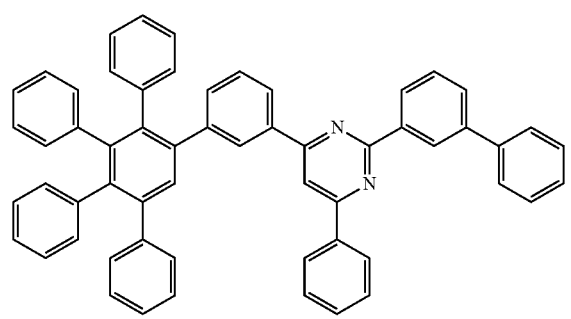
99
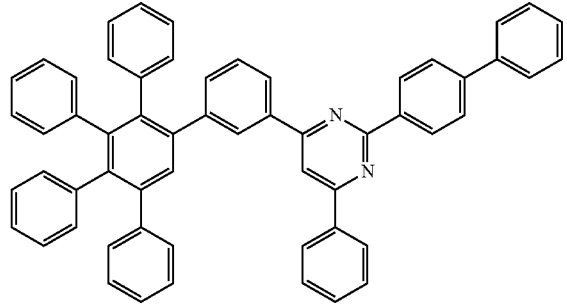
100
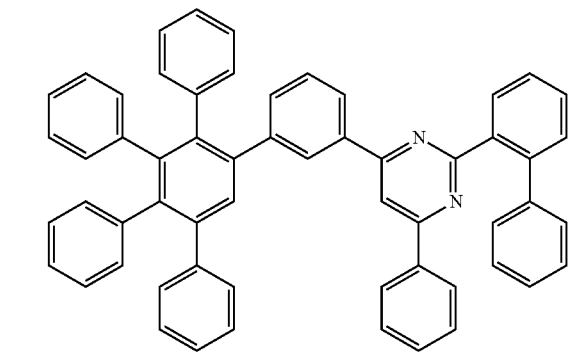
101
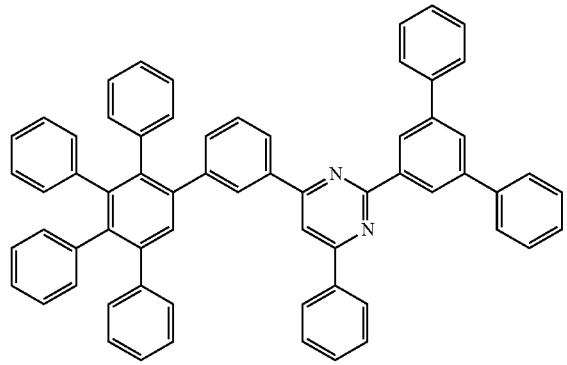
102
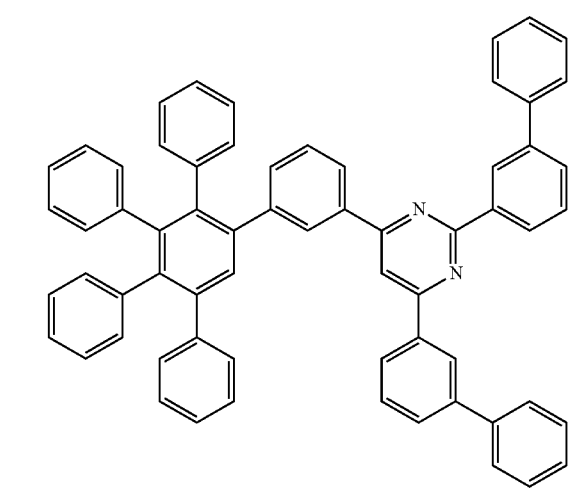

231
-continued
103
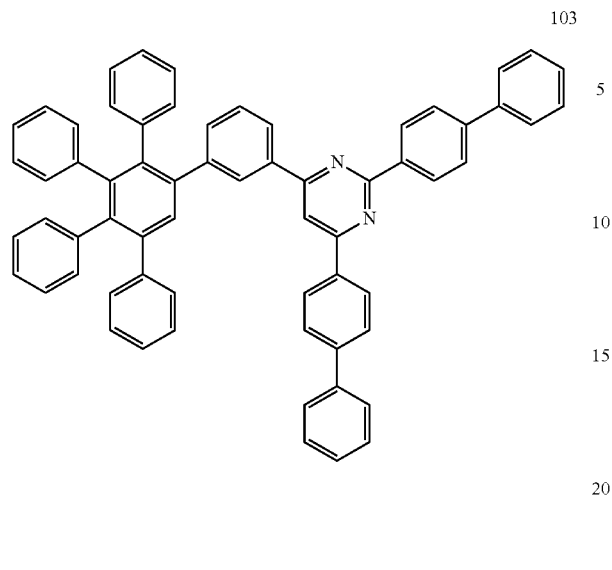
104
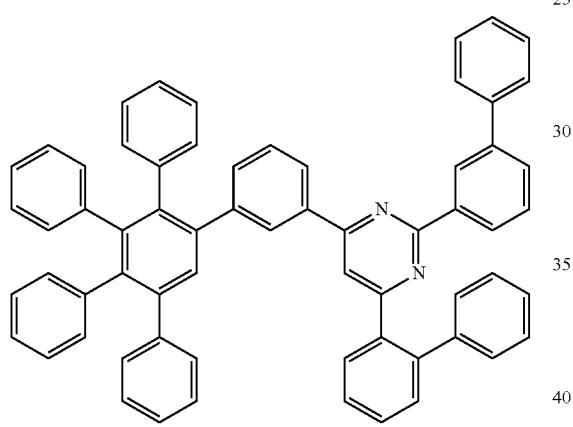
105
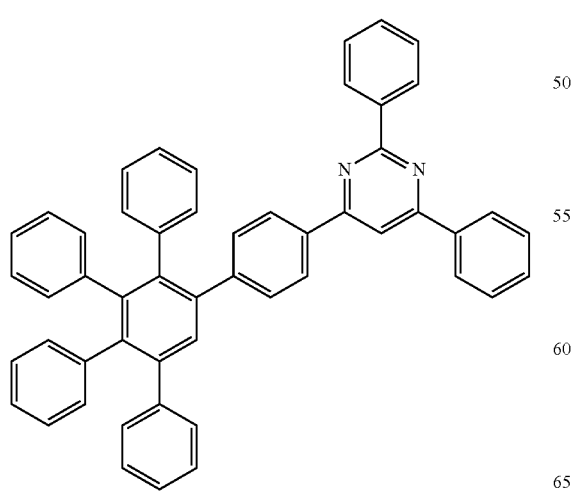
232
-continued
106
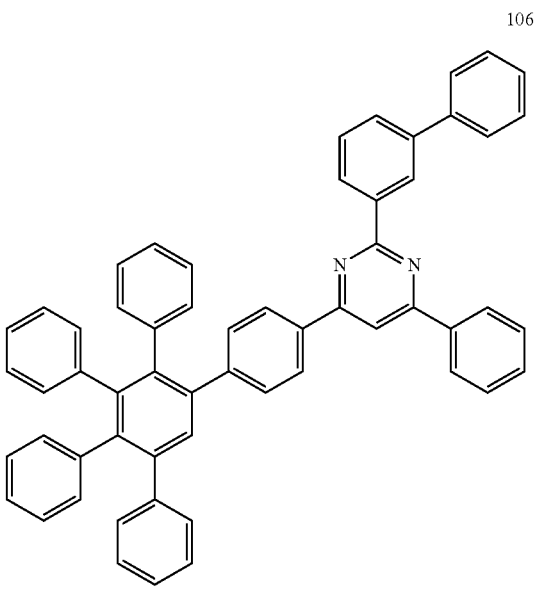
107
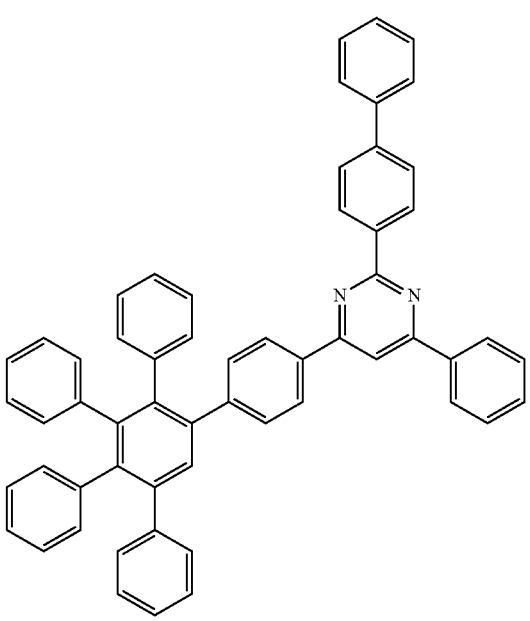

108
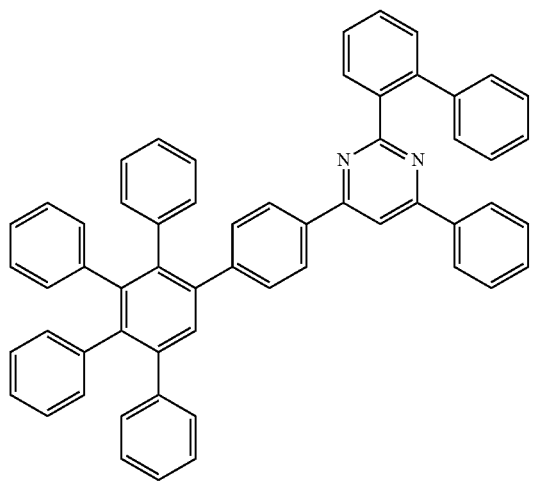
109
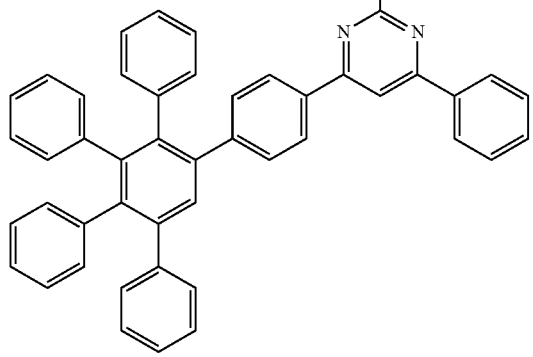
110
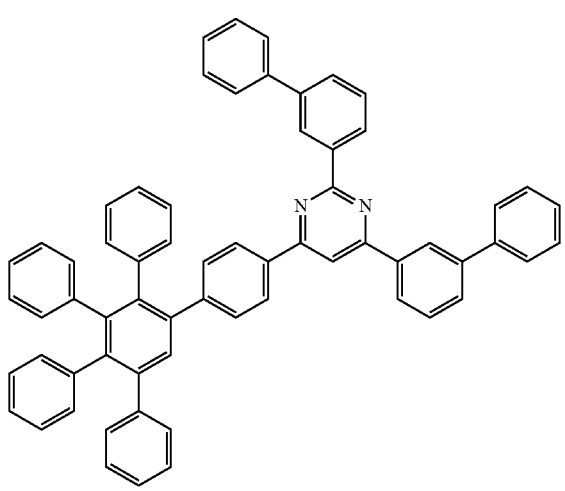
111
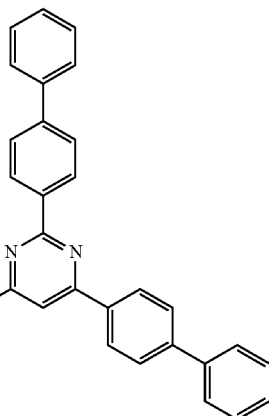
112
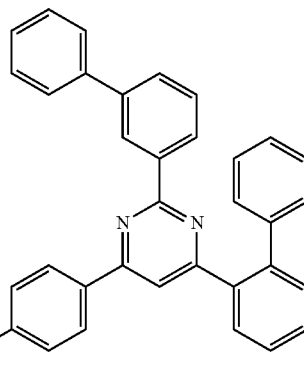
113
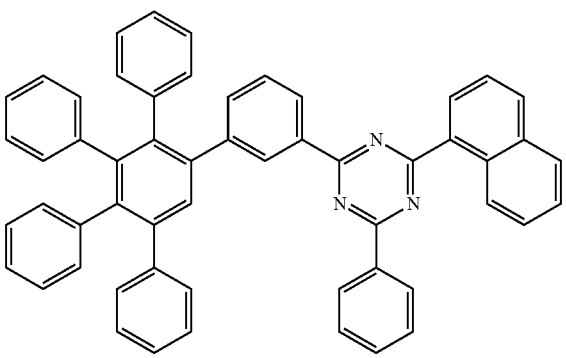

114
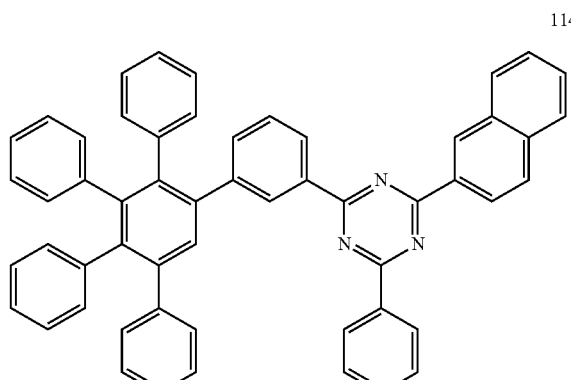
118
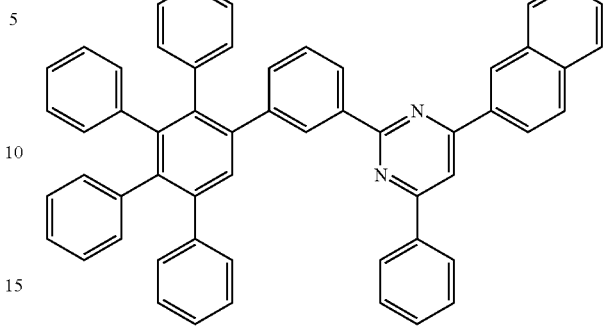
115
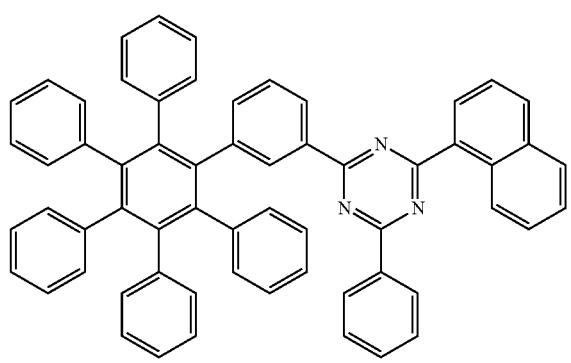
119
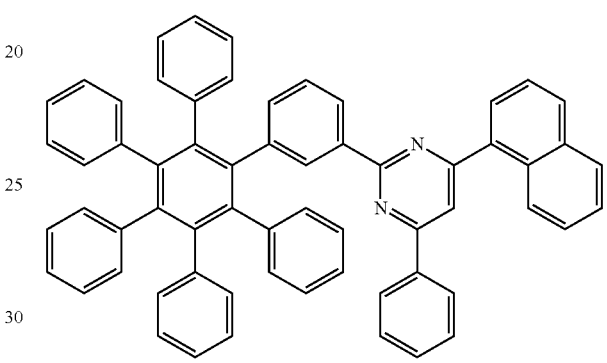
116
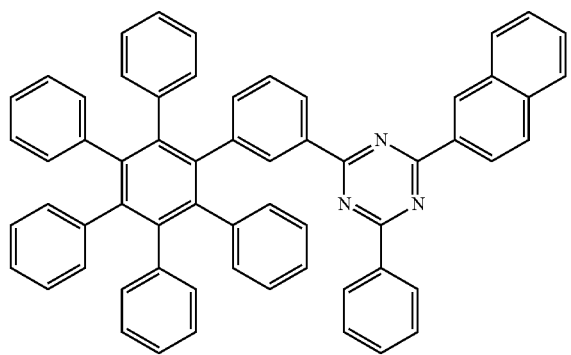
120
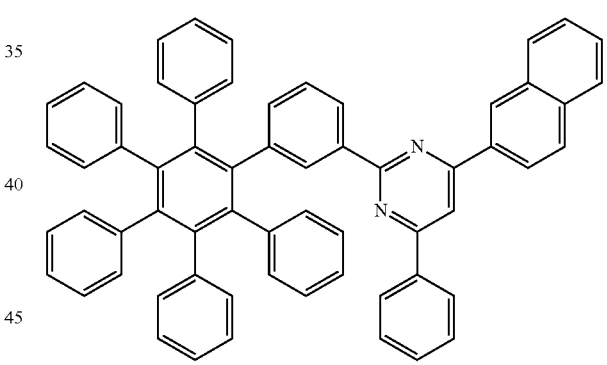
117
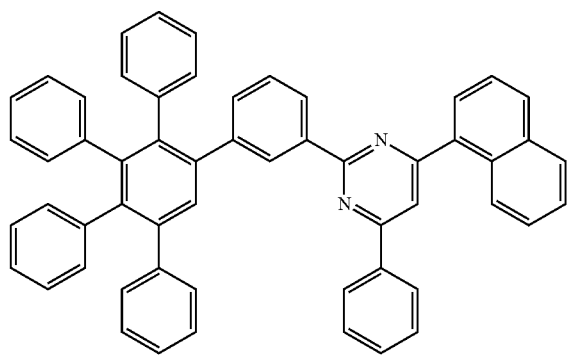
121
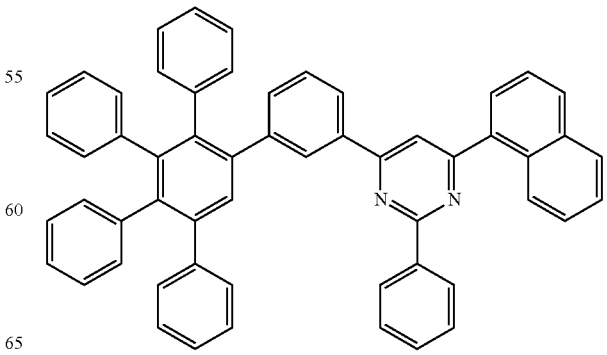

237
-continued
122
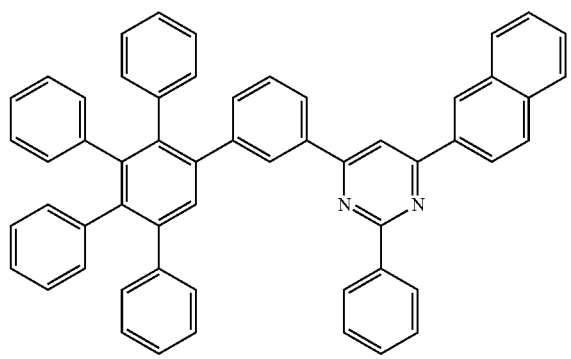
123
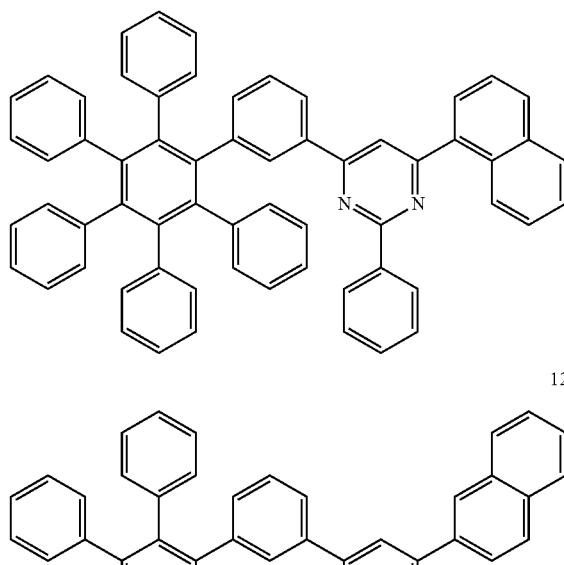
124
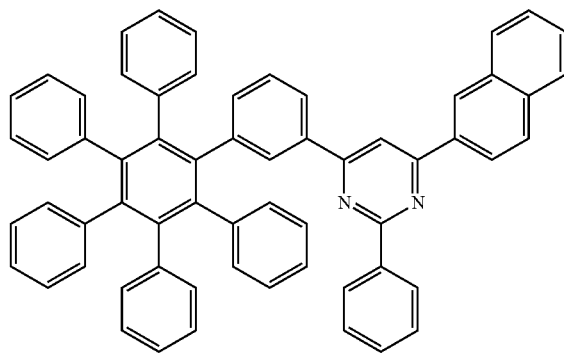
125
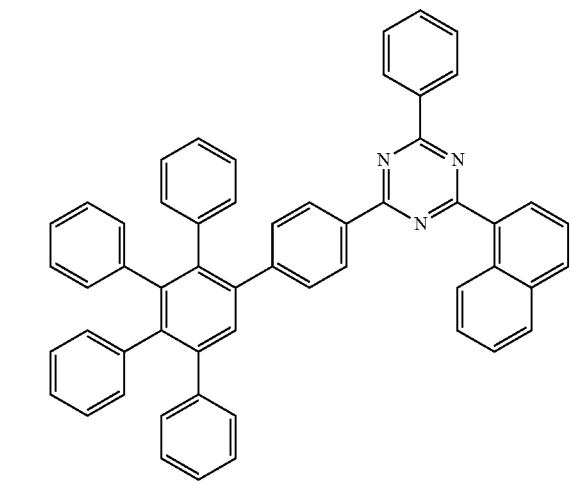
238
-continued
126
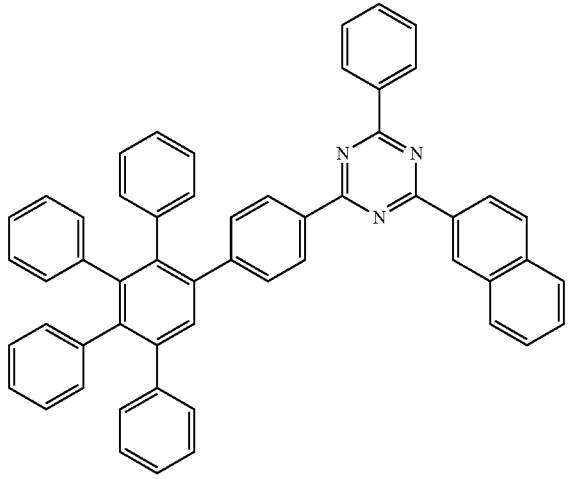
127
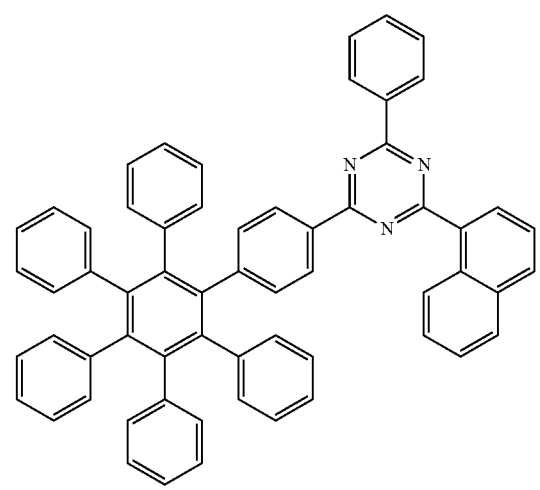
128
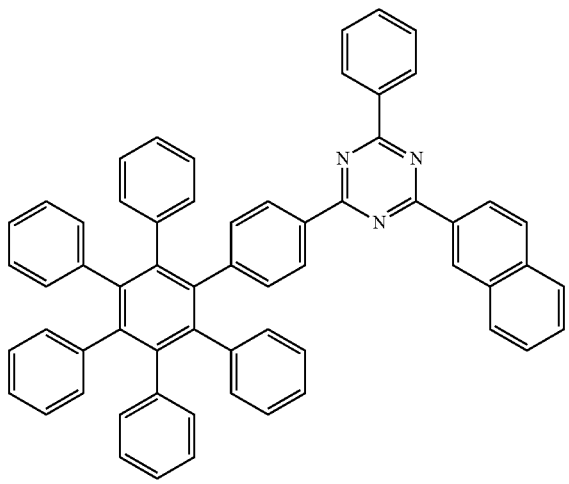

129
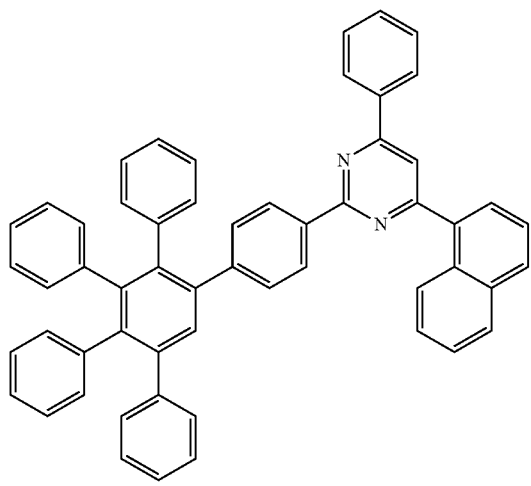
130
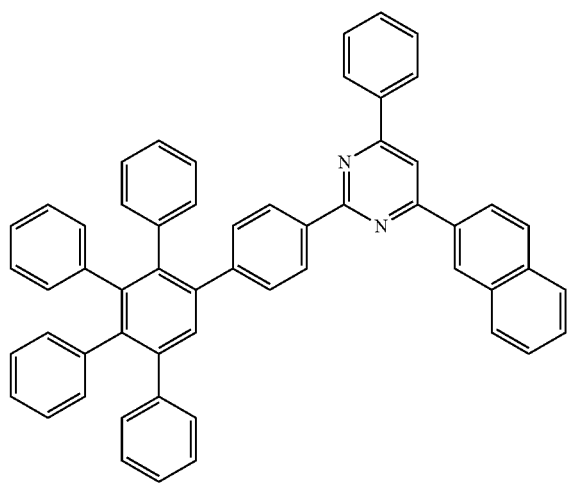
131
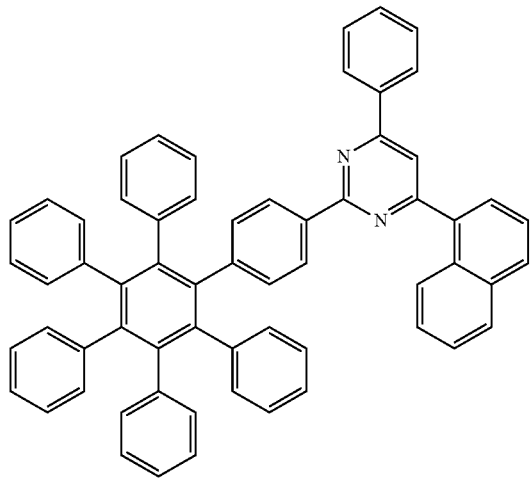
132
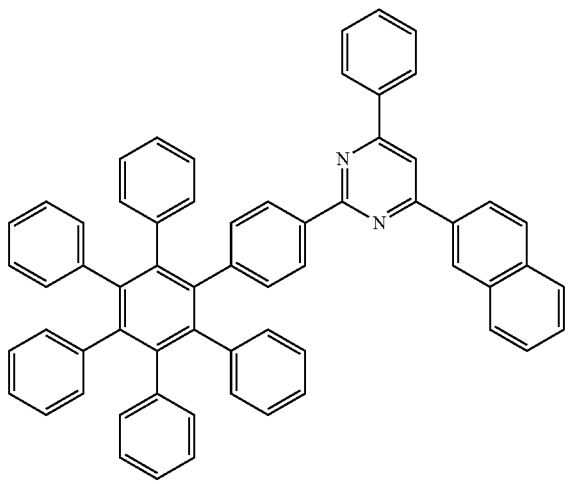
133
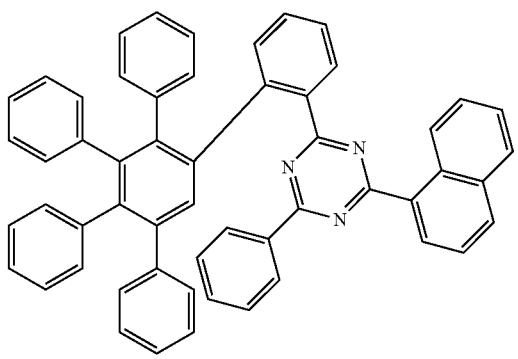
134
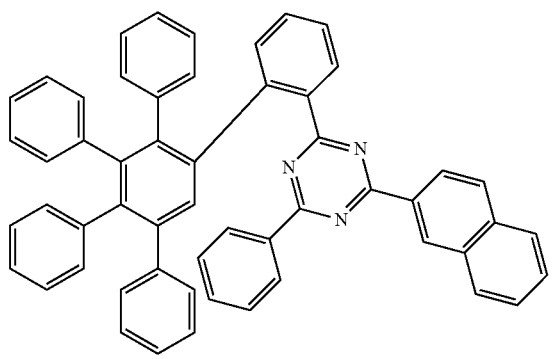

135
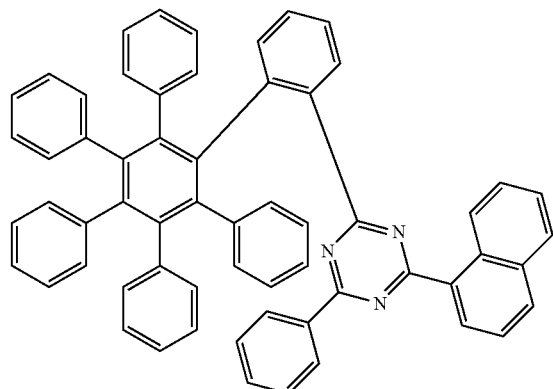
136
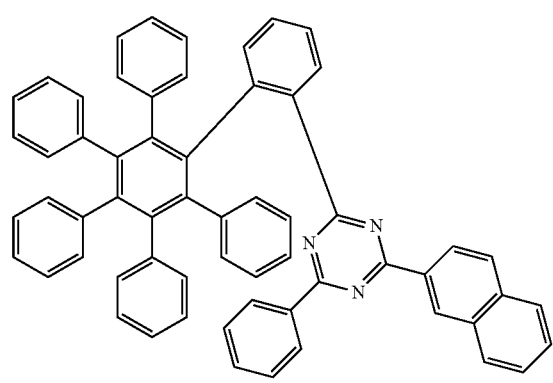
137
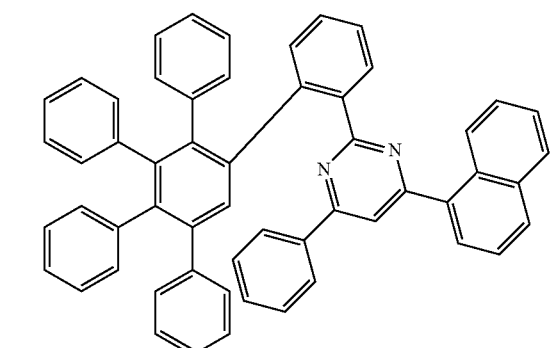
138
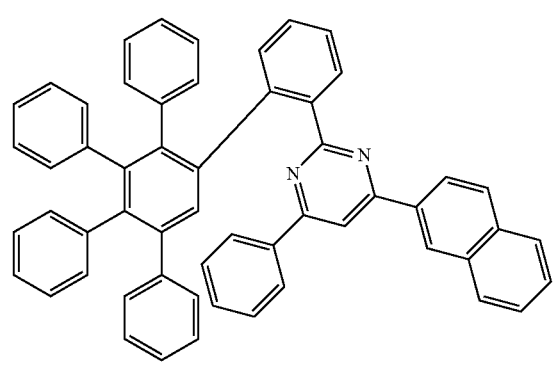
139

140
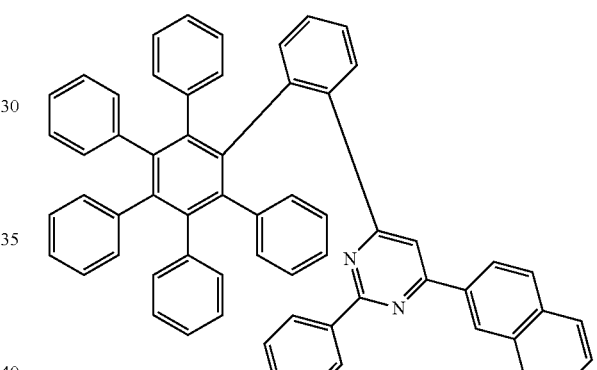
141
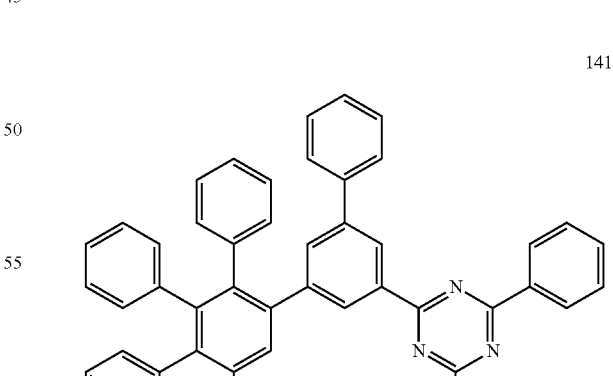

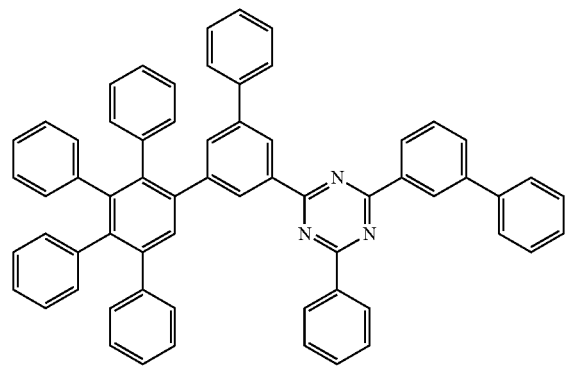
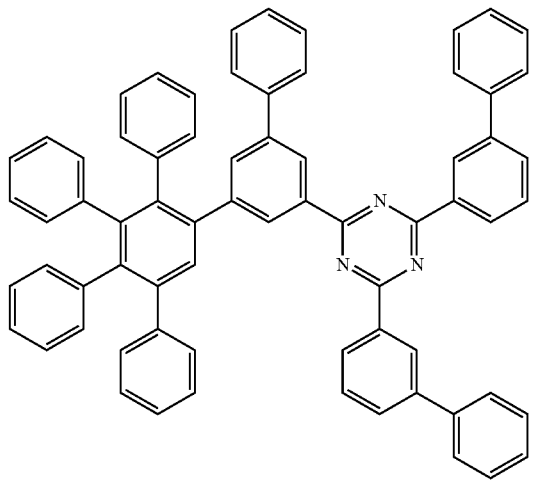
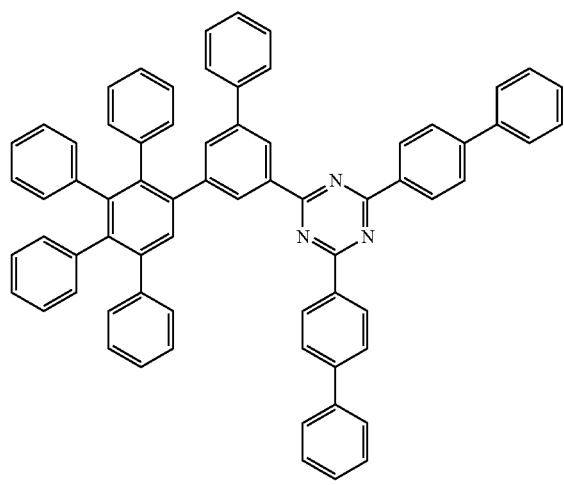
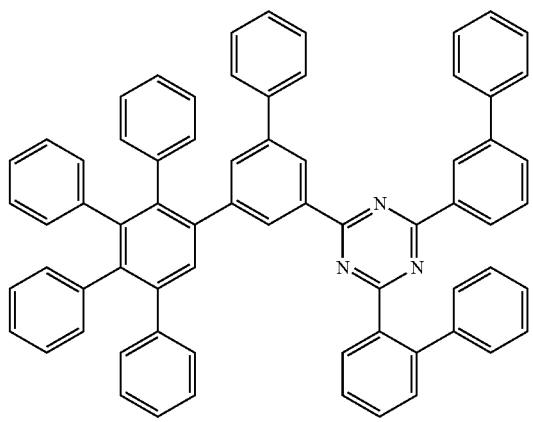

-continued

149

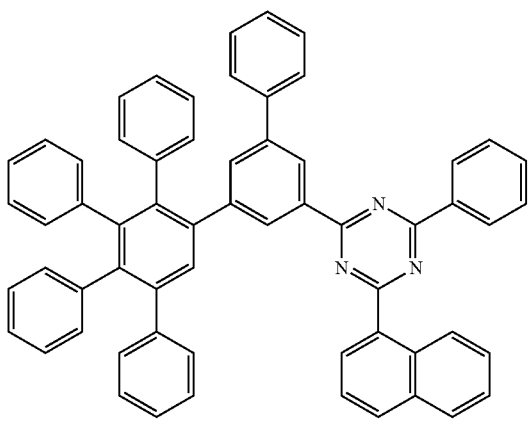

150

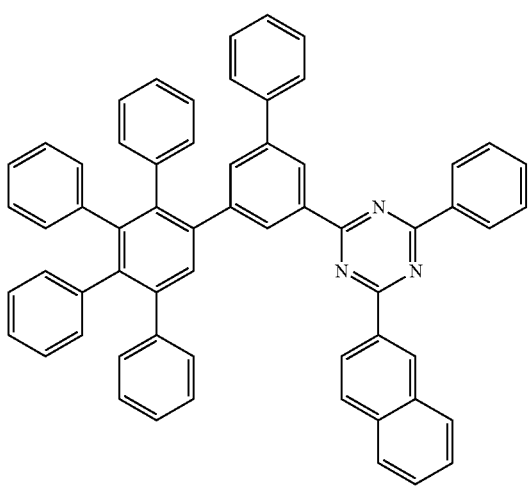

151

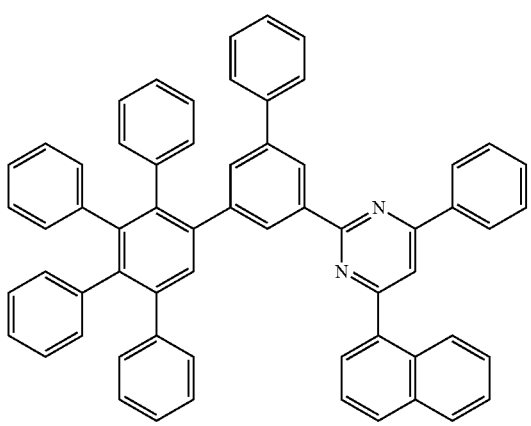

-continued

152

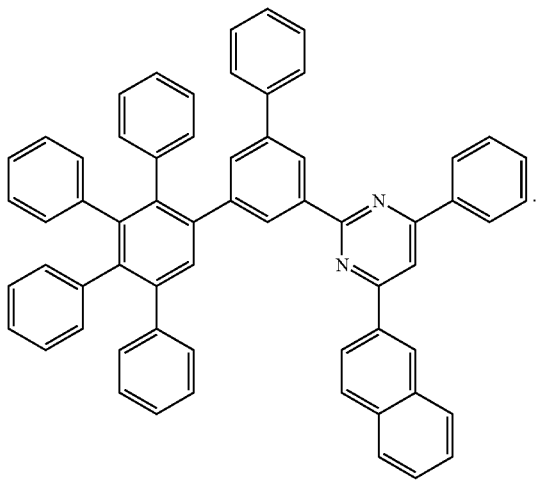

10. An organic optoelectronic device comprising
an anode and a cathode facing each other and
at least one organic layer between the anode and the cathode
wherein the organic layer includes the compound for an organic optoelectronic device of claim 1.

11. The organic optoelectronic device of claim 10, wherein the organic layer comprises an emission layer, an electron transport layer, and a hole transport layer,
wherein the electron transport layer or the emission layer comprises the compound for an organic optoelectronic device.

12. The organic optoelectronic device of claim 11, wherein the electron transport layer further comprises an electron transport auxiliary layer being adjacent to the emission layer, and
the electron transport auxiliary layer comprises the compound for an organic optoelectronic device.

13. The organic optoelectronic device of claim 11, wherein the emission layer further comprises at least one compound of a compound represented by Chemical Formula 2; and a compound consisting of a moiety represented by Chemical Formula 3 and a moiety represented by Chemical Formula 4:

[Chemical Formula 2]

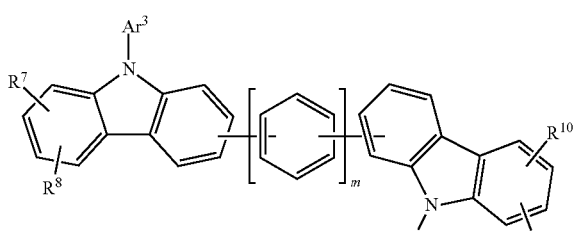

[Chemical Formula 3]

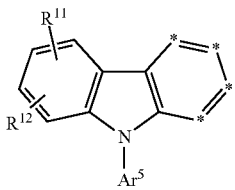

-continued

[Chemical Formula 4]

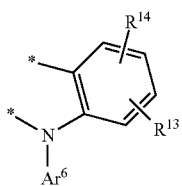

wherein, in Chemical Formulae 2 to 4, $Ar^3$ to $Ar^6$ are independently a substituted or unsubstituted C6 to C30 aryl group, or a substituted or unsubstituted C2 to C30 heteroaryl group, m is an integer of 0 or 1, adjacent two *'s of Chemical Formula 3 are combined with two *'s of Chemical Formula 4 to form a fused ring and * that does not form the fused ring of Chemical Formula 3 is independently $CR^b$, and $R^b$ and $R^7$ to $R^{14}$ are independently hydrogen, deuterium, a substituted or unsubstituted C1 to C10 alkyl group, C6 to C30 aryl group, or a substituted or unsubstituted C2 to C30 heteroaryl group.

14. The organic optoelectronic device of claim 13, wherein the substituted or unsubstituted C6 to C30 aryl group is a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted triphenylene group, or a substituted or unsubstituted fluorenyl group, and the substituted or unsubstituted C2 to C30 heteroaryl group is a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, or a substituted or unsubstituted quinazolyl group, wherein the "substituted" refers to replacement of at least one hydrogen by deuterium, a C1 to C10 alkyl group, a C6 to C18 aryl group, a C3 to C20 heteroaryl group.

15. A display device comprising the organic optoelectronic device of claim 10.

* * * * *